United States Patent
Xu et al.

(10) Patent No.: US 9,493,485 B2
(45) Date of Patent: Nov. 15, 2016

(54) SPIROCYCLIC DIHYDRO-THIAZINE AND DIHYDRO-OXAZINE BACE INHIBITORS, AND COMPOSITIONS AND USES THEREOF

(71) Applicant: Imago Pharmaceuticals, Inc., Jackson Hole, WY (US)

(72) Inventors: Ying-Zi Xu, Palo Alto, CA (US); Dean R. Artis, Kensington, CA (US); Simeon Bowers, Oakland, CA (US); Roy K. Hom, San Francisco, CA (US); Hing L. Sham, Palo Alto, CA (US); Shendong Yuan, San Ramon, CA (US)

(73) Assignee: Imago Pharmaceuticals, Inc., Jackson Hole, WY (US)

( * ) Notice: Subject to any disclaimer, the term of this patent is extended or adjusted under 35 U.S.C. 154(b) by 0 days.

(21) Appl. No.: 14/386,722

(22) PCT Filed: Mar. 20, 2013

(86) PCT No.: PCT/US2013/033177
§ 371 (c)(1),
(2) Date: Sep. 19, 2014

(87) PCT Pub. No.: WO2013/142613
PCT Pub. Date: Sep. 26, 2013

(65) Prior Publication Data
US 2015/0307518 A1     Oct. 29, 2015

Related U.S. Application Data

(60) Provisional application No. 61/613,377, filed on Mar. 20, 2012, provisional application No. 61/727,248, filed on Nov. 16, 2012.

(51) Int. Cl.
| | | |
|---|---|---|
| *C07D 513/10* | (2006.01) |
| *C07D 417/12* | (2006.01) |
| *C07D 413/14* | (2006.01) |
| *C07D 413/10* | (2006.01) |
| *C07D 413/12* | (2006.01) |
| *C07D 265/12* | (2006.01) |
| *C07D 265/18* | (2006.01) |
| *C07D 498/10* | (2006.01) |
| *C07D 279/16* | (2006.01) |

(52) U.S. Cl.
CPC ........... *C07D 513/10* (2013.01); *C07D 265/12* (2013.01); *C07D 265/18* (2013.01); *C07D 279/16* (2013.01); *C07D 413/10* (2013.01); *C07D 413/12* (2013.01); *C07D 413/14* (2013.01); *C07D 417/12* (2013.01); *C07D 498/10* (2013.01)

(58) Field of Classification Search
CPC ..................................... C07D 513/10
USPC ........................... 514/222.2; 544/6
See application file for complete search history.

(56) References Cited

U.S. PATENT DOCUMENTS

| | | |
|---|---|---|
| 2007/0185144 A1 | 8/2007 | Zhong et al. |
| 2009/0082560 A1 | 3/2009 | Kobayashi et al. |
| 2010/0075957 A1 | 3/2010 | Tamura et al. |
| 2010/0222338 A1 | 9/2010 | Zhong et al. |
| 2012/0016116 A1 | 1/2012 | Kobayashi et al. |
| 2012/0022249 A1 | 1/2012 | Kobayashi et al. |
| 2012/0172355 A1 | 7/2012 | Tamura et al. |
| 2013/0158260 A1 | 6/2013 | Kobayashi et al. |
| 2013/0303755 A1 | 11/2013 | Kobayashi et al. |
| 2014/0073815 A1 | 3/2014 | Tamura et al. |

FOREIGN PATENT DOCUMENTS

| | | |
|---|---|---|
| EP | 1 942 105 A1 | 7/2008 |
| WO | WO 2007/061670 A1 | 5/2007 |

OTHER PUBLICATIONS

Partial Supplementary European Search Report issued Nov. 2, 2015 in Patent Application No. 13764741.8.
Supplementary European Search Report issued Feb. 26, 2016, in European Patent Application No. 13764741.8 filed Mar. 20, 2013.

*Primary Examiner* — Kahsay Habte
(74) *Attorney, Agent, or Firm* — Oblon, McClelland, Maier & Neustadt, L.L.P.

(57) ABSTRACT

Compounds are provided having a structure according to Formula (I): wherein $A_1$, $A_2$, $A_3$, Y, $R^1$, $R^2$, $R^3$, $R^4$, $R^5$, $R^6$, m, n and p are defined herein. Further provided are pharmaceutical compositions including the compounds provided and methods of making and using the compounds and compositions as provided, e.g., in the treatment and prevention of various disorders, such as Alzheimer's disease.

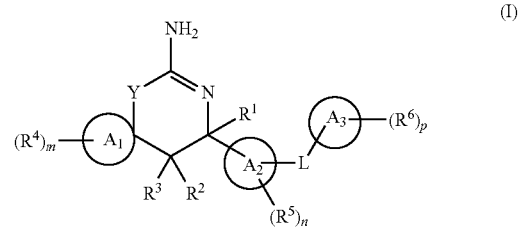

19 Claims, No Drawings

SPIROCYCLIC DIHYDRO-THIAZINE AND DIHYDRO-OXAZINE BACE INHIBITORS, AND COMPOSITIONS AND USES THEREOF

RELATED APPLICATIONS

This application claims priority to U.S. Provisional Patent Application No. 61/613,377, filed on Mar. 20, 2012, and 61/727,248, filed on Nov. 16, 2012 the entirety of which are incorporated herein by reference.

BACKGROUND OF THE INVENTION

Beta-secretase 1 (also known as beta-site amyloid precursor protein cleaving enzyme 1, BACE1, memapsin-2 and aspartyl protease 2) cleaves amyloid precursor protein (APP) to form an extracellular fragment (sAPPβ) and a 99 amino acid residue cell membrane bound fragment (CTFβ). The CTFβ fragment is further processed by gamma-secretase to form amyloid-β peptides of either 40 amino acids (Aβ-40) or 42 amino acids (Aβ-42). These amyloid-β peptides are involved in Alzheimer's disease pathology, with Aβ-42 considered the more detrimental species. In mutations of APP that are associated with Alzheimer's disease, the production of Aβ-42 is increased relative to Aβ-40. Aβ peptides are also relevant to the processing of tau. Alzheimer's disease, a common form of dementia, is a progressive degenerative disease that is characterized by two major pathologic observations in the brain which are (1) neurofibrillary tangles, which are aggregates of hyperphosphorylated tau proteins, and (2) amyloid-β plaques, which form from insoluble aggregates of amyloid-β peptides. See, for example, O'Brien and Wong, Annual Review of Neuroscience 2011, 34:185-204. The disease results in memory loss and impaired cognitive ability, and current therapy is limited to treating the symptoms. The inhibition of BACE1 is considered a desirable pharmaceutical target, as inhibition of BACE1 is likely to slow the progression of diseases resulting in β-amyloidosis, such as Alzheimer's disease.

An extra copy of chromosome 21 is found in individuals with Down syndrome. This chromosome contains the gene encoding APP, as well as the gene encoding BACE2 (a closely related homolog to BACE1). Down syndrome patients tend to develop Alzheimer's disease at an early age. The additional APP gene is believed to result in overexpression of APP resulting in an increase in Aβ peptides, which could explain the early onset of Alzheimer's disease in these individuals. As such, inhibition of BACE1 is considered a desirable pharmaceutical target in treating Down syndrome (Jiang et al., PNAS Jan. 26, 2010, 107(4):1630-1635).

Beta-secretase 2 (BACE2) is expressed in the pancreas, and is believed to be involved in the processing of pancreatic β-cells and may have a role in diabetes-associated amyloidogenesis. See, for example, Esterhazy et al, Cell Metab. 2011, Sep. 7, 14(3):365-77; and Finzi et al., Ultrastructural Pathology 2008, November-December, 32(6):246-51. The inhibition of BACE2 is considered a desirable pharmaceutical target, for example in the treatment of type 2 diabetes.

A number of other diseases involve β-amyloidosis, or are otherwise desirable targets for treatment with an inhibitor of BACE1 and/or BACE2. These include amyotrophic lateral sclerosis (Rabinovich-Toidman et al., Neurodegenerative Disease 2012, Jan. 21; Koistinen et al., Muscle Nerve 2006, October, 34(4):444-50), cerebral amyloid angiopathy (Blaise et al., The Aging Cell 2012, Jan. 19; Zipfel et al., Stroke 2009, March, 40(3 Suppl):S16-S19), retinal diseases, such as glaucoma and age-related macular degeneration (Guo et al., PNAS 2007, Aug. 14, 104(33):13444-13449; Bruban et al., Adv Exp Med Biol. 2012, 723:67-74; Ding et al., PNAS 2011, Jul. 12, 108(28):E279-E287), cardiovascular related disorders, such as cardiac arrest, stroke, or ischemia (Zetterberg et al., PLoS ONE 2011, 6(12):e28263; Xiong et al., Neurobiology of Disease 2008, 32:433-441; Wen et al., Brain Research 2004, May 29, 1009(1-2):1-8), disorders involving demyelination, such as nerve injury, spinal cord injury, and multiple sclerosis (Farah et al., The Journal of Neuroscience, 2011, Apr. 13, 31(15):5744-5754), and inclusion body myositis (Jin et al., American Journal of Pathology December 1998, 153(6):1679-1686; Nogalska et al., Neurosci. Lett. 2010, May 3, 474(3):140-143).

Alzheimer's disease affects a large population of elderly people, and there are few options available at this time to combat this disease. As such, a considerable effort has been made to find a suitable BACE1 inhibitor. For example, BACE1 and/or BACE2 inhibitors are described in a large number of patent applications, including PCT publication numbers WO 2012057247, WO 2012057248, WO 2012147762, WO 2012147763, WO 2011071135, WO 2011071057, WO 2011070781, WO 2011069934, WO 2011058763, WO 2011005738, and WO 2009134617, US patent application publication numbers US 2010190279, US 2010160290, US 2010093999, US 20100075957, US 2009209755, US 2009082560, and US 20070287692, and US patent numbers U.S. Pat. No. 7,964,594, U.S. Pat. No. 7,759,353, and U.S. Pat. No. 7,592,348. One such BACE1 inhibitor has been tested in human clinical trials (May et al., Journal of Neuroscience, 2011, Nov. 16, 31(46):16507-16516).

In spite of considerable effort from several companies to find a suitable BACE1 inhibitor, few have made it into the clinic. There remains a need to find a suitable BACE1 inhibitor that is pharmaceutically active in the brain without unwanted side effects.

SUMMARY OF THE INVENTION

In one aspect, a compound is provided having a structure according to Formula I:

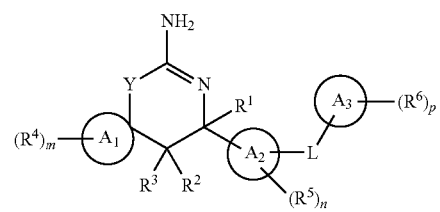

or a pharmaceutically acceptable salt thereof, wherein:
Y is O or S;
L is selected from the group consisting of a direct bond, —CR$^7$R$^8$—, —C(O)—, —O—, —S(O)$_z$—, —NR$^9$—, —CR$^7$R$^8$—CR$^{10}$R$^{11}$—, —CR$^7$R$^8$—C(O)—, —CR$^7$R$^8$—O—, —CR$^7$R$^8$—S(O)$_z$—, —CR$^7$R$^8$—NR$^9$—, —C(O)—CR$^{10}$R$^{11}$—, —C(O)—O—, —C(O)—NR$^9$—, —O—CR$^{10}$R$^{11}$—, —O—C(O)—, —S(O)$_z$—CR$^{10}$R$^{11}$—, —S(O)$_2$—NR$^9$—, —NR$^9$—CR$^{10}$R$^{11}$—, —NR$^9$—C(O)—, and —NR$^9$—S(O)$_2$—;
A$_1$ is a C$_{3-10}$ carbocyclic ring or a 3 to 10 membered heterocyclic ring;
A$_2$ is phenyl, naphthyl or a heteroaryl ring;
A$_3$ is phenyl, naphthyl or a heteroaryl ring;

$R^1$ is hydrogen, $C_{1-6}$ alkyl, or combines with $R^2$ to form a fused monocyclic $C_{3-7}$ carbocyclic ring or 3 to 7 membered heterocyclic ring;

$R^2$ and $R^3$ are independently hydrogen or halogen, or $R^3$ is hydrogen and $R^2$ combines with $R^1$ to form a fused monocyclic $C_{3-7}$ carbocyclic ring or a 3 to 7 membered heterocyclic ring;

$R^4$ at each occurrence is independently selected from the group consisting of halogen, —CN, $C_{1-6}$ alkyl, $C_{2-6}$ alkenyl, $C_{2-6}$ alkynyl, $C_{3-6}$ cycloalkyl, —OH, =O, —OR$^{12}$, —S(O)$_z$R$^{12}$, —C(O)R$^{12}$, —NR$^{13}$R$^{14}$, and =NR$^{14}$, wherein said $C_{1-6}$ alkyl, $C_{2-6}$ alkenyl, $C_{2-6}$ alkynyl, and $C_{3-6}$ cycloalkyl are optionally substituted with one or more fluoro, —OH, —NH$_2$, —OR$^a$, —S(O)$_z$R$^a$, —C(O)R$^a$, —NHR$^a$, —NR$^a$R$^b$, or optionally fluoro substituted $C_{3-6}$ cycloalkyl;

$R^5$ and $R^6$ at each occurrence are independently selected from the group consisting of halogen, —CN, —OH, —NH$_2$, —NO$_2$, —C(O)—OH, —C(O)—NH$_2$, —S(O)$_2$—NH$_2$, and L$_1$-R$^{15}$;

$R^7$, $R^8$, $R^9$, $R^{10}$, and $R^{11}$ are independently selected from the group consisting of hydrogen and $C_{1-6}$ alkyl;

$L_1$ at each occurrence is independently selected from the group consisting of a direct bond, —C(O)—, —O—, —S(O)$_z$—, —NR$^{16}$—, —C(O)—O—, —O—C(O)—, —C(O)—NR$^{16}$—, —NR$^{16}$—C(O)—, —S(O)$_2$—NR$^{16}$—, and —NR$^{16}$—S(O)$_2$—;

$R^{12}$ at each occurrence is independently selected from the group consisting of $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —NH$_2$, —OR$^a$, —S(O)$_z$R$^a$, —C(O)R$^a$, —NHR$^a$, —NR$^a$R$^b$, and optionally fluoro substituted $C_{3-6}$ cycloalkyl;

$R^{13}$ and $R^{14}$ at each occurrence are independently selected from the group consisting of hydrogen, $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl, are optionally substituted with one or more substituents independently selected from the group consisting of fluoro, —OH, —NH$_2$, —OR$^a$, —S(O)$_z$R$^a$, —C(O)R$^a$, —NHR$^a$, —NR$^a$R$^b$, and optionally fluoro substituted $C_{3-6}$ cycloalkyl, or $R^{13}$ and $R^{14}$ combine with the nitrogen to which they are attached to form a 4-7 membered monocyclic heterocyclic ring or a 5 or 7 membered heteroaryl ring, wherein said ring is optionally substituted with one or more substituents independently selected from the group consisting of halogen, —CN, =O, —OH, —NH$_2$, —OR$^a$, —S(O)$_z$R$^a$, —C(O)R$^a$, —NHR$^a$, —NR$^a$R$^b$, optionally fluoro substituted $C_{1-6}$ alkyl, optionally fluoro substituted $C_{2-6}$ alkenyl, optionally fluoro substituted $C_{2-6}$ alkynyl, and optionally fluoro substituted $C_{3-6}$ cycloalkyl;

$R^{15}$ at each occurrence is independently selected from the group consisting of $C_{1-6}$ alkyl, $C_{2-6}$ alkenyl, $C_{2-6}$ alkynyl, $C_{3-6}$ cycloalkyl, 3-7 membered heterocycloalkyl, phenyl, naphthyl, and heteroaryl, wherein phenyl, naphthyl, and heteroaryl are optionally substituted with one or more substituents independently selected from the group consisting of —CN, —OH, —NO$_2$, —C(O)—OH, $C_{1-6}$ alkyl, $C_{2-6}$ alkenyl, $C_{2-6}$ alkynyl, $C_{3-6}$ cycloalkyl, 3-7 membered heterocycloalkyl, phenyl, 5 or 6 membered heteroaryl, —OR$^{17}$, —S(O)$_z$R$^{17}$, —NR$^{18}$R$^{19}$, —C(O)R$^{17}$, —C(O)—OR$^{17}$, —O—C(O)R$^{17}$, —C(O)—NR$^{18}$R$^{19}$, —NR$^{16}$—C(O)R$^{17}$, —S(O)$_2$—NR$^{18}$R$^{19}$, and —NR$^{16}$—S(O)$_2$R$^{17}$, and wherein $C_{1-6}$ alkyl, $C_{2-6}$ alkenyl, $C_{2-6}$ alkynyl, $C_{3-6}$ cycloalkyl, and 3-7 membered heterocycloalkyl, as $R^{15}$ or as a substituent of phenyl, naphthyl, or heteroaryl, are optionally substituted with one or more substituents independently selected from the group consisting of fluoro, —CN, —OH, =O, =NH, —NO$_2$, —C(O)—OH, $C_{3-6}$ cycloalkyl, 3-7 membered heterocycloalkyl, —OR$^{17}$, —S(O)$_z$R$^{17}$, =NR$^{17}$, —NR$^{18}$R$^{19}$, —C(O)R$^{17}$, —C(O)—OR$^{17}$, —O—C(O)R$^{17}$, —C(O)—NR$^{18}$R$^{19}$, —NR$^{16}$—C(O)R$^{17}$, —S(O)$_2$—NR$^{18}$R$^{19}$, and —NR$^{16}$—S(O)$_2$R$^{17}$;

$R^{16}$ at each occurrence is independently selected from the group consisting of hydrogen and $C_{1-6}$ alkyl;

$R^{17}$ at each occurrence is independently selected from the group consisting of $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —NH$_2$, —OR$^a$, —S(O)$_z$R$^a$, —C(O)R$^a$, —NHR$^a$, —NR$^a$R$^b$, and optionally fluoro substituted $C_{3-6}$ cycloalkyl;

$R^{18}$ and $R^{19}$ at each occurrence are independently selected from the group consisting of hydrogen, $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —NH$_2$, —OR$^a$, —S(O)$_z$R$^a$, —C(O)R$^a$, —NHR$^a$, —NR$^a$R$^b$, and optionally fluoro substituted $C_{3-6}$ cycloalkyl, or $R^{18}$ and $R^{19}$ combine with the nitrogen to which they are attached to form a 4-7 membered monocyclic heterocyclic ring or a 5 or 7 membered heteaoryl ring, wherein said ring is optionally substituted with one or more substituents independently selected from the group consisting of halogen, —CN, =O, —OH, —NH$_2$, —OR$^a$, —S(O)$_z$R$^a$, —C(O)R$^a$, —NHR$^a$, —NR$^a$R$^b$, optionally fluoro substituted $C_{1-6}$ alkyl, optionally fluoro substituted $C_{2-6}$ alkenyl, optionally fluoro substituted $C_{2-6}$ alkynyl, and optionally fluoro substituted $C_{3-6}$ cycloalkyl;

$R^a$ and $R^b$ at each occurrence are independently selected from the group consisting of optionally fluoro substituted $C_{1-6}$ alkyl, optionally fluoro substituted $C_{2-6}$ alkenyl, optionally fluoro substituted $C_{2-6}$ alkynyl, and optionally fluoro substituted $C_{3-6}$ cycloalkyl, or $R^a$ and $R^b$ combine with the nitrogen to which they are attached to form N-linked-heterocycloalkyl;

m is 0, 1 or 2;

n is 0, 1, 2 or 3;

p is 0, 1, 2 or 3; and z is 0, 1 or 2.

In one aspect, a compound as provided herein is an inhibitor of BACE, including BACE1 and/or BACE2. The provided compound is useful for the treatment of a variety of diseases, including, but not limited to, Alzheimer's disease, Parkinson's disease, Down syndrome, glaucoma, age-related macular degeneration, cerebral amyloid angiopathy, amyotrophic lateral sclerosis, multiple sclerosis, nerve injury, spinal cord injury, cardiac arrest, stroke, ischemia, inclusion body myositis and type 2 diabetes. Also provided is a pharmaceutical composition comprising a compound of Formula I, and a method of utilizing the composition in the treatment and prevention of various diseases.

DETAILED DESCRIPTION OF THE INVENTION

Definitions

The definitions and explanations below are for the terms as used throughout this entire document including both the specification and the claims. Reference to compounds as described herein (e.g. a compound of Formula I), includes reference to Formula I including any sub-generic embodiments thereof, e.g. Formula Ia, Ib or Ic (including all sub-generic embodiments thereof). Similarly, reference to compounds of Formula II or Formula III includes reference to any subgeneric embodiments thereof, e.g. Formula IIa, IIb, or IIc and Formula IIIa-IIIh, respectively (including all sub-generic embodiments thereof). Throughout the specification and the appended claims, a given formula or name shall encompass all isomers thereof, such as stereoisomers (e.g. diastereomers, enantiomers, atropisomers), geometrical isomers, tautomers, and mixtures thereof where such isomers exist, unless the description designates a specific isomer.

It should be noted that, as used in this specification and the appended claims, the singular forms "a", "an", and "the" include plural referents unless the content clearly dictates otherwise. Thus, for example, reference to a composition containing "a compound" includes a composition containing a single compound, as well as a composition containing a mixture of two or more compounds. It should also be noted that the term "or" is generally employed in its sense including "and/or" unless the content clearly dictates otherwise.

Compounds were named using ChemDraw Ultra v. 10.0, (available from Cambridgesoft at 100 Cambridge Park Drive, Cambridge, Mass. 02140). Alternatively, the names were generated based on the IUPAC rules or were derived from names originally generated using the aforementioned nomenclature programs. In any instance where there may be any ambiguity between a name given to a compound structure, or if no name is provided for a given structure, the provided structure is intended to clearly define the compound, and those compounds only described by the given structure can be readily named using the above methods, or other methods known to one skilled in the art.

Where multiple substituents are indicated as being attached to a structure, those substituents are independently selected unless otherwise indicated. For example "$(R^5)_n$" indicates $R^5$ is an optional substituent (n=0, 1, 2, or 3) of ring $A_2$, and when n is 2 or 3 $R^5$ groups, each $R^5$ is independently selected from the Markush group of options (i.e., can be the same or different than another $R^5$ substituent of the ring, e.g. when n is 2, both $R^5$ could be independently halogen; both $R^5$ could be independently $C_{1-6}$ alkyl; one $R^5$ could be halogen, while the other $R^5$ could be $C_{1-6}$ alkyl, etc.). It is understood that for any optionally substituted group, any such substitution results in a stable molecule. Similarly, when different R groups are described as having the same Markush group of options, each R is independently selected from the Markush group of options. For example "$R^7$, $R^8$, $R^9$, . . . are independently selected from the group consisting of hydrogen and $C_{1-6}$ alkyl" means that $R^7$ is independently hydrogen or any $C_{1-6}$ alkyl group, $R^8$ is independently hydrogen or any $C_{1-6}$ alkyl group, etc. Similarly, where a designated R group is used in more than one Markush group member, for example $R^{17}$ in —$OR^{17}$ or —$S(O)_zR^{17}$, it is understood that each occurrence of $R^{17}$ is independently selected from the Markush group of options. As such, these R group definitions can be readily narrowed independently in a subsequent dependent claim.

The term "alkyl", by itself or as part of another substituent, means a straight or branched chain, saturated hydrocarbon radical having the number of carbon atoms as indicated. For example, "$C_{1-6}$ alkyl" means a straight or branched chain, saturated hydrocarbon radical having from 1 to 6 carbon atoms and "$C_{1-3}$ alkyl" means a straight or branched chain saturated hydrocarbon radical having from 1 to 3 carbon atoms. The alkyl group includes di- and multivalent radicals. For example, the alkyl group includes alkylene wherever appropriate, e.g., when the formula indicates that the alkyl group is divalent or when substituents are joined to form a ring. Examples of alkyl radicals include, but are not limited to methyl, ethyl, n-propyl, iso-propyl, n-butyl, tert-butyl, iso-butyl, sec-butyl, as well as homologs and isomers of, for example, n-pentyl or n-hexyl. Where it is indicated that alkyl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of alkyl, or alkyl substituted on another moiety, are attached at any available atom to provide a stable compound.

The term "alkenyl", by itself or as part of another substituent means a straight or branched chain, hydrocarbon radical that is unsaturated or polyunsaturated so as to have one, two or three double bonds, and having the number of carbon atoms as indicated. For example "$C_{2-6}$ alkenyl" means a straight or branched chain, hydrocarbon radical having from 2 to 6 carbon atoms and having one, two or three double bonds. Exemplary $C_{2-6}$ alkenyl includes vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like. Where it is indicated that alkenyl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of alkenyl, or alkenyl substituted on another moiety, are attached at any available atom to provide a stable compound.

The term "alkynyl", by itself or as part of another substituent means a straight or branched chain, hydrocarbon radical that is unsaturated or polyunsaturated so as to have one, two or three triple bonds, and having the number of carbon atoms as indicated. For example "$C_{2-6}$ alkynyl" means a straight or branched chain, hydrocarbon radical having from 2 to 6 carbon atoms and having one, two or three triple bonds. Exemplary $C_{2-6}$ alkynyl includes prop-1-ynyl, prop-2-ynyl (i.e., propargyl), ethynyl and 3-butynyl. Where it is indicated that alkynyl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of alkynyl, or alkynyl substituted on another moiety, are attached at any available atom to provide a stable compound.

The terms "alkoxy", "alkylamino", "dialkylamino", "alkylthio", "alkylsulfinyl", or "alkylsulfonyl" are used in their conventional sense, and refer to substituted or unsubstituted alkyl groups as described herein above, having the number of carbon atoms as indicated, that are attached to the remainder of the molecule via an oxygen atom, an amino group, a sulfur atom, S(O) or S(O)$_2$, respectively. For example, "C$_{1-6}$ alkylamino" refers to an amino group substituted with one C$_{1-6}$ alkyl group and "di-C$_{1-6}$ alkylamino" refers to an amino group substituted independently with two C$_{1-6}$ alkyl groups. Where it is indicated that an alkyl group within alkoxy, alkylamino, etc. is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of alkoxy, alkylamino, etc., or alkoxy, alkylamino, etc. substituted on another moiety, are attached at any available atom to provide a stable compound.

The term "N-linked-heterocycloalkyl", by itself or as part of another substituent, means the group —NR'R", where R' and R" combine with the nitrogen to form a 5-7 membered heterocycloalkyl, where the heterocycloalkyl optionally contains an additional heteroatom within the ring, such as O, N, or S, and optionally is further substituted with C$_{1-6}$ alkyl. The ring is bound to the group it is a substituent of via the nitrogen. Examples of N-linked-heterocycloalkyl include, but are not limited to, piperidine, piperazine, 4-methylpiperazine, morpholine, and thiomorpholine. Where it is indicated that N-linked-heterocycloalkyl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of N-linked-heterocycloalkyl, or N-linked-heterocycloalkyl substituted on another moiety, are attached at any available atom to provide a stable compound.

The term "carbocyclic" as used herein in describing a fused ring, means a monocyclic saturated or partially unsaturated, non-aromatic ring or a bicyclic saturated or partially unsaturated ring, wherein the bicyclic ring system is non-aromatic, wherein all of the ring atoms are carbon, and having the number of ring carbon atoms as indicated. For example a C$_3$-C$_{10}$ carbocyclic ring is a monocyclic or bicyclic ring having 3 to 10 carbon ring atoms and a monocyclic C$_3$-C$_7$ carbocyclic ring is a monocyclic ring having 3 to 7 carbon ring atoms. As used herein, the carbocyclic ring is fused to another ring system, i.e. one or two of the ring carbon atoms is common to an additional ring system. For example ring A$_1$ of a compound of Formula I is a spirocyclic ring, as one carbon atom is shared with the core ring system. It is understood that this common carbon atom of the spirocyclic ring is counted among the 3 to 10 carbons of the C$_3$-C$_{10}$ carbocyclic ring, and that reference to A$_1$ as mono or bicyclic refers only to the fused spiro portion, i.e. the fused Spiro portion designated as A$_1$ can be mono or bicyclic, not including the core thiazine or oxazine ring as part of bicyclic. In the case of A$_1$ as a bicyclic ring, the second ring (i.e. the ring portion that does not include the spiroatom) can be aromatic, e.g. a fused phenyl. Such a spirocyclic ring system includes, without limitation, monocyclic rings such as cyclopropyl, cyclobutyl, cyclopentyl, cyclohexyl, cyclopentenyl, cyclohexenyl, and the like as well as bicyclic rings such as bicyclo[4.1.0]heptyl, bicyclo[4.4.0]decyl, bicyclo[2.2.1]heptyl, bicyclo[2.2.1]heptenyl, spiro[4.5]decyl, adamantyl, 1,2-dihydronaphthalenyl, 1,2,3,4-tetrahydronapthalenyl, 1H-indenyl, 2,3-dihydro-1H-indenyl and the like. Similarly, when R$^1$ and R$^2$ of a compound of Formula I combine to form a fused monocyclic C$_3$-C$_7$ carbocyclic, there are two carbon atoms in common with the core ring system, and it is understood that both common carbon atoms of the fused ring are counted among the 3 to 7 carbons of the C$_3$-C$_7$ carbocyclic ring. Such a fused ring system includes, without limitation, monocyclic rings such as cyclopropyl, cyclobutyl, cyclopentyl, cyclohexyl, cyclopentenyl, cyclohexenyl, and the like. Where it is indicated that a carbocyclic ring is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of a carbocyclic ring, or carbocyclic ring substituted on another moiety, are attached at any available atom to provide a stable compound.

The term "cycloalkyl" by itself or in combination with other terms, means a monocyclic saturated or partially unsaturated, non-aromatic ring, wherein all of the ring atoms are carbon, and having the number of ring carbon atoms as indicated. For example, C$_3$-C$_6$ cycloalkyl is a monocyclic ring having 3 to 6 carbon atoms. Examples of C$_3$-C$_6$ cycloalkyl include, but are not limited to, cyclopropyl, cyclobutyl, cyclopentyl, cyclohexyl, 1-cyclohexenyl, 3-cyclohexenyl, and the like. Where it is indicated that cycloalkyl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of cycloalkyl, or cycloalkyl substituted on another moiety, are attached at any available atom to provide a stable compound.

The term "heterocyclic" as used herein in describing a ring, means a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, also 1, 2 or 3 members of the ring are heteroatoms selected from, e.g., N, O, S, Si, B and P, also N, O and S, and the remaining ring atoms are carbon atoms, in stable combinations known to those of skill in the art. Heterocyclic ring nitrogen, sulfur and phosphorus atoms are optionally oxidized, and the nitrogen atom(s) are optionally quaternized. For example, a 3-10 membered heterocyclic ring is a monocyclic or bicyclic ring having 1-5 ring atoms as heteroatoms, with the remaining ring atoms as carbon. As used herein, the heteroyclic ring may be a fused ring to another ring system, i.e. one or two of the heterocyclic ring carbon atoms is common to an additional ring system. For example ring A$_1$ of a compound of Formula I is a spirocyclic ring, as one carbon atom is shared with the core ring system. It is understood that this common carbon atom of the spirocyclic ring is counted among the 3 to 10 members of the heterocyclic ring. In the case of a bicyclic ring at this position, the second ring (i.e. the ring portion that does not include the spiroatom) can be aromatic, e.g. a fused phenyl, pyridyl, pyrazolyl, or the like. Such a spirocyclic ring system includes, without limitation, monocyclic rings such as oxirane, oxetane, tetrahydrofuran, tetrahydropyran, dihydropyran, azetidine, pyrrolidine, piperidine, tetrahydropyridine, piperazine, morpholine, thiomorpholine, and the like as well as bicyclic rings such as oxaspiro[4.5]decyl, azabicyclo[4.1.0]heptyl, azabicyclo[2.2.2]octyl, tetrahydropyridine, tetrahydroindole, dihydrobenzothiophene, dihydrobenzofuran, tetrahydrobenzofuran and the like. Similarly, when R$^1$ and R$^2$ of a compound of Formula I combine to form a fused monocyclic 3 to 7 membered heterocyclic ring, there are two carbon atoms in common with the core ring system, and it is understood that both common carbon atoms of the fused ring are counted among the 3 to 7 members of the heterocyclic ring. Such a fused ring system includes, without limitation, monocyclic rings such as oxirane, oxetane, tetrahydrofuran, tetrahydropyran, dihydropyran, azetidine, pyrrolidine, piperidine, tetrahydropyridine, piperazine, morpholine, thiomorpholine, and the like. A monocyclic 4-7 membered heterocyclic ring as used to describe formation of a ring with two substituents of an amine group includes, for example, azetidine, pyrrolidine, piperidine, tetrahydropyridine, tetrahydropyrimidine, piperazine, morpholine, thiomorpholine, and the like. Where it is indicated that a heterocyclic ring is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, or a sulfur atom is substituted with 1 or 2 =O, where multiple substituents are independently selected unless indicated otherwise. It is understood that any substitutions of a heterocyclic ring are attached at any available atom to provide a stable compound.

The term "heterocycloalkyl", as used herein in describing a ring, means a monocyclic saturated or partially unsaturated, non-aromatic ring having the indicated number of ring atoms (members), where at least one member and up to 3 members of the ring are heteroatoms selected from, e.g., N, O, S, Si, B and P, also N, O and S, and the remaining ring atoms are carbon atoms, in stable combinations known to those of skill in the art. Heterocycloalkyl ring nitrogen, sulfur and phosphorus atoms are optionally oxidized, and the nitrogen atom(s) are optionally quaternized. For example "3-7 membered heterocycloalkyl" means a monocyclic heterocyclic ring having 3 to 7 members, where 1, 2, or 3 members are N, O, S, Si, B or P, also N, O, or S. The point of attachment of heterocycloalkyl to the group it is a substituent of can be via a carbon atom or via a heteroatom. Exemplary 3-7 membered heterocycloalkyl groups for compounds described herein (e.g. a compound of Formula I) include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuranyl, dihydropyranyl, tetrahydrothienyl S-oxide, tetrahydrothienyl S,S-dioxide, homothiomorpholinyl S-oxide, tetrahydropyridyl, and the like. In one example, heterocycloalkyl is cycoalkylamino. Where it is indicated that heterocycloalkyl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, or a sulfur atom is substituted with 1 or 2 =O, where multiple substituents are independently selected unless indicated otherwise. It is understood that any substitutions of heterocycloalkyl, or heterocycloalkyl substituted on another moiety, are attached at any available atom to provide a stable compound.

The terms "phenyl" and "naphthyl" have their meaning as known in the art, i.e. a benzene and naphthylene radical, respectively. Where it is indicated that phenyl or naphthyl are optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of phenyl or napthyl, or phenyl or napthyl substituted on another moiety, are attached at any available atom to provide a stable compound.

The term "heteroaryl", as used herein means, unless otherwise stated, a polyunsaturated, monocyclic or bicyclic 5 to 10 membered aromatic moiety containing at least one and up to 5 heteroatoms, also 1, 2 or 3 heteroatoms selected from N, O, S, Si and B, also N, O and S, and the remaining ring atoms are carbon atoms, in stable combinations known to those of skill in the art. Heteroaryl ring nitrogen and sulfur atoms are optionally oxidized, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. A bicyclic heteroaryl can have the at least one heteroatom in either of the fused rings, i.e. it can be attached to the group it is a substituent of either via a heteroatom containing ring or a carbon only containing ring. The point of attachment of heteroaryl to the group it is a substituent of can be via a carbon atom or a heteroatom (e.g. nitrogen). In one example, the heteroaryl group has from 1 to 9 carbon atoms and from 1 to 5 heteroatoms selected from O, S and N. A 5 or 6 membered heteroaryl means a monocyclic heteroryl ring having 5- or 6-members, where 1, 2, 3, or 4, also 1, 2 or 3, also 1 or 2, also one member(s) is N, O or S and the remaining members are carbon atoms. A 5 or 7 membered heteroaryl, for example when used to describe an NRR group that forms a heteroaryl ring, means a monocyclic heteroryl ring having 5- or 7-members, where 1 member is N, and 1, 2, or 3, also 1 or 2, also one other member(s) is N and the remaining members are carbon atoms. Non-limiting examples of 5 to 10 membered heteroaryl groups include pyridyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzothienyl, benzoxazolyl, pyridopyridyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. In one example, heteroaryl groups include furanyl, thienyl, pyrrolyl, imidazolyl, pyrazolyl, thiadiazolyl, triazolyl, isoxazolyl, oxazolyl, isothiazolyl, thiazolyl, oxadiazolyl, pyridazinyl, pyrazinyl, pyrimidinyl, and pyridyl. Where it is indicated that heteroaryl is optionally substituted with one or more substituents, typically 1, 2, 3, 4, or 5, also 1, 2, 3, or 4, also 1, 2, or 3, also 1 or 2, or one, hydrogen atom(s) are replaced with an indicated substituent, where multiple substituents are independently selected unless indicated otherwise. It is understood that any substitutions of heteroaryl, or heteroaryl substituted on another moiety, are attached at any available atom to provide a stable compound.

The terms "halo" or "halogen," by themselves or as part of another substituent, mean at least one of fluorine, chlorine, bromine and iodine.

By "haloalkyl" or "haloalkoxy" is meant an alkyl or alkoxy radical, as defined above, wherein at least one hydrogen atom of alkyl or the alkyl chain of alkoxy is replaced by a halogen atom, where typically 1, 2, 3, 4, or 5, also 1, 2, 3, or 4, also 1, 2, or 3, also 1 or 2, or 1 hydrogen atom(s) is replaced by an independently selected halogen. More typically, 1, 2 or 3 hydrogen atoms on the same carbon are replaced with 1, 2 or 3 halogen atoms. In one example, the halogen is fluorine or chlorine, also fluorine. The term "haloalkyl" or "haloalkoxy" is meant to include monohaloalkyl and polyhaloalkyl. For example, the term "$C_{1-6}$ haloalkyl" is meant to include, but not limited to, chloromethyl, 1-bromoethyl, fluoromethyl, difluoromethyl, trifluoromethyl, 2,2,2-trifluoroethyl, perfluoroethyl, 4-chlorobutyl, and 3-bromopropyl; and the term "$C_{1-6}$ haloalkoxy" is meant to include, but not limited to, fluoromethoxy, difluoromethoxy, trifluoromethoxy, 2,2,2-trifluoroethoxy, and perfluoroethoxy. Similarly, when a group such as cycloalkyl, alkyl, alkenyl, alkoxy, alkylsulfonyl and the like is referred to as optionally fluoro substituted, at least one hydrogen atom attached to a carbon of said group is replaced by a fluorine atom, where typically 1, 2, 3, 4, or 5, also 1, 2, 3, or 4, also 1, 2, or 3, also 1 or 2, or 1 hydrogen atom(s) is replaced by a fluorine atom. For example, the term "optionally fluoro substituted $C_{1-6}$ alkyl" is meant to include, but not limited to, fluoromethyl, difluoromethyl, trifluoromethyl, 2,2,2-trifluoroethyl, perfluoroethyl, and the like, and "optionally fluoro substituted $C_{1-6}$ alkoxy" is meant to include, but not limited to, fluoromethoxy, difluoromethoxy, trifluoromethoxy, 2,2,2-trifluoroethoxy, perfluoroethoxy, and the like.

As used herein, the term "heteroatom" includes oxygen (O), nitrogen (N), sulfur (S), silicon (Si), boron (B) and phosphorus (P). In one example, heteroatoms are O, S and N.

By "oxo" is meant the group =O.

As used herein, the term "aromatic ring" or "non-aromatic ring" is consistent with the definition commonly used in the art. For example, aromatic rings include phenyl and pyridyl. Non-aromatic rings include cyclohexanes, cyclohexenes, and the like.

As used herein, the term "fused ring" means at least a second ring fused to a first to form at least a bicyclic ring, wherein the first and second rings have at least 1 atom in common. For example, a fused ring with 1 atom in common refers to a spirocyclic fused ring such as that described for ring $A_1$ of compounds of Formula I. Fused ring systems can include aromatic as well as non aromatic rings, for example naphthalene is an example of fused 6 membered rings having 2 atoms in common, where both rings are aromatic, while 1,2,3,4-tetrahydronaphthalene is an example of fused 6 membered rings having 2 atoms in common, where one ring is aromatic and the other is partially saturated. A fused ring can also have more than two atoms in common, for example bridged fused rings such as bicyclo[3.3.1]nonane, which is an example of fused 6 membered rings having 3 atoms in common. Fused rings include naphthalene, indole, quinoline, chromene and the like. When a fused ring is described as part of a substituent, for example in Formula I where $R^1$ and $R^2$ may form a fused ring, the description refers to only the portion of the resulting fused ring represented by $R^1$, $R^2$ and the common atoms of the existing core ring in Formula I. As such, the description of $R^1$ and $R^2$ combining to form a fused monocyclic ring means that a monocyclic ring is fused to the existing core ring, resulting in a tricyclic ring (as the core ring is already at least bicyclic with the fused spirocyclic ring $A_1$). Similarly, the description of $A_1$ as mono or bicyclic refers only to the fused spiro portion, i.e. the fused Spiro portion designated as $A_1$ can be mono or bicyclic, not including the core thiazine or oxazine ring as part of bicyclic. For example, when ring $A_1$ is monocyclic and $R^1$ and $R^2$ do not form a ring, the entire compound of Formula I is bicyclic due to the fusion of monocyclic Spiro ring $A_1$.

As used herein, the term "protecting group" as it relates to a nitrogen, oxygen, or thiol protecting group, is used as a term well known in the art of organic synthesis. For example, a nitrogen protecting group includes, without limitation, carbobenzyloxy (Cbz), p-methoxybenzyl carbonyl (Mox or MeOZ), tert-butyloxycarbonyl (Boc), 9-fluorenylmethyloxycarbonyl (FMOC), Acetyl (Ac), Benzoyl (Bz), Benzyl (Bn), Carbamate, p-methoxybenzyl (PMB), 3,4-dimethoxybenzyl (DMPM), p-methoxyphenyl (PMP), and Tosyl (Ts); an oxygen or thiol protecting group includes, without limitation, Acetyl (Ac), Benzoyl (Bz), Benzyl (Bn), p-methoxybenzyl (PMB), β-methoxyethyoxymethyl (MEM), dimethoxytrityl (DMT), methoxymethyl (MOM), methoxytrityl (MMT), methylthiomethyl, pivaloyl, tetrahydropyranyl (THP), trityl (Tr), timethylsilyl (TMS), tert-butyldimethylsilyl (TBDMS), tri-iso-propylsilyloxymethyl (TOM), and triisopropylsilyl (TIPS). Such protecting groups and their use are readily known to one of skill in the art.

As used herein, the term "selective" or "selectivity" as it relates to protease activity, means that a compound as described herein, e.g. a compound of Formula I, is a more potent inhibitor of a particular protease, such as BACE1, when compared to another protease. As such, selectivity of BACE1 relative to another protease can be represented as a comparison, for example, of the $IC_{50}$ of a compound on the protease activity of BACE1 to the $IC_{50}$ of the compound on the protease activity of another protease. For example, a compound that is 50 fold or 50× selective for BACE1 protease activity relative to another protease activity will have a ratio of $IC_{50}$(other protease)÷$IC_{50}$(BACE1)=50 (or a ratio of $IC_{50}$(BACE1)÷$IC_{50}$(other protease)=0.02).

The phrase "therapeutically effective amount" as used herein means that amount of a compound, material, or composition as described herein (e.g. a compound of Formula I and compositions thereof), which is effective for producing a desired therapeutic effect, at a reasonable benefit/risk ratio applicable to any medical treatment. For example, a "therapeutically effective amount" is an amount effective to reduce or lessen at least one symptom of the disease or condition being treated or to reduce or delay onset of one or more clinical markers or symptoms associated with the disease or condition, or to modify or reverse the disease process.

The terms "treatment" or "treating" when referring to a disease or condition, means producing a desired therapeutic effect. Exemplary therapeutic effects include delaying onset or reducing at least one symptom associated with the disease, positively affecting (e.g., reducing or delaying onset) of a clinical marker associated with the disease and slowing or reversing disease progression. Treatment includes preventative therapy, for example a subject that is at high risk of developing a disease or condition can be treated proactively to prevent or delay the onset of the disease. Treatment also includes therapeutic treatment of an existing disease or condition, for example, a subject having symptoms of a disease or condition can be treated to reduce or reverse the progression of the disease, or to alleviate the symptoms of the disease.

The term "pharmaceutically acceptable" refers to those properties and/or substances that are acceptable to a patient (e.g., human patient) from a toxicological and/or safety point of view.

The term "pharmaceutically acceptable salt" means any salt of a compound as described herein, e.g. a compound of Formula I, which is prepared with relatively nontoxic acids or bases, depending on the particular substituents found on a compound as described herein. A compound of Formula I may be prepared as a pharmaceutically acceptable salt. Such salts and their preparation for use as pharmaceuticals are readily known to those of skill in the art. Such salts may provide improved properties, e.g. solubility or pharmacokinetic properties, such that the pharmacological activity of the compound of Formula I is enhanced upon administration to a subject. It is understood that such pharmaceutically acceptable salts are effectively equivalent to compounds of Formula I, i.e. when such a salt is administered into a subject, the administration effectively encompasses the use of a compound of Formula I.

The term "pharmaceutically acceptable solvate" means any solvate, including any hydrate, of a compound as described herein, e.g. a compound of Formula I, which is prepared with a relatively nontoxic solvent or solvents. A compound as described herein, e.g. a compound of Formula I, can exist in unsolvated forms as well as solvated forms, including hydrated forms. Such solvates may provide improved properties, e.g. solubility or pharmacokinetic properties, such that the pharmacological activity of the compound of Formula I is enhanced upon administration to a subject. It is understood that such pharmaceutically acceptable solvated forms are effectively equivalent to compounds of Formula I, i.e. when such a solvated form is administered into a subject, the administration effectively encompasses the use of a compound of Formula I.

The term "pharmaceutically acceptable carrier" means any pharmaceutically acceptable ingredient known to those of skill in the art, which is typically considered a non-active ingredient.

The term "pharmaceutically acceptable derivative" or "prodrug" means any derivative of a compound of Formula I that is suitable for pharmaceutical use. For example, a prodrug of a compound as described herein which, upon administration to a recipient, is capable of providing, either directly or indirectly, a compound as described herein (e.g. a compound of Formula I). In some examples, a prodrug increases the bioavailability of a compound as described herein when such compound is administered to a mammal (e.g., by allowing an orally administered compound to be more readily absorbed into the blood stream) or which enhance delivery of the parent compound to a biological compartment (e.g., the brain) relative to the parent species. It is understood that such a prodrug form is effectively equivalent to a compound of Formula I, i.e. when such a prodrug form is administered into a subject, the administration effectively encompasses the use of a compound of Formula I.

The term "polymorph" refers to a crystal form of a compound as described herein. It is understood that a compound as described herein may occur in many different crystal forms, or polymorphs, or can be made into amorphous form (i.e. solid form without any defined crystal structure). While such varied solid forms may have different pharmaceutical properties, it is understood that any such crystal form comprises a compound as described herein, i.e. it is encompassed by a compound of Formula I. Similarly, a pharmaceutically acceptable salt or solvate of a compound of Formula I may exist as polymorphs, where any such polymorph is encompassed by a pharmaceutically acceptable salt or a pharmaceutically acceptable solvate of a compound of Formula I.

The term "metabolite" refers to a derivative of a compound as described herein resulting from administering such a compound to a recipient, wherein the metabolite results from metabolic processes in the body of a recipient. In some examples, a metabolite may be pharmaceutically active. Any metabolites may be identified using routine techniques known in the art, and their biological activity assessed as described herein.

The term "conjugate" refers to a derivative of a compound as described herein resulting in the linking of a suitable adjunct to provide additional features or uses. A compound of Formula I may be further conjugated via a suitably reactive group to link a moiety to the compound of Formula I, such that the linked moiety provides, for example, improved targeting to certain tissues, improved transport across the blood brain barrier, a suitable binding molecule for use as a probe, or the like. The portion of the conjugate that is derived from a compound of Formula I is expected to have similar properties to a compound of Formula I, for example such portion of the conjugate will readily bind to BACE1 and/or BACE2 in a similar manner to the non-derivative compound of Formula I. Such conjugates can be used, for example, for targeted drug delivery, improved delivery to the brain or CNS, as a probe for identifying BACE in a biological mixture or for isolating BACE from a biological mixture, or the like.

The term "isotopically enhanced" or "isotopically enhanced form" means that a compound as described herein, e.g. a compound of Formula I, may be modified to contain unnatural proportions of certain atomic isotopes at one or more of the atoms that constitute such a compound. For example, a compound can be radiolabeled with radioactive isotopes, such as for example tritium ($^3$H), iodine-125 ($^{125}$I) or carbon-14 ($^{14}$C). Such isotopic variations of a compound as described herein, whether radioactive or not, is effectively encompassed by compounds as described herein. For example, a compound in which one or more of the hydrogen atoms are replaced with another stable isotope of hydrogen (i.e., deuterium) or a radioactive isotope (i.e., tritium), is expected to have similar activity to the compound without isotopic enhancement as it relates to BACE inhibition, and such a compound is effectively equivalent to a compound of Formula I. Such an isotopically enhanced compound may be useful, for example, in detection of the compound in vivo or in biological tissue, such as a radiolabelled compound containing $^3$H or $^{14}$C to assess tissue distribution, or a positron emitting compound containing $^{11}$C, $^{15}$O, $^{13}$N, $^{18}$F or the like useful in positron emission tomography for in vivo imaging. Similarly, a deuterated compound may provide a compound with greater metabolic stability than the analogous non-deuterated compound, such that the deuterated compound has better pharmacokinetic properties. Any isotopically enhanced compound is expected to have similar inhibitory activity as it relates to BACE1 and or BACE2, and other proteases, such as Cathepsin D, Cathepsin E, Pepsin and Renin. Such a compound is readily prepared by those of skill in the art, for example by the methods as described herein or other methods known in the art, where suitable isotopically enhanced reagents may be used to provide the isotopically enhanced compounds.

As used herein, the term "chiral", "enantiomerically enriched" or "diastereomerically enriched" refers to a compound having an enantiomeric excess (ee) or a diastereomeric excess (de) of greater than about 50%, also greater than about 70% and also greater than about 90%. In one example, enantiomeric or diastereomeric excess is higher than about 90%, e.g., those compositions with greater than about 95%, greater than about 97% and greater than about 99% ee or de. The terms "enantiomeric excess" and "diastereomeric excess" are used in their conventional sense. Compounds with a single stereocenter are referred to as being present in "enantiomeric excess", those with at least two stereocenters are referred to as being present in "diastereomeric excess". The value of ee will be a number from 0 to 100, zero being racemic and 100 being enantiomerically pure. For example, a 90% ee reflects the presence of 95% of one enantiomer and 5% of the other(s) in the material in question. Stereoisomers are detectable if a concentration of such stereoisomer in the analyzed mixture can be determined using common analytical methods, such as chiral HPLC.

The terms "use in combination", "combination use" or the like, means use of a compound as described herein with one or more other therapeutics for the treatment, prevention, or amelioration of symptoms of a disease. Combination use includes use of a compound as described herein at any point before, during or after treatment with one or more other therapeutic treatments, for example a compound as described herein and another therapeutic agent can be administered essentially simultaneously, either in different vehicles, or can be administered in the same vehicle (e.g. can be manufactured into the same pill, tablet, solution, etc.); or a compound as described herein can be administered prior to (e.g. minutes, hours, days, or weeks before) administering another therapeutic agent; or a compound as described herein can be administered subsequently to (e.g. minutes, hours, days, or weeks after) administering another therapeutic agent.

The term "BACE-mediated condition" or any other variation thereof, as used herein means any disease or other condition in which BACE, including BACE1 and/or BACE2 is known to play a role, or a disease state that is associated with elevated activity or expression of BACE. For example, a "BACE1-mediated condition" may be relieved by inhibiting BACE1 protease activity. Such conditions include certain neurodegenerative diseases, such as Alzheimer's disease. For example, a "BACE2-mediated condition" may be relieved by inhibiting BACE2 protease activity. Such conditions include certain metabolic diseases, such as type 2 diabetes.

The term "β-amyloid related condition", or "amyloid-β related condition", "Aβ peptide related condition" or "Aβ related condition", or any other variation thereof, as used herein mean any disease or other condition in which abnormal Aα peptide (e.g. increased levels of Aβ peptide, including Aβ peptide aggregation, oligomerization, fibrillization or Aβ peptide containing plaques) are causative of or implicated in the disease, such that the disease or condition may be relieved by reduction in the production or level of Aβ peptide, including reduction in soluble Aβ levels and/or reduction in the levels of Aβ containing plaques (β-amyloid plaques). In one example, a β-amyloid related disease or condition is associated with Aβ peptide aggregation, oligomerization, fibrillization or plaque formation. In one example, a β-amyloid related condition is relieved by inhibiting BACE protease activity, including BACE1 and/or BACE2 protease activity. In one example, a β-amyloid related condition is relieved by inhibiting BACE1 protease activity.

The term "neurodegenerative diseases" or "neurological disease" includes any disease or condition characterized by problems with movements, such as ataxia, and conditions affecting cognitive abilities (e.g., memory) as well as conditions generally related to all types of dementia. "Neurodegenerative diseases" may be associated with impairment or loss of cognitive abilities, potential loss of cognitive abilities and/or impairment or loss of brain cells. Exemplary "neurodegenerative diseases" include Alzheimer's disease (including conditions associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, brain injuries, as well as ischemia and stroke. "Neurodegenerative diseases" also includes any undesirable condition associated with the disease. For instance, a method of treating a neurodegenerative disease includes methods of treating or preventing loss of neuronal function characteristic of neurodegenerative disease.

Certain spirocyclic thiazines and oxazines, e.g. a compound as described herein within the scope of Formula I, are potent inhibitors of BACE1 and/or BACE2. In some embodiments, such a compound exhibits properties conducive to good CNS exposure. A compound as described herein is characterized by one or more of the following properties:

(i) relatively low affinity for the P-glycoprotein (In one example, the compounds exhibit essentially no binding affinity/are not substrates for the P-glycoprotein);

(ii) relatively low molecular weight;

(iii) relatively low number of H-bond donors;

(iv) relatively low total polar surface area (TPSA);

(v) selectivity favoring BACE1, over other proteases, particularly over Cathepsin D; and (vi) appreciable solubility.

Furthermore, certain compounds as described herein are characterized by relatively high brain to plasma ratios and good brain exposure as indicated by in vivo experimental results (e.g., see Examples B, C). The presently described BACE1 and/or BACE2 inhibitors provide compounds with good CNS exposure properties and selectivity favoring BACE, in one example BACE1, over other proteases.

In one aspect, compounds are provided having a structure according to Formula I:

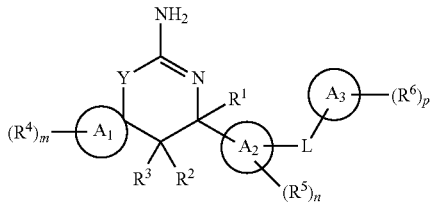

or a pharmaceutically acceptable salt thereof, wherein:
Y is O or S;
L is selected from the group consisting of a direct bond, —$CR^7R^8$—, —C(O)—, —O—, —S(O)$_z$—, —$NR^9$—, —$CR^7R^8$—$CR^{10}R^{11}$—, —$CR^7R^8$—C(O)—, —$CR^7R^8$—O—, —$CR^7R^8$—S(O)$_z$—, —$CR^7R^8$—$NR^9$—, —C(O)—$CR^{10}R^{11}$—, —C(O)—O—, —C(O)—$NR^9$—, —O—$CR^{10}R^{11}$—, —O—C(O)—, —S(O)$_z$—$CR^{10}R^{11}$—, —S(O)$_2$—$NR^9$—, —$NR^9$—$CR^{10}R^{11}$—, —$NR^9$—C(O)—, and —$NR^9$—S(O)$_2$—;
$A_1$ is a $C_{3-10}$ carbocyclic ring or a 3 to 10 membered heterocyclic ring;
$A_2$ is phenyl, naphthyl or a heteroaryl ring;
$A_3$ is phenyl, naphthyl or a heteroaryl ring;
$R^1$ is hydrogen, $C_{1-6}$ alkyl, or combines with $R^2$ to form a fused monocyclic $C_{3-7}$ carbocyclic ring or a 3 to 7 membered heterocyclic ring;
$R^2$ and $R^3$ are independently hydrogen or halogen, or $R^3$ is hydrogen and $R^2$ combines with $R^1$ to form a fused monocyclic $C_{3-7}$ carbocyclic ring or a 3 to 7 membered heterocyclic ring;
$R^4$ at each occurrence is independently selected from the group consisting of halogen, —CN, $C_{1-6}$ alkyl, $C_{2-6}$ alkenyl, $C_{2-6}$ alkynyl, $C_{3-6}$ cycloalkyl, —OH, =O, —$OR^{12}$, —S(O)$_z R^{12}$, —C(O)$R^{12}$, —$NR^{13}R^{14}$, and =$NR^{14}$, wherein said $C_{1-6}$ alkyl, $C_{2-6}$ alkenyl, $C_{2-6}$ alkynyl, and $C_{3-6}$ cycloalkyl are optionally substituted with one or more fluoro, —OH, —$NH_2$, —$OR^a$, —S(O)$_z R^a$, —C(O)$R^a$, —$NHR^a$, —$NR^a R^b$, or optionally fluoro substituted $C_{3-6}$ cycloalkyl;
$R^5$ and $R^6$ at each occurrence are independently selected from the group consisting of halogen, —CN, —OH, —$NH_2$, —$NO_2$, —C(O)—OH, —C(O)—$NH_2$, —S(O)$_2$—$NH_2$, and $L_1$-$R^{15}$;
$R^7$, $R^8$, $R^9$, $R^{10}$, and $R^{11}$ are independently selected from the group consisting of hydrogen and $C_{1-6}$ alkyl;
$L_1$ at each occurrence is independently selected from the group consisting of a direct bond, —C(O)—, —O—, —$NR^{16}$—, —C(O)—O—, —O—C(O)—, —C(O)—$NR^{16}$—, —$NR^{16}$—C(O)—, —S(O)$_2$—$NR^{16}$—, and —$NR^{16}$—S(O)$_2$—;
$R^{12}$ at each occurrence is independently selected from the group consisting of $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —$NH_2$, —$OR^a$, —S(O)$_z R^a$, —C(O)$R^a$, —$NHR^a$, —$NR^a R^b$, and optionally fluoro substituted $C_{3-6}$ cycloalkyl;
$R^{13}$ and $R^{14}$ at each occurrence are independently selected from the group consisting of hydrogen, $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl, are optionally substituted with one or more substituents independently selected from the group consisting of fluoro, —OH, —$NH_2$, —$OR^a$, —S(O)$_z R^a$, —C(O)$R^a$, —$NHR^a$, —$NR^a R^b$, and optionally fluoro substituted $C_{3-6}$ cycloalkyl, or $R^{13}$ and $R^{14}$ combine with the nitrogen to which they are attached to form a 4-7 membered monocyclic heterocyclic ring or a 5 or 7 membered heteroaryl ring, wherein said ring is optionally substituted with one or more substituents independently selected from the group consisting of halogen, —CN, =O, —OH, —$NH_2$, —$OR^a$, —S(O)$_z R^a$, —C(O)$R^a$, —$NHR^a$, —$NR^a R^b$, optionally fluoro substituted $C_{1-6}$ alkyl, optionally fluoro substituted $C_{2-6}$ alkenyl, optionally fluoro substituted $C_{2-6}$ alkynyl, and optionally fluoro substituted $C_{3-6}$ cycloalkyl;
$R^{15}$ at each occurrence is independently selected from the group consisting of $C_{1-6}$ alkyl, $C_{2-6}$ alkenyl, $C_{2-6}$ alkynyl, $C_{3-6}$ cycloalkyl, 3-7 membered heterocycloalkyl, phenyl, naphthyl, and heteroaryl, wherein phenyl, naphthyl, and heteroaryl are optionally substituted with one or more substituents independently selected from the group consisting of —CN, —OH, —$NO_2$, —C(O)—OH, $C_{1-6}$ alkyl, $C_{2-6}$ alkenyl, $C_{2-6}$ alkynyl, $C_{3-6}$ cycloalkyl, 3-7 membered heterocycloalkyl, phenyl, 5 or 6 membered heteroaryl, —$OR^{17}$, —S(O)$_z R^{17}$, —$NR^{18}R^{19}$, —C(O)$R^{17}$, —C(O)—$NR^{18}R^{19}$, —$NR^{16}$—C(O)$R^{17}$, —S(O)$_2$—$NR^{18}R^{19}$, and —$NR^{16}$—S(O)$_2 R^{17}$, and wherein $C_{1-6}$ alkyl, $C_{2-6}$ alkenyl, $C_{2-6}$ alkynyl, $C_{3-6}$ cycloalkyl, and 3-7 membered heterocycloalkyl, as $R^{15}$ or as a substituent of phenyl, naphthyl, or heteroaryl, are optionally substituted with one or more substituents independently selected from the group consisting of fluoro, —CN, —OH, =O, =NH, —$NO_2$, —C(O)—OH, $C_{3-6}$ cycloalkyl, 3-7 membered heterocycloalkyl, —$OR^{17}$, —S(O)$_z R^{17}$, =$NR^{17}$, —$NR^{18}R^{19}$, —C(O)$R^{17}$, —C(O)—$OR^{17}$, —O—C(O)$R^{17}$, —C(O)—$NR^{18}R^{19}$, —$NR^{16}$—C(O)$R^{17}$, —S(O)$_2$—$NR^{18}R^{19}$, and —$NR^{16}$—S(O)$_2 R^{17}$;
$R^{16}$ at each occurrence is independently selected from the group consisting of hydrogen and $C_{1-6}$ alkyl;
$R^{17}$ at each occurrence is independently selected from the group consisting of $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —$NH_2$, —$OR^a$, —S(O)$_z R^a$, —C(O)$R^a$, —$NHR^a$, —$NR^a R^b$, and optionally fluoro substituted $C_{3-6}$ cycloalkyl;
$R^{18}$ and $R^{19}$ at each occurrence are independently selected from the group consisting of hydrogen, $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —$NH_2$, —$OR^a$, —S(O)$_z R^a$, —C(O)$R^a$, —$NHR^a$, —$NR^a R^b$, and optionally fluoro substituted $C_{3-6}$ cycloalkyl, or $R^{18}$ and $R^{19}$ combine with the nitrogen to which they are attached to form a 4-7 membered monocyclic heterocyclic ring or a 5 or 7 membered heteroaryl ring, wherein said ring is optionally substituted with one or more substituents independently selected from the group consisting of halogen, —CN, =O, —OH, —NH$_2$, —OR$^a$, —S(O)$_z$R$^a$, —C(O)R$^a$, —NHR$^a$, —NR$^a$R$^b$, optionally fluoro substituted C$_{1-6}$ alkyl, optionally fluoro substituted C$_{2-6}$ alkenyl, optionally fluoro substituted C$_{2-6}$ alkynyl, and optionally fluoro substituted C$_{3-6}$ cycloalkyl;

R$^a$ and R$^b$ at each occurrence are independently selected from the group consisting of optionally fluoro substituted C$_{1-6}$ alkyl, optionally fluoro substituted C$_{2-6}$ alkenyl, optionally fluoro substituted C$_{2-6}$ alkynyl, and optionally fluoro substituted C$_{3-6}$ cycloalkyl, or R$^a$ and R$^b$ combine with the nitrogen to which they are attached to form N-linked-heterocycloalkyl;

m is 0, 1 or 2;

n is 0, 1, 2 or 3;

p is 0, 1, 2 or 3; and z is 0, 1 or 2.

In some embodiments of a compound of Formula I, Y is O. In some embodiments, Y is S.

In some embodiments of a compound of Formula I, L is a direct bond, —NR$^9$—, —C(O)—NR$^9$—, or —NR$^9$—C(O)—. In some embodiments, L is a direct bond, —NR$^9$—, or —NR$^9$—C(O)—. In some embodiments, L is —NR$^9$— or —NR$^9$—C(O)—. In some embodiments, L is a direct bond. In some embodiments, L is —C(O)—NR$^9$— or —NR$^9$—C(O)—. In some embodiments, L is —C(O)—NR$^9$—. In some embodiments, L is —NR$^9$—C(O)—. In some embodiments, L is —NR$^9$—.

In some embodiments of a compound of Formula I, A$_1$ is a C$_{3-10}$ carbocyclic ring. In some embodiments A$_1$ is a C$_{3-6}$ monocyclic carbocyclic ring. In some embodiments, A$_1$ is cyclohexane. In some embodiments, A$_1$ is cyclopentane. In some embodiments, A$_1$ is cyclobutane. In some embodiments, A$_1$ is cyclopropane.

In some embodiments of a compound of Formula I, A$_1$ is a 3 to 10 membered heterocyclic ring. In some embodiments A$_1$ is a 4 to 6 membered monocyclic heterocyclic ring. In some embodiments A$_1$ is a 4 to 6 membered monocyclic heterocyclic ring that contains one oxygen atom or one sulfur atom as the only heteroatom. In some embodiments A$_1$ is a 4 to 6 membered monocyclic heterocyclic ring that contains one oxygen atom. In some embodiments A$_1$ is tetrahydropyran. In some embodiments A$_1$ is tetrahydrofuran. In some embodiments A$_1$ is oxetane.

In some embodiments of a compound of Formula I, A$_2$ is phenyl, or a monocyclic 5-6 membered heteroaryl ring. In some embodiments A$_2$ is phenyl or a monocyclic 5 membered heteroaryl ring. In some embodiments A$_2$ is phenyl or thiophenyl. In some embodiments A$_2$ is a monocyclic 5 membered heteroaryl ring. In some embodiments A$_2$ is thiophenyl. In some embodiments A$_2$ is pyrazolyl. In some embodiments A$_2$ is phenyl.

In some embodiments of a compound of Formula I, A$_3$ is phenyl, or a monocyclic 5-6 membered heteroaryl ring. In some embodiments A$_3$ is phenyl, oxazolyl, pyridinyl, or pyrazinyl. In some embodiments A$_3$ is phenyl or a monocyclic 6 membered heteroaryl ring. In some embodiments A$_3$ is phenyl, pyridinyl, pyrazinyl, pyrimidinyl or pyridazinyl. In some embodiments A$_3$ is phenyl. In some embodiments A$_3$ is pyridinyl. In some embodiments A$_3$ is pyrazinyl. In some embodiments A$_3$ is pyrimidinyl. In some embodiments A$_3$ is pyridazinyl. In some embodiments A$_3$ is oxazolyl.

In some embodiments of a compound of Formula I, R$^1$ is hydrogen or C$_{1-3}$ alkyl. In some embodiments R$^1$ is methyl. In some embodiments, R$^1$ is hydrogen. In some embodiments, R$^1$ is ethyl. In some embodiments, R$^1$ is n-propyl. In some embodiments, R$^1$ is isopropyl.

In some embodiments of a compound of Formula I, R$^2$ and R$^3$ are independently hydrogen or halogen. In some embodiments, R$^2$ and R$^3$ are independently hydrogen or fluoro. In some embodiments, R$^2$ and R$^3$ are both hydrogen or both fluoro. In some embodiments, R$^2$ and R$^3$ are both hydrogen. In some embodiments, R$^2$ and R$^3$ are both halogen. In some embodiments, R$^2$ and R$^3$ are both fluoro.

In some embodiments of a compound of Formula I, R$^4$ is halogen. In some embodiments, R$^4$ is fluoro. In some embodiments, R$^4$ is fluoro and m is 1 or 2. In some embodiments, R$^4$ is fluoro and m is 2. In some embodiments, R$^4$ is fluoro, m is 2, and both fluoro are attached to the same carbon atom. In some embodiments, m is 0. In some embodiments, R$^4$ is —C(O)CH$_3$. In some embodiments, R$^4$ is —C(O)CH$_3$ and m is 1.

In some embodiments of a compound of Formula I, Y is O or S; L is a direct bond, —C(O)—NR$^9$—, or —NR$^9$—C(O)—; A$_1$ is a C$_{3-10}$ carbocyclic ring, in some embodiments a C$_{3-6}$ monocyclic carbocyclic ring or A$_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula I, Y is O or S; L is a direct bond, —C(O)—NR$^9$—, or —NR$^9$—C(O)—; A$_1$ is a C$_{3-10}$ carbocyclic ring, in some embodiments a C$_{3-6}$ monocyclic carbocyclic ring; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula I, Y is O or S; L is a direct bond, —C(O)—NR$^9$—, or —NR$^9$—C(O)—; A$_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula I, Y is O or S; L is a direct bond, —NR$^9$—, or —NR$^9$—C(O)—; A$_1$ is a C$_{3-10}$ carbocyclic ring, in some embodiments a C$_{3-6}$ monocyclic carbocyclic ring or A$_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom, in some embodiments, one oxygen atom as the only heteroatom; A$_2$ is phenyl, or a monocyclic 5-6 membered heteroaryl ring, in some embodiments phenyl or thiophenyl; and A$_3$ is phenyl, or a monocyclic 5-6 membered heteroaryl ring, in some embodiments phenyl, oxazolyl, pyridinyl, or pyrazinyl.

In some embodiments of a compound of Formula I, Y is O or S; L is a direct bond, —NR$^9$—, or —NR$^9$—C(O)—; A$_1$ is a C$_{3-10}$ carbocyclic ring, in some embodiments a C$_{3-6}$ monocyclic carbocyclic ring; A$_2$ is phenyl, or a monocyclic 5-6 membered heteroaryl ring, in some embodiments phenyl or thiophenyl; and A$_3$ is phenyl, or a monocyclic 5-6 membered heteroaryl ring, in some embodiments phenyl, oxazolyl, pyridinyl, or pyrazinyl.

In some embodiments of a compound of Formula I, Y is O or S; L is a direct bond, —NR$^9$—, or —NR$^9$—C(O)—; A$_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom, in some embodiments oxygen as the only heteroatom; A$_2$ is phenyl, or a monocyclic 5-6 membered heteroaryl ring, in some embodiments phenyl or thiophenyl; and A$_3$ is phenyl, or a monocyclic 5-6 membered heteroaryl ring, in some embodiments phenyl, oxazolyl, pyridinyl, or pyrazinyl.

In some embodiments of a compound of Formula I, further to any of the above embodiments, R$^1$ is methyl.

In some embodiments of a compound of Formula I, further to any of the above embodiments, Y is O. In some embodiment, further to any of the above embodiments, Y is S.

In some embodiments of a compound of Formula I, further to any of the above embodiments, n is 0, 1 or 2, p is 0, 1 or 2, and each R$^5$ and R$^6$ are independently selected from the group consisting of —CN, halogen, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, di-C$_{1-6}$ alkylamino, N-linked-heterocycloalkyl, and C$_{3-6}$ cycloalkyl, wherein C$_{1-6}$ alkyl, C$_{2-6}$ alkenyl, C$_{2-6}$ alkynyl, and the alkyl chains of C$_{1-6}$ alkoxy, C$_{1-6}$ alkylsulfonyl, C$_{1-6}$ alkylamino, or di-C$_{1-6}$ alkylamino are optionally substituted with one or more substituents independently selected from the group consisting of fluoro, —CN, C$_{3-6}$ cycloalkyl, C$_{1-6}$ alkoxy, C$_{1-6}$ haloalkoxy, C$_{1-6}$ alkylamino, alkylamino and N-linked-heterocycloalkyl. In some embodiments, n is 0 or 1; R$^5$ is halogen, —CN, C$_{1-6}$ alkyl, C$_{1-6}$ haloalkyl, C$_{1-6}$ alkoxy, or C$_{1-6}$ haloalkoxy; p is 0, 1, or 2; and R$^6$ at each occurrence is independently selected from the group consisting of halogen, —CN, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, di-C$_{1-6}$ alkylamino, N-linked-heterocycloalkyl, and C$_{3-6}$ cycloalkyl, wherein C$_{1-6}$ alkyl, C$_{2-6}$ alkenyl, C$_{2-6}$ alkynyl, and the alkyl chains of C$_{1-6}$ alkoxy, C$_{1-6}$ alkylsulfonyl, C$_{1-6}$ alkylamino, or di-C$_{1-6}$ alkylamino as R$^6$ are optionally substituted with one or more substituents independently selected from the group consisting of fluoro, —CN, C$_{3-6}$ cycloalkyl, C$_{1-6}$ alkoxy, C$_{1-6}$ haloalkoxy, C$_{1-6}$ alkylamino, alkylamino and N-linked-heterocycloalkyl. In some embodiments, further to any of the above embodiments, n is 1, R$^5$ is halogen, p is 0, 1 or 2, and each R$^6$ is independently selected from the group consisting of —CN, halogen, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ alkynyl, and C$_{3-6}$ cycloalkyl.

In some embodiments of a compound of Formula I, the compound has a structure according to Formula

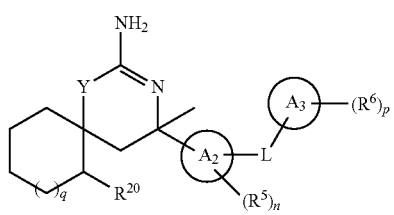

Ia or a pharmaceutically acceptable salt thereof, wherein:
q is 0 or 1;
R$^{20}$ is selected from the group consisting of hydrogen, —OH, =O, —OR$^{12}$, —S(O)$_z$R$^{12}$, —NR$^{13}$R$^{14}$, and =NR$^{14}$; and
A$_2$, A$_3$, Y, R$^5$, R$^6$, R$^{12}$, R$^{13}$, R$^{14}$, z, n and p are as defined for a compound of Formula I.

In some embodiments of a compound of Formula Ia, Y is O. In some embodiments, Y is S.

In some embodiments of a compound of Formula Ia, q is 0. In some embodiments q is 1.

In some embodiments of a compound of Formula Ia, L is a direct bond, —NR$^9$—, —C(O)—NR$^9$—, or —NR$^9$—C(O)—. In some embodiments, L is a direct bond, or —NR$^9$—C(O)—. In some embodiments, L is —NR$^9$— or —NR$^9$—C(O)—. In some embodiments, L is a direct bond. In some embodiments, L is —C(O)—NR$^9$— or —NR$^9$—C(O)—. In some embodiments, L is —C(O)—NR$^9$—. In some embodiments, L is —NR$^9$—C(O)—. In some embodiments, L is —NR$^9$—.

In some embodiments of a compound of Formula Ia, A$_2$ is phenyl, or a monocyclic 5-6 membered heteroaryl ring. In some embodiments A$_2$ is phenyl or a monocyclic 5 membered heteroaryl ring. In some embodiments A$_2$ is phenyl or thiophenyl. In some embodiments A$_2$ is a monocyclic 5 membered heteroaryl ring. In some embodiments A$_2$ is thiophenyl. In some embodiments A$_2$ is pyrazolyl. In some embodiments, A$_2$ is phenyl.

In some embodiments of a compound of Formula Ia, A$_3$ is phenyl, or a monocyclic 5-6 membered heteroaryl ring. In some embodiments A$_3$ is phenyl, oxazolyl, pyridinyl, or pyrazinyl. In some embodiments A$_3$ is phenyl or a monocyclic 6 membered heteroaryl ring. In some embodiments A$_3$ is phenyl, pyridinyl, pyrazinyl, pyrimidinyl or pyridazinyl. In some embodiments A$_3$ is phenyl. In some embodiments A$_3$ is pyridinyl. In some embodiments A$_3$ is pyrazinyl. In some embodiments A$_3$ is pyrimidinyl. In some embodiments A$_3$ is pyridazinyl. In some embodiments A$_3$ is oxazolyl.

In some embodiments of a compound of Formula Ia, R$^{20}$ is hydrogen. In some embodiments, R$^{20}$ is —OH, =O, or —OR$^{12}$. In some embodiments, R$^{20}$ is —S(O)$_z$R$^{12}$. In some embodiments, R$^{20}$ is —NR$^{13}$R$^{14}$, or =NR$^{14}$. In some embodiments, R$^{20}$ is —NR$^{13}$R$^{14}$.

In some embodiments of a compound of Formula Ia, Y is O or S; L is a direct bond, —C(O)—NR$^9$—, or —NR$^9$—C(O)—; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is O or S; q is 0; L is a direct bond, —C(O)—NR$^9$—, or —NR$^9$—C(O)—; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is O or S; q is 1; L is a direct bond, —C(O)—NR$^9$—, or —NR$^9$—C(O)—; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is S, $R^{20}$ is H, and L is a bond. In some embodiments Y is S; $R^{20}$ is H; L is a bond; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is O, $R^{20}$ is H, and L is a bond. In some embodiments Y is O; $R^{20}$ is H; L is a bond; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is S, q is 0, $R^{20}$ is H, and L is a bond. In some embodiments Y is S; q is 0; $R^{20}$ is H; L is a bond; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is O, q is 0, $R^{20}$ is H, and L is a bond. In some embodiments Y is O; q is 0; $R^{20}$ is H; L is a bond; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is S, q is 1, $R^{20}$ is H, and L is a bond. In some embodiments Y is S; q is 1; $R^{20}$ is H; L is a bond; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, Y is O, q is 1, $R^{20}$ is H, and L is a bond. In some embodiments Y is O; q is 1; $R^{20}$ is H; L is a bond; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ia, further to any of the above embodiments, $A_2$ is phenyl or thiophenyl; and $A_3$ is phenyl, oxazolyl, pyridinyl, or pyrazinyl.

In some embodiments of a compound of Formula I, the compound has a structure according to Formula Ib:

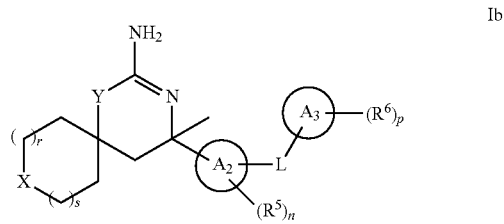

Ib or a pharmaceutically acceptable salt thereof, wherein:
X is O or $S(O)_2$;
r is 0, 1, or 2;
s is 0, 1, or 2; and
$A_2$, $A_3$, Y, $R^5$, $R^6$, n and p are as defined for a compound of Formula I.

In some embodiments of a compound of Formula Ib, Y is O. In some embodiments, Y is S.

In some embodiments of a compound of Formula Ib, X is O. In some embodiments, X is $S(O)_2$.

In some embodiments of a compound of Formula Ib, L is a direct bond, —$NR^9$—, —C(O)—$NR^9$—, or —$NR^9$—C(O)—. In some embodiments, L is a direct bond, —$NR^9$—, or —$NR^9$—C(O)—. In some embodiments, L is —$NR^9$— or —$NR^9$—C(O)—. In some embodiments, L is a direct bond. In some embodiments, L is —C(O)—$NR^9$— or —$NR^9$—C(O). In some embodiments, L is —C(O)—$NR^9$. In some embodiments, L is —$NR^9$—C(O). In some embodiments, L is —$NR^9$—.

In some embodiments of a compound of Formula Ib, $A_2$ is phenyl, or a monocyclic 5-6 membered heteroaryl ring. In some embodiments $A_2$ is phenyl or a monocyclic 5 membered heteroaryl ring. In some embodiments $A_2$ is phenyl or thiophenyl. In some embodiments $A_2$ is a monocyclic 5 membered heteroaryl ring. In some embodiments $A_2$ is thiophenyl. In some embodiments $A_2$ is pyrazolyl. In some embodiments, $A_2$ is phenyl.

In some embodiments of a compound of Formula Ib, $A_3$ is phenyl, or a monocyclic 5-6 membered heteroaryl ring. In some embodiments $A_3$ is phenyl, oxazolyl, pyridinyl, or pyrazinyl. In some embodiments $A_3$ is phenyl or a monocyclic 6 membered heteroaryl ring. In some embodiments $A_3$ is phenyl, pyridinyl, pyrazinyl, pyrimidinyl or pyridazinyl. In some embodiments $A_3$ is phenyl. In some embodiments $A_3$ is pyridinyl. In some embodiments $A_3$ is pyrazinyl. In some embodiments $A_3$ is pyrimidinyl. In some embodiments $A_3$ is pyridazinyl. In some embodiments $A_3$ is oxazolyl.

In some embodiments of a compound of Formula Ib, Y is O or S; L is a direct bond, —C(O)—$NR^9$—, or —$NR^9$—C(O)—; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is O or S; either r and s are both 0 or r and s are both 1; L is a direct bond, —C(O)—$NR^9$—, or —$NR^9$—C(O)—; $A_2$ is phenyl, or a monocyclic 5-6 membered heteroaryl ring, in some embodiments a monocyclic 5 membered heteroaryl ring; $A_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is O or S; r and s are both 0; L is a direct bond, —C(O)—NR$^9$—, or —NR$^9$—C(O)—; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is O or S; r and s are both 1; L is a direct bond, —C(O)—NR$^9$—, or —NR$^9$—C(O)—; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is O, L is a bond, and either r and s are both 0 or r and s are both 1. In some embodiments Y is O; L is a bond; either r and s are both 0 or r and s are both 1; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is O, L is a bond, and r and s are both 0. In some embodiments Y is O; L is a bond; r and s are both 0; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is O, L is a bond, and r and s are both 1. In some embodiments Y is O; L is a bond; r and s are both 1; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is S, L is a bond, and either r and s are both 0 or r and s are both 1. In some embodiments Y is S; L is a bond; either r and s are both 0 or r and s are both 1; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is S, L is a bond, and r and s are both 0. In some embodiments Y is S; L is a bond; r and s are both 0; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, Y is S, L is a bond, and r and s are both 1. In some embodiments Y is S; L is a bond; r and s are both 1; A$_2$ is phenyl, or a monocyclic 5-6 membered heteroaryl ring, in some embodiments a monocyclic 5 membered heteroaryl ring; A$_3$ is phenyl, or a monocyclic 5-6 membered heteroaryl ring, in some embodiments phenyl or a monocyclic 6 membered heteroaryl ring, in some embodiments phenyl, pyridinyl, pyrazinyl, pyrimidinyl or pyridazinyl.

In some embodiments of a compound of Formula Ib, further to any of the above embodiments of Formula Ib, X is O.

In some embodiments of a compound of Formula Ib, further to any of the above embodiments of Formula Ib, X is S(O)$_2$.

In some embodiments of a compound of Formula Ib, further to any of the above embodiments, A$_2$ is phenyl or thiophenyl; and A$_3$ is phenyl, oxazolyl, pyridinyl, or pyrazinyl.

In some embodiments of a compound of Formula I, Formula Ia or Formula Ib, further to any of the above embodiments, A$_2$ is phenyl, thiophenyl or pyrazolyl and A$_3$ is pyridinyl.

In some embodiments of a compound of Formula I, Formula Ia or Formula Ib, further to any of the above embodiments, L is a direct bond, A$_2$ is thiophenyl or pyrazolyl and A$_3$ is pyridinyl.

In some embodiments of a compound of Formula I, Formula Ia or Formula Ib, further to any of the above embodiments, L is —NR$^9$—C(O)—, A$_2$ is phenyl, and A$_3$ is pyridinyl.

In some embodiments of a compound of Formula I, Formula Ia or Formula Ib, further to any of the above embodiments, m is 0 or 1; R$^4$ is fluoro, =O, —OR$^{12}$, —S(O)$_z$R$^{12}$, —C(O)R$^{12}$, or —NR$^{13}$R$^{14}$, or R$^{20}$ is —OR$^{12}$, —S(O)$_z$R$^{12}$, or —NR$^{13}$R$^{14}$; n is 0 or 1; R$^5$ is halogen, —CN, C$_{1-6}$ alkyl, C$_{1-6}$ haloalkyl, C$_{1-6}$ alkoxy, or C$_{1-6}$ haloalkoxy; p is 0, 1, or 2; and R$^6$ at each occurrence is independently selected from the group consisting of halogen, —CN, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, di-C$_{1-6}$ alkylamino, and N-linked-heterocycloalkyl, wherein C$_{1-6}$ alkyl, C$_{2-6}$ alkenyl, C$_{2-6}$ alkynyl, and the alkyl chains of C$_{1-6}$ alkoxy, C$_{1-6}$ alkylsulfonyl, C$_{1-6}$ alkylamino, or di-C$_{1-6}$ alkylamino as R$^6$ are optionally substituted with one or more substituents independently selected from the group consisting of fluoro, —CN, C$_{3-6}$ cycloalkyl, C$_{1-6}$ alkoxy, C$_{1-6}$ haloalkoxy, C$_{1-6}$ alkylamino, di-C$_{1-6}$ alkylamino and N-linked-heterocycloalkyl.

In some embodiments of a compound of Formula I, Formula Ia, or Formula Ib, further to any of the above embodiments, n is 0, 1 or 2, p is 0, 1 or 2, and each R$^5$ and R$^6$ are independently selected from the group consisting of —CN, halogen, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, di-C$_{1-6}$ alkylamino, N-linked-heterocycloalkyl, and C$_{3-6}$ cycloalkyl, wherein C$_{1-6}$ alkyl, C$_{2-6}$ alkenyl, C$_{2-6}$ alkynyl, and the alkyl chains of C$_{1-6}$ alkoxy, C$_{1-6}$ alkylsulfonyl, C$_{1-6}$ alkylamino, or di-C$_{1-6}$ alkylamino are optionally substituted with one or more substituents independently selected from the group consisting of fluoro, —CN, C$_{3-6}$ cycloalkyl, C$_{1-6}$ alkoxy, C$_{1-6}$ haloalkoxy, C$_{1-6}$ alkylamino, di-C$_{1-6}$ alkylamino and N-linked-heterocycloalkyl. In some embodiments, n is 0 or 1; R$^5$ is halogen, —CN, C$_{1-6}$ alkyl, C$_{1-6}$ haloalkyl, C$_{1-6}$ alkoxy, or C$_{1-6}$ haloalkoxy; p is 0, 1, or 2; and R$^6$ at each occurrence is independently selected from the group consisting of halogen, —CN, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, di-C$_{1-6}$ alkylamino, N-linked-heterocycloalkyl, and C$_{3-6}$ cycloalkyl, wherein $C_{1-6}$ alkyl, $C_{2-6}$ alkenyl, $C_{2-6}$ alkynyl, and the alkyl chains of $C_{1-6}$ alkoxy, $C_{1-6}$ alkylsulfonyl, $C_{1-6}$ alkylamino, or di-$C_{1-6}$ alkylamino as $R^6$ are optionally substituted with one or more substituents independently selected from the group consisting of fluoro, —CN, $C_{3-6}$ cycloalkyl, $C_{1-6}$ alkoxy, $C_{1-6}$ haloalkoxy, $C_{1-6}$ alkylamino, di-$C_{1-6}$ alkylamino and N-linked-heterocycloalkyl. In some embodiments, further to any of the above embodiments, n is 1, $R^5$ is halogen, p is 0, 1 or 2, and each $R^6$ is independently selected from the group consisting of —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl.

In some embodiments of a compound of Formula I, the compound has a structure according to Formula Ic:

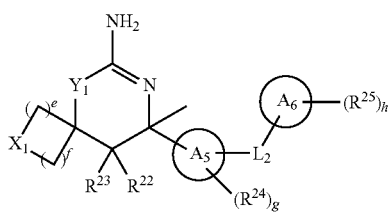

Ic or a pharmaceutically acceptable salt thereof, wherein:

$Y_1$ is O or S;

$L_2$ is selected from the group consisting of a direct bond, —NH—, and —NH—C(O)—;

$X_1$ is a direct bond and e and f are both 1; or $X_1$ is $CH_2$, $CF_2$, or O, and e and f are independently 1 or 2.

$A_5$ is phenyl or thiophenyl;

$A_6$ is phenyl, pyridinyl, pyrazinyl or oxazolyl;

$R^{22}$ and $R^{23}$ are both hydrogen or both fluoro;

$R^{24}$ at each occurrence is independently selected from the group consisting of —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl;

$R^{25}$ at each occurrence is independently selected from the group consisting of —CN, halogen, $C_{1-6}$ alkyl, $C_{2-6}$ alkenyl, $C_{2-6}$ alkynyl, $C_{1-6}$ alkoxy, $C_{1-6}$ alkylsulfonyl, $C_{1-6}$ alkylamino, di-$C_{1-6}$ alkylamino, N-linked-heterocycloalkyl, and $C_{3-6}$ cycloalkyl, wherein $C_{1-6}$ alkyl, $C_{2-6}$ alkenyl, $C_{2-6}$ alkynyl, and the alkyl chains of $C_{1-6}$ alkoxy, $C_{1-6}$ alkylsulfonyl, $C_{1-6}$ alkylamino, or di-$C_{1-6}$ alkylamino are optionally substituted with one or more substituents independently selected from the group consisting of fluoro, —CN, $C_{3-6}$ cycloalkyl, $C_{1-6}$ alkoxy, $C_{1-6}$ haloalkoxy, $C_{1-6}$ alkylamino, di-$C_{1-6}$ alkylamino and N-linked-heterocycloalkyl.

g is 0, 1, or 2; and h is 0, 1, or 2.

In some embodiments of a compound of Formula Ic, g is 0 or 1; $R^{24}$ is halogen, —CN, $C_{1-6}$ alkyl, $C_{1-6}$ haloalkyl, $C_{1-6}$ alkoxy, or $C_{1-6}$ haloalkoxy; h is 0, 1, or 2; and $R^{25}$ at each occurrence is independently selected from the group consisting of —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl.

In some embodiments, the compound of Formula Ic has a structure selected from the group consisting of:

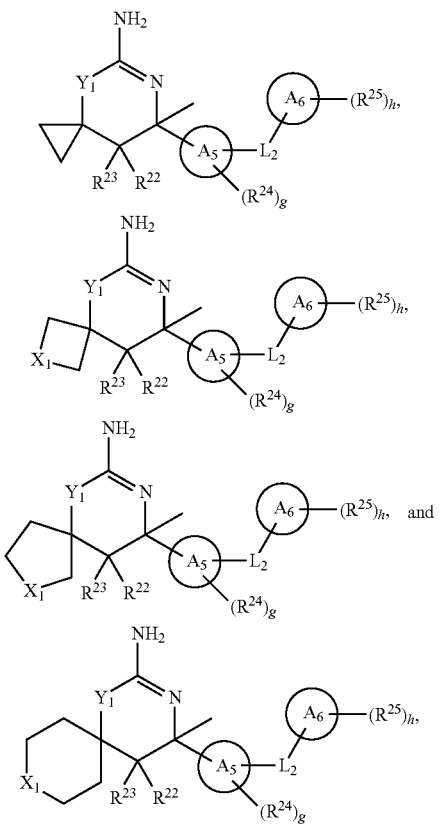

wherein $X_1$, $Y_1$, $L_2$, $A_5$, $A_6$, $R^{22}$, $R^{23}$, $R^{24}$, $R^{25}$, g and h are as defined for a compound of Formula Ic. In some embodiments,

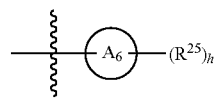

is

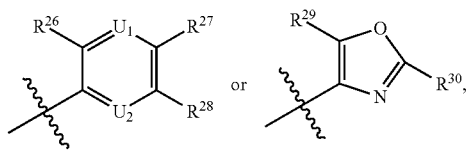

wherein

indicates the point of attachment of ring $A_6$ to $L_2$, or to ring $A_5$ when $L_2$ is a bond, and wherein $U_1$ and $U_2$ are independently CH or N; and $R^{26}$, $R^{27}$, $R^{28}$, $R^{29}$ and $R^{30}$ are independently selected from the group consisting of hydrogen, —CN, halogen, $C_{1-6}$ alkyl, $C_{2-6}$ alkenyl, $C_{2-6}$ alkynyl, $C_{1-6}$ alkoxy, $C_{1-6}$ alkylsulfonyl, $C_{1-6}$ alkylamino, di-$C_{1-6}$ alkylamino, N-linked-heterocycloalkyl, and $C_{3-6}$ cycloalkyl, wherein $C_{1-6}$ alkyl, $C_{2-6}$ alkenyl, $C_{2-6}$ alkynyl, and the alkyl chains of $C_{1-6}$ alkoxy, $C_{1-6}$ alkylsulfonyl, $C_{1-6}$ alkylamino, or di-$C_{1-6}$ alkylamino are optionally substituted with one or more substituents independently selected from the group consisting of fluoro, —CN, $C_{3-6}$ cycloalkyl, $C_{1-6}$ alkoxy, $C_{1-6}$ haloalkoxy, alkylamino, di-$C_{1-6}$ alkylamino and N-linked-heterocycloalkyl. In some embodiments, g is 0 or 1; $R^{24}$ is halogen, —CN, $C_{1-6}$ alkyl, $C_{1-6}$ haloalkyl, $C_{1-6}$ alkoxy, or $C_{1-6}$ haloalkoxy, in some embodiments halogen; and $R^{26}$, $R^{27}$, $R^{28}$, $R^{29}$ and $R^{30}$ are independently selected from the group consisting of hydrogen, —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl.

In some embodiments, the compound of Formula Ic has a structure selected from the group consisting of:

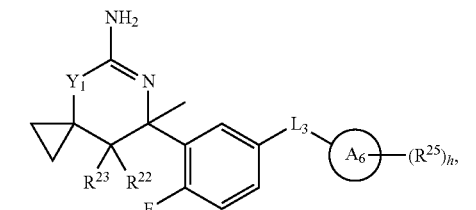

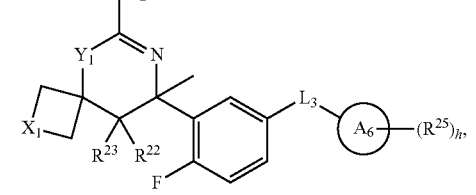

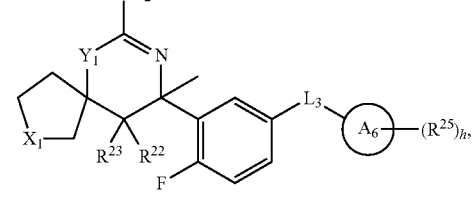

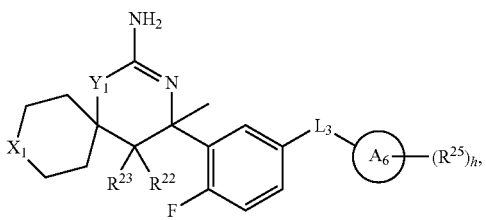

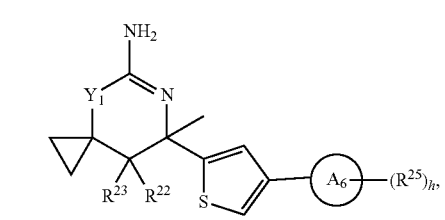

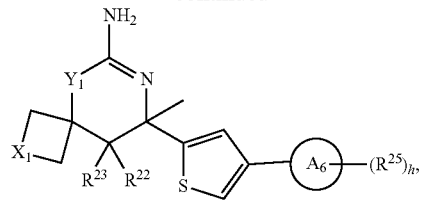

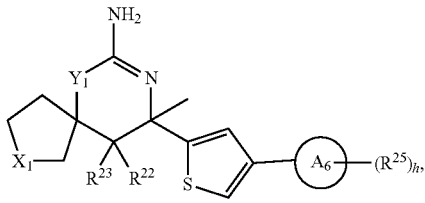

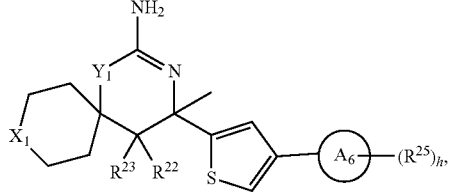

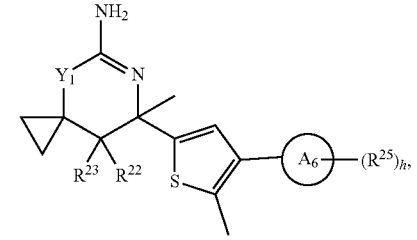

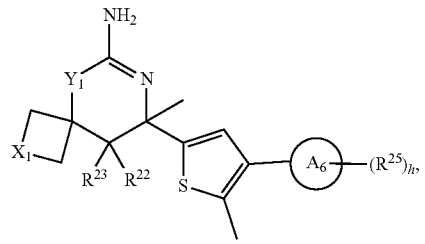

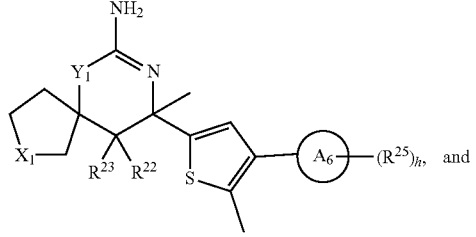 and

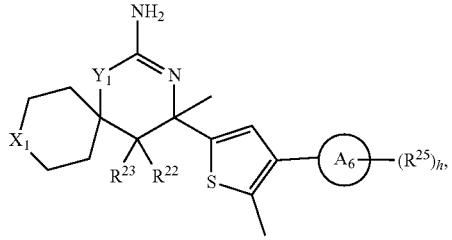

wherein $L_3$ is —NH— or —NH—C(O)—, and $X_1$, $Y_1$, $A_6$, $R^{22}$, $R^{23}$, $R^{25}$ and h are as defined for a compound of Formula Ic. In some embodiments,

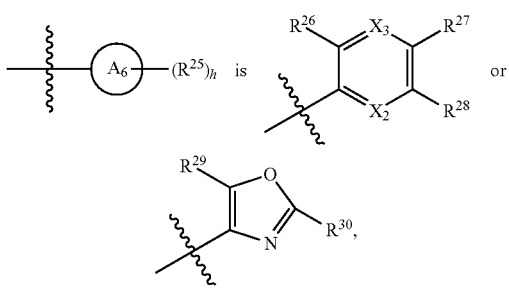 is 

wherein indicates the point of attachment of ring $A_6$ to $L_3$, or to the indicated thiophene ring, and wherein $U_1$ and $U_2$ are independently CH or N; and $R^{26}$, $R^{27}$, $R^{28}$, $R^{29}$ and $R^{30}$ are independently selected from the group consisting of hydrogen, —CN, halogen, $C_{1-6}$ alkyl, $C_{2-6}$ alkenyl, $C_{2-6}$ alkynyl, $C_{1-6}$ alkoxy, $C_{1-6}$ alkylsulfonyl, $C_{1-6}$ alkylamino, di-$C_{1-6}$ alkylamino, N-linked-heterocycloalkyl, and $C_{3-6}$ cycloalkyl, wherein $C_{1-6}$ alkyl, $C_{2-6}$ alkenyl, $C_{2-6}$ alkynyl, and the alkyl chains of $C_{1-6}$ alkoxy, $C_{1-6}$ alkylsulfonyl, $C_{1-6}$ alkylamino, or di-$C_{1-6}$ alkylamino are optionally substituted with one or more substituents independently selected from the group consisting of fluoro, —CN, $C_{3-6}$ cycloalkyl, $C_{1-6}$ alkoxy, $C_{1-6}$ haloalkoxy, $C_{1-6}$ alkylamino, di-$C_{1-6}$ alkylamino and N-linked-heterocycloalkyl. In some embodiments, g is 0 or 1; $R^{24}$ is halogen, —CN, $C_{1-6}$ alkyl, $C_{1-6}$ haloalkyl, $C_{1-6}$ alkoxy, or $C_{1-6}$ haloalkoxy, in some embodiments halogen; and $R^{26}$, $R^{27}$, $R^{28}$, $R^{29}$ and $R^{30}$ are independently selected from the group consisting of hydrogen, —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl.

In one embodiment, the compound of Formula I is selected from the group consisting of:
4-methyl-4-(4-(5-(prop-1-ynyl)pyridin-3-yl)thiophen-2-yl)-1-thia-3-azaspiro[5.5]undec-2-en-2-amine,
(S)-4-methyl-4-(4-(5-(prop-1-ynyl)pyridin-3-yl)thiophen-2-yl)-1-thia-3-azaspiro[5.5]undec-2-en-2-amine,
9-methyl-9-(4-(5-(prop-1-ynyl)pyridin-3-yl)thiophen-2-yl)-6-thia-8-azaspiro[4.5]dec-7-en-7-amine,
(S)-9-methyl-9-(4-(5-(prop-1-ynyl)pyridin-3-yl)thiophen-2-yl)-6-thia-8-azaspiro[4.5]dec-7-en-7-amine,
9-methyl-9-(4-(5-(prop-1-ynyl)pyridin-3-yl)thiophen-2-yl)-1-(pyrrolidin-1-yl)-6-thia-8-azaspiro[4.5]dec-7-en-7-amine,
4-(1-(5-bromopyridin-3-yl)-1H-pyrazol-4-yl)-4-methyl-1-thia-3-azaspiro[5.5]undec-2-en-2-amine,
(R)-5-(5-(2-amino-4-methyl-1-thia-3-azaspiro[5.5]undec-2-en-4-yl)thiophen-3-yl)nicotinonitrile,
4-methyl-4-(1-(5-(prop-1-ynyl)pyridin-3-yl)-1H-pyrazol-4-yl)-1-thia-3-azaspiro[5.5]undec-2-en-2-amine,
(S)-4-methyl-4-(1-(5-(prop-1-ynyl)pyridin-3-yl)-1H-pyrazol-4-yl)-1-thia-3-azaspiro[5.5]undec-2-en-2-amine,
4-methyl-4-(1-methyl-3-(5-(prop-1-ynyl)pyridin-3-yl)-1H-pyrazol-5-yl)-1-thia-3-azaspiro[5.5]undec-2-en-2-amine,
(S)-4-(3-chloro-5-(5-(prop-1-ynyl)pyridin-3-yl)thiophen-2-yl)-4-methyl-1-thia-3-azaspiro[5.5]undec-2-en-2-amine,
4-(3-chloro-5-(5-(prop-1-ynyl)pyridin-3-yl)thiophen-2-yl)-4-methyl-1-thia-3-azaspiro[5.5]undec-2-en-2-amine,
(S)-5-(5-(2-amino-4-methyl-1-thia-3-azaspiro[5.5]undec-2-en-4-yl)-4-chlorothiophen-2-yl)nicotinonitrile,
5-(5-(2-amino-4-methyl-1-thia-3-azaspiro[5.5]undec-2-en-4-yl)-4-chlorothiophen-2-yl)nicotinonitrile,
4-methyl-4-(4-(5-(prop-1-ynyl)pyridin-3-yl)thiophen-2-yl)-1,9-dioxa-3-azaspiro[5.5]undec-2-en-2-amine,
(S)-4-methyl-4-(4-(5-(prop-1-ynyl)pyridin-3-yl)thiophen-2-yl)-1,9-dioxa-3-azaspiro[5.5]undec-2-en-2-amine,
8-methyl-8-(4-(5-(prop-1-ynyl)pyridin-3-yl)thiophen-2-yl)-2-oxa-5-thia-7-azaspiro[3.5]non-6-en-6-amine,
2,2-difluoro-8-methyl-8-(4-(5-(prop-1-ynyl)pyridin-3-yl)thiophen-2-yl)-5-oxa-7-azaspiro[3.5]non-6-en-6-amine,
9,9-difluoro-4-methyl-4-(4-(5-(prop-1-ynyl)pyridin-3-yl)thiophen-2-yl)-1-oxa-3-azaspiro[5.5]undec-2-en-2-amine,
(S)-9,9-difluoro-4-methyl-4-(4-(5-(prop-1-ynyl)pyridin-3-yl)thiophen-2-yl)-1-oxa-3-azaspiro[5.5]undec-2-en-2-amine,
4-methyl-4-(4-(5-(prop-1-ynyl)pyridin-3-yl)thiophen-2-yl)-1-oxa-3-azaspiro[5.5]undec-2-en-2-amine,
N-(3-(2-amino-4-methyl-1-thia-3-azaspiro[5.5]undec-2-en-4-yl)-4-fluorophenyl)-5-fluoropicolinamide,
N-(3-(2-amino-4-methyl-1-thia-3-azaspiro[5.5]undec-2-en-4-yl)-4-fluorophenyl)-5-chloropicolinamide,
N-(3-(2-amino-4-methyl-1-thia-3-azaspiro[5.5]undec-2-en-4-yl)-4-fluorophenyl)-5-cyanopicolinamide,
7-methyl-7-(4-(5-(prop-1-ynyl)pyridin-3-yl)thiophen-2-yl)-4-thia-6-azaspiro[2.5]oct-5-en-5-amine,
7-methyl-7-(4-(5-(prop-1-ynyl)pyridin-3-yl)thiophen-2-yl)-4-oxa-6-azaspiro[2.5]oct-5-en-5-amine,
8-methyl-8-(4-(5-(prop-1-ynyl)pyridin-3-yl)thiophen-2-yl)-5-thia-7-azaspiro[3.5]non-6-en-6-amine,
8-methyl-8-(4-(5-(prop-1-ynyl)pyridin-3-yl)thiophen-2-yl)-5-oxa-7-azaspiro[3.5]non-6-en-6-amine,
4'-methyl-4'-(4-(5-(prop-1-ynyl)pyridin-3-yl)thiophen-2-yl)-4',5'-dihydrospiro[bicyclo[3.1.0]hexane-3,6'-[1,3]thiazin]-2'-amine,
7-methyl-7-(1-(5-(prop-1-ynyl)pyridin-3-yl)-1H-pyrazol-4-yl)-4-thia-6-azaspiro[2.5]oct-5-en-5-amine,
5-(5-(5-amino-7-methyl-4-thia-6-azaspiro[2.5]oct-5-en-7-yl)-4-chlorothiophen-2-yl)nicotinonitrile,
N-(3-(5-amino-7-methyl-4-thia-6-azaspiro[2.5]oct-5-en-7-yl)-4-fluorophenyl)-5-fluoropicolinamide,
N-(3-(5-amino-7-methyl-4-oxa-6-azaspiro[2.5]oct-5-en-7-yl)-4-fluorophenyl)-5-fluoropicolinamide,
N-(3-(6-amino-8-methyl-5-thia-7-azaspiro[3.5]non-6-en-8-yl)-4-fluorophenyl)-5-fluoropicolinamide,
(S)—N-(3-(6-amino-8-methyl-5-oxa-7-azaspiro[3.5]non-6-en-8-yl)-4-fluorophenyl)-5-fluoropicolinamide,
4-methyl-4-(4-(5-(prop-1-ynyl)pyridin-3-yl)thiophen-2-yl)-1,8-dioxa-3-azaspiro[5.5]undec-2-en-2-amine,
8-methyl-8-(4-(5-(prop-1-ynyl)pyridin-3-yl)thiophen-2-yl)-2,5-dioxa-7-azaspiro[3.5]non-6-en-6-amine,
5-(5-(6-amino-8-methyl-2,5-dioxa-7-azaspiro[3.5]non-6-en-8-yl)thiophen-3-yl)nicotinonitrile,
8-(4-(5-(cyclopropylethynyl)pyridin-3-yl)thiophen-2-yl)-8-methyl-2,5-dioxa-7-azaspiro[3.5]non-6-en-6-amine,
8-methyl-8-(1-(5-(prop-1-ynyl)pyridin-3-yl)-1H-pyrazol-4-yl)-2,5-dioxa-7-azaspiro[3.5]non-6-en-6-amine,
5-(5-(6-amino-8-methyl-2,5-dioxa-7-azaspiro[3.5]non-6-en-8-yl)-4-chlorothiophen-2-yl)nicotinonitrile,
N-(3-(6-amino-8-methyl-2,5-dioxa-7-azaspiro[3.5]non-6-en-8-yl)-4-fluorophenyl)-5-fluoropicolinamide,
4-methyl-4-(4-(5-(prop-1-ynyl)pyridin-3-yl)thiophen-2-yl)-9-oxa-1-thia-3-azaspiro[5.5]undec-2-en-2-amine, 4-methyl-4-(4-(5-(prop-1-ynyl)pyridin-3-yl)thiophen-2-yl)-8-oxa-1-thia-3-azaspiro[5.5]undec-2-en-2-amine,
5-(5-(6-amino-8-methyl-2-oxa-5-thia-7-azaspiro[3.5]non-6-en-8-yl)thiophen-3-yl)nicotinonitrile,
8-(4-(5-(cyclopropylethynyl)pyridin-3-yl)thiophen-2-yl)-8-methyl-2-oxa-5-thia-7-azaspiro[3.5]non-6-en-6-amine,
8-methyl-8-(1-(5-(prop-1-ynyl)pyridin-3-yl)-1H-pyrazol-4-yl)-2-oxa-5-thia-7-azaspiro[3.5]non-6-en-6-amine,
5-(5-(6-amino-8-methyl-2-oxa-5-thia-7-azaspiro[3.5]non-6-en-8-yl)-4-chlorothiophen-2-yl)nicotinonitrile,
N-(3-(6-amino-8-methyl-2-oxa-5-thia-7-azaspiro[3.5]non-6-en-8-yl)-4-fluorophenyl)-5-fluoropicolinamide,
(S)—N-(3-(6-amino-8-methyl-2-oxa-5-thia-7-azaspiro[3.5]non-6-en-8-yl)-4-fluorophenyl)-5-fluoropicolinamide,
8-methyl-8-(4-(5-(prop-1-ynyl)pyridin-3-yl)thiophen-2-yl)-2,5-dithia-7-azaspiro[3.5]non-6-en-6-amine-2,2-dioxide,
4-methyl-4-(4-(5-(prop-1-ynyl)pyridin-3-yl)thiophen-2-yl)-1-oxa-8-thia-3-azaspiro[5.5]undec-2-en-2-amine-8,8-dioxide,
8-methyl-8-(4-(5-(prop-1-ynyl)pyridin-3-yl)thiophen-2-yl)-5-oxa-2-thia-7-azaspiro[3.5]non-6-en-6-amine-2,2-dioxide,
5-(5-(6-amino-8-methyl-5-oxa-2-thia-7-azaspiro[3.5]non-6-en-8-yl-2,2-dioxide)thiophen-3-yl)nicotinonitrile,
8-(4-(5-(cyclopropylethynyl)pyridin-3-yl)thiophen-2-yl)-8-methyl-5-oxa-2-thia-7-azaspiro[3.5]non-6-en-6-amine-2,2-dioxide,
8-methyl-8-(1-(5-(prop-1-ynyl)pyridin-3-yl)-1H-pyrazol-4-yl)-5-oxa-2-thia-7-azaspiro[3.5]non-6-en-6-amine-2,2-dioxide,
5-(5-(6-amino-8-methyl-5-oxa-2-thia-7-azaspiro[3.5]non-6-en-8-yl-2,2-dioxide)-4-chlorothiophen-2-yl)nicotinonitrile,
N-(3-(6-amino-8-methyl-5-oxa-2-thia-7-azaspiro[3.5]non-6-en-8-yl-2,2-dioxide)-4-fluorophenyl)-5-fluoropicolinamide,
4-methyl-4-(4-(5-(prop-1-ynyl)pyridin-3-yl)thiophen-2-yl)-1,9-dithia-3-azaspiro[5.5]undec-2-en-2-amine-9,9-dioxide,
4-methyl-4-(4-(5-(prop-1-ynyl)pyridin-3-yl)thiophen-2-yl)-1-oxa-9-thia-3-azaspiro[5.5]undec-2-en-2-amine-9,9-dioxide,
4-methyl-4-(4-(5-(prop-1-ynyl)pyridin-3-yl)thiophen-2-yl)-1,8-dithia-3-azaspiro[5.5]undec-2-en-2-amine-8,8-dioxide,
5-(5-(6-amino-8-methyl-2,5-dithia-7-azaspiro[3.5]non-6-en-8-yl-2,2-dioxide)thiophen-3-yl) nicotinonitrile,
8-(4-(5-(cyclopropylethynyl)pyridin-3-yl)thiophen-2-yl)-8-methyl-2,5-dithia-7-azaspiro[3.5]non-6-en-6-amine-2,2-dioxide,
8-methyl-8-(1-(5-(prop-1-ynyl)pyridin-3-yl)-1H-pyrazol-4-yl)-2,5-dithia-7-azaspiro[3.5]non-6-en-6-amine-2,2-dioxide,
5-(5-(6-amino-8-methyl-2,5-dithia-7-azaspiro[3.5]non-6-en-8-yl-2,2-dioxide)-4-chlorothiophen-2-yl)nicotinonitrile,
N-(3-(6-amino-8-methyl-2,5-dithia-7-azaspiro[3.5]non-6-en-8-yl-2,2-dioxide)-4-fluorophenyl)-5-fluoropicolinamide,
1-(6-amino-8-methyl-8-(4-(5-(prop-1-ynyl)pyridin-3-yl)thiophen-2-yl)-5-thia-7-azaspiro[3.5]non-6-en-2-yl)ethanone,
1-(6-amino-8-methyl-8-(4-(5-(prop-1-ynyl)pyridin-3-yl)thiophen-2-yl)-5-oxa-7-azaspiro[3.5]non-6-en-2-yl)ethanone,
N-(3-(2-acetyl-6-amino-8-methyl-5-thia-7-azaspiro[3.5]non-6-en-8-yl)-4-fluorophenyl)-5-fluoropicolinamide,
N-(3-(2-acetyl-6-amino-8-methyl-5-oxa-7-azaspiro[3.5]non-6-en-8-yl)-4-fluorophenyl)-5-fluoropicolinamide,
N-(3-(6-amino-2,2-difluoro-8-methyl-5-oxa-7-azaspiro[3.5]non-6-en-8-yl)-4-fluorophenyl)-5-fluoropicolinamide,
N-(3-(2-amino-9,9-difluoro-4-methyl-1-oxa-3-azaspiro[5.5]undec-2-en-4-yl)-4-fluorophenyl)-5-fluoropicolinamide,
(S)—N-(3-(2-amino-9,9-difluoro-4-methyl-1-oxa-3-azaspiro[5.5]undec-2-en-4-yl)-4-fluorophenyl)-5-fluoropicolinamide,
N-(3-(6-amino-2,2-difluoro-8-methyl-5-thia-7-azaspiro[3.5]non-6-en-8-yl)-4-fluorophenyl)-5-fluoropicolinamide,
N-(3-(2-amino-9,9-difluoro-4-methyl-1-thia-3-azaspiro[5.5]undec-2-en-4-yl)-4-fluorophenyl)-5-fluoropicolinamide,
2,2-difluoro-8-methyl-8-(4-(5-(prop-1-ynyl)pyridin-3-yl)thiophen-2-yl)-5-thia-7-azaspiro[3.5]non-6-en-6-amine,
9,9-difluoro-4-methyl-4-(4-(5-(prop-1-ynyl)pyridin-3-yl)thiophen-2-yl)-1-thia-3-azaspiro[5.5]undec-2-en-2-amine,
2,2,9,9-tetrafluoro-8-methyl-8-(4-(5-(prop-1-ynyl)pyridin-3-yl)thiophen-2-yl)-5-thia-7-azaspiro[3.5]non-6-en-6-amine,
5,5,9,9-tetrafluoro-4-methyl-4-(4-(5-(prop-1-ynyl)pyridin-3-yl)thiophen-2-yl)-1-thia-3-azaspiro[5.5]undec-2-en-2-amine,
9,9-difluoro-8-methyl-8-(4-(5-(prop-1-ynyl)pyridin-3-yl)thiophen-2-yl)-5-thia-7-azaspiro[3.5]non-6-en-6-amine,
10,10-difluoro-9-methyl-9-(4-(5-(prop-1-ynyl)pyridin-3-yl)thiophen-2-yl)-6-thia-8-azaspiro[4.5]dec-7-en-7-amine,
5,5-difluoro-4-methyl-4-(4-(5-(prop-1-ynyl)pyridin-3-yl)thiophen-2-yl)-1-thia-3-azaspiro[5.5]undec-2-en-2-amine,
5,5-difluoro-4-methyl-4-(4-(5-(prop-1-ynyl)pyridin-3-yl)thiophen-2-yl)-9-oxa-1-thia-3-azaspiro[5.5]undec-2-en-2-amine,
N-(3-(6-amino-2,2,9,9-tetrafluoro-8-methyl-5-oxa-7-azaspiro[3.5]non-6-en-8-yl)-4-fluorophenyl)-5-fluoropicolinamide,
N-(3-(2-amino-5,5,9,9-tetrafluoro-4-methyl-1-oxa-3-azaspiro[5.5]undec-2-en-4-yl)-4-fluorophenyl)-5-fluoropicolinamide,
N-(3-(6-amino-9,9-difluoro-8-methyl-5-oxa-7-azaspiro[3.5]non-6-en-8-yl)-4-fluorophenyl)-5-fluoropicolinamide,
N-(3-(7-amino-10,10-difluoro-9-methyl-6-oxa-8-azaspiro[4.5]dec-7-en-9-yl)-4-fluorophenyl)-5-fluoropicolinamide,
N-(3-(2-amino-5,5-difluoro-4-methyl-1-oxa-3-azaspiro[5.5]undec-2-en-4-yl)-4-fluorophenyl)-5-fluoropicolinamide,
N-(3-(2-amino-5,5-difluoro-4-methyl-1,9-dioxa-3-azaspiro[5.5]undec-2-en-4-yl)-4-fluorophenyl)-5-fluoropicolinamide,
(R)—N-(3-(2-amino-5,5-difluoro-4-methyl-1,9-dioxa-3-azaspiro[5.5]undec-2-en-4-yl)-4-fluorophenyl)-5-fluoropicolinamide,
N-(3-(2-amino-4-methyl-9-oxa-1-thia-3-azaspiro[5.5]undec-2-en-4-yl)-4-fluorophenyl)-5-fluoropicolinamide,
N-(3-(2-amino-4-methyl-1,9-dioxa-3-azaspiro[5.5]undec-2-en-4-yl)-4-fluorophenyl)-5-fluoropicolinamide,
(S)—N-(3-(2-amino-4-methyl-1,9-dioxa-3-azaspiro[5.5]undec-2-en-4-yl)-4-fluorophenyl)-5-fluoropicolinamide,
3-(2-amino-4-methyl-9-oxa-1-thia-3-azaspiro[5.5]undec-2-en-4-yl)-4-fluoro-N-(5-fluoropyridin-2-yl)benzamide,
3-(2-amino-4-methyl-1,9-dioxa-3-azaspiro[5.5]undec-2-en-4-yl)-4-fluoro-N-(5-fluoropyridin-2-yl)benzamide,
3-(6-amino-8-methyl-5-oxa-7-azaspiro[3.5]non-6-en-8-yl)-4-fluoro-N-(5-fluoropyridin-2-yl)benzamide, 3-(6-amino-8-methyl-5-thia-7-azaspiro[3.5]non-6-en-8-yl)-4-fluoro-N-(5-fluoropyridin-2-yl)benzamide, (S)—N-(3-(2-amino-9,9-difluoro-4-methyl-1-oxa-3-azaspiro[5.5]undec-2-en-4-yl)-4-fluorophenyl)-5-chloropicolinamide, N-(3-(2-amino-4-methyl-9-oxa-1-thia-3-azaspiro[5.5]undec-2-en-4-yl)-4-fluorophenyl)-5-chloropicolinamide, (S)—N-(3-(2-amino-4-methyl-9-oxa-1-thia-3-azaspiro[5.5]undec-2-en-4-yl)-4-fluorophenyl)-5-chloropicolinamide, (S)—N-(3-(2-amino-4-methyl-9-oxa-1-thia-3-azaspiro[5.5]undec-2-en-4-yl)-4-fluorophenyl)-5-fluoropicolinamide, (S)—N-(3-(6-amino-8-methyl-5-thia-7-azaspiro[3.5]non-6-en-8-yl)-4-fluorophenyl)-5-chloropicolinamide, (S)—N-(3-(6-amino-8-methyl-5-oxa-7-azaspiro[3.5]non-6-en-8-yl)-4-fluorophenyl)-5-chloropicolinamide, (S)—N-(3-(6-amino-8-methyl-5-oxa-7-azaspiro[3.5]non-6-en-8-yl)-4-fluorophenyl)-5-cyanopicolinamide, (S)—N-(3-(6-amino-8-methyl-5-oxa-7-azaspiro[3.5]non-6-en-8-yl)-4-fluorophenyl)-5-chloro-3-fluoropicolinamide, (S)—N-(3-(2-amino-9,9-difluoro-4-methyl-1-oxa-3-azaspiro[5.5]undec-2-en-4-yl)-4-fluorophenyl)-5-(trifluoromethyl)picolinamide, (S)—N-(3-(2-amino-9,9-difluoro-4-methyl-1-oxa-3-azaspiro[5.5]undec-2-en-4-yl)-4-fluorophenyl)-5-chloro-3-fluoropicolinamide, (S)—N-(3-(2-amino-9,9-difluoro-4-methyl-1-oxa-3-azaspiro[5.5]undec-2-en-4-yl)-4-fluorophenyl)cyclopropanecarboxamide, (S)—N-(3-(5-amino-7-methyl-4-oxa-6-azaspiro[2.5]oct-5-en-7-yl)-4-fluorophenyl)-5-chloropicolinamide, (S,E)-8-(2-fluoro-5-(4-fluorostyryl)phenyl)-8-methyl-5-oxa-7-azaspiro[3.5]non-6-en-6-amine, (S)—N-(3-(6-amino-8-methyl-5-oxa-7-azaspiro[3.5]non-6-en-8-yl)-4-fluorophenyl)-5-methoxypyrazine-2-carboxamide, (S,E)-9,9-difluoro-4-(2-fluoro-5-(4-fluorostyryl)phenyl)-4-methyl-1-oxa-3-azaspiro[5.5]undec-2-en-2-amine, (S,E)-8-(5-(4-chlorostyryl)-2-fluorophenyl)-8-methyl-5-oxa-7-azaspiro[3.5]non-6-en-6-amine, (S)-8-(2-fluoro-5-(5-(prop-1-ynyl)pyridin-3-yl)phenyl)-8-methyl-5-oxa-7-azaspiro[3.5]non-6-en-6-amine, (S)—N-(3-(2-amino-9,9-difluoro-4-methyl-1-oxa-3-azaspiro[5.5]undec-2-en-4-yl)-4-fluorophenyl)-5-bromopicolinamide, (S)—N-(3-(2-amino-9,9-difluoro-4-methyl-1-oxa-3-azaspiro[5.5]undec-2-en-4-yl)-4-fluorophenyl)-5-cyclopropylpicolinamide, (S)—N-(3-(6-amino-8-methyl-5-oxa-7-azaspiro[3.5]non-6-en-8-yl)-4-fluorophenyl)-2-methyloxazole-4-carboxamide, N-(3-(2-amino-4-methyl-1,9-dioxa-3-azaspiro[5.5]undec-2-en-4-yl)-4-fluorophenyl)-5-chloropicolinamide, (S)—N-(3-(2-amino-4-methyl-1,9-dioxa-3-azaspiro[5.5]undec-2-en-4-yl)-4-fluorophenyl)-5-chloropicolinamide, (S)—N-(3-(6-amino-8-methyl-5-oxa-7-azaspiro[3.5]non-6-en-8-yl)-4-fluorophenyl)-4-chloro-2-methoxybenzamide, (S)—N-(3-(6-amino-8-methyl-5-oxa-7-azaspiro[3.5]non-6-en-8-yl)-4-fluorophenyl)-4-chlorobenzamide, N-(3-(2-amino-5,5-difluoro-4-methyl-1,9-dioxa-3-azaspiro[5.5]undec-2-en-4-yl)-4-fluorophenyl)-5-chloropicolinamide, N-(3-(6-amino-9,9-difluoro-8-methyl-5-oxa-7-azaspiro[3.5]non-6-en-8-yl)-4-fluorophenyl)-5-chloropicolinamide, N-(3-(6-amino-9,9-difluoro-8-methyl-5-oxa-7-azaspiro[3.5]non-6-en-8-yl)-4-fluorophenyl)-5-cyanopicolinamide, 5,5-difluoro-4-methyl-4-(4-(5-(prop-1-ynyl)pyridin-3-yl)thiophen-2-yl)-1,9-dioxa-3-azaspiro[5.5]undec-2-en-2-amine, (R)—N-(3-(6-amino-9,9-difluoro-8-methyl-5-oxa-7-azaspiro[3.5]non-6-en-8-yl)-4-fluorophenyl)-5-cyanopicolinamide, (S)-8-(2-fluoro-5-((5-fluoropyridin-2-yl)methylamino)phenyl)-8-methyl-5-oxa-7-azaspiro[3.5]non-6-en-6-amine, N-(3-(6-amino-9,9-difluoro-8-methyl-5-oxa-7-azaspiro[3.5]non-6-en-8-yl)-4-fluorophenyl)-5-methoxypyrazine-2-carboxamide, N-(3-(6-amino-9,9-difluoro-8-methyl-5-oxa-7-azaspiro[3.5]non-6-en-8-yl)-4-fluorophenyl)-2-methyloxazole-4-carboxamide, N-(3-(2-amino-4-methyl-1,9-dioxa-3-azaspiro[5.5]undec-2-en-4-yl)-4-fluorophenyl)-5-cyanopicolinamide, (S)-4-methyl-4-(5-methyl-4-(5-(prop-1-ynyl)pyridin-3-yl)thiophen-2-yl)-1,9-dioxa-3-azaspiro[5.5]undec-2-en-2-amine, 4-(2-fluoro-5-(1-propyl-1H-pyrazol-4-yl)phenyl)-4-methyl-1,9-dioxa-3-azaspiro[5.5]undec-2-en-2-amine, 4-(2-fluoro-5-(pyrimidin-5-yl)phenyl)-4-methyl-1,9-dioxa-3-azaspiro[5.5]undec-2-en-2-amine, (S)-8-(5-(7-chloroquinazolin-4-ylamino)-2-fluorophenyl)-8-methyl-5-oxa-7-azaspiro[3.5]non-6-en-6-amine, (S)—N-(3-(2-amino-4-methyl-9-oxa-1-thia-3-azaspiro[5.5]undec-2-en-4-yl)-4-fluorophenyl)-5-methoxypyrazine-2-carboxamide, (S)-4-(2-fluoro-5-(3-methoxypyridin-2-ylamino)phenyl)-4-methyl-9-oxa-1-thia-3-azaspiro[5.5]undec-2-en-2-amine, and any pharmaceutically acceptable salt thereof.

In one embodiment, the compound of Formula I is selected from the group consisting of:

4-methyl-4-(4-(5-(prop-1-ynyl)pyridin-3-yl)thiophen-2-yl)-1,9-dioxa-3-azaspiro[5.5]undec-2-en-2-amine, (S)-4-methyl-4-(4-(5-(prop-1-ynyl)pyridin-3-yl)thiophen-2-yl)-1,9-dioxa-3-azaspiro[5.5]undec-2-en-2-amine, 8-methyl-8-(4-(5-(prop-1-ynyl)pyridin-3-yl)thiophen-2-yl)-2-oxa-5-thia-7-azaspiro[3.5]non-6-en-6-amine, 9,9-difluoro-4-methyl-4-(4-(5-(prop-1-ynyl)pyridin-3-yl)thiophen-2-yl)-1-oxa-3-azaspiro[5.5]undec-2-en-2-amine, (S)-9,9-difluoro-4-methyl-4-(4-(5-(prop-1-ynyl)pyridin-3-yl)thiophen-2-yl)-1-oxa-3-azaspiro[5.5]undec-2-en-2-amine, N-(3-(2-amino-4-methyl-1-thia-3-azaspiro[5.5]undec-2-en-4-yl)-4-fluorophenyl)-5-fluoropicolinamide, 8-methyl-8-(4-(5-(prop-1-ynyl)pyridin-3-yl)thiophen-2-yl)-5-oxa-7-azaspiro[3.5]non-6-en-6-amine, (S)—N-(3-(6-amino-8-methyl-5-oxa-7-azaspiro[3.5]non-6-en-8-yl)-4-fluorophenyl)-5-fluoropicolinamide, 4-methyl-4-(4-(5-(prop-1-ynyl)pyridin-3-yl)thiophen-2-yl)-9-oxa-1-thia-3-azaspiro[5.5]undec-2-en-2-amine, (S)—N-(3-(6-amino-8-methyl-2-oxa-5-thia-7-azaspiro[3.5]non-6-en-8-yl)-4-fluorophenyl)-5-fluoropicolinamide, (S)—N-(3-(2-amino-9,9-difluoro-4-methyl-1-oxa-3-azaspiro[5.5]undec-2-en-4-yl)-4-fluorophenyl)-5-fluoropicolinamide, N-(3-(6-amino-9,9-difluoro-8-methyl-5-oxa-7-azaspiro[3.5]non-6-en-8-yl)-4-fluorophenyl)-5-fluoropicolinamide, N-(3-(2-amino-5,5-difluoro-4-methyl-1,9-dioxa-3-azaspiro[5.5]undec-2-en-4-yl)-4-fluorophenyl)-5-fluoropicolinamide, (R)—N-(3-(2-amino-5,5-difluoro-4-methyl-1,9-dioxa-3-azaspiro[5.5]undec-2-en-4-yl)-4-fluorophenyl)-5-fluoropicolinamide, N-(3-(2-amino-4-methyl-9-oxa-1-thia-3-azaspiro[5.5]undec-2-en-4-yl)-4-fluorophenyl)-5-fluoropicolinamide,
N-(3-(2-amino-4-methyl-1,9-dioxa-3-azaspiro[5.5]undec-2-en-4-yl)-4-fluorophenyl)-5-fluoropicolinamide,
(S)—N-(3-(2-amino-4-methyl-1,9-dioxa-3-azaspiro[5.5]undec-2-en-4-yl)-4-fluorophenyl)-5-fluoropicolinamide,
(S)—N-(3-(2-amino-9,9-difluoro-4-methyl-1-oxa-3-azaspiro[5.5]undec-2-en-4-yl)-4-fluorophenyl)-5-chloropicolinamide,
N-(3-(2-amino-4-methyl-9-oxa-1-thia-3-azaspiro[5.5]undec-2-en-4-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-fluoropicolinamide,
(S)—N-(3-(6-amino-8-methyl-5-thia-7-azaspiro[3.5]non-6-en-8-yl)-4-fluorophenyl)-5-chloropicolinamide,
(S)—N-(3-(6-amino-8-methyl-5-oxa-7-azaspiro[3.5]non-6-en-8-yl)-4-fluorophenyl)-5-chloropicolinamide,
(S)—N-(3-(6-amino-8-methyl-5-oxa-7-azaspiro[3.5]non-6-en-8-yl)-4-fluorophenyl)-5-cyanopicolinamide,
(S)—N-(3-(6-amino-8-methyl-5-oxa-7-azaspiro[3.5]non-6-en-8-yl)-4-fluorophenyl)-5-chloro-3-fluoropicolinamide,
(S)—N-(3-(2-amino-9,9-difluoro-4-methyl-1-oxa-3-azaspiro[5.5]undec-2-en-4-yl)-4-fluorophenyl)-5-(trifluoromethyl)picolinamide,
(S)—N-(3-(2-amino-9,9-difluoro-4-methyl-1-oxa-3-azaspiro[5.5]undec-2-en-4-yl)-4-fluorophenyl)-5-chloro-3-fluoropicolinamide,
(S)—N-(3-(2-amino-9,9-difluoro-4-methyl-1-oxa-3-azaspiro[5.5]undec-2-en-4-yl)-4-fluorophenyl)cyclopropanecarboxamide,
(S)—N-(3-(5-amino-7-methyl-4-oxa-6-azaspiro[2.5]oct-5-en-7-yl)-4-fluorophenyl)-5-chloropicolinamide,
(S,E)-8-(2-fluoro-5-(4-fluorostyryl)phenyl)-8-methyl-5-oxa-7-azaspiro[3.5]non-6-en-6-amine,
(S)—N-(3-(6-amino-8-methyl-5-oxa-7-azaspiro[3.5]non-6-en-8-yl)-4-fluorophenyl)-5-methoxypyrazine-2-carboxamide,
(S,E)-9,9-difluoro-4-(2-fluoro-5-(4-fluorostyryl)phenyl)-4-methyl-1-oxa-3-azaspiro[5.5]undec-2-en-2-amine,
(S,E)-8-(5-(4-chlorostyryl)-2-fluorophenyl)-8-methyl-5-oxa-7-azaspiro[3.5]non-6-en-6-amine,
(S)-8-(2-fluoro-5-(5-(prop-1-ynyl)pyridin-3-yl)phenyl)-8-methyl-5-oxa-7-azaspiro[3.5]non-6-en-6-amine,
(S)—N-(3-(2-amino-9,9-difluoro-4-methyl-1-oxa-3-azaspiro[5.5]undec-2-en-4-yl)-4-fluorophenyl)-5-bromopicolinamide,
(S)—N-(3-(2-amino-9,9-difluoro-4-methyl-1-oxa-3-azaspiro[5.5]undec-2-en-4-yl)-4-fluorophenyl)-5-cyclopropylpicolinamide,
(S)—N-(3-(6-amino-8-methyl-5-oxa-7-azaspiro[3.5]non-6-en-8-yl)-4-fluorophenyl)-2-methyloxazole-4-carboxamide,
N-(3-(2-amino-4-methyl-1,9-dioxa-3-azaspiro[5.5]undec-2-en-4-yl)-4-fluorophenyl)-5-chloropicolinamide,
(S)—N-(3-(2-amino-4-methyl-1,9-dioxa-3-azaspiro[5.5]undec-2-en-4-yl)-4-fluorophenyl)-5-chloropicolinamide,
(S)—N-(3-(6-amino-8-methyl-5-oxa-7-azaspiro[3.5]non-6-en-8-yl)-4-fluorophenyl)-4-chloro-2-methoxybenzamide,
(S)—N-(3-(6-amino-8-methyl-5-oxa-7-azaspiro[3.5]non-6-en-8-yl)-4-fluorophenyl)-4-chlorobenzamide,
N-(3-(2-amino-5,5-difluoro-4-methyl-1,9-dioxa-3-azaspiro[5.5]undec-2-en-4-yl)-4-fluorophenyl)-5-chloropicolinamide,
N-(3-(6-amino-9,9-difluoro-8-methyl-5-oxa-7-azaspiro[3.5]non-6-en-8-yl)-4-fluorophenyl)-5-chloropicolinamide,
N-(3-(6-amino-9,9-difluoro-8-methyl-5-oxa-7-azaspiro[3.5]non-6-en-8-yl)-4-fluorophenyl)-5-cyanopicolinamide,
5,5-difluoro-4-methyl-4-(4-(5-(prop-1-ynyl)pyridin-3-yl)thiophen-2-yl)-1,9-dioxa-3-azaspiro[5.5]undec-2-en-2-amine,
(R)—N-(3-(6-amino-9,9-difluoro-8-methyl-5-oxa-7-azaspiro[3.5]non-6-en-8-yl)-4-fluorophenyl)-5-cyanopicolinamide,
(S)-8-(2-fluoro-5-((5-fluoropyridin-2-yl)methylamino)phenyl)-8-methyl-5-oxa-7-azaspiro[3.5]non-6-en-6-amine,
N-(3-(6-amino-9,9-difluoro-8-methyl-5-oxa-7-azaspiro[3.5]non-6-en-8-yl)-4-fluorophenyl)-5-methoxypyrazine-2-carboxamide,
N-(3-(6-amino-9,9-difluoro-8-methyl-5-oxa-7-azaspiro[3.5]non-6-en-8-yl)-4-fluorophenyl)-2-methyloxazole-4-carboxamide,
N-(3-(2-amino-4-methyl-1,9-dioxa-3-azaspiro[5.5]undec-2-en-4-yl)-4-fluorophenyl)-5-cyanopicolinamide,
(S)-4-methyl-4-(5-methyl-4-(5-(prop-1-ynyl)pyridin-3-yl)thiophen-2-yl)-1,9-dioxa-3-azaspiro[5.5]undec-2-en-2-amine,
4-(2-fluoro-5-(1-propyl-1H-pyrazol-4-yl)phenyl)-4-methyl-1,9-dioxa-3-azaspiro[5.5]undec-2-en-2-amine,
4-(2-fluoro-5-(pyrimidin-5-yl)phenyl)-4-methyl-1,9-dioxa-3-azaspiro[5.5]undec-2-en-2-amine,
(S)-8-(5-(7-chloroquinazolin-4-ylamino)-2-fluorophenyl)-8-methyl-5-oxa-7-azaspiro[3.5]non-6-en-6-amine,
(S)—N-(3-(2-amino-4-methyl-9-oxa-1-thia-3-azaspiro[5.5]undec-2-en-4-yl)-4-fluorophenyl)-5-methoxypyrazine-2-carboxamide,
(S)-4-(2-fluoro-5-(3-methoxypyridin-2-ylamino)phenyl)-4-methyl-9-oxa-1-thia-3-azaspiro[5.5]undec-2-en-2-amine, and
any pharmaceutically acceptable salt thereof.

In one aspect, compounds are provided for use in making a compound of Formula I, having a structure according to Formula II:

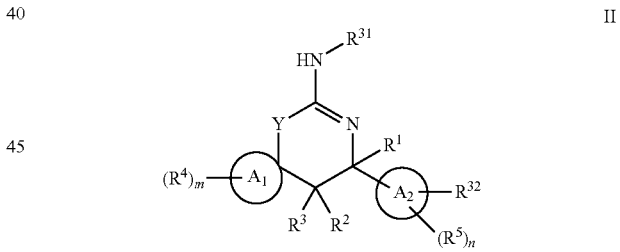

wherein:
$R^{31}$ is hydrogen or a nitrogen protecting group;
$R^{32}$ is halogen or $NH_2$; and
$A_1$, $A_2$, Y, $R^1$, $R^2$, $R^3$, $R^4$, $R^5$, m, and n are as defined for a compound of Formula I.

In some embodiments of a compound of Formula II, Y is O. In some embodiments, Y is S.

In some embodiments of a compound of Formula II, $A_1$ is a $C_{3-10}$ carbocyclic ring. In some embodiments $A_1$ is a $C_{3-6}$ monocyclic carbocyclic ring. In some embodiments, $A_1$ is cyclohexane. In some embodiments, $A_1$ is cyclopentane. In some embodiments, $A_1$ is cyclobutane. In some embodiments, $A_1$ is cyclopropane.

In some embodiments of a compound of Formula II, $A_1$ is a 3 to 10 membered heterocyclic ring. In some embodiments $A_1$ is a 4 to 6 membered monocyclic heterocyclic ring. In some embodiments $A_1$ is a 4 to 6 membered monocyclic heterocyclic ring that contains one oxygen atom or one sulfur atom as the only heteroatom. In some embodiments $A_1$ is a 4 to 6 membered monocyclic heterocyclic ring that contains one oxygen atom. In some embodiments $A_1$ is tetrahydropyran. In some embodiments $A_1$ is tetrahydrofuran. In some embodiments $A_1$ is oxetane.

In some embodiments of a compound of Formula II, $A_2$ is phenyl, or a monocyclic 5-6 membered heteroaryl ring. In some embodiments $A_2$ is phenyl or a monocyclic 5 membered heteroaryl ring. In some embodiments $A_2$ is phenyl or thiophenyl. In some embodiments $A_2$ is a monocyclic 5 membered heteroaryl ring. In some embodiments $A_2$ is thiophenyl. In some embodiments $A_2$ is pyrazolyl. In some embodiments, $A_2$ is phenyl.

In some embodiments of a compound of Formula II, $R^1$ is hydrogen or $C_{1-3}$ alkyl. In some embodiments $R^1$ is methyl. In some embodiments, $R^1$ is hydrogen. In some embodiments, $R^1$ is ethyl. In some embodiments, $R^1$ is n-propyl. In some embodiments, $R^1$ is isopropyl.

In some embodiments of a compound of Formula II, $R^2$ and $R^3$ are independently hydrogen or halogen. In some embodiments, $R^2$ and $R^3$ are independently hydrogen or fluoro. In some embodiments, $R^2$ and $R^3$ are both hydrogen or both fluoro. In some embodiments, $R^2$ and $R^3$ are both hydrogen. In some embodiments, $R^2$ and $R^3$ are both halogen. In some embodiments, $R^2$ and $R^3$ are both fluoro.

In some embodiments of a compound of Formula II, $R^4$ is halogen. In some embodiments, $R^4$ is fluoro. In some embodiments, $R^4$ is fluoro and m is 1 or 2. In some embodiments, $R^4$ is fluoro and m is 2. In some embodiments, $R^4$ is fluoro, m is 2, and both fluoro are attached to the same carbon atom. In some embodiments, m is 0. In some embodiments, $R^4$ is —C(O)CH$_3$. In some embodiments, $R^4$ is —C(O)CH$_3$ and m is 1.

In some embodiments of a compound of Formula II, $R^{32}$ is halogen. In some embodiments $R^{32}$ is NH$_2$.

In some embodiments of a compound of Formula II, Y is O or S; $A_1$ is a $C_{3-10}$ carbocyclic ring, in some embodiments a $C_{3-6}$ monocyclic carbocyclic ring or $A_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom; $A_2$ is phenyl, or a monocyclic 5-6 membered heteroaryl ring, in some embodiments a monocyclic 5 membered heteroaryl ring.

In some embodiments of a compound of Formula II, Y is O or S; $A_1$ is a $C_{3-10}$ carbocyclic ring, in some embodiments a $C_{3-6}$ monocyclic carbocyclic ring; $A_2$ is phenyl, or a monocyclic 5-6 membered heteroaryl ring, in some embodiments a monocyclic 5 membered heteroaryl ring.

In some embodiments of a compound of Formula II, Y is O or S; $A_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom; $A_2$ is phenyl, or a monocyclic 5-6 membered heteroaryl ring, in some embodiments a monocyclic 5 membered heteroaryl ring.

In some embodiments of a compound of Formula II, Y is O or S; $A_1$ is a $C_{3-10}$ carbocyclic ring, in some embodiments a $C_{3-6}$ monocyclic carbocyclic ring or $A_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom, in some embodiments, one oxygen atom as the only heteroatom; and $A_2$ is phenyl, or a monocyclic 5-6 membered heteroaryl ring, in some embodiments phenyl or thiophenyl.

In some embodiments of a compound of Formula II, Y is O or S; $A_1$ is a $C_{3-10}$ carbocyclic ring, in some embodiments a $C_{3-6}$ monocyclic carbocyclic ring; and $A_2$ is phenyl, or a monocyclic 5-6 membered heteroaryl ring, in some embodiments phenyl or thiophenyl.

In some embodiments of a compound of Formula II, Y is O or S; $A_1$ is a 3 to 10 membered heterocyclic ring, in some embodiments a 4 to 6 membered monocyclic heterocyclic ring, in some embodiments the 4 to 6 membered monocyclic heterocyclic ring contains one oxygen atom or one sulfur atom as the only heteroatom, in some embodiments oxygen as the only heteroatom; and $A_2$ is phenyl, or a monocyclic 5-6 membered heteroaryl ring, in some embodiments phenyl or thiophenyl.

In some embodiments of a compound of Formula II, further to any of the above embodiments, $R^1$ is methyl.

In some embodiments of a compound of Formula II, the compound has a structure according to Formula IIa:

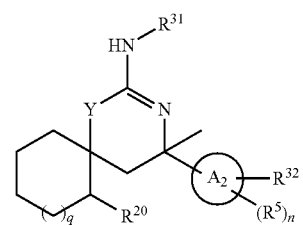

wherein:

$A_2$, Y, $R^5$, and n are as defined for a compound of Formula I;

q and $R^{20}$ are as defined for a compound of Formula Ia; and $R^{31}$ and $R^{32}$ are as definded for a compound of Formula II.

In some embodiments of a compound of Formula IIa, Y is O. In some embodiments, Y is S.

In some embodiments of a compound of Formula IIa, q is 0. In some embodiments q is 1.

In some embodiments of a compound of Formula IIa, $A_2$ is phenyl, or a monocyclic 5-6 membered heteroaryl ring. In some embodiments $A_2$ is a monocyclic 5 membered heteroaryl ring. In some embodiments $A_2$ is thiophenyl. In some embodiments $A_2$ is pyrazolyl. In some embodiments, $A_2$ is phenyl.

In some embodiments of a compound of Formula IIa, $R^{20}$ is hydrogen. In some embodiments, $R^{20}$ is —OH, =O, or —OR$^{12}$. In some embodiments, $R^{20}$ is —S(O)$_z$R$^{12}$. In some embodiments, $R^{20}$ is —NR$^{13}$R$^{14}$, or =NR$^{14}$. In some embodiments, $R^{20}$ is —NR$^{13}$R$^{14}$.

In some embodiments of a compound of Formula IIa, $R^{32}$ is halogen. In some embodiments $R^{32}$ is NH$_2$.

In some embodiments of a compound of Formula IIa, Y is O or S; $A_2$ is phenyl, or a monocyclic 5-6 membered heteroaryl ring, in some embodiments a monocyclic 5 membered heteroaryl ring.

In some embodiments of a compound of Formula IIa, Y is O or S; q is 0; $A_2$ is phenyl, or a monocyclic 5-6 membered heteroaryl ring, in some embodiments a monocyclic 5 membered heteroaryl ring.

In some embodiments of a compound of Formula IIa, Y is O or S; q is 1; $A_2$ is phenyl, or a monocyclic 5-6 membered heteroaryl ring, in some embodiments a monocyclic 5 membered heteroaryl ring.

In some embodiments of a compound of Formula IIa, Y is S, and $R^{20}$ is H. In some embodiments, Y is S; $R^{20}$ is H; $A_2$ is phenyl, or a monocyclic 5-6 membered heteroaryl ring, in some embodiments a monocyclic 5 membered heteroaryl ring.

In some embodiments of a compound of Formula IIa, Y is O, and $R^{20}$ is H. In some embodiments, Y is O; $R^{20}$ is H; $A_2$ is phenyl, or a monocyclic 5-6 membered heteroaryl ring, in some embodiments a monocyclic 5 membered heteroaryl ring.

In some embodiments of a compound of Formula IIa, Y is S, q is 0, and $R^{20}$ is H. In some embodiments, Y is S; q is 0; $R^{20}$ is H; $A_2$ is phenyl, or a monocyclic 5-6 membered heteroaryl ring, in some embodiments a monocyclic 5 membered heteroaryl ring.

In some embodiments of a compound of Formula IIa, Y is O, q is 0, and $R^{20}$ is H. In some embodiments, Y is O; q is 0; $R^{20}$ is H; $A_2$ is phenyl, or a monocyclic 5-6 membered heteroaryl ring, in some embodiments a monocyclic 5 membered heteroaryl ring.

In some embodiments of a compound of Formula IIa, Y is S, q is 1, and $R^{20}$ is H. In some embodiments, Y is S; q is 1; $R^{20}$ is H; $A_2$ is phenyl, or a monocyclic 5-6 membered heteroaryl ring, in some embodiments a monocyclic 5 membered heteroaryl ring.

In some embodiments of a compound of Formula IIa, Y is O, q is 1, and $R^{20}$ is H. In some embodiments, Y is O; q is 1; $R^{20}$ is H; $A_2$ is phenyl, or a monocyclic 5-6 membered heteroaryl ring, in some embodiments a monocyclic 5 membered heteroaryl ring.

In some embodiments of a compound of Formula II, the compound has a structure according to Formula IIb:

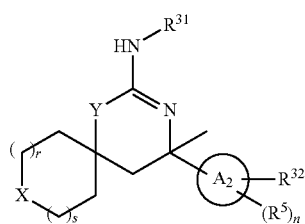

IIb wherein:
$A_2$, Y, $R^5$, and n are as defined for a compound of Formula I;
X, r and s are as defined for a compound of Formula Ib; and
$R^{31}$ and $R^{32}$ are as definded for a compound of Formula II.

In some embodiments of a compound of Formula IIb, Y is O. In some embodiments, Y is S.

In some embodiments of a compound of Formula IIb, X is O. In some embodiments, X is $S(O)_2$.

In some embodiments of a compound of Formula IIb, r and s are both 0. In some embodiments, r and s are both 1. In some embodiments, one of r and s is 0 and the other is 1.

In some embodiments of a compound of Formula IIb, $A_2$ is phenyl, or a monocyclic 5-6 membered heteroaryl ring. In some embodiments $A_2$ is a monocyclic 5 membered heteroaryl ring. In some embodiments $A_2$ is thiophenyl. In some embodiments $A_2$ is pyrazolyl. In some embodiments, $A_2$ is phenyl.

In some embodiments of a compound of Formula IIb, $R^{32}$ is halogen. In some embodiments of a compound of Formula IIb, $R^{32}$ is $NH_2$.

In some embodiments of a compound of Formula IIb, Y is O or S; $A_2$ is phenyl, or a monocyclic 5-6 membered heteroaryl ring, in some embodiments a monocyclic 5 membered heteroaryl ring.

In some embodiments of a compound of Formula IIb, Y is O or S; either r and s are both 0 or r and s are both 1; $A_2$ is phenyl, or a monocyclic 5-6 membered heteroaryl ring, in some embodiments a monocyclic 5 membered heteroaryl ring.

In some embodiments of a compound of Formula IIb, Y is O or S; r and s are both 0; $A_2$ is phenyl, or a monocyclic 5-6 membered heteroaryl ring, in some embodiments a monocyclic 5 membered heteroaryl ring.

In some embodiments of a compound of Formula IIb, Y is O or S; r and s are both 1; $A_2$ is phenyl, or a monocyclic 5-6 membered heteroaryl ring, in some embodiments a monocyclic 5 membered heteroaryl ring.

In some embodiments of a compound of Formula IIb, Y is O and either r and s are both 0 or r and s are both 1. In some embodiments Y is O; either r and s are both 0 or r and s are both 1; $A_2$ is phenyl, or a monocyclic 5-6 membered heteroaryl ring, in some embodiments a monocyclic 5 membered heteroaryl ring.

In some embodiments of a compound of Formula IIb, Y is S and either r and s are both 0 or r and s are both 1. In some embodiments Y is S; either r and s are both 0 or r and s are both 1; $A_2$ is phenyl, or a monocyclic 5-6 membered heteroaryl ring, in some embodiments a monocyclic 5 membered heteroaryl ring.

In some embodiments of a compound of Formula III), Y is O and r and s are both 0. In some embodiments Y is O; r and s are both 0; $A_2$ is phenyl, or a monocyclic 5-6 membered heteroaryl ring, in some embodiments a monocyclic 5 membered heteroaryl ring.

In some embodiments of a compound of Formula IIb, Y is S and r and s are both 1. In some embodiments Y is S; r and s are both 1; $A_2$ is phenyl, or a monocyclic 5-6 membered heteroaryl ring, in some embodiments a monocyclic 5 membered heteroaryl ring.

In some embodiments of a compound of Formula IIb, Y is O and r and s are both 1. In some embodiments Y is O; r and s are both 1; $A_2$ is phenyl, or a monocyclic 5-6 membered heteroaryl ring, in some embodiments a monocyclic 5 membered heteroaryl ring.

In some embodiments of a compound of Formula IIb, Y is S and r and s are both 0. In some embodiments Y is S; r and s are both 0; $A_2$ is phenyl, or a monocyclic 5-6 membered heteroaryl ring, in some embodiments a monocyclic 5 membered heteroaryl ring.

In some embodiments of a compound of Formula IIb, further to any of the above embodiments of Formula IIb, X is O.

In some embodiments of a compound of Formula IIb, further to any of the above embodiments of Formula IIb, X is $S(O)_2$.

In some embodiments of a compound of Formula II, Formula IIa or Formula IIb, further to any of the above embodiments, $A_2$ is phenyl, thiophenyl or pyrazolyl. In some embodiments, $A_2$ is phenyl. In some embodiments, $A_2$ is thiophenyl. In some embodiments, $A_2$ is pyrazolyl.

In some embodiments of a compound of Formula II, Formula IIa or Formula IIb, further to any of the above embodiments, m is 0 or 1; $R^4$ is fluoro, =O, —$OR^{12}$, —$S(O)_zR^{12}$, —$C(O)R^{12}$, or —$NR^{13}R^{14}$, or $R^{20}$ is —$OR^{12}$, —$S(O)_zR^{12}$, or —$NR^{13}R^{14}$; n is 0 or 1; and $R^5$ is halogen, —CN, $C_{1-6}$ alkyl, $C_{1-6}$ haloalkyl, $C_{1-6}$ alkoxy, or $C_{1-6}$ haloalkoxy.

In some embodiments of a compound of Formula II, Formula IIa or Formula IIb, further to any of the above embodiments, $R^{31}$ is hydrogen or a nitrogen protecting group, and the nitrogen protecting group is Boc. In some embodiments, $R^{31}$ is hydrogen. In some embodiments, $R^{31}$ is a nitrogen protecting group. In some embodiments, $R^{31}$ is Boc.

In some embodiments of a compound of Formula II, Formula IIa or Formula III), further to any of the above embodiments, Y is O. In some embodiment, further to any of the above embodiments, Y is S.

In some embodiments of a compound of Formula II, Formula IIa or Formula IIb, further to any of the above embodiments, n is 0, 1 or 2, and each $R^5$ is independently selected from the group consisting of —CN, halogen, $C_{1-6}$ alkyl, $C_{2-6}$ alkenyl, $C_{2-6}$ alkynyl, $C_{1-6}$ alkoxy, $C_{1-6}$ alkylsulfonyl, $C_{1-6}$ alkylamino, di-$C_{1-6}$ alkylamino, N-linked-heterocycloalkyl, and $C_{3-6}$ cycloalkyl, wherein $C_{1-6}$ alkyl, $C_{2-6}$ alkenyl, $C_{2-6}$ alkynyl, and the alkyl chains of $C_{1-6}$ alkoxy, $C_{1-6}$ alkylsulfonyl, $C_{1-6}$ alkylamino, or di-$C_{1-6}$ alkylamino are optionally substituted with one or more substituents independently selected from the group consisting of fluoro, —CN, $C_{3-6}$ cycloalkyl, $C_{1-6}$ alkoxy, $C_{1-6}$ haloalkoxy, $C_{1-6}$ alkylamino, di-$C_{1-6}$ alkylamino and N-linked-heterocycloalkyl. In some embodiments, n is 0 or 1; and $R^5$ is selected from the group consisting of halogen, —CN, $C_{1-6}$ alkyl, $C_{1-6}$ haloalkyl, $C_{1-6}$ alkoxy, and $C_{1-6}$ haloalkoxy. In some embodiments, further to any of the above embodiments, n is 1 and $R^5$ is halogen.

In some embodiments of a compound of Formula II, the compound has a structure according to Formula IIc:

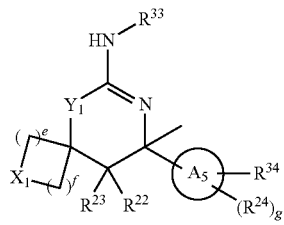

wherein:
$R^{33}$ is hydrogen or Boc;
$R^{34}$ is halogen or $NH_2$;
$Y_1$, $X_1$, e, f, g, $A_5$, $R^{22}$, $R^{23}$, and $R^{24}$ are as defined for a compound of Formula Ic.

In some embodiments of a compound of Formula IIc, g is 0 or 1; and $R^{24}$ is halogen, —CN, $C_{1-6}$ alkyl, $C_{1-6}$ haloalkyl, $C_{1-6}$ alkoxy, or $C_{1-6}$ haloalkoxy.

In some embodiments, the compound of Formula IIc has a structure selected from the group consisting of:

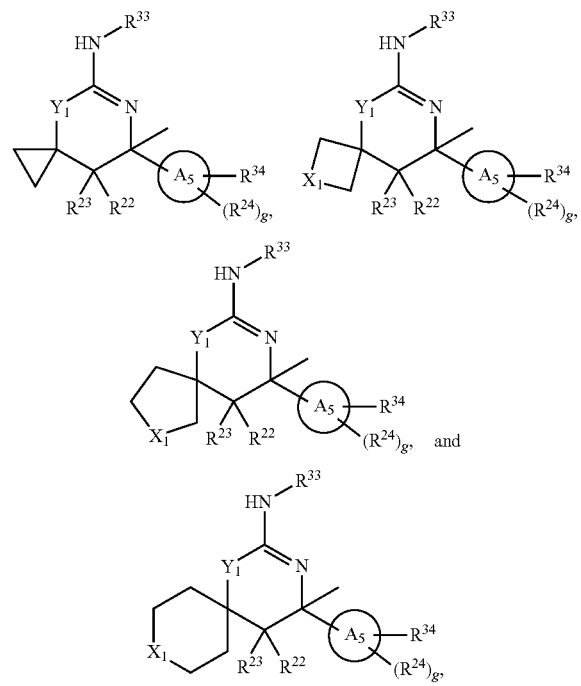

wherein $X_1$, $Y_1$, $A_5$, $R^{22}$, $R^{23}$, $R^{24}$, and g are as defined for a compound of Formula Ic and $R^{33}$ and $R^{34}$ are as defined for a compound of Formula IIc.

In some embodiments, the compound of Formula IIc has a structure selected from the group consisting of:

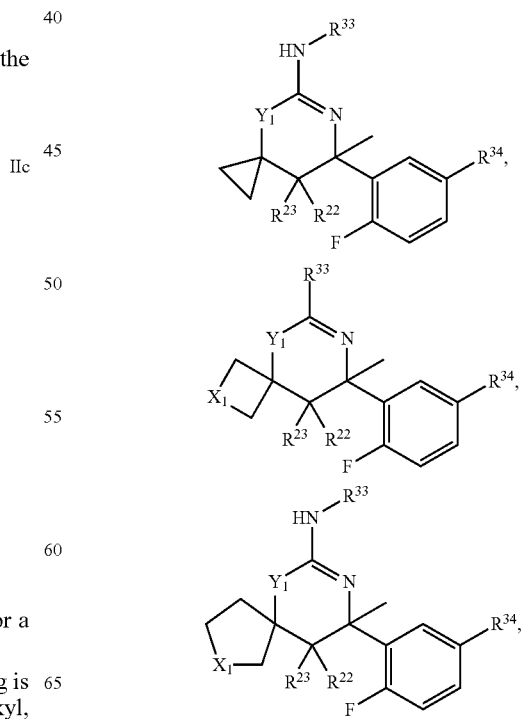

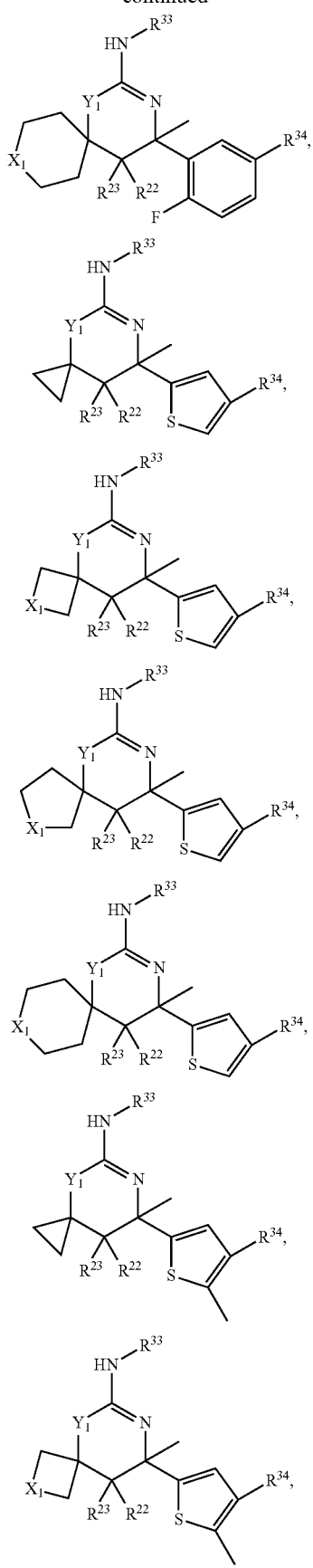

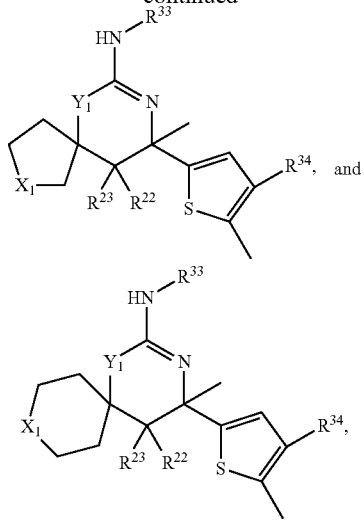

wherein $X_1$, $Y_1$, $R^{22}$, and $R^{23}$, are as defined for a compound of Formula Ic and $R^{33}$ and $R^{34}$ are as defined for a compound of Formula IIc.

In one embodiment, the compound of Formula II is selected from the group consisting of:
4-(4-bromothiophen-2-yl)-4-methyl-1,9-dioxa-3-azaspiro[5.5]undec-2-en-2-amine,
(S)-4-(4-bromothiophen-2-yl)-4-methyl-1,9-dioxa-3-azaspiro[5.5]undec-2-en-2-amine,
(R)-4-(4-bromothiophen-2-yl)-4-methyl-1,9-dioxa-3-azaspiro[5.5]undec-2-en-2-amine,
8-(4-bromothiophen-2-yl)-8-methyl-2-oxa-5-thia-7-azaspiro[3.5]non-6-en-6-amine,
(R)-4-(5-amino-2-fluorophenyl)-4-methyl-1-thia-3-azaspiro[5.5]undec-2-en-2-amine,
4-(5-bromo-2-fluorophenyl)-4-methyl-1-thia-3-azaspiro[5.5]undec-2-en-2-amine,
(S)-4-(5-bromo-2-fluorophenyl)-4-methyl-1-thia-3-azaspiro[5.5]undec-2-en-2-amine,
(S)-8-(5-bromo-2-fluorophenyl)-8-methyl-2-oxa-5-thia-7-azaspiro[3.5]non-6-en-6-amine,
(S)-8-(5-amino-2-fluorophenyl)-8-methyl-5-oxa-7-azaspiro[3.5]non-6-en-6-amine,
4-(5-bromo-2-fluorophenyl)-4-methyl-1,9-dioxa-3-azaspiro[5.5]undec-2-en-2-amine,
(S)-4-(5-bromo-2-fluorophenyl)-4-methyl-1,9-dioxa-3-azaspiro[5.5]undec-2-en-2-amine
8-(4-bromothiophen-2-yl)-8-methyl-5-oxa-7-azaspiro[3.5]non-6-en-6-amine,
(S)-4-(4-bromo-5-methylthiophen-2-yl)-4-methyl-1,9-dioxa-3-azaspiro[5.5]undec-2-en-2-amine,
4-(4-bromothiophen-2-yl)-9,9-difluoro-4-methyl-1-oxa-3-azaspiro[5.5]undec-2-en-2-amine,
(S)-4-(4-bromothiophen-2-yl)-9,9-difluoro-4-methyl-1-oxa-3-azaspiro[5.5]undec-2-en-2-amine,
8-(5-bromo-2-fluorophenyl)-8-methyl-5-oxa-7-azaspiro[3.5]non-6-en-6-amine,
(S)-8-(5-bromo-2-fluorophenyl)-8-methyl-5-oxa-7-azaspiro[3.5]non-6-en-6-amine,
(R)-8-(5-bromo-2-fluorophenyl)-8-methyl-5-oxa-7-azaspiro[3.5]non-6-en-6-amine,
(S)-4-(5-bromo-2-fluorophenyl)-9,9-difluoro-4-methyl-1-oxa-3-azaspiro[5.5]undec-2-en-2-amine,
(R)-8-(5-bromo-2-fluorophenyl)-8-methyl-5-thia-7-azaspiro[3.5]non-6-en-6-amine, (S)-8-(5-bromo-2-fluorophenyl)-8-methyl-5-thia-7-azaspiro[3.5]non-6-en-6-amine,
(4S)-4-(3-bromothiophen-2-yl)-7,7,8,8,9,9,10,10,11-nonadeutero-4-methyl-1-thia-3-azaspiro[5.5]undec-2-en-2-amine,
4-(5-bromo-2-fluorophenyl)-4-methyl-9-oxa-1-thia-3-azaspiro[5.5]undec-2-en-2-amine,
(S)-4-(5-bromo-2-fluorophenyl)-4-methyl-9-oxa-1-thia-3-azaspiro[5.5]undec-2-en-2-amine,
(R)-4-(5-bromo-2-fluorophenyl)-4-methyl-9-oxa-1-thia-3-azaspiro[5.5]undec-2-en-2-amine,
4-(4-bromothiophen-2-yl)-4-methyl-9-oxa-1-thia-3-azaspiro[5.5]undec-2-en-2-amine,
(S)-7-(5-bromo-2-fluorophenyl)-7-methyl-4-oxa-6-azaspiro[2.5]oct-5-en-5-amine,
4-(5-bromo-2-fluorophenyl)-5,5-difluoro-4-methyl-1,9-dioxa-3-azaspiro[5.5]undec-2-en-2-amine,
4-(4-bromothiophen-2-yl)-5,5-difluoro-4-methyl-1,9-dioxa-3-azaspiro[5.5]undec-2-en-2-amine,
(S)-4-(5-bromo-2-fluorophenyl)-5,5-difluoro-4-methyl-1,9-dioxa-3-azaspiro[5.5]undec-2-en-2-amine,
(R)-4-(5-bromo-2-fluorophenyl)-5,5-difluoro-4-methyl-1,9-dioxa-3-azaspiro[5.5]undec-2-en-2-amine,
8-(5-bromo-2-fluorophenyl)-9,9-difluoro-8-methyl-5-oxa-7-azaspiro[3.5]non-6-en-6-amine,
(S)-8-(5-bromo-2-fluorophenyl)-9,9-difluoro-8-methyl-5-oxa-7-azaspiro[3.5]non-6-en-6-amine,
(R)-8-(5-bromo-2-fluorophenyl)-9,9-difluoro-8-methyl-5-oxa-7-azaspiro[3.5]non-6-en-6-amine,
tert-butyl 4-(5-bromo-2-fluorophenyl)-4-methyl-1,9-dioxa-3-azaspiro[5.5]undec-2-en-2-ylcarbamate,
(S)-tert-butyl 4-(5-bromo-2-fluorophenyl)-4-methyl-1,9-dioxa-3-azaspiro[5.5]undec-2-en-2-ylcarbamate,
tert-butyl 4-(5-amino-2-fluorophenyl)-4-methyl-1,9-dioxa-3-azaspiro[5.5]undec-2-en-2-ylcarbamate,
(S)-tert-butyl 4-(5-amino-2-fluorophenyl)-4-methyl-1,9-dioxa-3-azaspiro[5.5]undec-2-en-2-ylcarbamate,
(S)-tert-butyl 4-(5-bromo-2-fluorophenyl)-9,9-difluoro-4-methyl-1-oxa-3-azaspiro[5.5]undec-2-en-2-ylcarbamate,
(S)-tert-butyl 4-(5-amino-2-fluorophenyl)-9,9-difluoro-4-methyl-1-oxa-3-azaspiro[5.5]undec-2-en-2-ylcarbamate,
tert-butyl 8-(5-bromo-2-fluorophenyl)-8-methyl-5-oxa-7-azaspiro[3.5]non-6-en-6-ylcarbamate,
(S)-tert-butyl 8-(5-bromo-2-fluorophenyl)-8-methyl-5-oxa-7-azaspiro[3.5]non-6-en-6-ylcarbamate,
(R)-tert-butyl 8-(5-bromo-2-fluorophenyl)-8-methyl-5-oxa-7-azaspiro[3.5]non-6-en-6-ylcarbamate,
tert-butyl 8-(5-amino-2-fluorophenyl)-8-methyl-5-oxa-7-azaspiro[3.5]non-6-en-6-ylcarbamate,
(S)-tert-butyl 8-(5-amino-2-fluorophenyl)-8-methyl-5-oxa-7-azaspiro[3.5]non-6-en-6-ylcarbamate,
(R)-tert-butyl 8-(5-amino-2-fluorophenyl)-8-methyl-5-oxa-7-azaspiro[3.5]non-6-en-6-ylcarbamate,
tert-butyl 4-(5-bromo-2-fluorophenyl)-4-methyl-1-thia-3-azaspiro[5.5]undec-2-en-2-ylcarbamate,
tert-butyl 4-(5-amino-2-fluorophenyl)-4-methyl-1-thia-3-azaspiro[5.5]undec-2-en-2-ylcarbamate,
(S)-tert-butyl 8-(5-bromo-2-fluorophenyl)-8-methyl-5-thia-7-azaspiro[3.5]non-6-en-6-ylcarbamate,
(R)-tert-butyl 8-(5-bromo-2-fluorophenyl)-8-methyl-5-thia-7-azaspiro[3.5]non-6-en-6-ylcarbamate,
(S)-tert-butyl 8-(5-amino-2-fluorophenyl)-8-methyl-5-thia-7-azaspiro[3.5]non-6-en-6-ylcarbamate,
(R)-tert-butyl 8-(5-amino-2-fluorophenyl)-8-methyl-5-thia-7-azaspiro[3.5]non-6-en-6-ylcarbamate,
(S)-tert-butyl 8-(5-bromo-2-fluorophenyl)-8-methyl-2-oxa-5-thia-7-azaspiro[3.5]non-6-en-6-ylcarbamate,
(S)-tert-butyl 8-(5-amino-2-fluorophenyl)-8-methyl-2-oxa-5-thia-7-azaspiro[3.5]non-6-en-6-ylcarbamate,
tert-butyl 4-(5-bromo-2-fluorophenyl)-4-methyl-9-oxa-1-thia-3-azaspiro[5.5]undec-2-en-2-ylcarbamate,
(S)-tert-butyl 4-(5-bromo-2-fluorophenyl)-4-methyl-9-oxa-1-thia-3-azaspiro[5.5]undec-2-en-2-ylcarbamate,
(R)-tert-butyl 4-(5-bromo-2-fluorophenyl)-4-methyl-9-oxa-1-thia-3-azaspiro[5.5]undec-2-en-2-ylcarbamate,
tert-butyl 4-(5-amino-2-fluorophenyl)-4-methyl-9-oxa-1-thia-3-azaspiro[5.5]undec-2-en-2-ylcarbamate,
(S)-tert-butyl 4-(5-amino-2-fluorophenyl)-4-methyl-9-oxa-1-thia-3-azaspiro[5.5]undec-2-en-2-ylcarbamate,
(R)-tert-butyl 4-(5-amino-2-fluorophenyl)-4-methyl-9-oxa-1-thia-3-azaspiro[5.5]undec-2-en-2-ylcarbamate,
(S)-tert-butyl 7-(5-bromo-2-fluorophenyl)-7-methyl-4-oxa-6-azaspiro[2.5]oct-5-en-5-ylcarbamate,
(S)-tert-butyl 7-(5-amino-2-fluorophenyl)-7-methyl-4-oxa-6-azaspiro[2.5]oct-5-en-5-ylcarbamate,
tert-butyl 4-(5-bromo-2-fluorophenyl)-5,5-difluoro-4-methyl-1,9-dioxa-3-azaspiro[5.5]undec-2-en-2-ylcarbamate,
(R)-tert-butyl 4-(5-bromo-2-fluorophenyl)-5,5-difluoro-4-methyl-1,9-dioxa-3-azaspiro[5.5]undec-2-en-2-ylcarbamate,
(S)-tert-butyl 4-(5-bromo-2-fluorophenyl)-5,5-difluoro-4-methyl-1,9-dioxa-3-azaspiro[5.5]undec-2-en-2-ylcarbamate,
tert-butyl 4-(5-amino-2-fluorophenyl)-5,5-difluoro-4-methyl-1,9-dioxa-3-azaspiro[5.5]undec-2-en-2-ylcarbamate,
(R)-tert-butyl 4-(5-amino-2-fluorophenyl)-5,5-difluoro-4-methyl-1,9-dioxa-3-azaspiro[5.5]undec-2-en-2-ylcarbamate,
(S)-tert-butyl 4-(5-amino-2-fluorophenyl)-5,5-difluoro-4-methyl-1,9-dioxa-3-azaspiro[5.5]undec-2-en-2-ylcarbamate,
tert-butyl 8-(5-bromo-2-fluorophenyl)-9,9-difluoro-8-methyl-5-oxa-7-azaspiro[3.5]non-6-en-6-ylcarbamate,
(R)-tert-butyl 8-(5-bromo-2-fluorophenyl)-9,9-difluoro-8-methyl-5-oxa-7-azaspiro[3.5]non-6-en-6-ylcarbamate,
(S)-tert-butyl 8-(5-bromo-2-fluorophenyl)-9,9-difluoro-8-methyl-5-oxa-7-azaspiro[3.5]non-6-en-6-ylcarbamate,
tert-butyl 8-(5-amino-2-fluorophenyl)-9,9-difluoro-8-methyl-5-oxa-7-azaspiro[3.5]non-6-en-6-ylcarbamate,
(R)-tert-butyl 8-(5-amino-2-fluorophenyl)-9,9-difluoro-8-methyl-5-oxa-7-azaspiro[3.5]non-6-en-6-ylcarbamate, and
(S)-tert-butyl 8-(5-amino-2-fluorophenyl)-9,9-difluoro-8-methyl-5-oxa-7-azaspiro[3.5]non-6-en-6-ylcarbamate.

In one aspect, compounds are provided for use in making a compound of Formula I, having a structure according to Formula III, wherein Formula III is selected from the group consisting of:

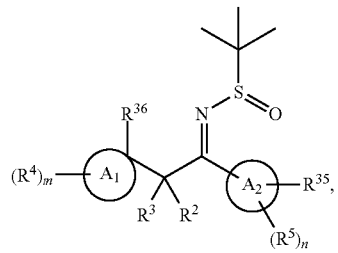

IIIa

-continued

IIIb
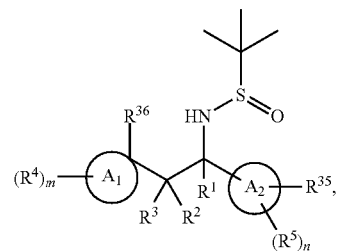

IIIc
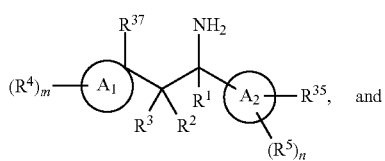
and

IIId
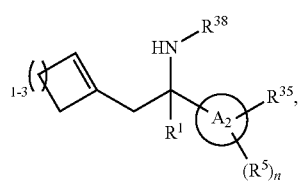

wherein:
$R^{35}$ is halogen;
$R^{36}$ is OH, $OR^{39}$, SH, or $SR^{40}$;
$R^{37}$ is OH, SH, or $SR^{40}$;
$R^{38}$ is hydrogen or

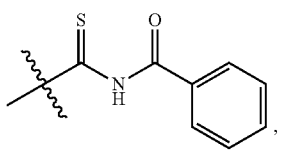 [SMILES: *C(=S)NC(=O)c1ccccc1], wherein

indicates the attachment point to NH;
$R^{39}$ is an oxygen protecting group;
$R^{40}$ is a thiol protecting group; and
$A_1$, $A_2$, $R^1$, $R^2$, $R^3$, $R^4$, m, and n are as defined for a compound of Formula I.

In some embodiments of a compound of Formula III, the compound has a structure selected from the group consisting of:

IIIe
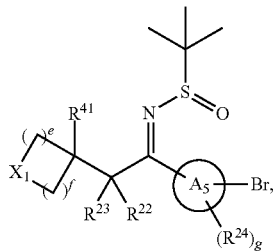

IIIf
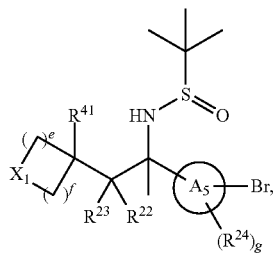

IIIg
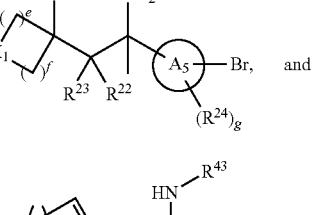
and

IIIh
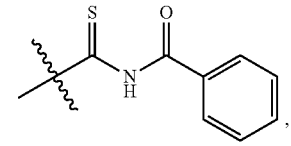

wherein:
$R^{41}$ is OH, TBDMS protected O, SH, or p-methoxybenzyl protected S;
$R^{42}$ is OH, SH, or p-methoxybenzyl protected S;
$R^{43}$ is hydrogen or

, wherein indicates the attachment point to NH;
$X_1$, e, f, g, $A_5$, $R^{22}$, $R^{23}$, and $R^{24}$ are as defined for compounds of Formula Ic.

In some embodiments of a compound of Formula III selected from IIIe, IIIf, IIIg and IIIh, g is 0 or 1; and $R^{24}$ is halogen, —CN, $C_{1-6}$ alkyl, $C_{1-6}$ haloalkyl, $C_{1-6}$ alkoxy, or $C_{1-6}$ haloalkoxy.

In some embodiments of a compound of Formula III,

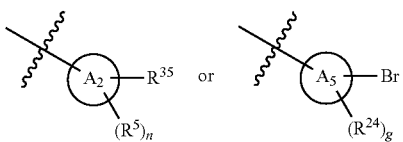

is selected from the group consisting of:

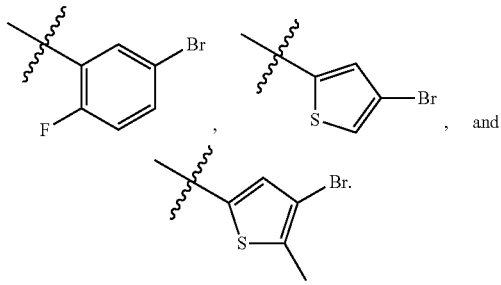

In one embodiment, a compound as described herein, e.g. a compound of Formula I, is an inhibitor of BACE1 and/or BACE2 protease activity, with an $IC_{50}$ of less than about 1.0 µM, less than about 0.9 µM, less than about 0.8 µM, less than about 0.7 µM, less than about 0.6 µM, less than about 0.5 µM, less than about 0.4 µM, less than about 0.3 µM, or less than about 0.2 µM in a BACE1 and/or BACE2 protease activity assay. In one embodiment, a compound of Formula I has an $IC_{50}$ of less than about 100 nM, less than about 90 nM, less than about 80 nM, less than about 70 nM, less than about 60 nM, less than about 50 nM, less than about 40 nM, less than about 30 nM, less than about 20 nM or less than about 10 nM in a BACE1 and/or BACE2 protease activity assay.

In one embodiment, a compound as described herein, e.g. a compound of Formula I, is an inhibitor of BACE1 protease activity, with an $IC_{50}$ of less than about 1.0 µM, less than about 0.9 µM, less than about 0.8 less than about 0.7 µM, less than about 0.6 µM, less than about 0.5 µM, less than about 0.4 µM, less than about 0.3 µM, or less than about 0.2 µM in a BACE1 protease activity assay. In one embodiment, a compound of Formula I has an $IC_{50}$ of less than about 100 nM, less than about 90 nM, less than about 80 nM, less than about 70 nM, less than about 60 nM, less than about 50 nM, less than about 40 nM, less than about 30 nM, less than about 20 nM or less than about 10 nM in a BACE1 protease activity assay.

In one embodiment, a compound as described herein, e.g. a compound of Formula I, is an inhibitor of BACE2 protease activity, with an $IC_{50}$ of less than about 1.0 µM, less than about 0.9 µM, less than about 0.8 µM, less than about 0.7 µM, less than about 0.6 µM, less than about 0.5 less than about 0.4 µM, less than about 0.3 µM, or less than about 0.2 µM in a BACE2 protease activity assay. In one embodiment, a compound of Formula I has an $IC_{50}$ of less than about 100 nM, less than about 90 nM, less than about 80 nM, less than about 70 nM, less than about 60 nM, less than about 50 nM, less than about 40 nM, less than about 30 nM, less than about 20 nM or less than about 10 nM in a BACE2 protease activity assay.

In one embodiment, a compound as described herein, e.g. a compound of Formula I, is an inhibitor of BACE1 protease activity, and is selective compared to the activity of one or more other proteases, including, but not limited to, one or more of Cathepsin D protease activity, Cathepsin E protease activity, Renin protease activity, HIV protease activity, Pepsin protease activity, and/or BACE2 protease activity. In some instances, a compound of Formula I is an inhibitor of BACE1 protease activity, and is selective compared to Cathepsin D protease activity. In some instances, a compound of Formula I is an inhibitor of BACE1 protease activity, and is selective compared to Cathepsin E protease activity. In some instances, a compound of Formula I is an inhibitor of BACE1 protease activity, and is selective compared to Renin protease activity. In some instances, a compound of Formula I is an inhibitor of BACE1 protease activity, and is selective compared to HIV protease activity. In some instances, a compound of Formula I is an inhibitor of BACE1 protease activity, and is selective compared to Pepsin protease activity. In some instances, a compound of Formula I is an inhibitor of BACE1 protease activity, and is selective compared to BACE2 protease activity. In some instances, a compound of Formula I is an inhibitor of BACE1 protease activity, and is selective compared to Cathepsin D protease activity and BACE2 protease activity. For the purpose of this application the selectivity of the instant compounds for BACE1 over another protease, such as Cathepsin D or BACE2 is expressed as a ratio of $IC_{50}$ values for a suitable activity assay or in some instances as a ratio of % inhibition at a given concentration of compound, such as at 10 µM. These values can be determined using assays known in the art or those described herein (see e.g., Example A).

In one embodiment, a compound as described herein, e.g. a compound of Formula I, is characterized by the following inhibitory activities involving BACE1 protease activity. In one embodiment, the ratio of $IC_{50}(BACE1) \div IC_{50}(Cathepsin\ D)$ is less than about 1, less than about 0.9, less than about 0.8, less than about 0.7, less than about 0.6, less than about 0.5, less than about 0.4, less than about 0.3, less than about 0.2 or less than about 0.1. In one embodiment, the ratio of $IC_{50}(BACE1) \div IC_{50}(Cathepsin\ D)$ is less than about 0.09, less than about 0.08, less than about 0.07, less than about 0.06, less than about 0.05, less than about 0.04, less than about 0.03, less than about 0.02 or less than about 0.01. In one embodiment, the ratio of $IC_{50}(BACE1) \div IC_{50}(Cathepsin\ D)$ is less than about 0.009, less than about 0.008, less than about 0.007, less than about 0.006, less than about 0.005, less than about 0.004, less than about 0.003, less than about 0.002 or less than about 0.001. In one embodiment, the ratio of $IC_{50}(BACE1) \div IC_{50}(Cathepsin\ D)$ is less than about 0.0009, less than about 0.0008, less than about 0.0007, less than about 0.0006, less than about 0.0005, less than about 0.0004, less than about 0.0003, less than about 0.0002 or less than about 0.0001.

In one embodiment, a compound as described herein, e.g. a compound of Formula I, is characterized by the following inhibitory activities involving BACE1 protease activity. In one embodiment, the ratio of $IC_{50}(BACE1) \div IC_{50}(BACE2)$ is less than about 1, less than about 0.9, less than about 0.8, less than about 0.7, less than about 0.6, less than about 0.5, less than about 0.4, less than about 0.3, less than about 0.2 or less than about 0.1. In one embodiment, the ratio of $IC_{50}(BACE1)\ IC_{50}(BACE2)$ is less than about 0.09, less than about 0.08, less than about 0.07, less than about 0.06, less than about 0.05, less than about 0.04, less than about 0.03, less than about 0.02 or less than about 0.01. In one embodiment, the ratio of $IC_{50}(BACE1) \div IC_{50}(BACE2)$ is less than about 0.009, less than about 0.008, less than about 0.007, less than about 0.006, less than about 0.005, less than about 0.004, less than about 0.003, less than about 0.002 or less than about 0.001. In one embodiment, the ratio of $IC_{50}(BACE1) \div IC_{50}(BACE2)$ is less than about 0.0009, less than about 0.0008, less than about 0.0007, less than about 0.0006, less than about 0.0005, less than about 0.0004, less than about 0.0003, less than about 0.0002 or less than about 0.0001.

In one aspect, any tautomer, stereoisomer, prodrug, derivative, conjugate, polymorph, isotopically enhanced form, pharmaceutically acceptable salt or pharmaceutically acceptable solvate of a compound of Formula I is provided. In one embodiment, any tautomer of a compound of Formula I is provided. In one embodiment, any stereoisomer of a compound of Formula I is provided. In one embodiment, any prodrug of a compound of Formula I is provided. In one embodiment, any derivative of a compound of Formula I is provided. In one embodiment, any conjugate of a compound of Formula I is provided. In one embodiment, any polymorph of a compound of Formula I is provided. In one embodiment, any isotopically enhanced form of a compound of Formula I is provided. In one embodiment, any pharmaceutically acceptable salt of a compound of Formula I is provided. In one embodiment, any polymorph of any pharmaceutically acceptable salt of a compound of Formula I is provided. In one embodiment, any pharmaceutically acceptable solvate of a compound of Formula I is provided. In one embodiment, any polymorph of any pharmaceutically acceptable solvate of a compound of Formula I is provided.

In one aspect, a pharmaceutical composition comprising a compound as described herein, e.g. a compound of Formula I, and a pharmaceutically acceptable carrier is provided. In one embodiment, a pharmaceutical composition comprising any tautomer of a compound of Formula I and a pharmaceutically acceptable carrier is provided. In one embodiment, a pharmaceutical composition comprising any stereoisomer of a compound of Formula I and a pharmaceutically acceptable carrier is provided. In one embodiment, a pharmaceutical composition comprising any prodrug of a compound of Formula I and a pharmaceutically acceptable carrier is provided. In one embodiment, a pharmaceutical composition comprising any derivative of a compound of Formula I and a pharmaceutically acceptable carrier is provided. In one embodiment, a pharmaceutical composition comprising any conjugate of a compound of Formula I and a pharmaceutically acceptable carrier is provided. In one embodiment, a pharmaceutical composition comprising any polymorph of a compound of Formula I and a pharmaceutically acceptable carrier is provided. In one embodiment, a pharmaceutical composition comprising any isotopically enhanced form of a compound of Formula I and a pharmaceutically acceptable carrier is provided. In one embodiment, a pharmaceutical composition comprising any pharmaceutically acceptable salt of a compound of Formula I and a pharmaceutically acceptable carrier is provided. In one embodiment, a pharmaceutical composition comprising any polymorph of any pharmaceutically acceptable salt of a compound of Formula I and a pharmaceutically acceptable carrier is provided. In one embodiment, a pharmaceutical composition comprising any pharmaceutically acceptable solvate of a compound of Formula I and a pharmaceutically acceptable carrier is provided. In one embodiment, a pharmaceutical composition comprising any polymorph of any pharmaceutically acceptable solvate of a compound of Formula I and a pharmaceutically acceptable carrier is provided.

In one aspect, a kit is provided that includes a compound or composition thereof as described herein, e.g. a compound of Formula I, or a pharmaceutically acceptable salt or solvate thereof, or a composition comprising such a compound or pharmaceutically acceptable salt or solvate thereof. In some embodiments, the kit includes a compound of Formula I, or a pharmaceutically acceptable salt thereof, or a composition comprising such a compound or pharmaceutically acceptable salt thereof. In some embodiments, the compound or composition thereof is packaged, e.g., in a vial, bottle or similar container, which may be further packaged, e.g., within a box, envelope, or similar container. In some embodiments, the compound or composition thereof is approved by the U.S. Food and Drug Administration or similar regulatory agency for administration to a mammal, e.g., a human. In some embodiments the compound or composition thereof is approved for administration to a mammal, e.g., a human, for a BACE mediated disease or condition, including a BACE1 and/or BACE2 mediated condition. In one embodiment, such a kit includes written instructions for use and/or other indication that the compound or composition is suitable or approved for administration to a mammal, e.g., a human, for a suitable disease or condition. In some embodiments, the compound or composition is packaged in unit dose or single dose form, e.g., single dose pills, capsules, or the like.

In one aspect, a compound of Formula I, or a pharmaceutically acceptable salt or solvate thereof, or a composition comprising such a compound or pharmaceutically acceptable salt or solvate thereof, is useful in the treatment and/or prevention of a BACE mediated disorder, or an Aβ peptide related disorder. In some embodiments, a compound of Formula I, or a pharmaceutically acceptable salt thereof, or a composition comprising such a compound or pharmaceutically acceptable salt thereof, is useful in the treatment and/or prevention of a BACE mediated disorder, or an Aβ peptide related disorder. In one embodiment, use of a compound of Formula I, or a pharmaceutically acceptable salt or solvate thereof, or a composition comprising such a compound or pharmaceutically acceptable salt or solvate thereof, for the treatment of a disease is provided; in some embodiments the use of a compound of Formula I, or a pharmaceutically acceptable salt thereof, or a composition comprising such a compound or pharmaceutically acceptable salt thereof, for the treatment of a disease is provided; wherein the disease is selected from the group consisting of neurological diseases, such as Alzheimer's disease (including any disorders associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, and demyelinating diseases (including multiple sclerosis, idiopathic inflammatory demyelinating disease, chronic inflammatory demyelinating polyneuropathy, Guillain-Barre syndrome, progressive multifocal leukoencephalopathy, and Charcot-Marie-Tooth Disease); other CNS disorders, such as traumatic brain injury, brain inflammation, spinal cord injury, and nerve injury; anxiety disorders (including obsessive-compulsive disorder, general anxiety disorder and post-traumatic disorder); ocular diseases including glaucoma and age-related macular degeneration; cardiovascular diseases such as myocardial infarction, arterial thrombosis, transient ischemic attack, and stroke (including dementia associated with stroke and neurodegeneration associated with stroke); other amyloidoses, such as familial amyloidotic polyneuropathy, hemodialysis associated amyloidosis (accumulation of β2-microglobulins and complications arising therefrom); prion diseases such as Creutzfeldt-Jakob disease, Gerstmann-Sträussler-Scheinker syndrome, scrapie (including Kuru scrapie and animal scrapie), and bovine spongiform encephalitis; cancers, such as glioblastoma multiforme, multiple myeloma, malignant melanoma, Kaposi sarcoma, and breast cancer; autoimmune diseases such as rheumatoid arthritis, Sjogren syndrome, lupus erythematosus, and Graves disease; inflammatory diseases such as inclusion body myositis, dermatomyositis, macrophagic myofasciitis, juvenile idiopathic arthritis, granulomatous arthritis, and inflammatory reactions; and other diseases, including narcolepsy, type 2 diabetes, hypertension, Wilson's disease, Whipple's disease, spinocerebellar ataxia 1, spinocerebellar ataxia 7, and Kostmann disease.

In one embodiment, use of a compound of Formula I, or a pharmaceutically acceptable salt or solvate thereof, or a composition comprising such a compound or pharmaceutically acceptable salt or solvate thereof, for the treatment of a disease is provided; in some embodiments the use of a compound of Formula I, or a pharmaceutically acceptable salt thereof, or a composition comprising such a compound or pharmaceutically acceptable salt thereof, for the treatment of a disease is provided; wherein the disease is selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, amyotrophic lateral sclerosis, multiple sclerosis, traumatic brain injury, brain inflammation, spinal cord injury, nerve injury, glaucoma, age-related macular degeneration, myocardial infarction, arterial thrombosis, transient ischemic attack, and stroke. In one embodiment, the disease is selected from the group consisting of Alzheimer's disease, Down syndrome, amyotrophic lateral sclerosis, multiple sclerosis, traumatic brain injury, spinal cord injury, nerve injury, glaucoma, age-related macular degeneration, myocardial infarction, transient ischemic attack, and stroke. In one embodiment, the disease is Alzheimer's disease.

In one embodiment, use of a compound of Formula I, or a pharmaceutically acceptable salt or solvate thereof, or a composition comprising such a compound or pharmaceutically acceptable salt or solvate thereof, in the preparation of a medicament for the treatment of a disease is provided; in some embodiments the use of a compound of Formula I, or a pharmaceutically acceptable salt thereof, or a composition comprising such a compound or pharmaceutically acceptable salt thereof, in the preparation of a medicament for the treatment of a disease is provided; wherein the disease is selected from the group consisting of neurological diseases, such as Alzheimer's disease (including any disorders associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, and demyelinating diseases (including multiple sclerosis, idiopathic inflammatory demyelinating disease, chronic inflammatory demyelinating polyneuropathy, Guillain-Barre syndrome, progressive multifocal leukoencephalopathy, and Charcot-Marie-Tooth Disease); other CNS disorders, such as traumatic brain injury, brain inflammation, spinal cord injury, and nerve injury; anxiety disorders (including obsessive-compulsive disorder, general anxiety disorder and post-traumatic disorder); ocular diseases including glaucoma and age-related macular degeneration; cardiovascular diseases such as myocardial infarction, arterial thrombosis, transient ischemic attack, and stroke (including dementia associated with stroke and neurodegeneration associated with stroke); other amyloidoses, such as familial amyloidotic polyneuropathy, hemodialysis associated amyloidosis (accumulation of β2-microglobulins and complications arising therefrom); prion diseases such as Creutzfeldt-Jakob disease, Gerstmann-Sträussler-Scheinker syndrome, scrapie (including Kuru scrapie and animal scrapie), and bovine spongiform encephalitis; cancers, such as glioblastoma multiforme, multiple myeloma, malignant melanoma, Kaposi sarcoma, and breast cancer; autoimmune diseases such as rheumatoid arthritis, Sjogren syndrome, lupus erythematosus, and Graves disease; inflammatory diseases such as inclusion body myositis, dermatomyositis, macrophagic myofasciitis, juvenile idiopathic arthritis, granulomatous arthritis, and inflammatory reactions; and other diseases, including narcolepsy, type 2 diabetes, hypertension, Wilson's disease, Whipple's disease, spinocerebellar ataxia 1, spinocerebellar ataxia 7, and Kostmann disease.

In one embodiment, use of a compound of Formula I, or a pharmaceutically acceptable salt or solvate thereof, or a composition comprising such a compound or pharmaceutically acceptable salt or solvate thereof, in the preparation of a medicament for the treatment of a disease is provided; in some embodiments the use of a compound of Formula I, or a pharmaceutically acceptable salt thereof, or a composition comprising such a compound or pharmaceutically acceptable salt thereof, in the preparation of a medicament for the treatment of a disease is provided; wherein the disease is selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, amyotrophic lateral sclerosis, multiple sclerosis, traumatic brain injury, brain inflammation, spinal cord injury, nerve injury, glaucoma, age-related macular degeneration, myocardial infarction, arterial thrombosis, transient ischemic attack, and stroke. In one embodiment, the disease is selected from the group consisting of Alzheimer's disease, Down syndrome, amyotrophic lateral sclerosis, multiple sclerosis, traumatic brain injury, spinal cord injury, nerve injury, glaucoma, age-related macular degeneration, myocardial infarction, transient ischemic attack, and stroke. In one embodiment, the disease is Alzheimer's disease.

In one aspect, a method is provided for treating a disease. The method includes administering to a mammalian subject (e.g., human subject or patient) in need thereof a therapeutically effective amount of a compound of Formula I, or a pharmaceutically acceptable salt or solvate thereof, or a composition comprising such a compound or pharmaceutically acceptable salt or solvate thereof. In one embodiment, the method includes administering to a mammalian subject (e.g., human subject or patient) in need thereof a therapeutically effective amount of a compound of Formula I, or a pharmaceutically acceptable salt thereof, or a composition comprising such a compound or pharmaceutically acceptable salt thereof. In one embodiment, a method of treating or preventing a BACE mediated disorder, or Aβ peptide related disorder is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment the method is provided comprising administering to a mammalian subject in need thereof a therapeutically effective amount of a compound of Formula I, or a pharmaceutically acceptable salt thereof, or a composition comprising such a compound or pharmaceutically acceptable salt thereof. In one embodiment, a method of treating a disease is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment the method is provided comprising administering to a mammalian subject in need thereof a therapeutically effective amount of a compound of Formula I, or a pharmaceutically acceptable salt thereof, or a composition comprising such a compound or pharmaceutically acceptable salt thereof; wherein the disease is selected from the group consisting of neurological diseases, such as Alzheimer's disease (including any disorders associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, and demyelinating diseases (including multiple sclerosis, idiopathic inflammatory demyelinating disease, chronic inflammatory demyelinating polyneuropathy, Guillain-Barre syndrome, progressive multifocal leukoencephalopathy, and Charcot-Marie-Tooth Disease); other CNS disorders, such as traumatic brain injury, brain inflammation, spinal cord injury, and nerve injury; anxiety disorders (including obsessive-compulsive disorder, general anxiety disorder and post-traumatic disorder); ocular diseases including glaucoma and age-related macular degeneration; cardiovascular diseases such as myocardial infarction, arterial thrombosis, transient ischemic attack, and stroke (including dementia associated with stroke and neurodegeneration associated with stroke); other amyloidoses, such as familial amyloidotic polyneuropathy, hemodialysis associated amyloidosis (accumulation of β2-microglobulin and complications arising therefrom); prion diseases such as Creutzfeldt-Jakob disease, Gerstmann-Sträussler-Scheinker syndrome, scrapie (including Kuru scrapie and animal scrapie), and bovine spongiform encephalitis; cancers, such as glioblastoma multiforme, multiple myeloma, malignant melanoma, Kaposi sarcoma, and breast cancer; autoimmune diseases such as rheumatoid arthritis, Sjogren syndrome, lupus erythematosus, and Graves disease; inflammatory diseases such as inclusion body myositis, dermatomyositis, macrophagic myofasciitis, juvenile idiopathic arthritis, granulomatous arthritis, and inflammatory reactions; and other diseases, including narcolepsy, type 2 diabetes, hypertension, Wilson's disease, Whipple's disease, spinocerebellar ataxia 1, spinocerebellar ataxia 7, and Kostmann disease.

In one embodiment, a method of treating a disease is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment, the method is provided comprising administering to a mammalian subject in need thereof a therapeutically effective amount of a compound of Formula I, or a pharmaceutically acceptable salt thereof, or a composition comprising such a compound or pharmaceutically acceptable salt thereof; wherein the disease is selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, amyotrophic lateral sclerosis, multiple sclerosis, traumatic brain injury, brain inflammation, spinal cord injury, nerve injury, glaucoma, age-related macular degeneration, myocardial infarction, arterial thrombosis, transient ischemic attack, and stroke. In one embodiment, the disease is selected from the group consisting of Alzheimer's disease, Down syndrome, amyotrophic lateral sclerosis, multiple sclerosis, traumatic brain injury, spinal cord injury, nerve injury, glaucoma, age-related macular degeneration, myocardial infarction, transient ischemic attack, and stroke. In one embodiment, the disease is Alzheimer's disease.

In one embodiment, a method of treating a neurodegenerative disease is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment, the method is provided comprising administering to a mammalian subject in need thereof a therapeutically effective amount of a compound of Formula I, or a pharmaceutically acceptable salt thereof, or a composition comprising such a compound or pharmaceutically acceptable salt thereof; wherein the neurodegenerative disease is selected from the group consisting of Alzheimer's disease (including any disorders associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, and demyelinating diseases (including multiple sclerosis, idiopathic inflammatory demyelinating disease, chronic inflammatory demyelinating polyneuropathy, Guillain-Barre syndrome, progressive multifocal leukoencephalopathy, and Charcot-Marie-Tooth Disease); and other CNS disorders, such as traumatic brain injury, brain inflammation, spinal cord injury, and nerve injury. In one embodiment, the neurodegenerative disease is selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, amyotrophic lateral sclerosis, multiple sclerosis, traumatic brain injury, brain inflammation, spinal cord injury, and nerve injury. In one embodiment, the neurodegenerative disease is selected from the group consisting of Alzheimer's disease, Down syndrome, amyotrophic lateral sclerosis, multiple sclerosis, traumatic brain injury, spinal cord injury, and nerve injury. In one embodiment, the neurodegenerative disease is Alzheimer's disease.

In one embodiment, a method of treating Alzheimer's disease is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof. In one embodiment, the method of treating Alzheimer's disease is provided comprising administering to a mammalian subject in need thereof a therapeutically effective amount of a compound of Formula I, or a pharmaceutically acceptable salt thereof, or a composition comprising such a compound or pharmaceutically acceptable salt thereof.

In one embodiment, a method of reducing the level of Aβ peptide in the brain of a mammalian subject is provided comprising administering to the mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment the method is provided comprising administering to the mammalian subject in need thereof a therapeutically effective amount of a compound of Formula I, or a pharmaceutically acceptable salt thereof, or a composition comprising such a compound or pharmaceutically acceptable salt thereof. In one embodiment, the method of reducing the level of Aβ peptide in the brain of a mammalian subject provides treatment of a disease selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, traumatic brain injury, and brain inflammation.

In one embodiment, a method of reducing the level of CTFβ fragment in the brain of a mammalian subject is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment the method is provided comprising administering to the mammalian subject in need thereof a therapeutically effective amount of a compound of Formula I, or a pharmaceutically acceptable salt thereof, or a composition comprising such a compound or pharmaceutically acceptable salt thereof. In one embodiment, the method of reducing the level of CTFβ fragment in the brain of a mammalian subject provides treatment of a disease selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, traumatic brain injury, and brain inflammation.

In one embodiment, a method of reducing the level of sAPPβ fragment in the brain of a mammalian subject is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment the method is provided comprising administering to the mammalian subject in need thereof a therapeutically effective amount of a compound of Formula I, or a pharmaceutically acceptable salt thereof, or a composition comprising such a compound or pharmaceutically acceptable salt thereof. In one embodiment, the method of reducing the level of sAPPβ fragment in the brain of a mammalian subject provides treatment of a disease selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, traumatic brain injury, and brain inflammation.

In one embodiment, a method of preventing Aβ peptide aggregation, oligomerization, fibrillization or plaque formation in a mammalian subject is provided comprising administering to a mammalian subject in need thereof a therapeutically effective amount of a compound of Formula I, or a pharmaceutically acceptable salt or solvate thereof, or a composition comprising such a compound or pharmaceutically acceptable salt or solvate thereof; in one embodiment the method is provided comprising administering to the mammalian subject in need thereof a therapeutically effective amount of a compound of Formula I, or a pharmaceutically acceptable salt thereof, or a composition comprising such a compound or pharmaceutically acceptable salt thereof. In one embodiment, the method of preventing Aβ peptide aggregation, oligomerization, fibrillization or plaque formation in a mammalian subject provides treatment of a disease selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, traumatic brain injury, and brain inflammation.

In one embodiment, the use of a pharmaceutically acceptable prodrug of a compound of Formula I to treat or prevent any of the above-identified disorders is provided. In one embodiment, use of a composition comprising a pharmaceutically acceptable prodrug of a compound of Formula I to treat or prevent any of the above-identified disorders is provided. In one embodiment, use of a pharmaceutically acceptable prodrug of a compound of Formula I in the preparation of a medicament for the treatment or prevention of any of the above-identified disorders is provided.

In one aspect, a compound of Formula I, or a pharmaceutically acceptable salt or solvate thereof, or a composition comprising such a compound or pharmaceutically acceptable salt or solvate thereof, may be used in combination with another agent for the treatment of a disease or the treatment of a symptom associated with a disease. In one embodiment, a compound of Formula I, or a pharmaceutically acceptable salt thereof, or a composition comprising such a compound or pharmaceutically acceptable salt thereof, may be used in combination with another agent for the treatment of a disease or the treatment of a symptom associated with a disease. In some embodiments of the use in combination with one or more agents for the treatment of Alzheimer's disease, the one or more other agents is selected from the group consisting of a cholinesterase inhibitor, an NMDA receptor antagonist, an antioxidant, an antidepressant, an anxiolytic, an antipsychotic, an anti-Aβ peptide vaccine, an anti-Aβ peptide antibody, a retinoid X receptor activator, a gamma secretase inhibitor, another BACE1 inhibitor, inhibitors of β-amyloid aggregation, inhibitors of tau aggregation, and tau kinase inhibitors.

In one embodiment, a compound of Formula I, or a pharmaceutically acceptable salt or solvate thereof, or a composition comprising such a compound or pharmaceutically acceptable salt or solvate thereof; in some embodiments a compound of Formula I, or a pharmaceutically acceptable salt thereof, or a composition comprising such a compound or pharmaceutically acceptable salt thereof; may be used in combination with one or more agents for the treatment of Alzheimer's disease, wherein the one or more agents is selected from the group consisting of donepezil, galantamine, revastigmine, tactrine, memantine, vitamin E, citalopram, fluoxetine, paroseine, setraline, trazodone, nortriptyline, lorazepam, oxazepam, temazepam, aripiprazole, clozapine, haloperidol, olanzapine, quetiapine, risperidone, ziprasidone, bexarotene, bapineuzumab, solanezumab, clioquinol, resveratrol, methylene blue, IV immunoglobulin, docosahexanenoic acid, latrepirdine, and davunetide.

Exemplary compounds as described herein, e.g. compounds of Formula I, are provided in Examples 1-14 below, including testing of their in vitro and/or in vivo biological activities and pharmaceutical properties (e.g. Example A, B and C).

Compound Forms and Derivatives

In one aspect, various forms or derivatives of compounds as described herein are provided. In on example, a compound of Formula I may exist in a number of different forms or derivatives, for example, tautomers, isomers, racemic mixtures, prodrugs, active metabolites, pharmaceutically acceptable salts, pharmaceutically acceptable solvates, isotopically enhanced forms, conjugates, and other solid forms thereof, including different crystal forms, polymorphs or amorphous solids.

A compound as described herein, e.g. a compound of Formula I, can exist in particular geometric, conformational or stereoisomeric forms. The compound of Formula I includes all such isomeric forms, including cis- and trans-isomers, atropisomers, (−)- and (+)-enantiomers, diastereomers, (D)-isomers, (L)-isomers, the racemic mixtures thereof, and other mixtures thereof, such as enantiomerically or diastereomerically enriched mixtures. Such regioisomers and stereoisomers may be isolated in enriched form by standard separation methods known to those skilled in the art. Additional asymmetric carbon atoms can be present in a substituent such as an alkyl group. When the compounds described herein contain olefinic double bonds or other centers of geometric asymmetry, and unless specified otherwise, it is intended that the compounds include both E and Z geometric isomers. Compounds may also include regions that are sterically constrained such that atropisomers may be isolated by standard separation methods known to those skilled in the art. Likewise, all tautomeric forms and mixtures of tautomers are included.

Optically active (R)- and (S)-isomers and d and l isomers can be prepared using chiral synthons or chiral reagents, or resolved using conventional techniques. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound. If, for instance, a particular enantiomer of a compound as described herein is desired, it can be prepared by asymmetric synthesis, or by derivatization with a chiral auxiliary, where the resulting diastereomeric mixture is separated and the auxiliary group cleaved to provide the desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the enantiomers in enriched form. In addition, separation of enantiomers and diastereomers is frequently accomplished using chromatography employing chiral, stationary phases, optionally in combination with chemical derivatization (e.g., formation of carbamates from amines).

A compound as described herein, e.g. a compound of Formula I, can exist in a prodrug form. A prodrug of a compound as described herein is a pharmaceutically acceptable derivative of a compound of Formula I that readily undergoes chemical changes under physiological conditions to provide the compound as described herein (e.g. a compound of Formula I). It is understood that such prodrugs are effectively equivalent to a compound of Formula I, i.e. when such a prodrug is administered into a subject, such administration effectively encompasses the use of a compound of Formula I. Non-limiting examples of a pharmaceutically acceptable derivative or prodrug include pharmaceutically acceptable esters, phosphate esters or sulfonate esters thereof as well as other derivatives of a compound as described herein which, upon administration to a recipient, is capable of providing, either directly or indirectly, a compound as described herein (e.g. a compound of Formula I). Particularly favored derivatives or prodrugs are those that increase the bioavailability of a compound as described herein when such compound is administered to a mammal (e.g., by allowing an orally administered compound to be more readily absorbed into the blood stream) or which enhance delivery of the parent compound to a biological compartment (e.g., the brain or lymphatic system) relative to the parent species.

Prodrugs include a variety of esters (e.g. carboxylic acid ester) or protected amines (e.g. acylated amine groups). Ester groups that are suitable as prodrug groups are generally known in the art and include benzyloxy, di($C_{1-6}$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and $C_{1-6}$ alkoxy esters, optionally substituted by N-morpholino and amide-forming groups such as di($C_{1-6}$)alkylamino. In one example, ester prodrug groups include $C_{1-6}$ alkoxy esters. Those skilled in the art will recognize various synthetic methodologies that may be employed to form a pharmaceutically acceptable prodrug of the compound of Formula I (e.g., via esterification of a carboxylic acid or hydroxyl group, acylation of an amine group).

In one example, the prodrug is suitable for treatment/prevention of those diseases and conditions that require the drug molecule to cross the blood brain barrier. In one example, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to a compound as described herein (e.g. a compound of Formula I) by chemical or biochemical methods in an ex vivo environment. For example, a prodrug can be slowly converted to the compound of Formula I when placed in a transdermal patch reservoir with a suitable enzyme or chemical reagent.

A compound as described herein, e.g. a compound of Formula I, when used in vivo may form an active metabolite. Thus, such metabolites are provided as pharmacologically active compounds or compounds that further metabolize to pharmacologically active compounds that are derivatives of compounds as described herein resulting from metabolic processes in the body of a subject. Such metabolites are readily identified by those of skill in the art, and may further be prepared similarly to the methods as described herein, such that a suitable metabolite can be prepared and isolated for pharmaceutical use.

A compound as described herein, e.g. a compound of Formula I, can exist in a pharmaceutically acceptable salt form. A compound of Formula I may be prepared with relatively nontoxic acids or bases, depending on the particular substituents found on the compounds described herein. Such salts and their preparation for use as pharmaceuticals are readily known to those of skill in the art. Such salts may provide improved properties, e.g. solubility or pharmacokinetic properties, such that the pharmacological activity of the compound of Formula I is enhanced upon administration to a subject. It is understood that such salts are effectively equivalent to a compound of Formula I, i.e. when such a salt is administered into a subject, such administration effectively encompasses the use of a compound of Formula I. When a compound as described herein (e.g. a compound of Formula I) contains relatively acidic functionalities (e.g., —COOH group), base addition salts can be obtained by contacting the compound (e.g., neutral form of such compound) with a sufficient amount of the desired base, either neat or in a suitable inert solvent. Examples of pharmaceutically acceptable base addition salts include lithium, sodium, potassium, calcium, ammonium, organic amino (e.g. ethylenediamine, diethylamine, piperazine, ethanolamine, diethanolamine, triethanolamine, tromethamine, choline, meglumine, benzathine, 4-phenylcyclohexylamine), zinc, magnesium and aluminum salts and the like. When a compound as described herein (e.g. a compound of Formula I) contains relatively basic functionalities (e.g., amines), acid addition salts can be obtained, e.g., by contacting the compound (e.g., neutral form of such compound) with a sufficient amount of the desired acid, either neat or in a suitable inert solvent. Examples of pharmaceutically acceptable acid addition salts include those derived from inorganic acids like hydrochloric, hydrobromic, hydroiodic, nitric, carbonic, monohydrogencarbonic, phosphoric, diphosphoric, monohydrogenphosphoric, dihydrogenphosphoric, sulfuric, monohydrogensulfuric, thiocyanic, hydriodic and the like, as well as the salts derived from relatively nontoxic organic acids like formic, acetic, alginic, propionic, isobutyric, ascorbic, aspartic, gentisic, galactaric, D-glucoheptanoic, D-gluconic, D-glucoronic, D-galactunoric, malic, maleic, malonic, benzoic, succinic, suberic, fumaric, glutaric, 2-oxoglutaric, adipic, capric, caproic, caprylic, dodecylsulfuric, lactic, lactobionic, mandelic, naphthylene-1,5-disulfonic, naphthalene-2-sulfonic, 1-hydroxy-2-napthoic, orotic, oxalic, phthalic, pyroglutamic, glycerophosphoric, hippuric, benzenesulfonic, p-toluenesulfonic, camphorsulfonic, camphoric, cinnamic, citric, tartaric, methanesulfonic, nicotinic, ethanesulfonic, ethane-1,2-disulfonic, 2-hydroxyethanesulfonic, salicylic, lauric, oleic, palmitic, pamoic, sebacic, undecylenic, stearic and the like. Also included are salts of amino acids such as glutamate, lysinate, arginate and the like (see, for example, Berge et al., Journal of Pharmaceutical Science 1977, 66:1-19). Certain specific compounds as described herein (e.g. a compound of Formula I) contain both basic and acidic functionalities that allow the compounds to be converted into either base or acid addition salts.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound as described herein.

When a substituent includes a negatively charged oxygen atom "$O^-$", e.g., in "—$COO^-$", then the formula is meant to optionally include a proton or an organic or inorganic cationic counterion. In one example, the resulting salt form of the compound is pharmaceutically acceptable. Further, when a compound of Formula I includes an acidic group, such as a carboxylic acid group, e.g., written as the substituent "—COOH", "—CO₂H" or "—C(O)₂H", then the formula is meant to optionally include the corresponding "de-protonated" form of that acidic group, e.g., "—COO⁻", "—CO₂⁻" or "—C(O)₂⁻", respectively.

A compound as described herein, e.g. a compound of Formula I, can exist in unsolvated forms as well as solvated forms, including hydrated forms. Such solvates may provide improved properties, e.g. solubility or pharmacokinetic properties, such that the pharmacological activity of the compound of Formula I is enhanced upon administration to a subject. It is understood that such solvated forms are effectively equivalent to a compound of Formula I, i.e. when such a solvate is administered into a subject, such administration effectively encompasses the use of a compound of Formula I.

A compound as described herein, e.g. a compound of Formula I, can exist in multiple crystalline forms, i.e. polymorphs, or in an amorphous form, and a compound of Formula I encompasses all such forms of the compound. In general, all physical forms are of use in the methods contemplated herein. Such physical forms may provide improved properties, e.g. solubility or pharmacokinetic properties, such that the pharmacological activity of the compound of Formula I is enhanced upon administration of the particular form to a subject.

A compound as described herein, e.g. a compound of Formula I, can contain natural or unnatural proportions of atomic isotopes at one or more of the atoms that constitute such compounds. For example, the compounds can be radiolabeled with radioactive isotopes, such as for example tritium ($^3$H), iodine-125 ($^{125}$I) or carbon-14 ($^{14}$C). All isotopic variations of a compound as described herein, whether radioactive or not, are effectively encompassed by a compound as described herein, e.g., a compound in which one or more of the hydrogen atoms are replaced with another stable isotope of hydrogen (i.e., deuterium) or a radioactive isotope (i.e., tritium), is expected to have similar activity as it relates to BACE inhibition, and is effectively equivalent to a compound of Formula I. Such an isotopically enhanced compound may be useful, for example, in detection of the compound in vivo or in biological tissue, such as a radiolabelled compound containing $^3$H or $^{14}$C to assess tissue distribution, or a positron emitting compound containing $^{11}$C, $^{15}$O, $^{13}$N, $^{18}$F or the like useful in positron emission tomography for in vivo imaging. Similarly, a deuterated compound may provide the compound with greater metabolic stability relative to the non-deuterated compound to provide improved pharmacokinetic properties. Such a compound is readily prepared by the methods as described herein, where suitable isotopically enhanced reagents may be used in place of non enhanced reagents. For example, alkyl groups may include isotopic variants of hydrogen and carbon, such that methyl, for example, includes —CH₃, or may include the analogous structure in which any atoms can include any isotopes thereof, for example —CD₃, —$^{14}$CH₃, and the like.

Pharmaceutical Compositions:

Pharmaceutical compositions are provided, including a compound as described herein, e.g. a compound of Formula I, including any forms thereof, such as any isomers, polymorphs, pharmaceutically acceptable salts or solvates thereof, and at least one pharmaceutically acceptable carrier. A pharmaceutically acceptable carrier includes solvents, solid or liquid diluents, vehicles, adjuvants, excipients, glidants, binders, granulating agents, dispersing agents, suspending agents, wetting agents, lubricating agents, disintegrants, solubilizers, stabilizers, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., *Handbook of Pharmaceutical Manufacturing Formulations*, Volumes 1-6, Niazi, Sarfaraz K., Taylor & Francis Group 2005, which is incorporated herein by reference in its entirety. A pharmaceutical composition may include one or more compounds of Formula I, including any forms thereof, such as any isomers, polymorphs, pharmaceutically acceptable salts or solvates thereof, in association with one or more pharmaceutically acceptable carrier and optionally other active ingredients.

The compounds of Formula I may be administered orally, topically, parenterally, by inhalation or spray or rectally in dosage unit formulations containing at least one pharmaceutically acceptable carrier. Parenteral administration includes percutaneous, subcutaneous, intravascular (e.g., intravenous), intramuscular, or intrathecal injection or infusion techniques and the like. The pharmaceutical compositions containing a compound of Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of a compound of Formula I, or any salts or solvates thereof, may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, a flavoring agent or a coloring agent. The pharmaceutical compositions may be in the form of a sterile, injectable, aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

A compound of Formula I may be administered parenterally in a sterile medium. The compound, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations may be applied as a topical gel, spray, ointment or cream, or as a scleral suppository, containing the active ingredients in a total amount of, for example, 0.075 to 30% w/w, also 0.2 to 20% w/w and also 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compound of Formula I can also be administered by a transdermal device. In one example, topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions may be constituted from known ingredients in a known manner. While the phase may comprise merely an emulsifier, it may comprise a mixture of at least one emulsifier with a fat or oil or with both a fat and an oil. In one example, a hydrophilic emulsifier is included together with a lipophilic emulsifier, which acts as a stabilizer. In one example, both an oil and a fat are included. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of compounds as described herein include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. In one example, the cream is a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. In one example, the anti-inflammatory active ingredients are present in such formulations in a concentration of 0.5 to 20%, also about 0.5 to 10% and also about 1.5% w/w. For therapeutic purposes, the active compounds, i.e. a compound of Formula I, are ordinarily combined with one or more adjuvants appropriate to the indicated route of administration. The compound may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compound may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

Dosage levels of the order of from about 0.005 mg to about 100 mg per kilogram of body weight per day are useful in the treatment of the diseases and conditions described herein (e.g., about 0.35 mg to about 7 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In one example, in the case of skin conditions, a topical preparation of a compound of Formula I may be applied to the affected area one to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

A compound as described herein, e.g. a compound of Formula I, can be formulated as described herein in combination with one or more other agents, for example one or more other agents for the treatment of Alzheimer's disease. For example, formulations may include a compound of Formula I and one or more other agents selected from the group consisting of a cholinesterase inhibitor, an NMDA receptor antagonist, an antioxidant, an antidepressant, an anxiolytic, an antipsychotic, an anti-Aβ peptide vaccine, an anti-Aβ peptide antibody, a retinoid X receptor activator, a gamma secretase inhibitor, another BACE1 inhibitor, inhibitors of β-amyloid aggregation, inhibitors of tau aggregation, and tau kinase inhibitors. In one example, a formulation includes a compound of Formula I and one or more agents selected from the group consisting of donepezil, galantamine, revastigmine, tactrine, memantine, vitamin E, citalopram, fluoxetine, paroseine, setraline, trazodone, nortriptyline, lorazepam, oxazepam, temazepam, aripiprazole, clozapine, haloperidol, olanzapine, quetiapine, risperidone, ziprasidone, bexarotene, bapineuzumab, solanezumab, clioquinol, resveratrol, methylene blue, IV immunoglobulin, docosahexanenoic acid, latrepirdine, and davunetide.

Methods of Use:

BACE1 involvement in the processing of APP provides a suitable drug target for the treatment of diseases associated with Aβ peptide toxicity. A BACE1 inhibitor can be used to reduce the amount of various products of the processing of amyloid precursor protein in vivo, including the reduction of sAPPβ, CTFβ, Aβ-40 and Aβ-42, as well as reduction in or prevention of Aβ peptide aggregation, oligomerization, fibrillization or plaque formation. Reduction of levels of Aβ peptide includes reduction in levels of soluble Aβ peptide and/or reduction in levels of insoluble Aβ peptide aggregates (Aβ plaques). In one example, compounds as described herein are useful in the reduction of sAPPβ, CTFβ, Aβ-40 and Aβ-42 in a mammalian subject, including in the brain of a mammalian subject. In one example, compounds as described herein are useful in the prevention of Aβ peptide aggregation, oligomerization, fibrillization or plaque formation in a mammalian subject including in the brain of a mammalian subject. In one example, the resulting reduction of Aβ-42 in particular is desirable to treat a variety of disease where high levels of Aβ-42 are detrimental. In one example, compounds as described herein are useful in the reduction in the levels of Aβ plaques in the brain. In one example, compounds as described herein are useful in the reduction in or prevention of Aβ peptide aggregation, oligomerization, fibrillization or plaque formation in the brain. BACE2 is involvement in the processing of pancreatic β-cells provides a suitable drug target, for example, in the treatment of type 2 diabetes.

The variety of diseases associated with Aβ peptide toxicity, or diseases amenable to treatment with a BACE1 and/or BACE2 inhibitor includes, for example, neurological diseases, such as Alzheimer's disease (including any disorders associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, and demyelinating diseases (including multiple sclerosis, idiopathic inflammatory demyelinating disease, chronic inflammatory demyelinating polyneuropathy, Guillain-Barre syndrome, progressive multifocal leukoencephalopathy, and Charcot-Marie-Tooth Disease); other CNS disorders, such as traumatic brain injury, brain inflammation, spinal cord injury, and nerve injury; anxiety disorders (including obsessive-compulsive disorder, general anxiety disorder and post-traumatic disorder); ocular diseases including glaucoma and age-related macular degeneration; cardiovascular diseases such as myocardial infarction, arterial thrombosis, transient ischemic attack, and stroke (including dementia associated with stroke and neurodegeneration associated with stroke); other amyloidoses, such as familial amyloidotic polyneuropathy, hemodialysis associated amyloidosis (accumulation of β2-microglobulins and complications arising therefrom); prion diseases such as Creutzfeldt-Jakob disease, Gerstmann-Sträussler-Scheinker syndrome, scrapie (including Kuru scrapie and animal scrapie), and bovine spongiform encephalitis; cancers, such as glioblastoma multiforme, multiple myeloma, malignant melanoma, Kaposi sarcoma, and breast cancer; autoimmune diseases such as rheumatoid arthritis, Sjogren syndrome, lupus erythematosus, and Graves disease; inflammatory diseases such as inclusion body myositis, dermatomyositis, macrophagic myofasciitis, juvenile idiopathic arthritis, granulomatous arthritis, and inflammatory reactions; and other diseases, including narcolepsy, type 2 diabetes, hypertension, Wilson's disease, Whipple's disease, spinocerebellar ataxia 1, spinocerebellar ataxia 7, and Kostmann disease.

In one example, compounds of Formula I can be used to reduce in vivo levels of any one or more of sAPPβ, CTFβ, Aβ-40 and Aβ-42. In one example, compounds of Formula I can be used to reduce levels of any one or more of sAPPβ, CTFβ, Aβ-40 and Aβ-42 in the brain. In one example, compounds of Formula I can be used to reduce the levels of Aβ plaques in the brain.

A compound as described herein is useful in the treatment and/or prevention of a disease selected from the group consisting of neurological diseases, such as Alzheimer's disease (including any disorders associated with Alzheimer's disease, such as dementia, attention deficit, depression, agitation, mild cognitive impairment, cognitive decline, memory loss, senility, neurodegeneration, olfactory impairment), diffuse Lewy body type Alzheimer's disease, Parkinson's disease (including dementia associated with Parkinson's disease), frontotemporal dementias with parkinsonism, progressive supranuclear palsy (including dementia associated with supranuclear palsy), cortical basal degeneration (including dementia associated with cortical basal degeneration), dementia with Lewy bodies, presenile dementia, senile dementia, multi-infarct dementia, dementia of mixed vascular and degenerative origin, mild cognitive impairment, Down syndrome (including dementia and cognitive impairment associated with Down syndrome), hereditary cerebral hemorrhage with amyloidosis of the Dutch-Type, cerebral amyloid angiopathy, amyotrophic lateral sclerosis, Huntington's disease, and demyelinating diseases (including multiple sclerosis, idiopathic inflammatory demyelinating disease, chronic inflammatory demyelinating polyneuropathy, Guillain-Barre syndrome, progressive multifocal leukoencephalopathy, and Charcot-Marie-Tooth Disease); other CNS disorders, such as traumatic brain injury, brain inflammation, spinal cord injury, and nerve injury; anxiety disorders (including obsessive-compulsive disorder, general anxiety disorder and post-traumatic disorder); ocular diseases including glaucoma and age-related macular degeneration; cardiovascular diseases such as myocardial infarction, arterial thrombosis, transient ischemic attack, and stroke (including dementia associated with stroke and neurodegeneration associated with stroke); other amyloidoses, such as familial amyloidotic polyneuropathy, hemodialysis associated amyloidosis (accumulation of β2-microglobulins and complications arising therefrom); prion diseases such as Creutzfeldt-Jakob disease, Gerstmann-Sträussler-Scheinker syndrome, scrapie (including Kuru scrapie and animal scrapie), and bovine spongiform encephalitis; cancers, such as glioblastoma multiforme, multiple myeloma, malignant melanoma, Kaposi sarcoma, and breast cancer; autoimmune diseases such as rheumatoid arthritis, Sjogren syndrome, lupus erythematosus, and Graves disease; inflammatory diseases such as inclusion body myositis, dermatomyositis, macrophagic myofasciitis, juvenile idiopathic arthritis, granulomatous arthritis, and inflammatory reactions; and other diseases, including narcolepsy, type 2 diabetes, hypertension, Wilson's disease, Whipple's disease, spinocerebellar ataxia 1, spinocerebellar ataxia 7, and Kostmann disease.

The methods of use of a compound or composition thereof as described herein in treatment of various diseases includes administering to a mammalian subject (e.g., human) in need thereof a therapeutically effective amount of a compound of Formula I, or pharmaceutically acceptable salt or solvate thereof, including any form thereof, or a composition comprising such a compound, pharmaceutically acceptable salt or solvate thereof, including any form thereof.

Activity of Compounds:

Compounds as described herein, e.g., a compound of Formula I, are tested for their activity in vitro to inhibit cleavage of APP between Met595 and Asp596 numbered for the APP695 isoform, or a mutant thereof, or at a corresponding site of a different isoform, such as APP751 or APP770, or a mutant thereof. Inhibitory activity is demonstrated in one of a variety of inhibition assays, for example whereby cleavage of an APP substrate in the presence of BACE1 enzyme is analyzed in the presence of the inhibitory compound, under conditions normally sufficient to result in cleavage at the BACE1 cleavage site. Reduction of APP cleavage at the BACE1 cleavage site compared with an untreated or inactive control is correlated with inhibitory activity. Assay systems that can be used to demonstrate efficacy of the compounds as described herein are known. Similar assays can be used to assess activity of BACE2 and other proteases for comparison, such as Cathepsin D. Representative assay systems are described, for example, in U.S. Pat. Nos. 5,942,400 and 5,744,346, PCT publication number WO 2011/069934, PCT publication number WO 2011/

029803, and PCT Publication Number WO 2007047306, the disclosures of which are hereby incorporated by reference with respect to such assays.

The enzymatic activity of BACE1 and the production of Aβ can be analyzed using natural, mutated, and/or synthetic APP substrates, natural, mutated, and/or synthetic enzyme, and a compound as described herein. The analysis can involve a biochemical assay, or a cellular assay involving primary or secondary cells expressing native, mutant, and/or synthetic APP and enzyme. Detection of enzymatic activity can be by analysis of at least one of the cleavage products, for example, by immunoassay, fluorometric or chromogenic assay, HPLC, or other means of detection. Inhibitory compounds are determined as those able to decrease the amount of BACE1 cleavage product produced in comparison to a control, where BACE1 mediated cleavage in the reaction system is observed and measured in the absence of inhibitory compounds. The efficacy of the compounds as described herein is determined as a percentage inhibition at a particular concentration, or the percentage inhibition as a function of compound concentration can be used to calculate an $IC_{50}$ for the compound in a particular assay.

A compound as described herein is useful in inhibiting the protease activity of BACE, including BACE1 and/or BACE2. Protease activity can be determined using any suitable assay, as are known in the art or described herein, where such assays typically employ a suitable protease substrate as known in the art or as described herein. In one example, a method (e.g., an in vitro assay) is provided that includes: (i) contacting a compound of Formula I with a BACE kinase, thereby forming a mixture. The method may further include (ii) contacting the mixture with a protease substrate (e.g., peptide substrate) thereby forming an amount of protease cleavage product. The method can further include (iii) measuring the amount of protease cleavage product. The amount of protease cleavage product may be measured using a detection reagent. Suitable detection reagents can include a metal reagent, such as a lanthanoid (e.g., Eu-63), a radioactive probe, a labeled (e.g., fluorescently labelled) antibody and combinations thereof. Exemplary assays include a fluorescence resonance energy transfer (FRET) assay (e.g., TR-FRET), an AlphaScreen® assay, or the like. Examples of such assays are described in Example A. In one example, a compound of Formula I is used as a reference standard to determine the in vitro activity of other compounds in a protease assay as described above. Thus, in another example, the compound of Formula I is used in an in vitro assay for identifying candidate compounds that are capable of inhibiting BACE protease activity, including BACE1 and/or BACE2 activity.

The activity of a compound as described herein can also be assessed in other proteases, including cathepsin D, cathepsin E, renin and pepsin. In vitro assays for the determination of such other protease activities are known in the art and exemplary assay formats are described herein (see e.g., Example A). Assays for BACE1 and other protease activities are also described, for example, in PCT publication number WO 2011/069934, PCT publication number WO 2011/029803, PCT publication number WO 2007/047306, the disclosures of which are hereby incorporated by reference with respect to such assays.

Certain compounds as described herein, e.g. compounds of Formula I, exhibit various in vitro cellular activities, such as the inhibition of BACE1 activity in a suitable cellular system, or cellular systems to assess other proteases, including BACE2 and cathepsin D. For example, numerous cell-based assays can be used to analyze BACE1 activity and/or processing of APP to release Aβ. Contact of an APP substrate with a BACE1 enzyme within the cell and in the presence or absence of a compound as described herein can be used to demonstrate BACE1 inhibitory activity of the compound. In one example, the assay in the presence of a useful inhibitory compound provides at least about 10% inhibition of the enzymatic activity, as compared with a non-inhibited control. In one example, cells that naturally express BACE1 are used. Alternatively, cells are modified to express a recombinant BACE1 or synthetic variant enzyme. The APP substrate can be added to the culture medium or is expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the BACE1 APP cleavage site can be used, provided that the expressed APP is permitted to contact the enzyme and enzymatic cleavage activity can be analyzed. Human cell lines that normally process Aβ from APP provide useful means to assay inhibitory activities of the compounds employed in the methods of treatment as described herein. Production and release of Aβ and/or other cleavage products into the culture medium can be measured, for example by immunoassay, such as Western blot or enzyme-linked immunoassay (EIA) such as by ELISA. For example, the inhibition of BACE1 activity can be assessed in human embryonic kidney cell line HEKp293 (ATCC Accession No. CRL-1573) transfected with APP751 containing the naturally occurring double mutation Lys651Met652 to Asn651Leu652, commonly called the Swedish mutation shown to overproduce Aβ (Citron et al., Nature 1992, 360:672-674). Aβ levels in treated or untreated cells are measured by immunoassay with Aβ specific antibodies, which can be assessed for the compounds as described herein (see e.g., Example A). Similarly, inhibition of BACE2 can be assessed by monitoring the cleavage of TMEM27, for example in an INS1E rat cell line. Assays are also described, for example, in PCT publication number WO 2011/069934, PCT publication number WO 2011/029803, PCT publication number WO 2007/047306, the disclosures of which are hereby incorporated by reference with respect to such assays.

Although both neural and non-neural cells process and release Aβ, levels of endogenous BACE1 activity are low and often difficult to detect by EIA. The use of cell types known to have enhanced BACE1 activity, enhanced processing of APP to Aβ, and/or enhanced production of Aβ are suited to use in cellular assays. For example, transfection of cells with the Swedish Mutant form of APP (APP-SW), with APP-KK, or with APP-SW-KK provides cells having enhanced BACE1 activity and producing amounts of Aβ that can be readily measured. In such assays, for example, the cells expressing APP and BACE1 are incubated in a culture medium under conditions suitable for BACE1 enzymatic activity at its cleavage site on the APP substrate. On exposure of the cells to the compound inhibitor employed in the methods of treatment, the amount of Aβ released into the medium and/or the amount of CTFβ fragments of APP in the cell lysates is reduced as compared with the control. The cleavage products of APP can be analyzed, for example, by immune reactions with specific antibodies, as discussed above. In one example, cells for analysis of BACE1 activity include primary human neuronal cells, primary transgenic animal neuronal cells where the transgene is APP, and other cells such as those of a stable human embryonic kidney cell line HEKp293 (ATCC Accession No. CRL-1573) expressing APP, for example, APP-SW. In one example, the level of Aβ in HEKp293 cells transfected with APP751 treated with a compound of Formula I will be less than 90%, less than 80%, less than 70%, less than 60%, less than 50%, less than 40%, less than 30%, less than 20%, less than 10%, less than 5%, or less than 1% of the level in control cells that are not treated with compound.

A compound as described herein can exhibit in vivo biological activity, such as reduction in the levels of Aβ peptide in a mouse model. Various animal models can be used to analyze BACE1 activity and/or processing of APP to release Aβ, as described above. For example, transgenic animals expressing APP substrate and BACE1 enzyme can be used to demonstrate inhibitory activity of the compounds as described herein. Certain transgenic animal models have been described, for example, in U.S. Pat. Nos. 5,877,399, 5,612,486, 5,387,742, 5,720,936, 5,850,003, 5,877,015, and 5,811,633, and in Games et al., Nature 1995, 373:523. Animals that exhibit characteristics associated with the pathophysiology of Alzheimer's disease are suitable for use in assessing in vivo biological activity. Administration of the compounds as described herein to the transgenic mice described herein provides an alternative method for demonstrating the inhibitory activity of the compounds. In one example, administration of the compounds as described herein in a pharmaceutically effective carrier and via an administrative route that reaches the target tissue in an appropriate therapeutic amount is suitable. For example, following peritoneal injection of a compound of Formula I (e.g., at a dose of about 50 mg, about 100 mg, about 200 mg or about 300 mg/kg), or a vehicle control, plasma and brain tissue can be harvested and assessed for the level of Aβ peptide (Aβ-40 and/or Aβ-42) by immunoassay detection. Assays are described, for example, in PCT publication number WO 2011/115938 and PCT publication number WO 2007/047306, the disclosures of which are hereby incorporated by reference with respect to such assays. In one example, the level of Aβ peptide in the brain or plasma of mice treated with a compound of Formula I will be less than 90%, less than 80%, less than 70%, less than 60%, less than 50%, less than 40%, less than 30%, less than 20%, less than 10%, less than 5%, or less than 1% of the Aβ peptide levels from the brain or plasma of control mice that are not treated with compound.

Synthesis of the Compounds:

The compounds as described herein, e.g. compounds of Formula I, can be prepared using methods known in the art of organic synthesis and those described herein in the Examples. The starting materials and various intermediates may be obtained from commercial sources, prepared from commercially available compounds, and/or prepared using known synthetic methods. For example, the compounds as described herein, as well as all intermediates, can be synthesized by processes using either solution or solid phase techniques. Exemplary procedures for preparing compounds as described herein are outlined in the following schemes. It is understood that for the exemplary procedures, variations and modifications are readily available, for example, any of solvents, reaction times, reagents, temperatures, work up conditions, or other reaction parameters may be varied employing alternate solvents, reagents, reaction times, temperatures, work up conditions, and the like, as are readily available to one skilled in the art.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

The sulfinamide compound C, which can be used in the synthesis of a compound of Formula I, is prepared from compound A, a suitable acetyl, bromo substituted ring $A_2$, and 2-methylpropane-2-sulfinamide compound B, in one step according to Scheme 1.

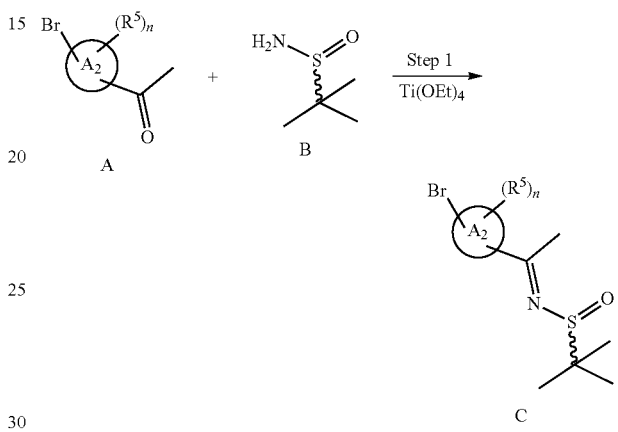

Scheme 1

Compound A ($A_2$, $R^5$ and n are as described for compounds of Formula I) is reacted with 2-methylpropane-2-sulfinamide B (wherein the wavy line bond to the sulfur indicates this compound can be a racemic mixture, or the specific R or S isomer) and tetraethoxytitanium in a suitable solvent, such as THF, with heating (e.g. 75° C.) to provide compound C. Alternatively, compound A can be replaced with a compound already containing ring $A_3$ (as described for compounds of Formula I), either as a compound readily available, or by reacting compound A to replace the bromine with ring $A_3$ via a Suzuki reaction with a suitable boronic acid (as described in Scheme 8).

The compound J, which can be used in the synthesis of a compound of Formula I wherein $A_1$ is carbocyclic or heterocyclic, Y is O, $R^2$ and $R^3$ are H, and $R^1$ is methyl, is prepared from compound A, a suitable acetyl, bromo substituted ring $A_2$, and a cyclic ketone compound D, in six steps according to Scheme 2.

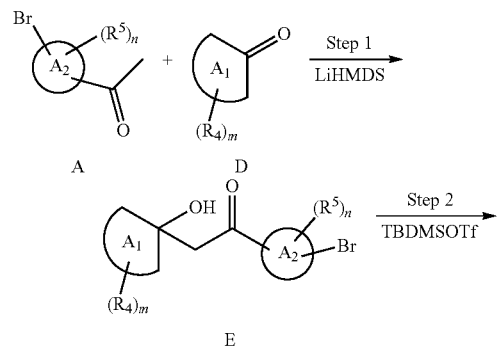

Scheme 2

-continued

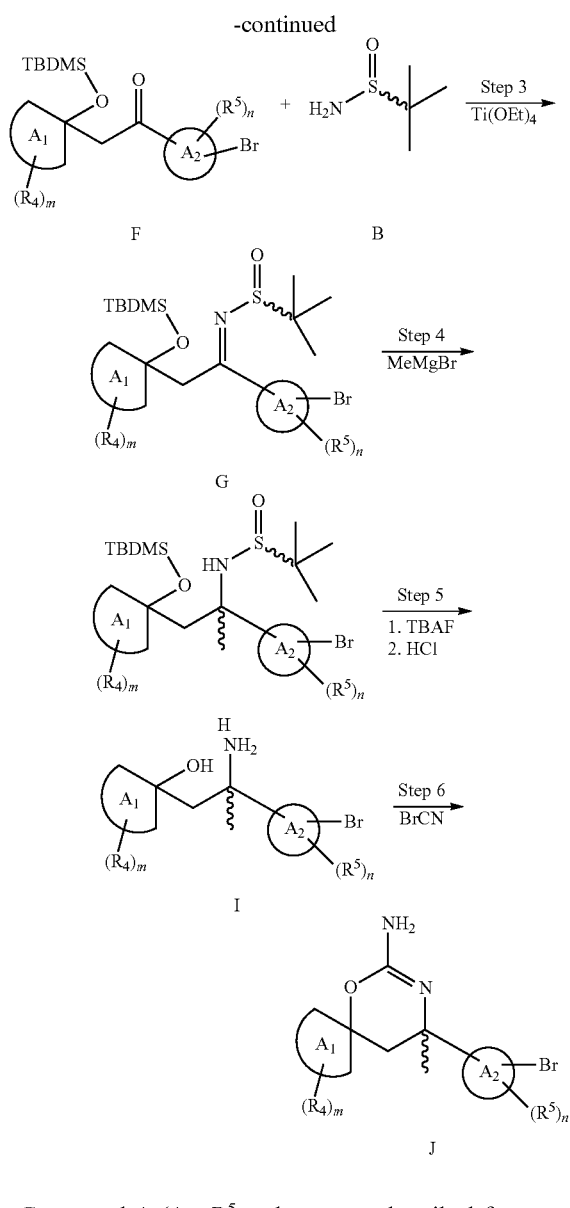

stepwise with TBAF in THF at room temperature followed by HCl in dioxane to provide compound I, which is cyclized to form the dihydro-oxazine J, for example by heating in a sealed tube with cyanic bromide, e.g. at 65° C. for 18 hours.

The compound T, which can be used in the synthesis of a compound of Formula I wherein $A_1$ is cyclobutane, cyclopentane or cyclohexane, Y is S, $R^2$ and $R^3$ are H, and $R^1$ is methyl, is prepared from carboxylic acid compound K, in nine steps according to Scheme 3.

Scheme 3

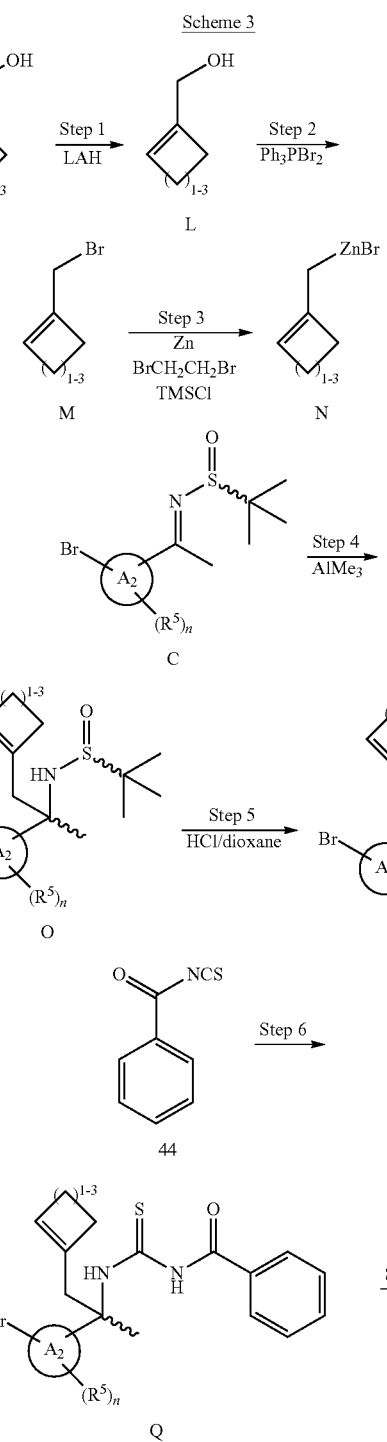

Compound A ($A_2$, $R^5$ and n are as described for compounds of Formula I) can be treated with base (e.g. LiHMDS) in a suitable solvent, such as THF, at low temperature (e.g. −78° C.) and reacted with Compound D ($A_1$, $R^4$ and m are as described for compounds of Formula I) to provide compound E upon warming to room temperature. The OH of compound E is protected with a suitable protecting group, for example with TBDMS group, by reacting with tert-butyldimethylsilyl triflate in the presence of 2,6-lutidine in $CH_2Cl_2$ at low temperature (e.g. 0° C.), then warming to room temperature to provide compound F. Compound F is combined with tetraethoxytitanium and 2-methylpropane-2-sulfinamide B (wherein the wavy line bond to the sulfur indicates this compound can be a racemic mixture, or the specific R or S isomer) in, for example, dry THF and heated, e.g. to reflux, to provide compound G, which is then treated with a Grignard reagent, e.g. methyl magnesium bromide in, for example, THF and ether to provide compound H (when the S or R isomer of B is used in Step 3, this reaction can be done under conditions to provide a specific stereoisomer on the chiral carbon as indicated by the second wavy line). The nitrogen of Compound H is deprotected, for example The compound Z, which can be used in the synthesis of a compound of Formula I wherein $A_1$ is oxetane, Y is S, $R^2$ and $R^3$ are H, and $R^1$ is methyl, is prepared from 2-methylenepropane-1,3-diol 53 in nine steps according to Scheme 4.

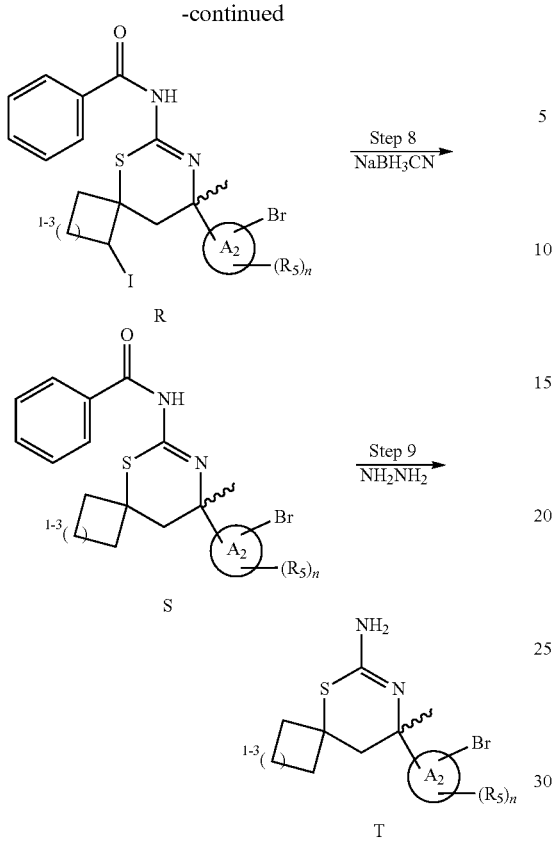

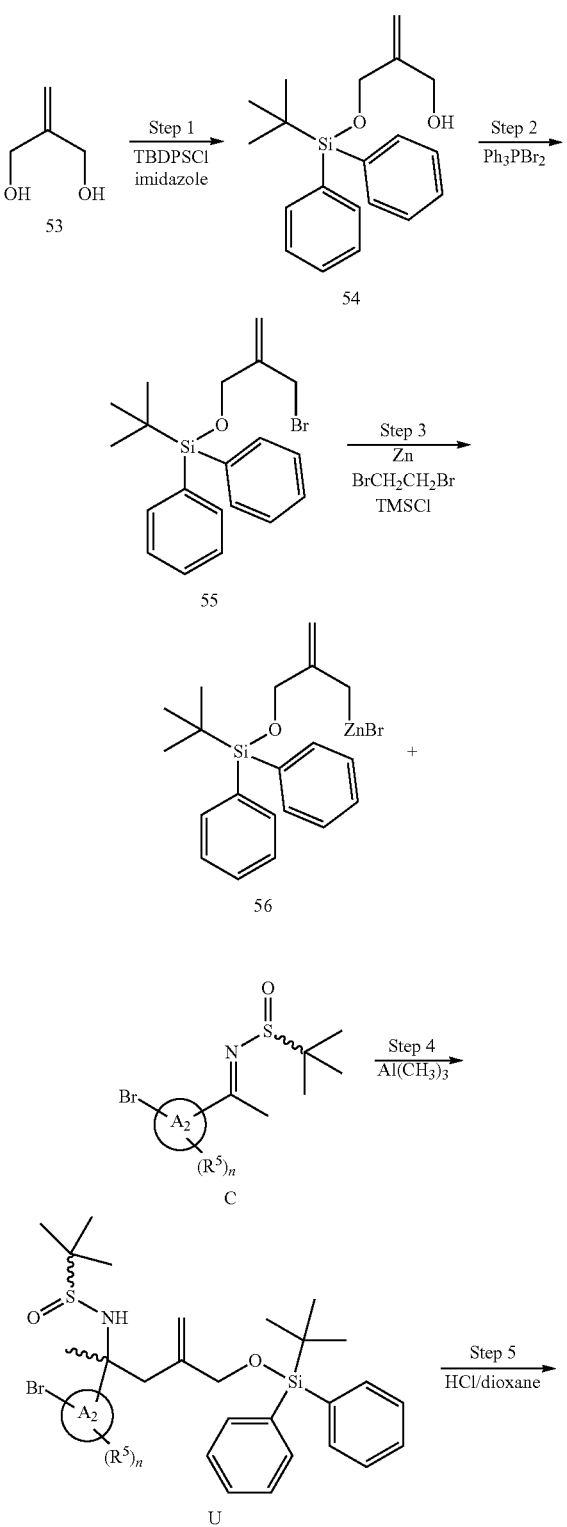

$C_{4-6}$ Cycloalk-1-enecarboxylic acid K is reacted with a suitable reducing agent (e.g. lithium aluminum hydride) in ether or other suitable solvent, heating to reflux under nitrogen. The resulting alcohol L is reacted with a suitable bromination reagent, such as dibromo(triphenyl)-phosphane, in $CH_2Cl_2$ or other suitable solvent to provide the bromomethyl substituted cycloalkene M, which is further reacted with zinc, 1,2-dibromoethane and chloro(trimethyl) silane, for example in dry THF, to provide the bromo zinc compound N. A suitable sulfinamide compound C ($A_2$, $R^5$ and n are as described for compounds of Formula I, prepared by the methods provided in Scheme 1) is reacted with compound N, where the reaction is performed by dropwise addition of N to a solution of compound C with $AlMe_3$ in THF or other suitable solvent at low temperature (e.g. −78° C.) to provide compound O. The compound C can be either a racemic mixture, or can be the specific stereoisomer at the indicated wavy line bond to the sulfur, where under suitable conditions the stereoisomer may selectively provide a particular stereoisomer in compound O at the indicated wavy line bond to the stereocenter carbon. Note that, alternatively, compound C can be substituted with a suitable compound already including ring $A_3$ in this reaction. Compound O is reacted with HCl in dioxane in a suitable solvent such as MeOH to provide compound P, which is reacted with benzoyl isothiocyanate 44 in dry THF or other suitable solvent to provide compound Q. Cyclization of compound Q to provide the substituted dihydro-thiazine R is performed at low temperature (e.g. 0° C.), reacting with iodine in a suitable solvent such as dry $CH_2Cl_2$. Compound R can be reacted with sodium cyanoborohydride, for example in MeOH and HOAc, to provide compound S, which is then reacted with hydrazine in a suitable solvent, such as $CH_2Cl_2$, to remove the amine protecting group, providing compound T.

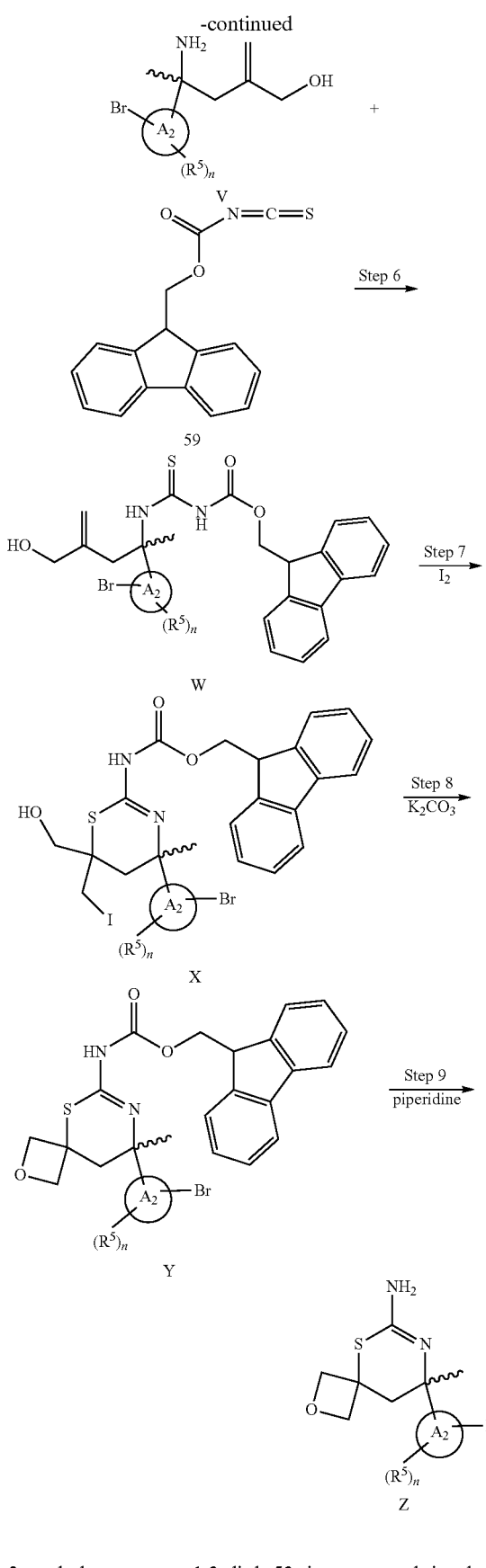

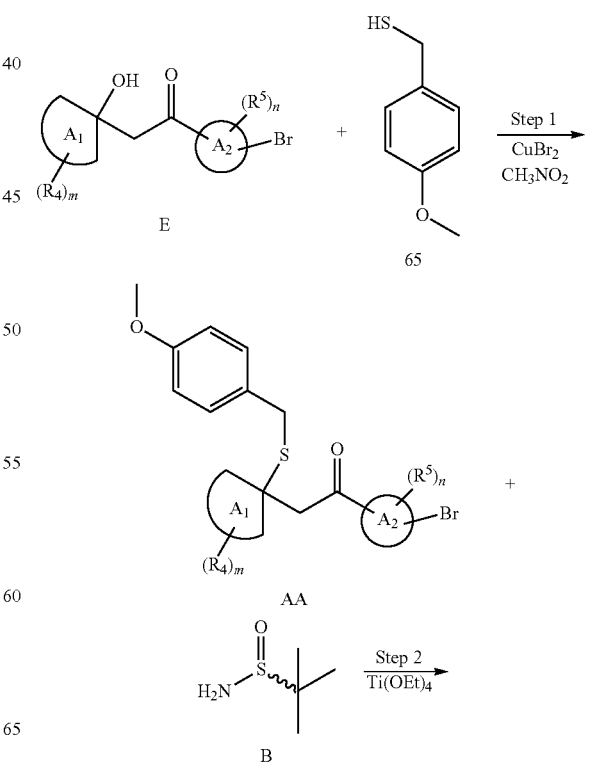

ethyl]allyl]zinc 56 by the methods described in Example 4 below. A suitable sulfinamide compound C ($A_2$, $R^5$ and n are as described for compounds of Formula I, prepared by the methods provided in Scheme 1) is reacted with bromo-[2-[[tert-butyl(diphenyl)silyl]oxymethyl]allyl]zinc 56, where the reaction is performed by dropwise addition of 56 to a solution of compound C with $AlMe_3$ in THF or other suitable solvent at low temperature (e.g. −78° C.) to provide compound U. The compound C can be either a racemic mixture, or can be a specific stereoisomer at the indicated wavy line bond to the sulfur, where under suitable conditions the stereoisomer may selectively provide a specific stereoisomer in compound U at the indicated wavy line bond to the chiral carbon. Note that, alternatively, compound C can be substituted with a suitable compound already including ring $A_3$ in this reaction. Compound U is reacted with HCl in dioxane in a suitable solvent such as MeOH to provide compound V, which is reacted with O-(9H-fluoren-9-yl)methyl carbonisothiocyanatidate 59 in dry THF or other suitable solvent to provide compound W, which is reacted with iodine in a suitable solvent such as THF to provide compound X. Compound X can be reacted with potassium carbonate in a suitable solvent, such as dioxane/water, to form the oxetane spirocycle, providing Compound Y, which is deprotected by reaction with piperidine in a suitable solvent such as $CH_2Cl_2$, to provide Compound Z.

The compound FF, which can be used in the synthesis of a compound of Formula I wherein $A_1$ is carbocyclic or heterocyclic, Y is S, $R^2$ and $R^3$ are H, and $R^1$ is methyl, is prepared from (4-methoxyphenyl)methanethiol 65 and Compound E (see Scheme 2) in six steps according to Scheme 5.

Scheme 5

2-methylenepropane-1,3-diol 53 is converted in three steps to provide bromo-[2-[[tert-butyl(diphenyl)silyl]oxym-

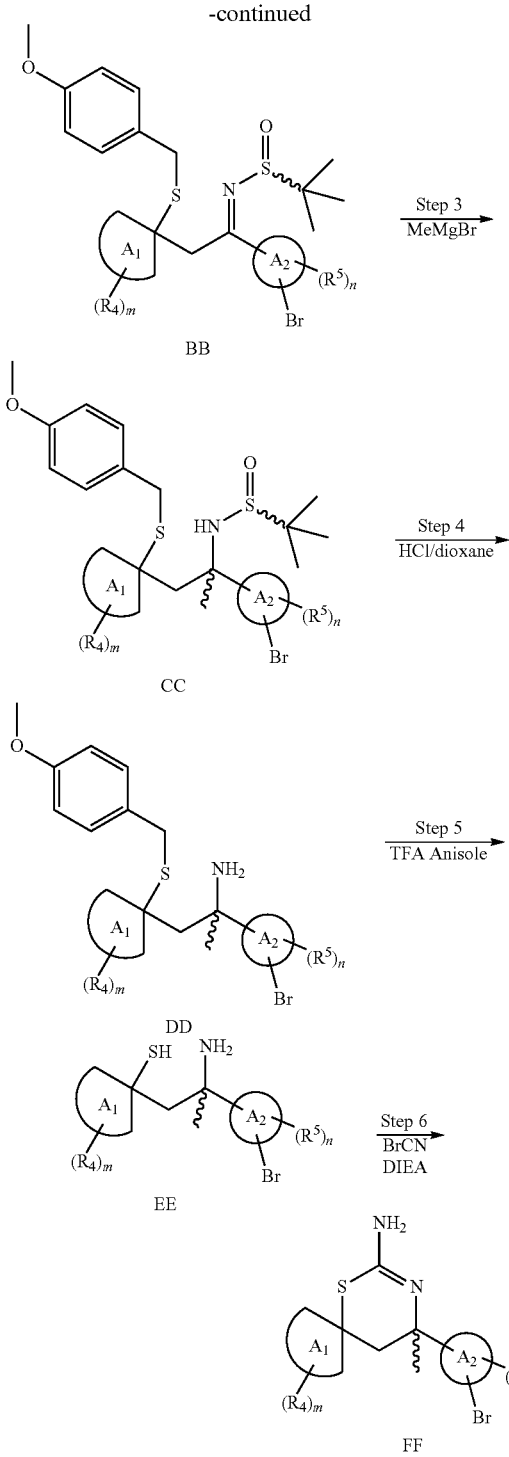

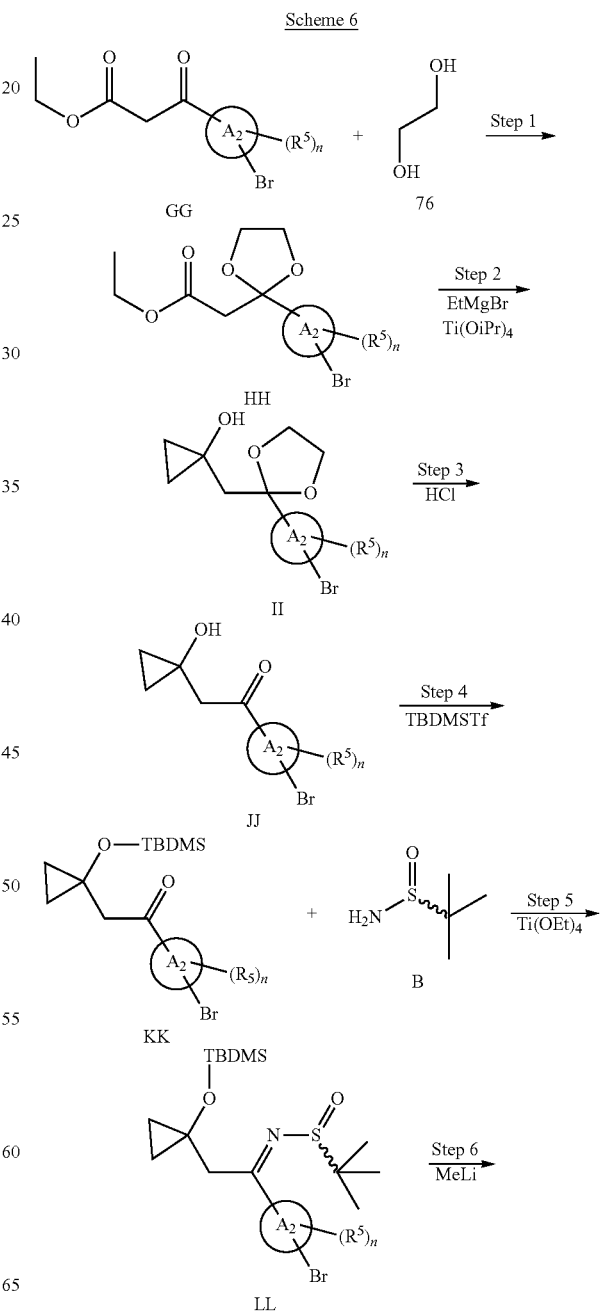

THF and ether to provide compound CC (when the S or R isomer of B is used in Step 2, this reaction can be done under conditions to provide a specific stereoisomer on the chiral carbon as indicated by the second wavy line). The nitrogen is deprotected by reacting with HCl in dioxane in a suitable solvent, such as $CH_2Cl_2$, to provide Compound DD, which upon reacting with anisole in TFA results in Compound EE. Compound EE is then reacted with cyanic bromide and DIEA in a suitable solvent such as EtOH for provide the desired compound FF.

The compound PP, which can be used in the synthesis of a compound of Formula I wherein $A_1$ is cyclopropane, Y is O, $R^2$ and $R^3$ are H, and $R^1$ is methyl, is prepared from ethane-1,2-diol 76 and Compound GG in nine steps according to Scheme 6.

Compound E (prepared as described in Scheme 2; $A_2$, $A_1$, $R^4$, $R^5$, m and n are as described for compounds of Formula I) is reacted with (4-methoxyphenyl)methanethiol 65 and dibromocopper in $CH_3NO_2$, to provide Compound AA, which is then reacted with tetraethoxytitanium and 2-methylpropane-2-sulfinamide B (wherein the wavy line bond to the sulfur indicates this compound can be a racemic mixture, or the specific R or S isomer) in a suitable solvent such as dry THF and heated, e.g. to reflux, to provide compound BB. Compound BB is treated with a Grignard reagent, e.g. methyl magnesium bromide in a suitable solvent such as

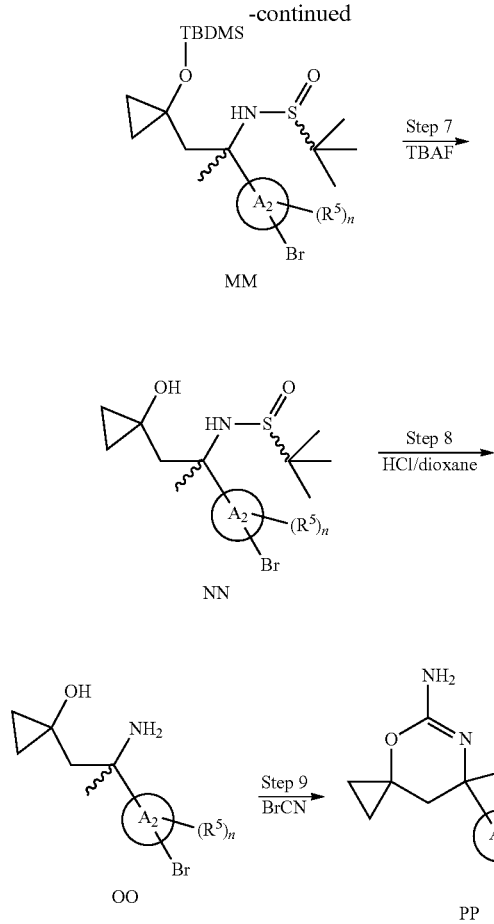

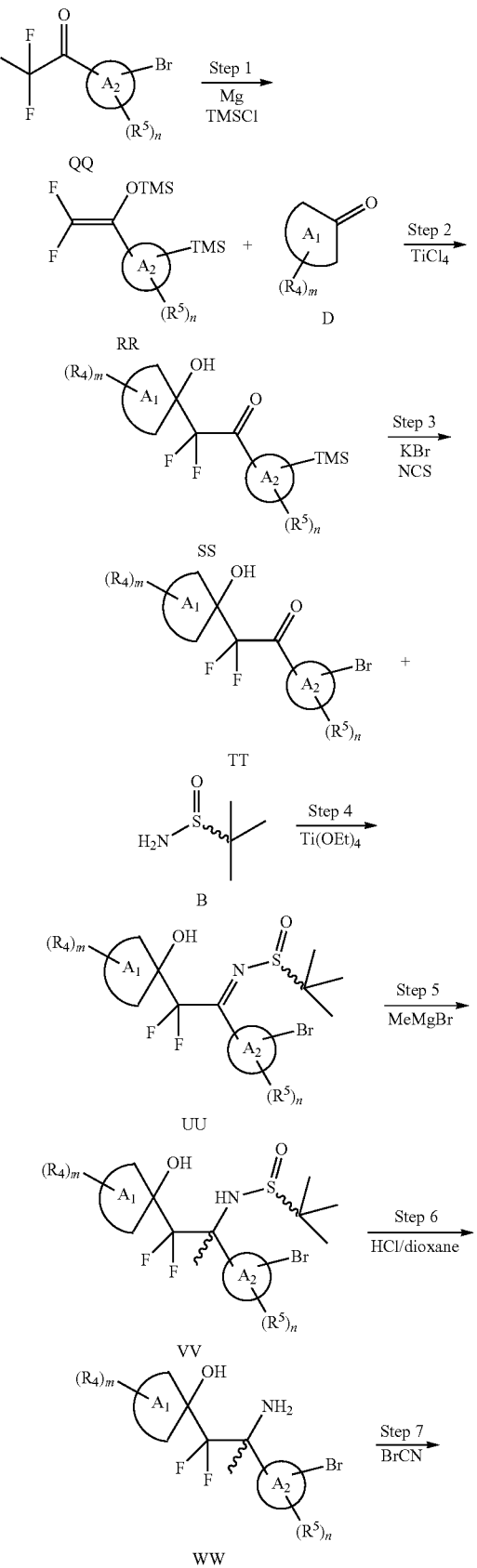

Scheme 7

Compound GG (A$_2$, R$^5$ and n are as described for compounds of Formula I) is reacted with ethane-1,2-diol 76 and p-toluenesulfonic acid in a suitable solvent, such as toluene to provide Compound HH. Compound HH is combined with tetraisoproxytitanium in a suitable solvent such as THF/Et$_2$O and reacted with EtMgBr to provide Compound II, which is then reacted with HCl, for example in MeOH to provide Compound JJ. The resulting OH group is protected by reacting, for example, with tert-butyldimethylsilyl triflate and 2,6-lutedine in a suitable solvent such as CH$_2$Cl$_2$, to provide compound KK, which is then reacted with tetra-ethoxytitanium and 2-methylpropane-2-sulfinamide B (wherein the wavy line bond to the sulfur indicates this compound can be a racemic mixture, or the specific R or S isomer) in a suitable solvent such as dry THF and heated, e.g. to reflux, to provide Compound LL. Reaction of Compound LL in a suitable solvent such as THF under nitrogen at low temperature (e.g. −20° C.) with dropwise addition of MeLi in ether results in Compound MM, which is then reacted with tetrabutylammonium fluoride in a suitable solvent such as THF to provide Compound NN. The nitrogen is deprotected with HCl in dioxane in a suitable solvent such as CH$_2$Cl$_2$ to provide Compound OO, which is reacted with cyanic bromide in a suitable solvent such as EtOH for provide the desired compound PP.

The compound XX, which can be used in the synthesis of a compound of Formula I wherein A$_1$ is carbocyclic or heterocyclic, Y is O, R$^2$ and R$^3$ are F, and R$^1$ is methyl, is prepared from Compound QQ in seven steps according to Scheme 7.

87
-continued

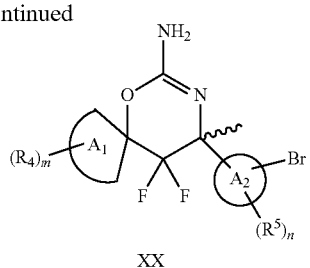

XX

Magnesium and chloro(trimethyl)silane are combined in a suitable solvent such as THF and reacted with dropwise addition of Compound QQ ($A_2$, $R^5$ and n are as described for compounds of Formula I) at low temperature (e.g. 0° C.) to provide Compound RR. Compound D ($A_1$, $R^4$ and m are as described for compounds of Formula I) is added to a solution of tetrachlorotitanium in a suitable solvent such as $CH_2Cl_2$ under nitrogen at e.g. −78° C., then reacted with dropwise addition of Compound RR to provide Compound SS. Compound SS is dissolved in a suitable solvent such as HOAc and MeOH, with addition of KBr, then 1-chloropyrrolidine-2,5-dione, and reacted at elevated temperature (e.g. 60° C.), resulting in Compound TT. Compound TT is then reacted with tetraethoxytitanium and 2-methylpropane-2-sulfinamide B (wherein the wavy line bond to the sulfur indicates this compound can be a racemic mixture, or the specific R or S isomer) in a suitable solvent such as dry THF and heated, e.g. to reflux, to provide Compound UU. Reaction of Compound UU in THF under nitrogen at low temperature (e.g. 0° C.) with dropwise addition of $CH_3MgBr$ in ether results in Compound VV. The nitrogen is deprotected with HCl in dioxane in a suitable solvent such as $CH_2Cl_2$ to provide Compound WW, which is reacted with cyanic bromide in a suitable solvent such as EtOH for provide the desired compound XX.

The Compound AB (e.g. Compounds J, T, Z, FF, PP or XX prepared as described in Schemes 2-7) can be reacted with a suitable boronic acid Compound AC or Compound AD (Suzuki reaction) to provide Compound AE or Compound AF, e.g. a compound of Formula I wherein L is a direct bond or —CH═CH—, respectively, $R^1$ is methyl and $R^2$ and $R^3$ are both hydrogen or both F, in one step according to Scheme 8/8a.

88

The bromine on ring $A_2$ of Compound AB (e.g. Compounds J, T, Z, FF, PP or XX prepared as described in Schemes 2-7, $R^2$ and $R^3$ are either both H or both F, Y, $A_1$, $A_2$, $R^4$, $R^5$, m and n are as described for compounds of Formula I) can be replaced in a Suzuki reaction with a suitable boronic acid AC or AD ($A_3$, $R^6$ and p are as described for compounds of Formula I, $B(OR)_2$ is e.g. $B(OH)_2$ or a suitable ester thereof), reacting in a suitable solvent, such as DME/water, with a suitable base, such as cesium carbonate, and a suitable palladium catalyst, such as 1,1'-bis(diphenylphosphino)ferrocene palladium (II) dichloride, with heating (e.g. 90° C.) under nitrogen, to provide the desired compound AE or AF.

The Compound AB (e.g. Compounds J, T, Z, FF, PP or XX prepared as described in Schemes 2-7) can be reacted to convert the bromine to an amine, and subsequently modified to provide Compound AL, e.g. a compound of Formula I wherein L is —NH—C(O)—, $R^1$ is methyl and $R^2$ and $R^3$ are both hydrogen or both F, in five steps according to Scheme 9.

Scheme 9

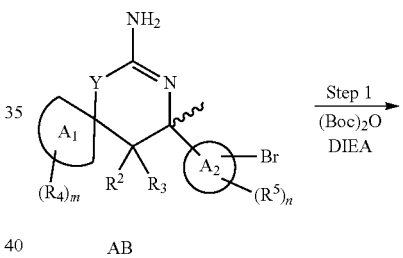

AB

Scheme 8/8a

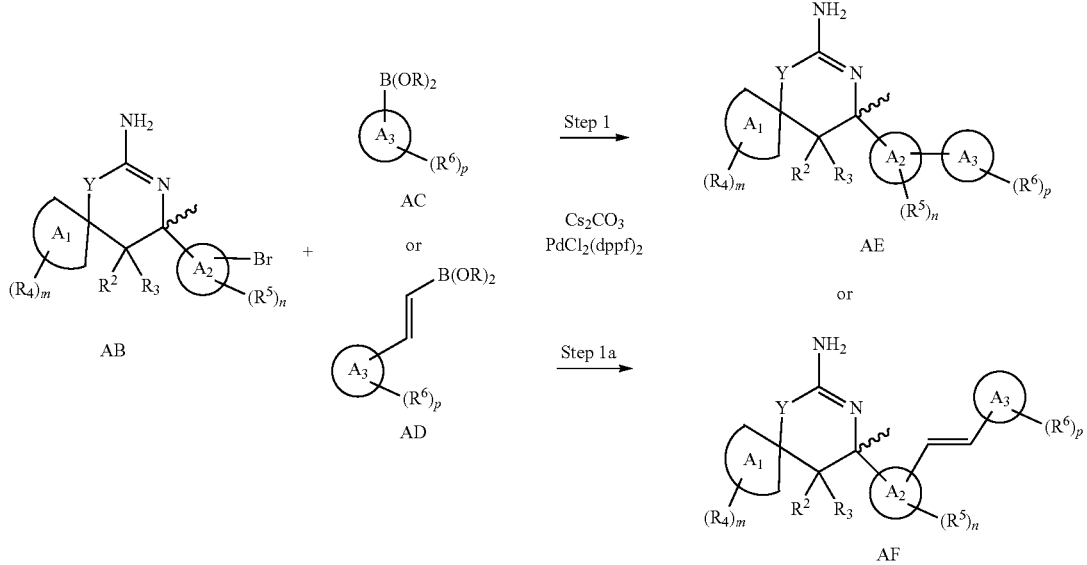

-continued

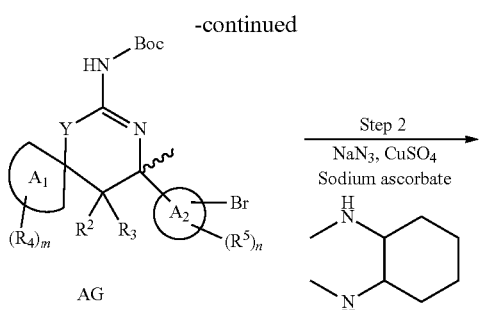

AG

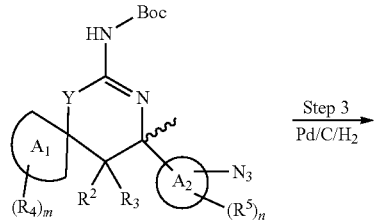

AH

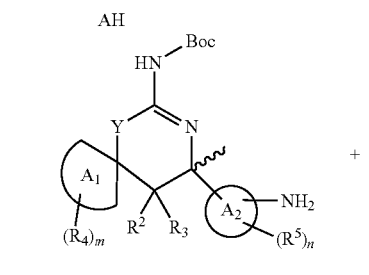

AI

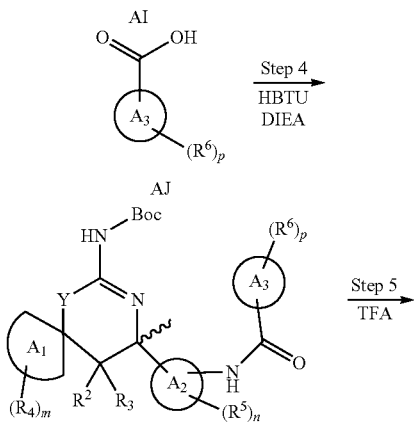

AK

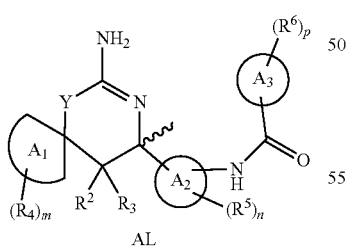

AL

The free amine of Compound AB (e.g. Compounds J, T, Z, FF, PP and XX prepared as described in Schemes 2-7, $R^2$ and $R^3$ are either both H or both F, Y, $A_1$, $A_2$, $R^4$, $R^5$, m and n are as described for compounds of Formula I) is Boc protected by reacting with tert-butoxycarbonyl tert-butyl carbonate and N-ethyl-N-isopropylpropan-2-amine in a suitable solvent such as $CH_2Cl_2$. The resulting Compound AG is reacted with sodium azide, sodium ascorbate, copper sulfate and N1,N2-dimethylcyclohexane-1,2-diamine in a suitable solvent such as EtOH/water to provide the azido Compound AH, which is converted to the amino Compound AI by hydrogenation, for example reacting with $H_2$ and 10% Pd/C catalyst in a suitable solvent such as EtOH. Reaction of Compound AI with a suitable carboxylic acid Compound AJ ($A_3$, $R^6$ and p are as described for compounds of Formula I) in the presence of [benzotriazol-1-yloxy(dimethylamino) methylene]-dimethyl-ammonium hexafluorophosphate and N-ethyl-N-isopropyl-propan-2-amine in a suitable solvent such as DMF results in the amide linked Compound AK which is subsequently deprotected with TFA, for example in $CH_2Cl_2$, to provide the desired Compound AL.

Alternatively, Compound AI as prepared by the methods of Scheme 9 can be reacted in two steps to provide Compound AO, e.g. a compound of Formula I wherein L is —NH—$CH_2$—, $R^1$ is methyl and $R^2$ and $R^3$ are both hydrogen or both F, according to Scheme 10.

Scheme 10

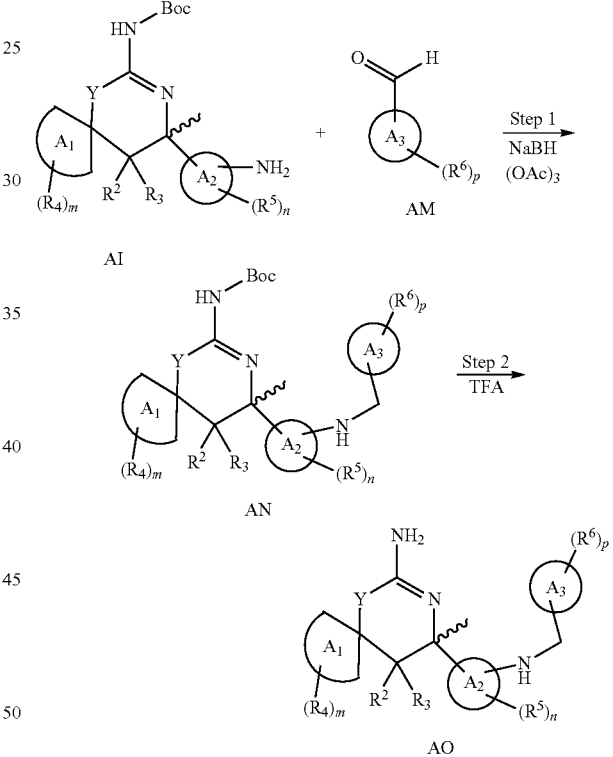

Reaction of Compound AI with a suitable aldehyde Compound AM ($A_3$, $R^6$ and p are as described for compounds of Formula I) in the presence of sodium triacetoxyborohydride in a suitable solvent such as $CH_3OH$ results in Compound AN, which is subsequently deprotected with TFA, for example in $CH_2Cl_2$, to provide the desired Compound AO.

Compound AI as prepared by the methods of Scheme 9 can be reacted in one or two steps to provide Compound AR, e.g. a compound of Formula I wherein L is —NH—, $R^1$ is methyl and $R^2$ and $R^3$ are both hydrogen or both F, according to Scheme 11/11a.

Scheme 11/11a

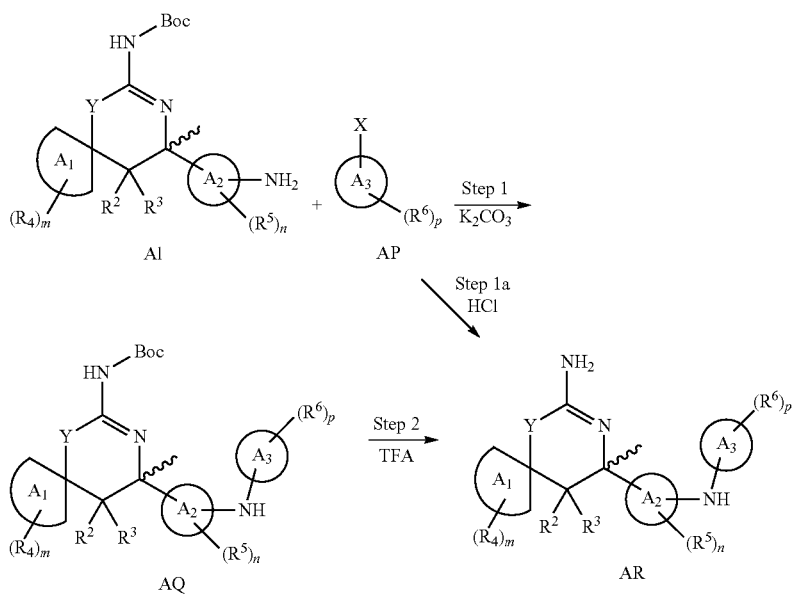

Reaction of Compound AI with a suitable halogenated Compound AP ($A_3$, $R^6$ and p are as described for compounds of Formula I, X is a halogen) in the presence of potassium carbonate in a suitable solvent such as isopropanol results in Compound AQ, which is subsequently deprotected with TFA, for example in $CH_2Cl_2$, to provide the desired Compound AR. Alternatively, the reaction of Compound AI with a suitable halogenated Compound AP ($A_3$, $R^6$ and p are as described for compounds of Formula I, X is a halogen) in the presence of HCl in dioxane in a suitable solvent such as isopropanol, in addition to forming the amine linked ring $A_3$, results in removal of the amine protecting group to provide the desired Compound AR in a single step 1a.

Compounds as described herein, including compositions and methods of use thereof, are illustrated further by the following examples, which are not to be construed as limiting the invention in scope or spirit to the specific procedures described in them. Analogous structures and alternative synthetic routes within the scope of the invention will be apparent to those skilled in the art.

EXAMPLES

General

Reagents and solvents obtained from commercial suppliers are used without further purification unless otherwise stated. Thin layer chromatography is performed on pre-coated 0.25 mm silica gel plates (E. Merck, silica gel 60, $F_{254}$) or similar. Visualization is achieved using UV illumination or staining with phosphomolybdic acid, ninhydrin or other common staining reagents. Flash column chromatography is performed using an ISCO system and prepacked silica gel columns. Preparatory HPLC is performed on a Varian Prepstar high performance liquid chromatograph. $^1$H NMR spectra are recorded at 400 MHz on a Bruker Avance spectrometer. Chemical shifts are reported in parts per million (ppm) downfield relative to tetramethylsilane (TMS) or to proton resonances resulting from incomplete deuteration of the NMR solvent (δ scale). Mass spectra (LCMS) are recorded on an Agilent series 1100 mass spectrometer connected to an Agilent series 1100 HPLC. In some instances the synthetic examples give a racemic mixture of stereoisomers, which are readily separated by chiral HPLC.

LCMS is performed on an Agilent 1100 Series HPLC with a Series 1100 MSD with electrospray ionization using a Phenomenex Luna C18 4.6 mm i.d.×30 mm length, 3μ particle size column or similar. Compound purity is typically determined by HPLC/MS analysis using a variety of analytical methods.

The examples are intended to be illustrative and are not limiting or restrictive to the scope of the invention. For example, where additional compounds are prepared similarly to synthetic methods of another example, or in the same manner as another example, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art.

Example 1

Synthesis of (E)-N-(1-(4-bromothiophen-2-yl)ethylidene)-2-methylpropane-2-sulfinamide (3)

(E)-N-(1-(4-Bromothiophen-2-yl)ethylidene)-2-methylpropane-2-sulfinamide 3 was prepared from 1-(4-bromothiophen-2-yl)ethanone 1 and 2-methylpropane-2-sulfinamide 2 in one Step as follows:

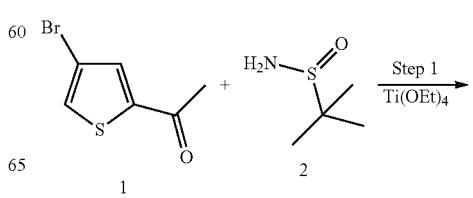

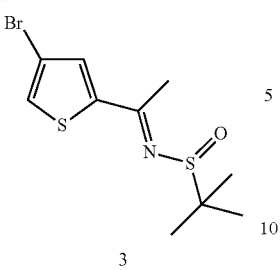

3

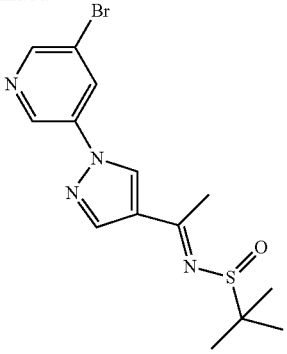

7

Step 1—synthesis of (E)-N-(1-(4-bromothiophen-2-yl)ethylidene)-2-methylpropane-2-sulfinamide (3)

1-(4-Bromothiophen-2-yl)ethanone (1, 4 g, 19.5 mmol), 2-methylpropane-2-sulfinamide (2, 2.6 g, 21.5 mmol) and tetraethoxytitanium (9.7 g, 25.4 mmol) were combined in 100 mL of THF. The mixture was heated at 75° C. overnight, then concentrated under vacuum and the residue was dissolved in 100 mL of $CH_2Cl_2$. The mixture was poured into 200 mL of ice-water and stirred for 5 minutes, then filtered through a celite pad and the solid was washed with 2×30 mL of $CH_2Cl_2$. The organic phase was separated from the filtrate and washed with brine, then dried, filtered and the filtrate was concentrated under vacuum. The resulting material was purified by flash column chromatography (hexane/EtOAc). Appropriate fractions were combined and concentrated under vacuum to provide the desired compound as a yellow solid (3, 4.1 g, 16 mmol).

(E)-N-(1-(1-(5-Bromopyridin-3-yl)-1H-pyrazol-4-yl)ethylidene)-2-methylpropane-2-sulfinamide 7 was prepared from 3-bromo-5-fluoropyridine 4 and 1-(1H-pyrazol-4-yl)ethanone 5 in two Steps as follows:

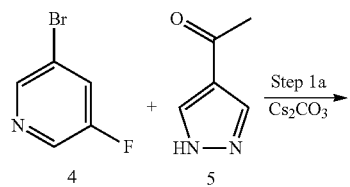

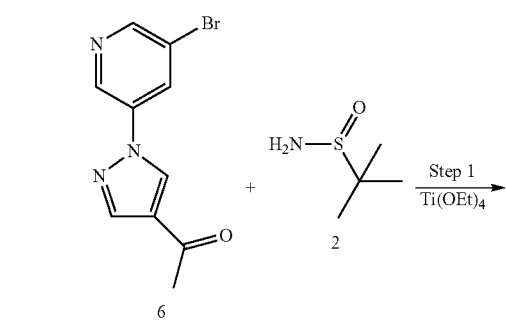

Step 1a—synthesis of 1-(1-(5-bromopyridin-3-yl)-1H-pyrazol-4-yl)ethanone (6)

A mixture of 3-bromo-5-fluoropyridine (4, 1 g, 9.1 mmol), 1-(1H-pyrazol-4-yl)ethanone (5, 1.6 g, 9.1 mmol) and $Cs_2CO_3$ (3.55 g, 10.9 mmol) in 15 mL of DMF was heated at 120° C. in a microwave oven for 30 minutes. The reaction was cooled to room temperature and diluted with 150 mL of water and filtered. The solid was collected and dried to provide the desired compound (6, 2 g, 7.5 mmol, 83% yield).

Step 1—synthesis of (E)-N-(1-(1-(5-bromopyridin-3-yl)-1H-pyrazol-4-yl)ethylidene)-2-methylpropane-2-sulfinamide (7)

1-(1-(5-Bromopyridin-3-yl)-1H-pyrazol-4-yl)ethanone (6) is reacted similarly to the above Step 1 to provide (E)-N-(1-(1-(5-bromopyridin-3-yl)-1H-pyrazol-4-yl)ethylidene)-2-methylpropane-2-sulfinamide 7.

Additional sulfinamide compounds are prepared similarly to this method, optionally replacing 1-(4-bromothiophen-2-yl)ethanone 1 with a suitable ethanone in Step 1, or replacing 1-(1H-pyrazol-4-yl)ethanone 5 with a suitable ethanone compound in Step 1a, and/or optionally replacing 2-methylpropane-2-sulfinamide 2 with the (S) or (R) isomer thereof in Step 1. The following compounds are prepared:
(S,E)-N-(1-(4-bromothiophen-2-yl)ethylidene)-2-methylpropane-2-sulfinamide (8),
(R,E)-N-(1-(4-bromothiophen-2-yl)ethylidene)-2-methylpropane-2-sulfinamide (9),
(S,E)-N-(1-(5-bromo-3-chlorothiophen-2-yl)ethylidene)-2-methylpropane-2-sulfinamide (10),
(E)-N-(1-(5-bromo-3-chlorothiophen-2-yl)ethylidene)-2-methylpropane-2-sulfinamide (11),
(S,E)-N-(1-(1-(5-bromopyridin-3-yl)-1H-pyrazol-4-yl)ethylidene)-2-methylpropane-2-sulfinamide (12),
(S,E)-N-(1-(5-bromo-2-fluorophenyl)ethylidene)-2-methylpropane-2-sulfinamide (13),
(E)-N-(1-(5-bromo-2-fluorophenyl)ethylidene)-2-methylpropane-2-sulfinamide (14),
(R,E)-N-(1-(5-bromo-2-fluorophenyl)ethylidene)-2-methylpropane-2-sulfinamide (15), and
(S,E)-N-(1-(3-bromothiophen-2-yl)ethylidene)-2-methylpropane-2-sulfinamide (16).

The following table provides the compound number (column 1), compound used in Step 1 or 1a (column 2 ethanone Step 1 unless Step 1a is indicated), sulfinamide used in Step 1 (column 3, as (S), (R), or racemic (2)) to give the compound shown in column 4.

| Comp. No. | ethanone | sul-fina-mide | Compound structure |
|---|---|---|---|
| 8 | | (S) | 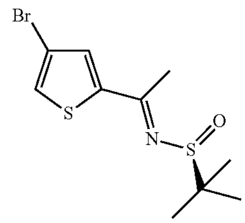 |
| 9 | | (R) | 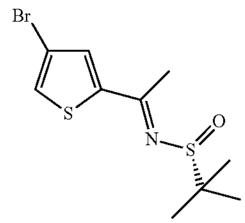 |
| 10 | | (S) | 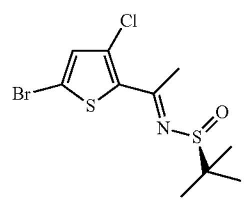 [SMILES: C/C(=N\[S@@](=O)C(C)(C)C)c1sc(Br)cc1Cl] |
| 11 | | racemic | 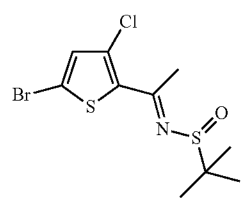 [SMILES: C/C(=N\S(=O)C(C)(C)C)c1sc(Br)cc1Cl] |
| 12 | Step 1a | (S) | 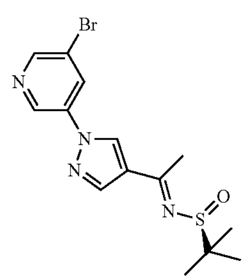 [SMILES: C/C(=N\[S@@](=O)C(C)(C)C)c1cnn(-c2cncc(Br)c2)c1] |
| 13 | | (S) | 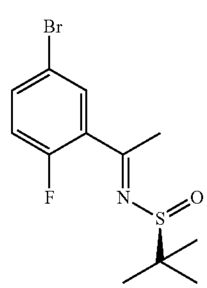 [SMILES: C/C(=N\[S@@](=O)C(C)(C)C)c1cc(Br)ccc1F] |

-continued

| Comp. No. | ethanone | sul-fina-mide | Compound structure |
|---|---|---|---|
| 14 | | racemic | 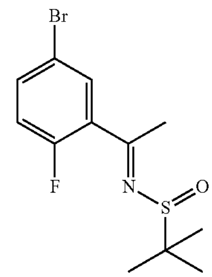 [SMILES: C/C(=N\S(=O)C(C)(C)C)c1cc(Br)ccc1F] |
| 15 | | (R) | 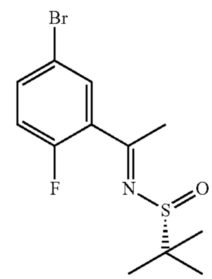 [SMILES: C/C(=N\[S@](=O)C(C)(C)C)c1cc(Br)ccc1F] |
| 16 | | (S) | 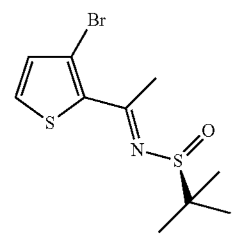 |

Example 2

Synthesis of 4-(5-bromo-2-fluorophenyl)-4-methyl-1,9-dioxa-3-azaspiro[5.5]undec-2-en-2-amine (25)

4-(5-Bromo-2-fluorophenyl)-4-methyl-1,9-dioxa-3-azaspiro[5.5]undec-2-en-2-amine 25 was prepared from 1-(5-bromo-2-fluorophenyl)ethanone 17 and dihydro-2H-pyran-4(3H)-one 18 in seven Steps as follows:

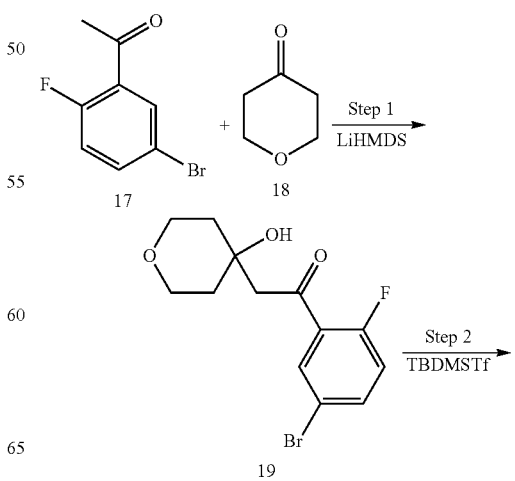

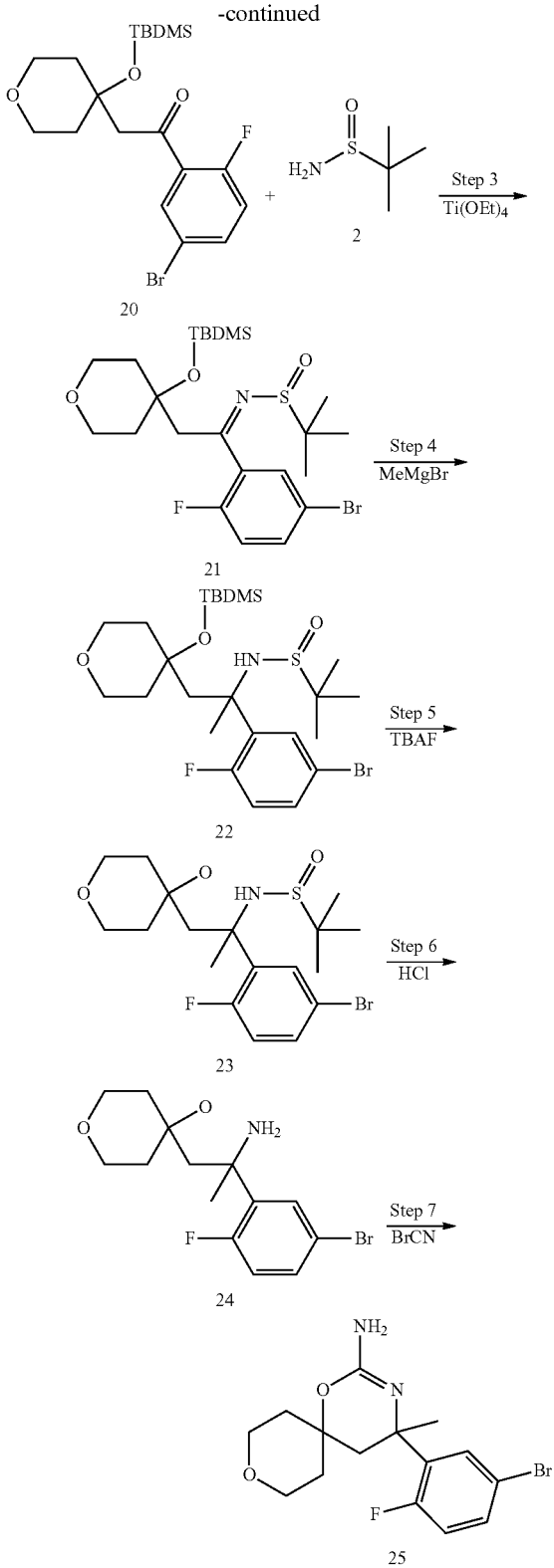

Step 1—synthesis of 1-(5-bromo-2-fluorophenyl)-2-(4-hydroxytetrahydro-2H-pyran-4-yl)ethanone (19)

Lithium bis(trimethylsilyl)amide (12 mL, 1M in THF, 12 mmol) was diluted with 12 mL of dry THF, and the solution was cooled to −78° C. for 5 minutes under nitrogen. A solution of 1-(5-bromo-2-fluoro-phenyl)ethanone (17, 2 g, 9.21 mmol) in 4 mL of THF was added dropwise over 10 minutes and the mixture was stirred at −78° C. for 30 minutes. Dihydro-2H-pyran-4(3H)-one (18, 1.2 g, 12 mmol) in 2 mL of THF was added dropwise and the mixture was stirred at −78° C. for 15 minutes, and then gradually warmed to room temperature over 2 hours. The reaction was quenched with saturated aqueous NH$_4$Cl and extracted with 2×60 mL of EtOAc. The organic portion was dried, filtered and the filtrate concentrated under vacuum and the residue purified by flash column chromatography (hexane/EtOAc 0-50%). Appropriate fractions were combined and concentrated under vacuum to provide the desired compound as a white solid (19, 2.1 g, 6.6 mmol).

Step 2—synthesis of 1-(5-bromo-2-fluorophenyl)-2-(4-(tert-butyldimethylsilyloxy)tetrahydro-2H-pyran-4-yl)ethanone (20)

tert-Butyldimethylsilyl triflate (2.5 g, 9.46 mmol) was added to a 0° C. solution of 1-(5-bromo-2-fluoro-phenyl)-2-(4-hydroxytetrahydropyran-4-yl)ethanone (19, 2.0 g, 6.31 mmol) and 2,6-lutidine (1.35 g, 12.61 mmol) in 20 mL of CH$_2$Cl$_2$. The mixture stood at 0° C. for 2 hours, followed by 3 hours at room temperature, then was poured into saturated aqueous NaHCO$_3$. The organic portion was separated, washed with aqueous 10% HCl, saturated NaHCO$_3$, and brine, then dried with MgSO$_4$, filtered and the filtrate concentrated under vacuum. The resulting material was purified by flash column chromatography (hexane/EtOAc 0-40%). Appropriate fractions were combined and concentrated under vacuum to provide the desired compound (20, 2.55 g, 5.91 mmol).

Step 3—synthesis of (Z)—N-(1-(5-bromo-2-fluorophenyl)-2-(4-(tert-butyldimethylsilyloxy)tetrahydro-2H-pyran-4-yl)ethylidene)-2-methylpropane-2-sulfinamide (21)

1-(5-Bromo-2-fluorophenyl)-2-(4-(tert-butyldimethylsilyloxy)tetrahydro-2H-pyran-4-yl)ethanone (20, 2.0 g, 4.64 mmol), 2-methylpropane-2-sulfinamide (2, 1.40 g, 11.6 mmol) and tetraethoxytitanium (4.2 g, 18.54 mmol) were combined in 20 mL of dry THF and heated at refluxing for overnight. This was concentrated under vacuum and the residue was dissolved in 100 mL of CH$_2$Cl$_2$, then the mixture was poured into 100 mL of ice-water and stirred for 5 minutes. The inorganic solid was removed by filtration through a celite pad, then the solid was washed with 2×15 mL of CH$_2$Cl$_2$. The organic phase was separated from the filtrate and washed with brine, dried and filtered and the filtrate concentrated under vacuum. The resulting material was purified by flash column chromatography (hexane/EtOAc 0-50%). Appropriate fractions were combined and concentrated under vacuum to provide the desired compound (21, 2.4 g, 4.5 mmol).

Step 4—synthesis of N-(2-(5-bromo-2-fluorophenyl)-1-(4-(tert-butyldimethylsilyloxy)tetrahydro-2H-pyran-4-yl)propan-2-yl)-2-methylpropane-2-sulfinamide (22)

(Z)—N-(1-(5-Bromo-2-fluorophenyl)-2-(4-(tert-butyldimethylsilyloxy)tetrahydro-2H-pyran-4-yl)ethylidene)-2-methylpropane-2-sulfinamide (21, 2.2 g, 4.1 mmol) was dissolved in 20 mL of dry THF and stirred at −20° C. under nitrogen for 5 minutes, then CH₃MgBr (4.1 mL, 3M in ether, 12.3 mmol) was added dropwise. The resulting mixture was stirred at 0° C. for 1 hour. The reaction mixture was quenched with saturated aqueous NH₄Cl at 0° C., extracted with 2×80 mL of EtOAc, and the organic portion was dried, filtered and the filtrate concentrated under vacuum. The resulting material was purified by flash column chromatography (hexane/EtOAc 0-80%). Appropriate fractions were combined and concentrated under vacuum to provide the desired compound as a white solid (22, 1.1 g, 2.0 mmol).

Step 5—synthesis of N-(2-(5-bromo-2-fluorophenyl)-1-(4-hydroxytetrahydro-2H-pyran-4-yl)propan-2-yl)-2-methylpropane-2-sulfinamide (23)

N-(2-(5-Bromo-2-fluorophenyl)-1-(4-(tert-butyldimethylsilyloxy)tetrahydro-2H-pyran-4-yl)propan-2-yl)-2-methylpropane-2-sulfinamide (22, 1.3 g, 2.4 mmol) was dissolved in 8 mL of dry THF, then 7.1 mL of tetrabutylammonium fluoride (1N in THF) was added and the mixture stirred for 3 hours at room temperature. The reaction was diluted with 80 mL of EtOAc, then washed with saturated aqueous NH₄Cl, water and brine. The organic portion was dried, filtered and the filtrate concentrated under vacuum and the resulting material was purified by flash column chromatography (hexane/EtOAc 0-100%). Appropriate fractions were combined and concentrated under vacuum to provide the desired compound as a white solid (23, 1.0 g, 2.11 mmol).

Step 6—synthesis of 4-(2-amino-2-(5-bromo-2-fluorophenyl)propyl)tetrahydro-2H-pyran-4-ol (24)

N-(2-(5-Bromo-2-fluorophenyl)-1-(4-hydroxytetrahydro-2H-pyran-4-yl)propan-2-yl)-2-methylpropane-2-sulfinamide (23, 0.91 g, 2.09 mmol) was dissolved in 10 mL of dry CH₂Cl₂, and 15 mL of HCl (4N in dioxane) was added. The mixture was stirred at room temperature for 30 minutes, then concentrated under vacuum. The residue was dissolved in 80 mL of EtOAc, washed with saturated aqueous NaHCO₃, and the aqueous layer was extracted with 2×20 mL of EtOAc. The combined organic phase was washed with brine and dried over Na₂SO₄, filtered and the filtrate concentrated under vacuum to provide the desired compound (24, 690 mg, 2.08 mmol).

Step 7—synthesis of 4-(5-bromo-2-fluorophenyl)-4-methyl-1,9-dioxa-3-azaspiro[5.5]undec-2-en-2-amine (25)

4-(2-Amino-2-(5-bromo-2-fluorophenyl)propyl)tetrahydro-2H-pyran-4-ol (24, 690 mg, 2.05 mmol), and BrCN (435 mg, 4.1 mmol) were combined in 10 mL of dry EtOH and heated at 80° C. in a sealed-tube for 24 hours. The reaction mixture was diluted with 80 mL of EtOAc, washed with saturated aqueous NaHCO₃, and brine. The organic portion was dried, filtered and the filtrate concentrated under vacuum and the resulting material was purified by flash column chromatography (hexane/EtOAc 20-100%). Appropriate fractions were combined and concentrated under vacuum to provide the desired compound as a white solid (25, 0.3 g, 0.8 mmol).

Additional compounds are prepared following the methods of this example, wherein 1-(5-bromo-2-fluoro-phenyl) ethanone 17 is optionally replaced with a suitable (hetero) aryl ethanone and dihydro-2H-pyran-4(3H)-one 18 is optionally replaced with a suitable cyclic ketone in Step 1. In addition, 2-methylpropane-2-sulfinamide 2 is optionally replaced with the (S) or (R) isomer thereof, which under suitable conditions results a specific (S) or (R) isomer on the chiral ring carbon (e.g. the 4 position of compound 25). The following compounds were prepared by this method:
8-(4-bromothiophen-2-yl)-8-methyl-5-oxa-7-azaspiro[3.5]non-6-en-6-amine (26),
4-(4-bromothiophen-2-yl)-4-methyl-1,9-dioxa-3-azaspiro[5.5]undec-2-en-2-amine (27),
(S)-4-(4-bromothiophen-2-yl)-4-methyl-1,9-dioxa-3-azaspiro[5.5]undec-2-en-2-amine (28),
(R)-4-(4-bromothiophen-2-yl)-4-methyl-1,9-dioxa-3-azaspiro[5.5]undec-2-en-2-amine (29),
(S)-4-(4-bromo-5-methylthiophen-2-yl)-4-methyl-1,9-dioxa-3-azaspiro[5.5]undec-2-en-2-amine (30),
4-(4-bromothiophen-2-yl)-9,9-difluoro-4-methyl-1-oxa-3-azaspiro[5.5]undec-2-en-2-amine (31),
(S)-4-(4-bromothiophen-2-yl)-9,9-difluoro-4-methyl-1-oxa-3-azaspiro[5.5]undec-2-en-2-amine (32),
(S)-8-(5-bromo-2-fluorophenyl)-8-methyl-5-oxa-7-azaspiro[3.5]non-6-en-6-amine (33),
(R)-8-(5-bromo-2-fluorophenyl)-8-methyl-5-oxa-7-azaspiro[3.5]non-6-en-6-amine (34),
8-(5-bromo-2-fluorophenyl)-8-methyl-5-oxa-7-azaspiro[3.5]non-6-en-6-amine (35),
(S)-4-(5-bromo-2-fluorophenyl)-9,9-difluoro-4-methyl-1-oxa-3-azaspiro[5.5]undec-2-en-2-amine (36), and
(S)-4-(5-bromo-2-fluorophenyl)-4-methyl-1,9-dioxa-3-azaspiro[5.5]undec-2-en-2-amine (37).

The following table provides the compound number (column 1) and compounds used in Step 1 (column 2) to give the compound shown in column 3. An asterisk by the compound number indicates this was prepared using (S)-2-methylpropane-2-sulfinamide in Step 3 resulting in the (S) isomer in Step 4 as indicated in the structure of column 3. Two asterisks similarly indicate use of (R)-2-methylpropane-2-sulfinamide in Step 3 resulting in the (R) isomer in Step 4.

| Comp. number | Step 1 reactants | Structure |
|---|---|---|
| 26 | 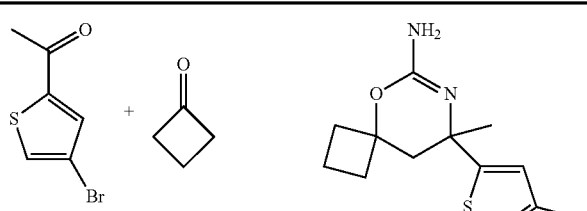 | 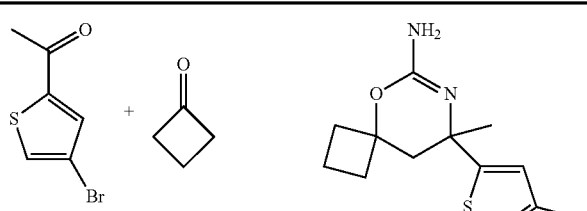 |

-continued
| Comp. number | Step 1 reactants | Structure |
|---|---|---|
| 27 | 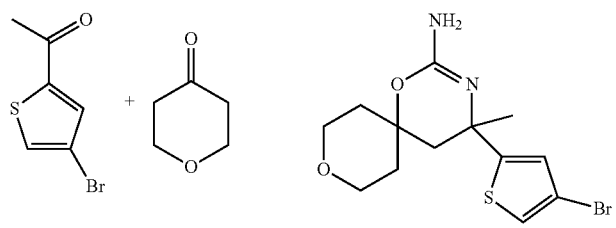 | 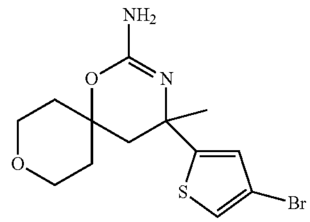 [SMILES: CC1(c2cc(Br)cs2)CC2(CCOCC2)OC(N)=N1] |
| 28* | | 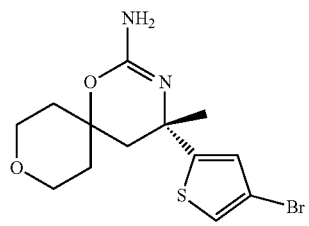 [SMILES: C[C@@]1(c2cc(Br)cs2)CC2(CCOCC2)OC(N)=N1] |
| 29** | | 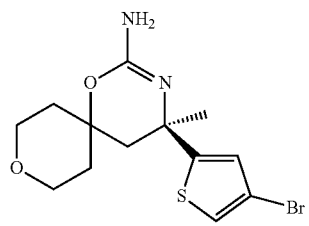 [SMILES: C[C@]1(c2cc(Br)cs2)CC2(CCOCC2)OC(N)=N1] |
| 30* | 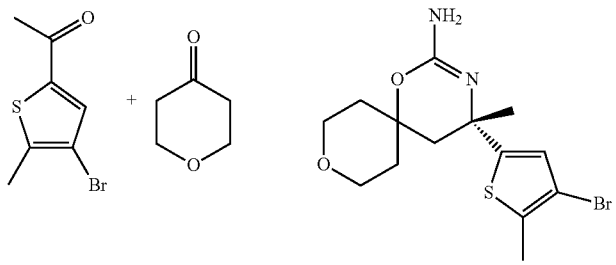 | 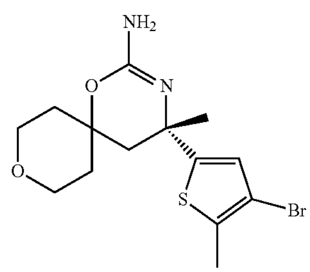 [SMILES: Cc1sc([C@]2(C)CC3(CCOCC3)OC(N)=N2)cc1Br] |
| 31 | 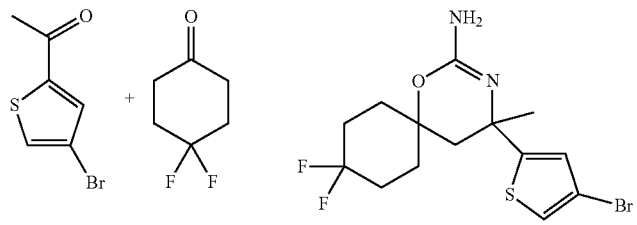 | 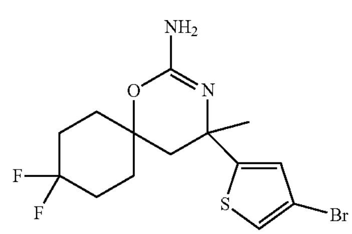 [SMILES: CC1(c2cc(Br)cs2)CC2(CCC(F)(F)CC2)OC(N)=N1] |
| 32* | | 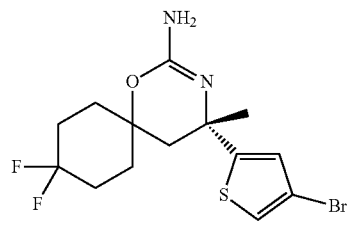 [SMILES: C[C@@]1(c2cc(Br)cs2)CC2(CCC(F)(F)CC2)OC(N)=N1] |

-continued
| Comp. number | Step 1 reactants | Structure |
|---|---|---|
| 33* | 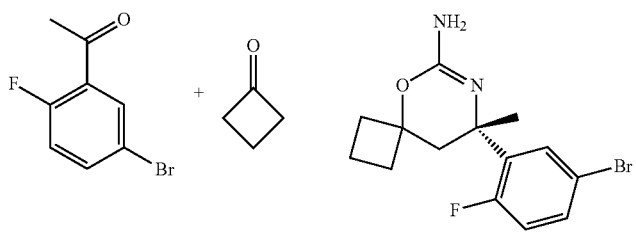 | 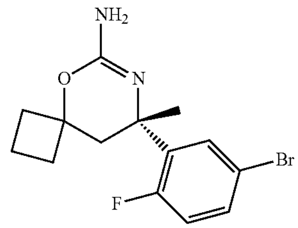 [SMILES: C[C@@]1(c2cc(Br)ccc2F)CC2(CCC2)OC(N)=N1] |
| 34** | | 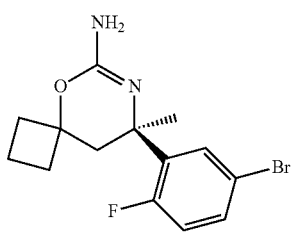 [SMILES: C[C@]1(c2cc(Br)ccc2F)CC2(CCC2)OC(N)=N1] |
| 35 | | 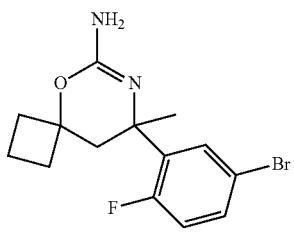 [SMILES: CC1(c2cc(Br)ccc2F)CC2(CCC2)OC(N)=N1] |
| 36* | 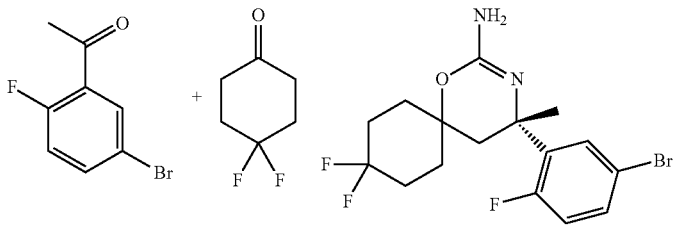 | 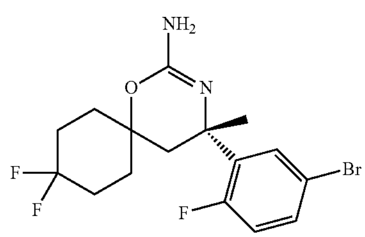 [SMILES: C[C@@]1(c2cc(Br)ccc2F)CC2(CCC(F)(F)CC2)OC(N)=N1] |
| 37* | 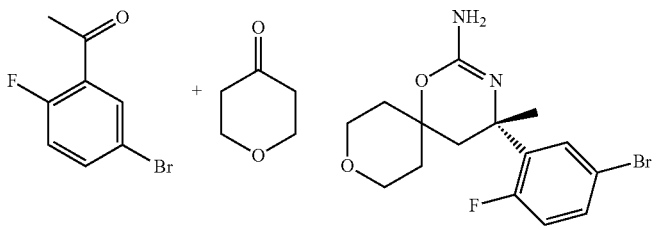 | 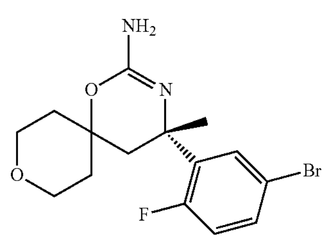 [SMILES: C[C@@]1(c2cc(Br)ccc2F)CC2(CCOCC2)OC(N)=N1] |

Example 3

Synthesis of 4-(5-bromo-2-fluorophenyl)-4-methyl-1-thia-3-azaspiro[5.5]undec-2-en-2-amine (48)

4-(5-Bromo-2-fluorophenyl)-4-methyl-1-thia-3-azaspiro[5.5]undec-2-en-2-amine 48 was prepared from cyclohex-1-enecarboxylic acid 38 in nine Steps as follows:

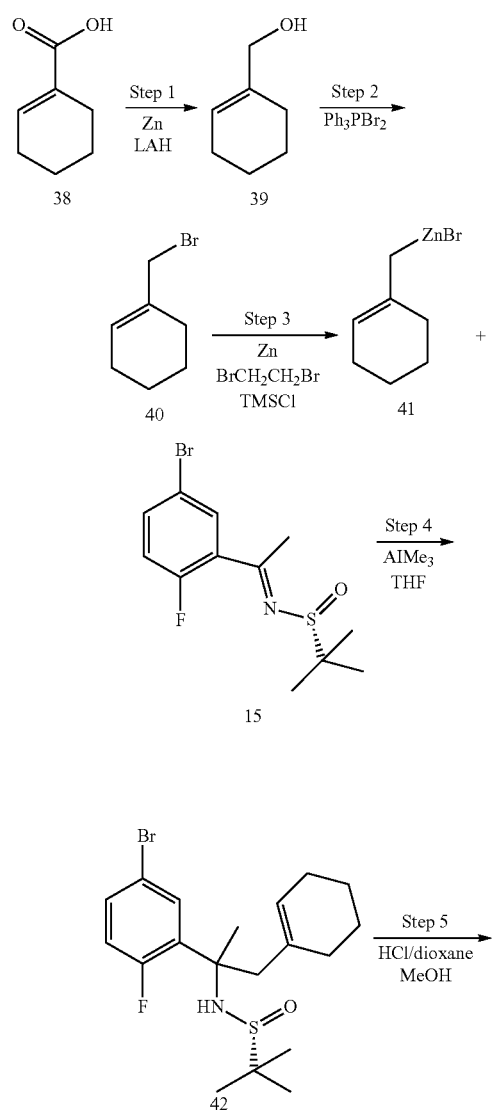

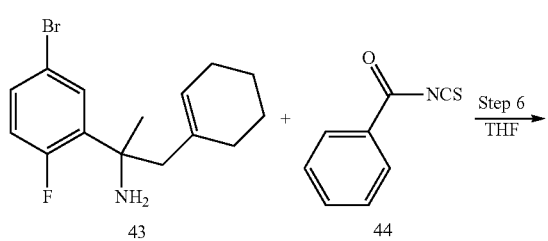

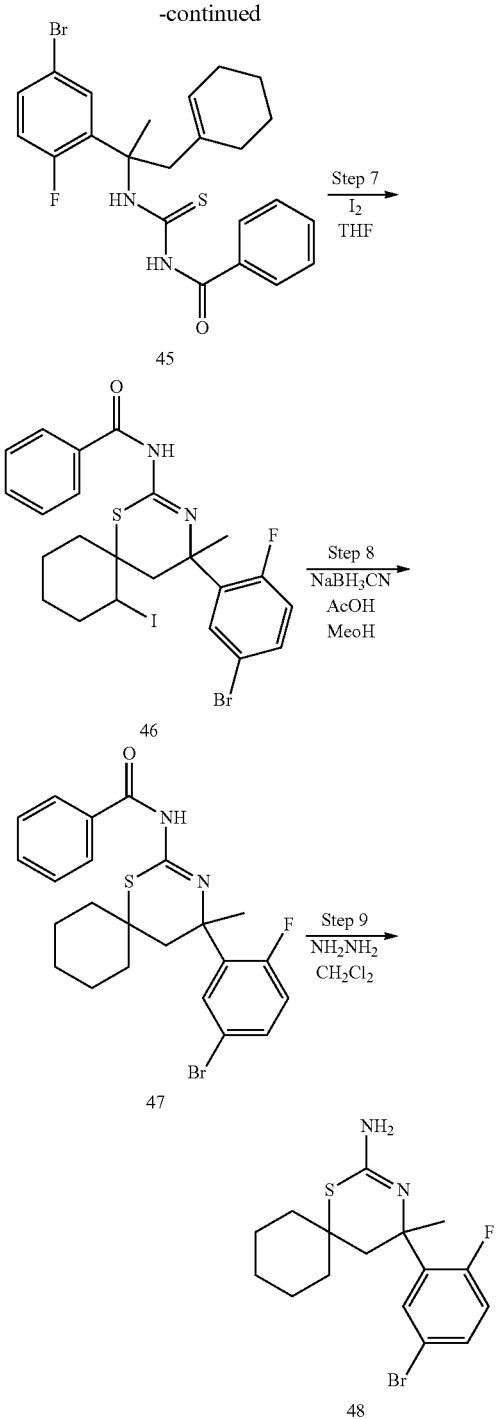

Step 1—Synthesis of Cyclohexenylmethanol (39)

Cyclohex-1-enecarboxylic acid (38, 2.9 g, 23 mmol) was dissolved in 50 mL of ether, then 28 mL of lithium aluminum hydride (1 M in THF, 28 mmol) was added dropwise under nitrogen. The mixture was heated at refluxing for 1 hour, then cooled to 0° C. and quenched with 4 mL of water, followed by 35 mL of aqueous 10% $H_2SO_4$. The organic phase was separated and the aqueous layer was extracted with 30 mL of ether. The combined organic portions were dried over Na$_2$SO$_4$, filtered and the filtrate concentrated under vacuum to provide the desired compound as a liquid (39, 2.6 g, 23 mmol).

Step 2—synthesis of 1-(bromomethyl)cyclohex-1-ene (40)

Dibromo(triphenyl)-phosphane (22 g, 53 mmol) was dissolved in 120 mL of dry CH$_2$Cl$_2$, cooled with an ice-water bath and a solution of cyclohexenylmethanol (39, 5.5 g, 49 mmol) in 10 mL of CH$_2$Cl$_2$ was added dropwise. The mixture was stirred at 0° C. for 3 hours, then 100 g silica-gel was added to the mixture, concentrated under vacuum and purified by flash column chromatography (100% hexane). Appropriate fractions were combined and concentrated under vacuum to provide the desired compound (40, 5.7 g, 33 mmol).

Step 3—synthesis of bromo(cyclohexen-1-ylmethyl)zinc (41)

Zinc dust (1.5 g, 22.8 mmol) was suspended in 10 mL of dry THF, and 1,2-dibromoethane (0.16 g, 0.85 mmol) was added to the suspension. The mixture was heated at 60° C. for 5 minutes, then cooled to room temperature and chloro(trimethyl)silane (0.1 g, 0.85 mmol) was added. The mixture was stirred at room temperature for 10 minutes, then a solution of 1-(bromomethyl)cyclohex-1-ene (40, 1 g, 5.7 mmol) in 2 mL of THF was added dropwise over 20 minutes. The resulting mixture was stirred at room temperature for 15 hours. The zinc was removed by filtration and the filtrate containing the desired compound 41 was used in the next step.

Step 4—synthesis of (R)—N-(2-(5-bromo-2-fluorophenyl)-1-cyclohexenylpropan-2-yl)-2-methylpropane-2-sulfinamide (42)

A solution of (R,E)-N-(1-(5-bromo-2-fluorophenyl)ethylidene)-2-methylpropane-2-sulfinamide (15, 0.5 g, 1.562 mmol) was dissolved in 3 mL of THF and cooled to −30° C., then AlMe$_3$ (0.9369 mL, 1.874 mmol) was added and the reaction was stirred for 30 minutes. Bromo(cyclohexen-1-ylmethyl)zinc (41, 6 mL, 3.123 mmol in THF) was added slowly and the reaction was stirred at −30° C. for 1 hour, then warmed to room temperature. The reaction mixture was diluted with EtOAc, and the resulting solution was washed with saturated aqueous NaHCO$_3$. The organic phase was dried with Na$_2$SO$_4$, filtered and the filtrate concentrated under vacuum to give a mixture of containing the desired compound 42. MS: 416.1 m/z (M+H)$^+$.

Step 5—synthesis of 2-(5-bromo-2-fluorophenyl)-1-cyclohexenylpropan-2-amine (43)

(R)—N-(2-(5-Bromo-2-fluorophenyl)-1-cyclohexenyl-propan-2-yl)-2-methylpropane-2-sulfinamide (42, 0.62 g, 1.489 mmol) was dissolved in 3 mL of MeOH and 3 mL of HCl (4N in dioxane) was added. The reaction was stirred at room temperature for 2 hours, then concentrated under vacuum and the residue re-dissolved in EtOAc. The resulting solution was washed with saturated aqueous NaHCO$_3$, and the organic phase was dried with Na$_2$SO$_4$, filtered and the filtrate concentrated under vacuum. The resulting material was purified by silica gel chromatography (ISCO, hexane/EtOAc 0-100%). Appropriate fractions were combined and concentrated under vacuum to provide the desired compound (43, 0.189 g, 0.6054 mmol, 40.66%). MS: 312.1 m/z (M+H)$^+$.

Step 6—synthesis of N-(2-(5-bromo-2-fluorophenyl)-1-cyclohexenylpropan-2-ylcarbamothioyl)benzamide (45)

2-(5-Bromo-2-fluorophenyl)-1-cyclohexenylpropan-2-amine (43, 0.185 g, 0.5926 mmol) was dissolved in THF and benzoyl isothiocyanate (44, 0.08704 g, 0.5333 mmol) was added. The reaction was stirred at room temperature for 1 hour, then concentrated under vacuum. The resulting material was purified by silica gel chromatography (ISCO, hexane/EtOAc 0-50%). Appropriate fractions were combined and concentrated under vacuum to provide the desired compound (45, 0.271 g, 0.5700 mmol, 96.20%). MS: 475.1 m/z (M+H)$^+$.

Step 7—synthesis of N-(4-(5-bromo-2-fluorophenyl)-7-iodo-4-methyl-1-thia-3-azaspiro[5.5]undec-2-en-2-yl)benzamide (46)

Iodine (0.2883 g, 1.136 mmol) was added to a solution of N-(2-(5-bromo-2-fluorophenyl)-1-cyclohexenylpropan-2-ylcarbamothioyl)benzamide (45, 0.27 g, 0.5679 mmol) in 2 mL of THF and the resulting solution was stirred at room temperature for 3 hours. The reaction was diluted with EtOAc and washed with 1 N aqueous Na$_2$SO$_3$. The organic phase was dried with Na$_2$SO$_4$, filtered and the filtrate concentrated under vacuum. The resulting material was purified by silica gel chromatography (ISCO, hexane/EtOAc 0-50%). Appropriate fractions were combined and concentrated under vacuum to provide the desired compound (46, 0.32 g, 0.5322 mmol, 93.70%). MS: 600.9 m/z (M+H)$^+$.

Step 8—synthesis of N-(4-(5-bromo-2-fluorophenyl)-4-methyl-1-thia-3-azaspiro[5.5]undec-2-en-2-yl)benzamide (47)

Sodium cyanoborohydride (0.09144 g, 1.455 mmol) was added to a solution of N-(4-(5-bromo-2-fluorophenyl)-7-iodo-4-methyl-1-thia-3-azaspiro[5.5]undec-2-en-2-yl)benzamide (46, 0.175 g, 0.2910 mmol) in 3 mL of MeOH and HOAc (0.03495 g, 0.5821 mmol) and the resulting mixture was stirred at room temperature for 18 hours. A further addition of sodium cyanoborohydride (0.09144 g, 1.455 mmol) was made and the reaction was stirred for another 6 hours. The mixture was concentrated under vacuum and the residue was re-dissolved in EtOAc and washed with saturated NaHCO$_3$. The organic phase was dried with Na$_2$SO$_4$, filtered and the filtrate concentrated under vacuum. The resulting material was purified by silica gel chromatography (ISCO, hexane/EtOAc 0-100%). Appropriate fractions were combined and concentrated under vacuum to provide the desired compound (47, 0.105 g, 0.2209 mmol, 75.89%). MS: 475.0 m/z (M+H)$^+$.

Step 9—synthesis of 4-(5-bromo-2-fluorophenyl)-4-methyl-1-thia-3-azaspiro[5.5]undec-2-en-2-amine (48)

Hydrazine (0.1416 g, 4.417 mmol) was added to a solution of N-(4-(5-bromo-2-fluorophenyl)-4-methyl-1-thia-3-azaspiro[5.5]undec-2-en-2-yl)benzamide (47, 0.105 g, 0.2209 mmol) in 1 mL of CH$_2$Cl$_2$ and the resulting solution was stirred at room temperature for 18 hours. The mixture was diluted with CH$_2$Cl$_2$ and washed with brine. The organic phase was dried with Na$_2$SO$_4$, filtered and the filtrate concentrated under vacuum. The resulting material was purified by silica gel chromatography (ISCO, hexane/EtOAc 0-100%). Appropriate fractions were combined and concentrated under vacuum to provide the desired compound (48, 0.08 g, 0.2155 mmol, 97.55%). MS: 371.0 m/z (M+H)$^+$.

Additional compounds are prepared following the methods of this example, wherein cyclohex-1-enecarboxylic acid 38 is optionally replaced with cyclobut-1-enecarboxylic acid in Step 1 and (R,E)-N-(1-(5-bromo-2-fluorophenyl)ethylidene)-2-methylpropane-2-sulfinamide 15 is optionally replaced with a suitable sulfinamide in Step 4. When the (S) or (R) isomer of the sulfonamide compound is used under suitable conditions, Step 5 results in the (S) or (R) isomer on the chiral ring carbon (e.g. the 4 position of compound 48). The following compounds were prepared by this method:

(R)-8-(5-bromo-2-fluorophenyl)-8-methyl-5-thia-7-azaspiro[3.5]non-6-en-6-amine (49),
(S)-8-(5-bromo-2-fluorophenyl)-8-methyl-5-thia-7-azaspiro[3.5]non-6-en-6-amine (50),
(4S)-4-(3-bromothiophen-2-yl)-7,7,8,8,9,9,10,10,11-nonadeutero-4-methyl-1-thia-3-azaspiro[5.5]undec-2-en-2-amine (51), and
(S)-4-(5-bromo-2-fluorophenyl)-4-methyl-1-thia-3-azaspiro[5.5]undec-2-en-2-amine (52).

The following table provides the compound number (column 1), compound used in Step 1 (column 2), and compound used in Step 4 (column 3) to give the compound shown in column 4.

Example 4

Synthesis of 8-(4-bromothiophen-2-yl)-8-methyl-2-oxa-5-thia-7-azaspiro[3.5]non-6-en-6-amine (63)

8-(4-Bromothiophen-2-yl)-8-methyl-2-oxa-5-thia-7-azaspiro[3.5]non-6-en-6-amine 63 was prepared from 2-methylenepropane-1,3-diol 53 in nine Steps as follows:

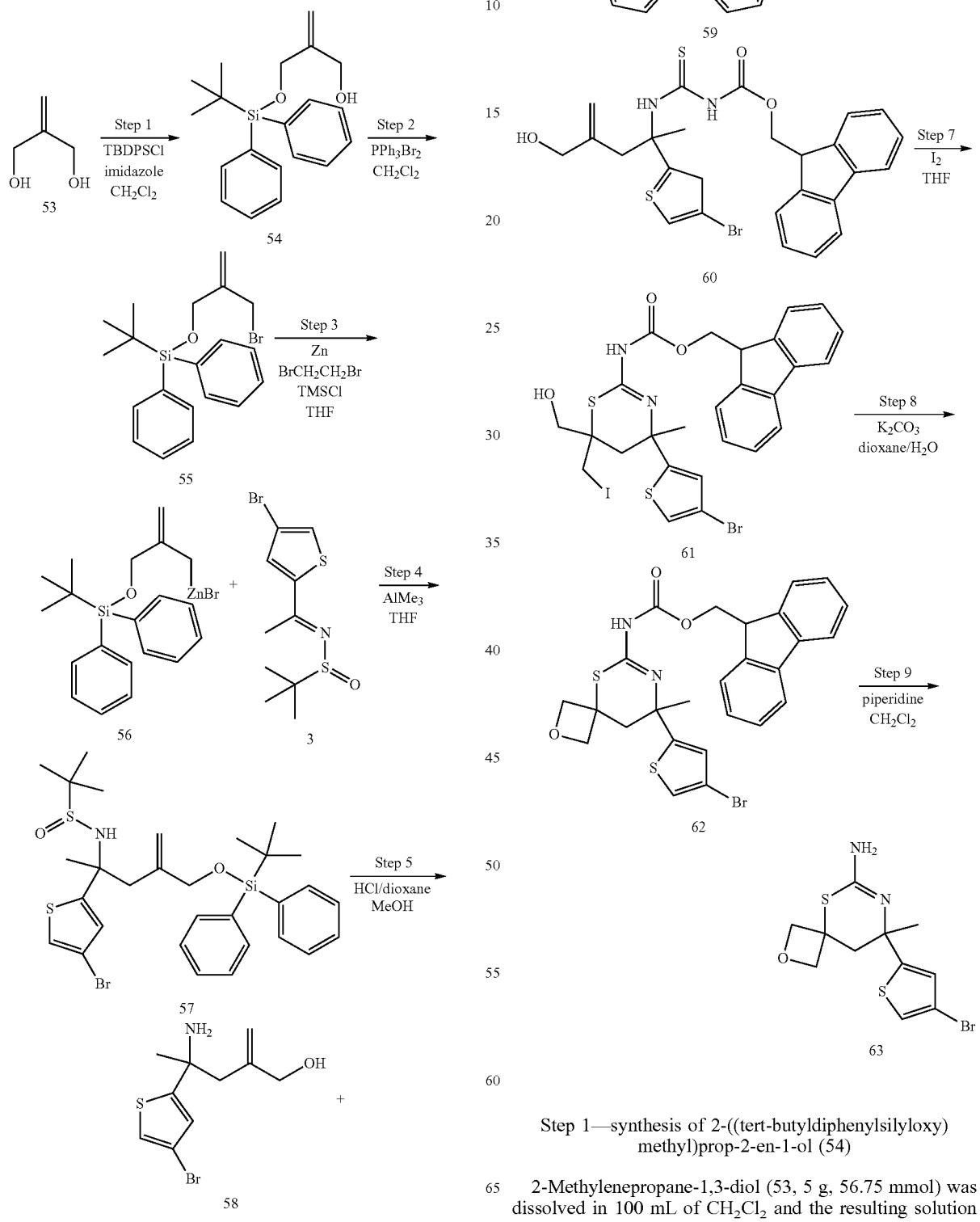

Step 1—synthesis of 2-((tert-butyldiphenylsilyloxy)methyl)prop-2-en-1-ol (54)

2-Methylenepropane-1,3-diol (53, 5 g, 56.75 mmol) was dissolved in 100 mL of $CH_2Cl_2$ and the resulting solution was cooled to 0° C. Imidazole (7.728 g, 113.5 mmol) was added followed by tert-butyl-chloro-diphenyl-silane (14.04 g, 13.07 mL, 51.08 mmol) and the resulting solution was stirred at room temperature for 18 hours. The reaction mixture was washed with water and the organic phase was dried with $Na_2SO_4$, filtered and the filtrate concentrated under vacuum. The resulting material was purified by silica gel chromatography (hexane/EtOAc 0-100%). Appropriate fractions were combined and concentrated under vacuum to provide the desired compound (54, 5.62 g, 17.2 mmol, 30.3%). MS: 349.1 m/z $(M+Na)^+$.

Step 2—synthesis of (2-(bromomethyl)allyloxy) (tert-butyl)diphenylsilane (55)

2-((tert-Butyldiphenylsilyloxy)methyl)prop-2-en-1-ol (54, 2.1 g, 6.4 mmol) was dissolved in 20 mL of $CH_2Cl_2$ and the resulting solution was cooled to 0° C. Triphenylphosphine dibromide (3.3 g, 7.7 mmol) was added and the resulting reaction was stirred for 2 hours after which the reaction mixture was washed with saturated aqueous $NaHCO_3$. The organic phase was dried with $Na_2SO_4$, filtered and the filtrate concentrated under vacuum. The resulting material was purified by silica gel chromatography (hexane). Appropriate fractions were combined and concentrated under vacuum to provide the desired compound (55, 2.3 g, 5.9 mmol, 92%).

Step 3—synthesis of bromo-[2-[[tert-butyl(diphenyl)silyl]oxymethyl]allyl]zinc (56)

Zinc (1.4 g, 22 mmol) was suspended in 5 mL of THF and 1,2-dibromoethane (0.15 g, 0.070 mL, 0.81 mmol) was added. The mixture was heated to 60° C. for 10 minutes then cooled to room temperature. Chloro(trimethyl)silane (0.088 g, 0.10 mL, 0.81 mmol) was added and the mixture was stirred at room temperature for 15 minutes. A solution of (2-(bromomethyl)allyloxy)(tert-butyl)diphenylsilane (55, 2.1 g, 5.4 mmol) in 5 mL of THF was added dropwise over 15 minutes and the resulting mixture was stirred at room temperature for 4 hours to give a 0.5 M solution of the desired compound 56.

Step 4—synthesis of N-(2-(4-bromothiophen-2-yl)-4-((tert-butyldiphenylsilyloxy)methyl)pent-4-en-2-yl)-2-methylpropane-2-sulfinamide (57)

(E)-N-(1-(4-Bromothiophen-2-yl)ethylidene)-2-methylpropane-2-sulfinamide (3, 0.12 g, 0.3892 mmol) was dissolved in 1 mL of THF and the resulting solution was cooled to −30° C. Trimethylaluminum (0.2335 mL, in toluene 0.4670 mmol) was added slowly and the resulting solution was stirred at −30° C. for 15 minutes. Bromo-[2-[[tert-butyl (diphenyl)silyl]oxymethyl]allyl]zinc (56, 2 mL, 0.7785 mmol) in THF was added slowly and resulting solution was stirred at −30° C. for 1 hour and then warmed to room temperature. After stirring at room temperature for 1 hour, the reaction was diluted with EtOAc and washed with saturated aqueous $NaHCO_3$. The organic phase was dried with $Na_2SO_4$, filtered and the filtrate concentrated under vacuum and the residue was purified by silica gel chromatography (hexane/EtOAc 0-100%). Appropriate fractions were combined and concentrated under vacuum to provide the desired compound (57, 0.192 g, 0.3103 mmol, 79.72%). MS: 640.1 m/z $(M+Na)^+$.

Step 5—synthesis of 4-amino-4-(4-bromothiophen-2-yl)-2-methylenepentan-1-ol (58)

HCl (10 mL, 40 mmol, 4 N in dioxane) was added to a solution of N-(2-(4-bromothiophen-2-yl)-4-((tert-butyldiphenylsilyloxy)methyl)pent-4-en-2-yl)-2-methylpropane-2-sulfinamide (57, 2.42 g, 3.91 mmol) in 10 mL of MeOH and the resulting solution was stirred at room temperature for 2 hours. The solution was diluted with $CH_2Cl_2$ and washed with saturated aqueous $NaHCO_3$. The organic phase was dried with $Na_2SO_4$, filtered and the filtrate concentrated under vacuum to provide the desired compound (58, 0.696 g, 2.520 mmol, 64.4%). MS: 258.9 m/z $(M-NH_2)^+$.

Step 6—synthesis of 9H-fluoren-9-ylmethyl N-[[1-(4-bromo-2-thienyl)-3-(hydroxymethyl)-1-methyl-but-3-enyl]carbamothioyl]carbamate (60)

O-(9H-fluoren-9-yl)methyl carbonisothiocyanatidate (59, 0.7028 g, 2.4983 mmol) was added to a solution of 4-amino-4-(4-bromothiophen-2-yl)-2-methylenepentan-1-ol (58, 0.69 g, 2.4983 mmol) in 5 mL of THF and the resulting solution was stirred at room temperature for 1 hour. The reaction mixture was diluted with EtOAc and washed with water. The organic phase was dried with $Na_2SO_4$, filtered and the filtrate concentrated under vacuum. The resulting material was purified by silica gel chromatography (hexane/EtOAc 0-100%). Appropriate fractions were combined and concentrated under vacuum to provide the desired compound (60, 0.725 g, 1.300 mmol, 52.05%). MS: 578.9 m/z $(M+Na)^+$.

Step 7—synthesis of (9H-fluoren-9-yl)methyl 4-(4-bromothiophen-2-yl)-6-(hydroxymethyl)-6-(iodomethyl)-4-methyl-5,6-dihydro-4H-1,3-thiazin-2-ylcarbamate (61)

Iodine (0.3770 g, 1.485 mmol) was added to a solution of 9H-fluoren-9-ylmethyl N-[[1-(4-bromo-2-thienyl)-3-(hydroxymethyl)-1-methyl-but-3-enyl]carbamothioyl]carbamate (60, 0.69 g, 1.238 mmol) in 6 mL of THF and the resulting solution was stirred at room temperature for 4 hours. The reaction mixture was diluted with EtOAc and washed with 1N aqueous $Na_2SO_3$. The organic phase was dried with $Na_2SO_4$, filtered and the filtrate concentrated under vacuum and the residue was purified by silica gel chromatography (hexane/EtOAc 0-100%). Appropriate fractions were combined and concentrated under vacuum to provide the desired compound (61, 0.652 g, 0.9541 mmol, 77.08%). MS: 683.9 m/z $(M+H)^+$.

Step 8—synthesis of (9H-fluoren-9-yl)methyl 8-(4-bromothiophen-2-yl)-8-methyl-2-oxa-5-thia-7-azaspiro[3.5]non-6-en-6-ylcarbamate (62)

Potassium carbonate (0.08899 g, 0.6438 mmol) was added to a solution of (9H-fluoren-9-yl)methyl 4-(4-bromothiophen-2-yl)-6-(hydroxymethyl)-6-(iodomethyl)-4-methyl-5,6-dihydro-4H-1,3-thiazin-2-ylcarbamate (61, 0.22 g, 0.3219 mmol) in 2 mL of dioxane and 0.2 mL of water and the resulting solution was stirred at room temperature for 18 hours. The reaction mixture was diluted with EtOAc and washed with water. The organic phase was dried with $Na_2SO_4$, filtered and the filtrate concentrated under vacuum to give the desired compound (62, 0.152 g, 0.2736 mmol, 85.00%). MS: 555.1 m/z $(M+H)^+$.

Step 9—synthesis of 8-(4-bromothiophen-2-yl)-8-methyl-2-oxa-5-thia-7-azaspiro[3.5]non-6-en-6-amine (63)

(9H-fluoren-9-yl)methyl 8-(4-bromothiophen-2-yl)-8-methyl-2- oxa-5-thia-7-azaspiro[3.5]non-6-en-6-ylcarbamate (62, 0.12 g, 0.2160 mmol) was dissolved in $CH_2Cl_2$ and piperidine (0.09197 g, 1.080 mmol) was added. The reaction mixture was stirred at room temperature for 4 hours, then concentrated under vacuum and the residue purified by silica gel chromatography (hexane/EtOAc 0-100%). Appropriate fractions were combined and concentrated under vacuum and the resulting material was further purified by HPLC. Appropriate fractions were combined and concentrated under vacuum to give the desired compound (63, 0.025 g, 0.07501 mmol, 34.72%). MS: 333.0 m/z $(M+H)^+$. $^1$H NMR (400 MHz, $CD_3OD$) δ: 7.44 (d, J=1.4 Hz, 1H), 7.11 (d, J=1.4 Hz, 1H), 3.71 (d, J=10.3 Hz, 1H), 3.35 (m, 3H), 2.55 (s, 2H), 1.79 (s, 3H).

(S)-8-(5-bromo-2-fluorophenyl)-8-methyl-2-oxa-5-thia-7-azaspiro[3.5]non-6-en-6-amine 64,

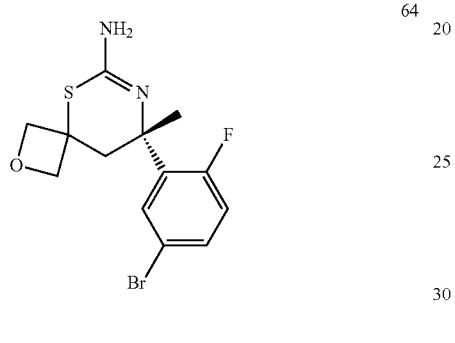

was prepared by this method, replacing (E)-N-(1-(4-bromothiophen-2-yl)ethylidene)-2-methylpropane-2-sulfinamide 3 with (S,E)-N-(1-(5-bromo-2-fluorophenyl)ethylidene)-2-methylpropane-2-sulfinamide 13 in Step 4.

Example 5

Synthesis of 4-(5-bromo-2-fluorophenyl)-4-methyl-9-oxa-1-thia-3-azaspiro[5.5]undec-2-en-2-amine (71)

4-(5-Bromo-2-fluorophenyl)-4-methyl-9-oxa-1-thia-3-azaspiro[5.5]undec-2-en-2-amine 71 was prepared from 1-(5-bromo-2-fluorophenyl)-2-(4-hydroxytetrahydro-2H-pyran-4-yl)ethanone 19 (prepared as described in Example 2) and (4-methoxyphenyl)methanethiol 65 in six Steps as follows:

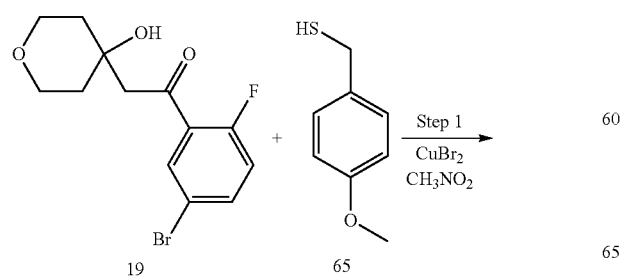

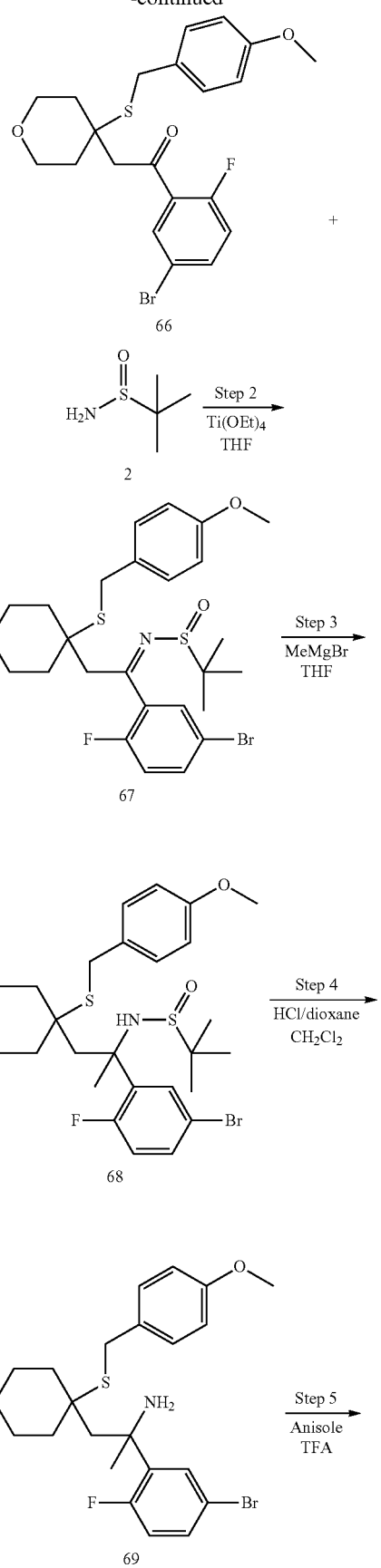

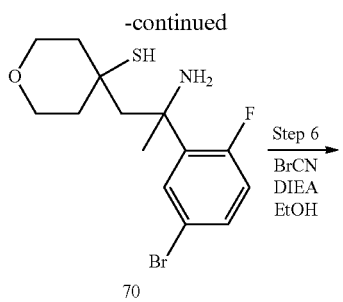

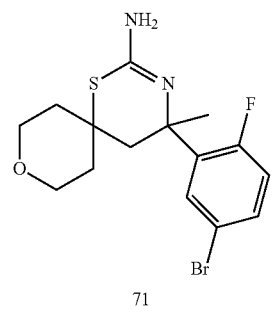

Step 1—synthesis of 1-(5-bromo-2-fluorophenyl)-2-(4-(4-methoxybenzylthio)tetrahydro-2H-pyran-4-yl)ethanone (66)

1-(5-Bromo-2-fluorophenyl)-2-(4-hydroxytetrahydro-2H-pyran-4-yl)ethanone (19, 550 mg, 1.73 mmol) and (4-methoxyphenyl)methanethiol (65, 802 mg, 5.2 mmol) were combined in 10 mL of dry $CH_3NO_2$, and dibromocopper (39 mg, 0.17 mmol) was added. The resulting mixture was sonicated with Aquasonic (Model 50D) for 5 minutes. The reaction mixture was concentrated under vacuum and the residue was purified by flash column chromatography (hexane/EtOAc 0-20%). Appropriate fractions were combined and concentrated under vacuum to provide the desired compound (66, 770 mg, 1.70 mmol).

Step 2—synthesis of (Z)—N-(1-(5-bromo-2-fluorophenyl)-2-(4-(4-methoxybenzylthio)tetrahydro-2H-pyran-4-yl)ethylidene)-2-methylpropane-2-sulfinamide (67)

1-(5-Bromo-2-fluorophenyl)-2-(4-(4-methoxybenzylthio)tetrahydro-2H-pyran-4-yl)ethanone (66, 800 mg, 1.76 mmol), 2-methylpropane-2-sulfinamide (2, 535 mg, 4.41 mmol) and tetraethoxytitanium (2.4 g, 10.6 mmol) were combined in 12 mL of dry THF and heated at refluxing for overnight. The reaction was concentrated under vacuum and the residue dissolved in 150 mL of $CH_2Cl_2$, then the mixture was poured into 50 mL of ice-water and stirred for 5 minutes. The inorganic solid was removed by filtration through a celite pad, then the solid was washed with 2×15 mL of $CH_2Cl_2$. The organic phase was separated from the filtrate and washed with brine, dried and filtered and the filtrate concentrated under vacuum. The resulting material was purified by flash column chromatography (hexane/EtOAc 0-50%). Appropriate fractions were combined and concentrated under vacuum to provide the desired compound (67, 870 mg, 1.56 mmol).

Step 3—synthesis of N-(2-(5-bromo-2-fluorophenyl)-1-(4-(4-methoxybenzylthio)tetrahydro-2H-pyran-4-yl)propan-2-yl)-2-methylpropane-2-sulfinamide (68)

(Z)—N-(1-(5-Bromo-2-fluorophenyl)-2-(4-(4-methoxybenzylthio)tetrahydro-2H-pyran-4-yl)ethylidene)-2-methylpropane-2-sulfinamide (67, 1.1 g, 1.98 mmol) was dissolved in 20 mL of dry THF and stirred at −20° C. under nitrogen for 5 minutes, then $CH_3MgBr$ (5.27 mL, 3M in ether, 15.8 mmol) was added dropwise. The resulting mixture was stirred at −20° C. for 1 hour. The reaction mixture was quenched with saturated aqueous $NH_4Cl$ at 0° C., extracted with 2×80 mL of EtOAc, and the organic portion was dried, filtered and the filtrate concentrated under vacuum. The resulting material was purified by flash column chromatography (hexane/EtOAc 0-80%). Appropriate fractions were combined and concentrated under vacuum to provide the desired compound as an oil (68, 335 mg, 0.58 mmol).

Step 4—synthesis of 2-(5-bromo-2-fluorophenyl)-1-(4-(4-methoxybenzylthio)tetrahydro-2H-pyran-4-yl)propan-2-amine (69)

N-(2-(5-Bromo-2-fluorophenyl)-1-(4-(4-methoxybenzylthio)tetrahydro-2H-pyran-4-yl)propan-2-yl)-2-methylpropane-2-sulfinamide (68, 335 mg, 0.58 mmol) was dissolved in 3 mL of dry $CH_2Cl_2$, and 1 mL of HCl (4N in dioxane) was added. The mixture was stirred at room temperature for 30 minutes, then concentrated under vacuum. The residue was dissolved in 50 mL of EtOAc, washed with saturated aqueous $NaHCO_3$, and the aqueous layer was extracted with 2×20 mL of EtOAc. The combined organic phase was washed with brine and dried over $Na_2SO_4$, filtered and the filtrate concentrated under vacuum to provide the desired compound (69, 270 mg, 0.57 mmol).

Step 5—synthesis of 4-(2-amino-2-(5-bromo-2-fluorophenyl)propyl)tetrahydro-2H-pyran-4-thiol (70)

2-(5-Bromo-2-fluorophenyl)-1-(4-(4-methoxybenzylthio)tetrahydro-2H-pyran-4-yl)propan-2-amine (69, 270 mg, 0.57 mmol) and anisole (187 mg, 1.73 mmol) were combined in 6 mL TFA and heated at 90° C. in a sealed tube for 3 hours. The reaction mixture was concentrated under vacuum and the resulting material was purified by HPLC (acetonitrile/water with 0.1% TFA). Appropriate fractions were combined and concentrated under vacuum to provide the desired compound as a TFA salt (70, 220 mg, 0.47 mmol).

Step 6—synthesis of 4-(5-bromo-2-fluorophenyl)-4-methyl-9-oxa-1-thia-3-azaspiro[5.5]undec-2-en-2-amine (71)

4-(2-amino-2-(5-bromo-2-fluorophenyl)propyl)tetrahydro-2H-pyran-4-thiol (70, 90 mg, 0.26 mmol), BrCN (27.5 mg, 0.26 mmol), and N-ethyl-N-isopropyl-propan-2-amine (40 mg, 0.31 mmol) were combined in 2 mL of dry EtOH and flushed with nitrogen. The mixture was stirred at room temperature for 1 hour, then heated at 75° C. in a sealed tube for 6 hours. The reaction mixture was diluted with 25 mL of EtOAc, washed with saturated aqueous $NaHCO_3$, and brine and the organic portion was dried, filtered and concentrated under vacuum. The resulting material was purified by flash column chromatography (hexane/EtOAc 20-100%). Appropriate fractions were combined and concentrated under vacuum to provide the desired compound as a white solid (71, 70 mg, 0.18 mmol).

4-(4-bromothiophen-2-yl)-4-methyl-9-oxa-1-thia-3-azaspiro[5.5]undec-2-en-2-amine 72,

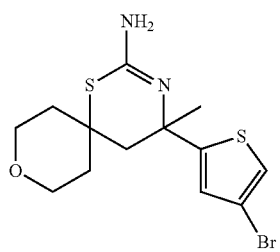

72 was prepared following the methods of this example, where 1-(5-bromo-2-fluorophenyl)-2-(4-hydroxytetrahydro-2H-pyran-4-yl)ethanone 19 is replaced with 1-(4-bromothiophen-2-yl)-2-(4-hydroxytetrahydro-2H-pyran-4-yl)ethanone (prepared by the methods of Example 2, isolated after Step 1 in the preparation of 4-(4-bromothiophen-2-yl)-4-methyl-1,9-dioxa-3-azaspiro[5.5]undec-2-en-2-amine 27.

(S)-4-(5-bromo-2-fluorophenyl)-4-methyl-9-oxa-1-thia-3-azaspiro[5.5]undec-2-en-2-amine 73, and (R)-4-(5-bromo-2-fluorophenyl)-4-methyl-9-oxa-1-thia-3-azaspiro[5.5]undec-2-en-2-amine 74

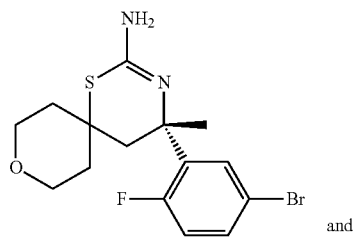

73 and

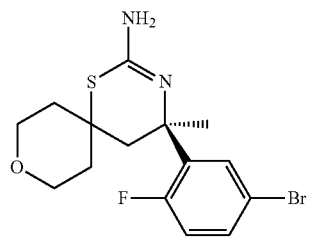

74 were prepared following the methods of this example, where 2-methylpropane-2-sulfinamide 2 is replaced with either the (S) or (R) isomer thereof in Step 2, respectively, resulting in the (S) or (R) isomer, respectively, on the chiral carbon generated in step 3.

Example 6

Synthesis of (S)-7-(5-bromo-2-fluorophenyl)-7-methyl-4-oxa-6-azaspiro[2.5]oct-5-en-5-amine (86)

(S)-7-(5-bromo-2-fluorophenyl)-7-methyl-4-oxa-6-azaspiro[2.5]oct-5-en-5-amine 86 was prepared from ethyl 3-(5-bromo-2-fluorophenyl)-3-oxopropanoate 75 and ethane-1,2-diol 76 in nine Steps as follows:

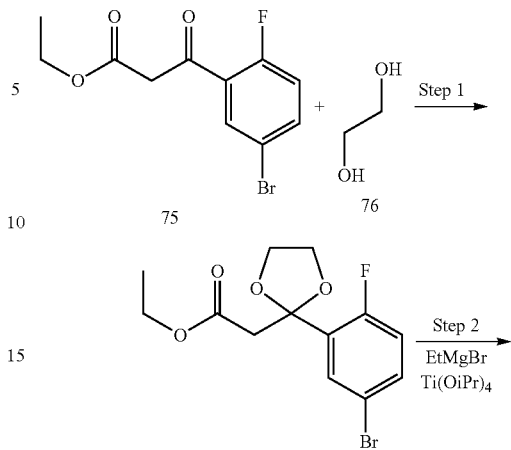

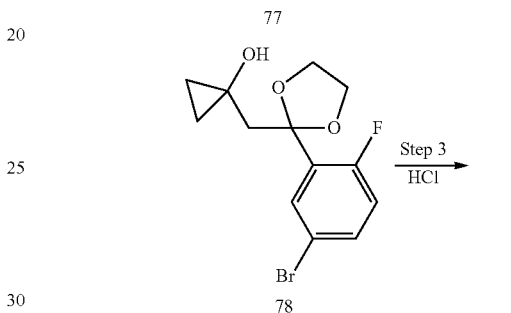

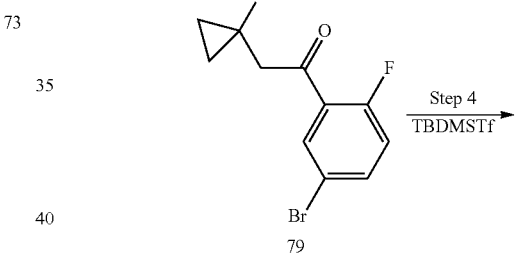

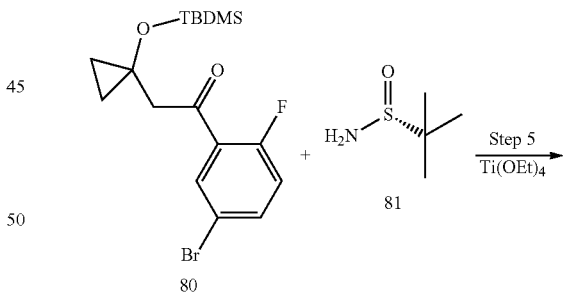

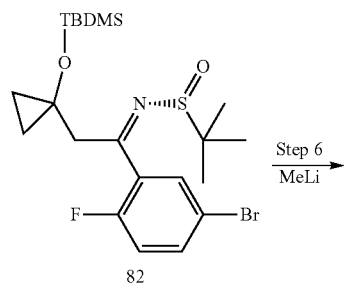

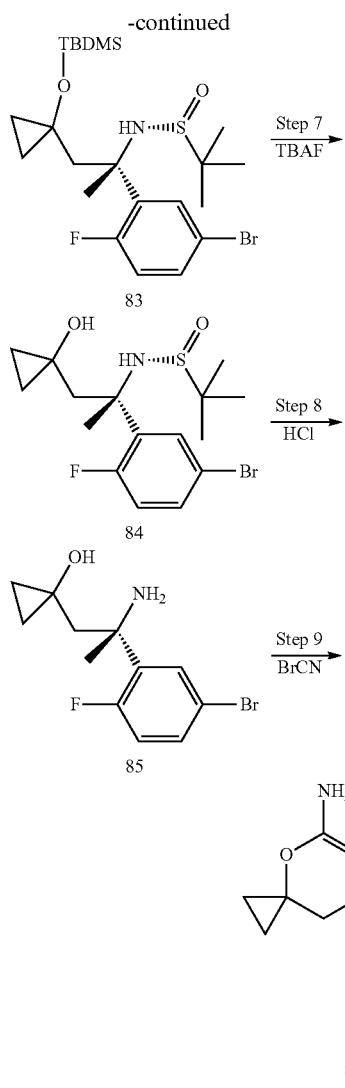

Step 1—synthesis of ethyl 2-(2-(5-bromo-2-fluorophenyl)-1,3-dioxolan-2-yl)acetate (77)

Ethyl 3-(5-bromo-2-fluorophenyl)-3-oxopropanoate (75, 6 g, 20.75 mmol) was dissolved in 100 mL of toluene, then ethane-1,2-diol (76, 7.72 g, 124.2 mmol) and p-toluenesulfonic acid (285 mg, 1.66 mmol) were added. The resulting mixture was heated at refluxing by using Dean-Stark apparatus to remove water. After 5 hours, the reaction mixture was diluted with 100 mL of EtOAc, washed with saturated aqueous $NaHCO_3$, water and brine. The organic portion was dried, filtered and the filtrate concentrated under vacuum and the residue purified by flash column chromatography (hexane/EtOAc 0-25%). Appropriate fractions were combined and concentrated under vacuum to provide the desired compound as an oil (77, 1.9 g, 5.1 mmol).

Step 2—synthesis of 1-((2-(5-bromo-2-fluorophenyl)-1,3-dioxolan-2-yl)methyl)cyclopropanol (78)

Ethyl 2-(2-(5-bromo-2-fluorophenyl)-1,3-dioxolan-2-yl)acetate (77, 1.65 g, 4.95 mmol) was dissolved in 30 mL of THF and 10 mL of $Et_2O$, and tetraisopropoxytitanium (0.42 g, 1.49 mmol) was added. The mixture was stirred at 10° C. for 5 minutes, then $CH_3CH_2MgBr$ (5 mL, 3M in ether, 14.9 mmol) was added dropwise over 25 minutes and the resulting mixture was stirred at room temperature for 3 hours. The reaction mixture was quenched with saturated aqueous $NH_4Cl$ at 0° C., extracted with 2×50 mL of EtOAc, and the organic portion was dried, filtered and the filtrate concentrated under vacuum. The resulting material was purified by flash column chromatography (hexane/EtOAc 0-40%). Appropriate fractions were combined and concentrated under vacuum to provide the desired compound as a white solid (78, 1.45 g, 4.57 mmol).

Step 3—synthesis of 1-(5-bromo-2-fluorophenyl)-2-(1-hydroxycyclopropyl)ethanone (79)

1-((2-(5-Bromo-2-fluorophenyl)-1,3-dioxolan-2-yl)methyl)cyclopropanol (78, 1.45 g, 4.57 mmol) was dissolved in 40 mL of MeOH, and 1.5 mL of concentrated HCl was added. The mixture was stirred at room temperature for 24 hours. The reaction mixture was diluted with 150 mL of EtOAc, washed with 2×80 mL of water and brine, and the organic portion was dried, filtered and the filtrate concentrated under vacuum provide the desired compound as a white solid (79, 1.18 g, 4.32 mmol).

Step 4—synthesis of 1-(5-bromo-2-fluorophenyl)-2-(1-(tert-butyldimethylsilyloxy)cyclopropyl)ethanone (80)

tert-Butyldimethylsilyl triflate (1.34 g, 5.21 mmol) was added to a 0° C. solution of 1-(5-bromo-2-fluorophenyl)-2-(1-hydroxycyclopropyl)ethanone (79, 0.95 g, 3.48 mmol) and 2,6-lutidine (0.75 g, 7.0 mmol) in 15 mL of $CH_2Cl_2$. The mixture stood at 0° C. for 2 hour, followed by 3 hours at room temperature, then was poured into saturated aqueous $NaHCO_3$. The organic portion was separated, washed with aqueous 10% HCl, saturated $NaHCO_3$, and brine, then dried with $MgSO_4$, filtered and the filtrate concentrated under vacuum. The resulting material was purified by flash column chromatography (hexane/EtOAc 0-40%). Appropriate fractions were combined and concentrated under vacuum to provide the desired compound (80, 1.3 g, 3.4 mmol).

Step 5—synthesis of (R,Z)—N-(1-(5-bromo-2-fluorophenyl)-2-(1-(tert-butyldimethylsilyloxy)cyclopropyl)ethylidene)-2-methylpropane-2-sulfinamide (82)

1-(5-Bromo-2-fluorophenyl)-2-(1-(tert-butyldimethylsilyloxy)cyclopropyl)ethanone (80, 1.3 g, 3.4 mmol), (R)-2-methylpropane-2-sulfinamide (81, 1.2 g, 10 mmol) and tetraethoxytitanium (3.1 g, 13 mmol) were combined in 12 mL of dry THF and heated at refluxing for overnight. This was concentrated under vacuum and the residue was dissolved in 100 mL of $CH_2Cl_2$, then the mixture was poured into 100 mL of ice-water and stirred for 5 minutes. The inorganic solid was removed by filtration through a celite pad, then the solid was washed with 2×15 mL of $CH_2Cl_2$. The organic phase was separated from the filtrate and washed with brine, dried and filtered and the filtrate concentrated under vacuum. The resulting material was purified by flash column chromatography (hexane/EtOAc 0-50%). Appropriate fractions were combined and concentrated under vacuum to provide the desired compound (82, 1.4 g, 2.9 mmol).

Step 6—synthesis of (R)—N—((S)-2-(5-bromo-2-fluorophenyl)-1-(1-(tert-butyldimethylsilyloxy)cyclopropyl)propan-2-yl)-2-methylpropane-2-sulfinamide (83)

(R,Z)—N-(1-(5-Bromo-2-fluorophenyl)-2-(1-(tert-butyldimethylsilyloxy)cyclopropyl)ethylidene)-2-methylpropane-2-sulfinamide (82, 1.39 g, 2.83 mmol) was dissolved in 20 mL of dry THF and stirred at −20° C. under nitrogen for 5 minutes, then MeLi (2.3 mL, 1.6 M in ether, 3.68 mmol) was added dropwise. The resulting mixture was stirred at −20° C. for 1 hour. The reaction mixture was quenched with saturated aqueous NH₄Cl at 0° C., extracted with 2×80 mL of EtOAc, and the organic portion was dried, filtered and the filtrate concentrated under vacuum. The resulting material was purified by flash column chromatography (hexane/EtOAc 0-80%). Appropriate fractions were combined and concentrated under vacuum to provide the desired compound as a white solid (83, 0.25 g, 0.49 mmol).

Step 7—synthesis of (R)—N—((S)-2-(5-bromo-2-fluorophenyl)-1-(1-hydroxycyclopropyl)propan-2-yl)-2-methylpropane-2-sulfinamide (84)

(R)—N—((S)-2-(5-Bromo-2-fluorophenyl)-1-(1-(tert-butyldimethylsilyloxy)cyclopropyl)propan-2-yl)-2-methylpropane-2-sulfinamide (83, 0.25 g, 0.49 mmol) was dissolved in 3 mL of dry THF, then 1.5 mL of tetrabutylammonium fluoride (1N in THF) was added and the mixture stirred for 3 hours at room temperature. The reaction was diluted with 50 mL of EtOAc, then washed with saturated aqueous NH₄Cl, water and brine, and the organic portion was dried, filtered and the filtrate concentrated under vacuum. The resulting material was purified by flash column chromatography (hexane/EtOAc 0-100%). Appropriate fractions were combined and concentrated under vacuum to provide the desired compound as a white solid (84, 0.15 g, 0.38 mmol).

Step 8—synthesis of (S)-1-(2-amino-2-(5-bromo-2-fluorophenyl)propyl)cyclopropanol (85)

(R)—N—((S)-2-(5-Bromo-2-fluorophenyl)-1-(1-hydroxycyclopropyl)propan-2-yl)-2-methylpropane-2-sulfinamide (84, 0.15 g, 0.38 mmol) was dissolved in 4 mL of dry CH₂Cl₂, and 2 mL of HCl (4N in dioxane) was added. The mixture was stirred at room temperature for 30 minutes, then concentrated under vacuum. The residue was dissolved in 40 mL of EtOAc, washed with saturated aqueous NaHCO₃, and the aqueous layer was extracted with 2×10 mL of EtOAc. The combined organic phase was washed with brine and dried over Na₂SO₄, filtered and the filtrate concentrated under vacuum to provide the desired compound (85, 0.11 g, 0.38 mmol).

Step 9—synthesis of (S)-7-(5-bromo-2-fluorophenyl)-7-methyl-4-oxa-6-azaspiro[2.5]oct-5-en-5-amine (86)

(S)-1-(2-Amino-2-(5-bromo-2-fluorophenyl)propyl)cyclopropanol (85, 170 mg, 0.59 mmol), and BrCN (94 mg, 0.88 mmol) were combined in 5 mL of dry EtOH and heated at 60° C. in a sealed-tube for 24 hours. The reaction mixture was diluted with 50 mL of EtOAc, washed with saturated aqueous NaHCO₃, and brine and the organic portion was dried, filtered and the filtrate concentrated under vacuum. The resulting material was purified by flash column chromatography (hexane/EtOAc 20-100%). Appropriate fractions were combined and concentrated under vacuum to provide the desired compound as a white solid (86, 93 mg, 0.30 mmol).

Example 7

Synthesis of 4-(5-bromo-2-fluorophenyl)-5,5-difluoro-4-methyl-1,9-dioxa-3-azaspiro[5.5]undec-2-en-2-amine (94)

4-(5-bromo-2-fluorophenyl)-5,5-difluoro-4-methyl-1,9-dioxa-3-azaspiro[5.5]undec-2-en-2-amine 94 was prepared from 1-(5-bromo-2-fluorophenyl)-2,2,2-trifluoroethanone 87 in seven Steps as follows:

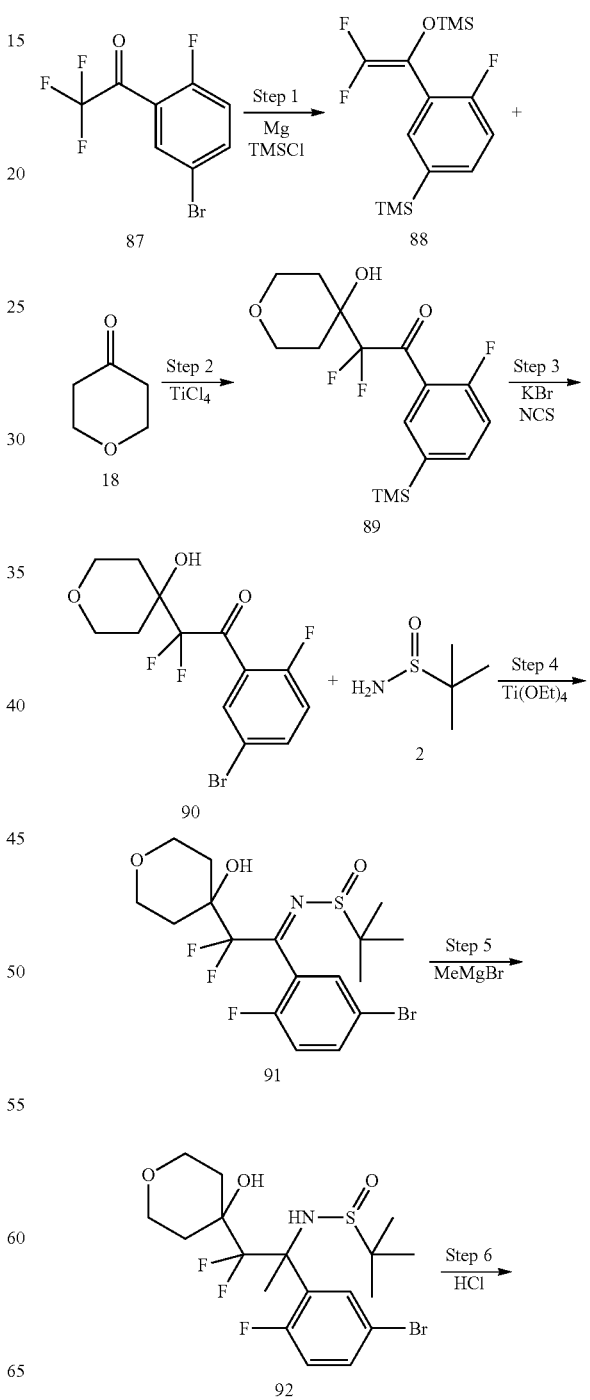

-continued

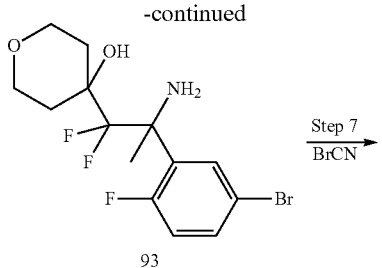

93

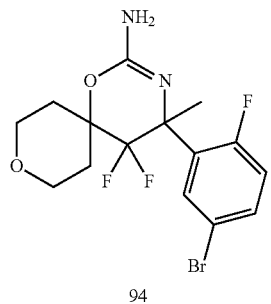 [SMILES: CC1(c2cc(Br)ccc2F)N=C(N)OC2(CCOCC2)C1(F)F]

94

Step 1—synthesis of (2,2-difluoro-1-(2-fluoro-5-(trimethylsilyl)phenyl)vinyloxy)trimethylsilane (88)

To a dry flask with 15 mL of dry THF, magnesium turning (0.4 g, 17 mmol) and chloro(trimethyl)silane (2.4 g, 22 mmol), were added and cooled down to 0° C. 1-(5-bromo-2-fluorophenyl)-2,2,2-trifluoroethanone (87, 1.5 g, 22 mmol) was added dropwise. After addition, the mixture was stirred for additional 2 hours at 0° C. The reaction was concentrated under vacuum, and the residue was suspended in 20 mL of dry $CH_2Cl_2$, and insoluble solid was removed with filtration through a celite pad. The filtrate solution containing compound 88 was used in the next step.

Step 2—synthesis of 2,2-difluoro-1-(2-fluoro-5-(trimethylsilyl)phenyl)-2-(4-hydroxytetrahydro-2H-pyran-4-yl)ethanone (89)

Tetrachlorotitanium (0.79 g, 4.1 mmol) was dissolved in 10 mL of dry $CH_2Cl_2$, then cooled to −78° C. under nitrogen. A solution of dihydro-2H-pyran-4(3H)-one (18, 0.83 g, 8.3 mmol) in 5 mL of dry $CH_2Cl_2$ was added dropwise. The mixture was stirred at −78° C. for 15 minutes, then a solution of (2,2-difluoro-1-(2-fluoro-5-(trimethylsilyl)phenyl)vinyloxy)trimethylsilane (88, 1.1 g, 3.5 mmol) in 15 mL $CH_2Cl_2$ was added dropwise. The resulting mixture was stirred at −78° C. for 4 hours, then at room temperature overnight. The reaction was quenched with 30 mL saturated $NH_4Cl$, extracted with 100 mL $CH_2Cl_2$, and the organic portion was dried, filtered and the filtrate concentrated under vacuum. The resulting material was purified by flash column chromatography (hexane/EtOAc 0-25%). Appropriate fractions were combined and concentrated under vacuum to provide the desired compound as a white solid (89, 0.48 g, 1.38 mmol).

Step 3—synthesis of 1-(5-bromo-2-fluorophenyl)-2,2-difluoro-2-(4-hydroxytetrahydro-2H-pyran-4-yl)ethanone (90)

2,2-Difluoro-1-(2-fluoro-5-(trimethylsilyl)phenyl)-2-(4-hydroxytetrahydro-2H-pyran-4-yl)ethanone (89, 0.45 g, 1.31 mmol) was dissolved in 8 mL of HOAc and 3 mL of MeOH and KBr (0.31 g, 2.62 mmol) was added. The mixture was stirred at 60° C. for 20 minutes, then 1-chloropyrrolidine-2,5-dione (0.28 g, 2.1 mmol) was added. The resulting mixture was stirred at 60° C. 15 hours. The reaction mixture was diluted with 60 mL of EtOAc, washed with 3×30 mL water and brine, and the organic portion was dried, filtered and the filtrate concentrated under vacuum. The resulting material was purified by flash column chromatography (hexane/EtOAc 0-40%). Appropriate fractions were combined and concentrated under vacuum to provide the desired compound as a white solid (90, 0.41 g, 1.16 mmol).

Step 4—synthesis of (E)-N-(1-(5-bromo-2-fluorophenyl)-2,2-difluoro-2-(4-hydroxytetrahydro-2H-pyran-4-yl)ethylidene)-2-methylpropane-2-sulfinamide (91)

1-(5-Bromo-2-fluorophenyl)-2,2-difluoro-2-(4-hydroxytetrahydro-2H-pyran-4-yl)ethanone (90, 0.35, 0.99 mmol), 2-methylpropane-2-sulfinamide (2, 0.3 g, 2.48 mmol) and tetraethoxytitanium (1.14 g, 5.0 mmol) were combined in 8 mL of dry THF and heated at refluxing for overnight. This was concentrated under vacuum and the residue was dissolved in 50 mL of $CH_2Cl_2$, then the mixture was poured into 40 mL of ice-water and stirred for 5 minutes. The inorganic solid was removed by filtration through a celite pad, then the solid was washed with 2×20 mL of $CH_2Cl_2$. The organic phase was separated from the filtrate and washed with brine, dried and filtered and the filtrate concentrated under vacuum. The resulting material was purified by flash column chromatography (hexane/EtOAc 0-50%). Appropriate fractions were combined and concentrated under vacuum to provide the desired compound (91, 0.304 g, 0.66 mmol).

Step 5—synthesis of N-(2-(5-bromo-2-fluorophenyl)-1,1-difluoro-1-(4-hydroxytetrahydro-2H-pyran-4-yl)propan-2-yl)-2-methylpropane-2-sulfinamide (92)

(E)-N-(1-(5-Bromo-2-fluorophenyl)-2,2-difluoro-2-(4-hydroxytetrahydro-2H-pyran-4-yl)ethylidene)-2-methylpropane-2-sulfinamide (91, 0.304 g, 0.66 mmol) was dissolved in 10 mL of dry THF and stirred at 0° C. under nitrogen for 5 minutes, then $CH_3MgBr$ (1.1 mL, 3M in ether, 3.3 mmol) was added dropwise. The resulting mixture was stirred at 0° C. for 2 hour. The reaction mixture was quenched with saturated aqueous $NH_4Cl$ at 0° C., extracted with 2×50 mL of EtOAc, and the organic portion was dried, filtered and the filtrate concentrated under vacuum. The resulting material was purified by flash column chromatography (hexane/EtOAc 0-80%). Appropriate fractions were combined and concentrated under vacuum to provide the desired compound as a white solid (92, 0.25 g, 0.53 mmol).

Step 6—synthesis of 4-(2-amino-2-(5-bromo-2-fluorophenyl)-1,1-difluoropropyl)tetrahydro-2H-pyran-4-ol (93)

N-(2-(5-Bromo-2-fluorophenyl)-1,1-difluoro-1-(4-hydroxytetrahydro-2H-pyran-4-yl)propan-2-yl)-2-methylpropane-2-sulfinamide (92, 0.25 g, 0.53 mmol) was dissolved in 2 mL of dry $CH_2Cl_2$, and 2 mL of HCl (4N in dioxane) was added. The mixture was stirred at room temperature for 30 minutes, then concentrated under vacuum. The residue was dissolved in 50 mL of EtOAc, washed with saturated aqueous NaHCO₃, and the aqueous layer was extracted with 2×20 mL of EtOAc. The combined organic phase was washed with brine and dried over Na₂SO₄, filtered and the filtrate concentrated under vacuum to provide the desired compound (93, 0.18 g, 0.51 mmol).

Step 7—synthesis of 4-(5-bromo-2-fluorophenyl)-5,5-difluoro-4-methyl-1,9-dioxa-3-azaspiro[5.5]undec-2-en-2-amine (94)

4-(2-Amino-2-(5-bromo-2-fluorophenyl)-1,1-difluoropropyl)tetrahydro-2H-pyran-4-ol (93, 190 mg, 0.516 mmol), and BrCN (164 mg, 1.55 mmol) were combined in 6 mL of dry EtOH and heated at 80° C. in a sealed-tube for 24 hours. The reaction mixture was diluted with 50 mL of EtOAc, washed with saturated aqueous NaHCO₃, and brine and the organic portion was dried, filtered and the filtrate concentrated under vacuum. The resulting material was purified by flash column chromatography (hexane/EtOAc 20-100%). Appropriate fractions were combined and concentrated under vacuum to provide the desired compound as a white solid (94, 118 g, 0.3 mmol).

Additional compounds are prepared following the methods of this example, wherein 1-(5-bromo-2-fluorophenyl)-2,2,2-trifluoroethanone 87 is optionally replaced with a suitable trifluoroethanone in Step 1 and dihydro-2H-pyran-4(3H)-one 18 is optionally replaced with a suitable cyclic ketone in Step 2. The (S) or (R) isomer of the 2-methylpropane-2-sulfinamide 2 is optionally used in Step 4, with the result that Step 5 provides a specific (S) or (R) isomer ultimately providing a specific isomer of the chiral ring carbon (e.g. the 4 position of compound 94). The following compounds were prepared by this method:

4-(4-bromothiophen-2-yl)-5,5-difluoro-4-methyl-1,9-dioxa-3-azaspiro[5.5]undec-2-en-2-amine (95),
(S)-4-(5-bromo-2-fluorophenyl)-5,5-difluoro-4-methyl-1,9-dioxa-3-azaspiro[5.5]undec-2-en-2-amine (96),
(R)-4-(5-bromo-2-fluorophenyl)-5,5-difluoro-4-methyl-1,9-dioxa-3-azaspiro[5.5]undec-2-en-2-amine (97),
8-(5-bromo-2-fluorophenyl)-9,9-difluoro-8-methyl-5-oxa-7-azaspiro[3.5]non-6-en-6-amine (98),
(S)-8-(5-bromo-2-fluorophenyl)-9,9-difluoro-8-methyl-5-oxa-7-azaspiro[3.5]non-6-en-6-amine (99), and
(R)-8-(5-bromo-2-fluorophenyl)-9,9-difluoro-8-methyl-5-oxa-7-azaspiro[3.5]non-6-en-6-amine (100).

The following table provides the compound number (column 1), compound used in Step 1 (column 2), and compound used in Step 2 (column 3) to give the compound shown in column 4. An asterisk by the compound number indicates the (S) isomer of 2-methylpropane-2-sulfinamide was used, while two asterisks indicated the (R) isomer was used.

| Comp. number | Step 1 | Step 2 | Structure |
|---|---|---|---|
| 95 | | | 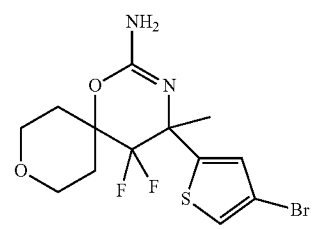 [SMILES: CC1(c2cc(Br)cs2)N=C(N)OC2(CCOCC2)C1(F)F] |
| 96** | | | 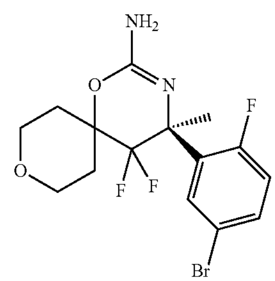 [SMILES: C[C@@]1(c2cc(Br)ccc2F)N=C(N)OC2(CCOCC2)C1(F)F] |
| 97* | | | 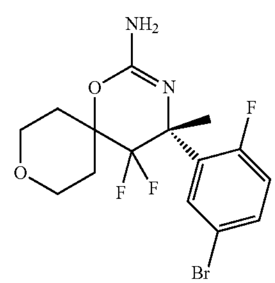 [SMILES: C[C@]1(c2cc(Br)ccc2F)N=C(N)OC2(CCOCC2)C1(F)F] |

-continued

| Comp. number | Step 1 | Step 2 | Structure |
|---|---|---|---|
| 98 | | | 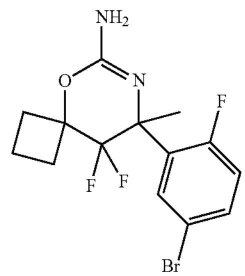 [SMILES: CC1(c2cc(Br)ccc2F)N=C(N)OC2(CCC2)C1(F)F] |
| 99** | | | 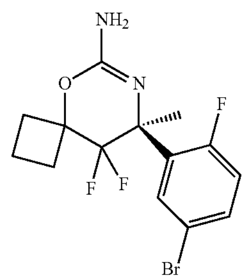 [SMILES: C[C@@]1(c2cc(Br)ccc2F)N=C(N)OC2(CCC2)C1(F)F] |
| 100* | | | 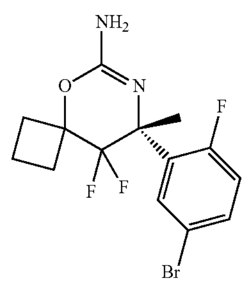 [SMILES: C[C@]1(c2cc(Br)ccc2F)N=C(N)OC2(CCC2)C1(F)F] |

Example 8

Synthesis of 4-methyl-4-(4-(5-(prop-1-ynyl)pyridin-3-yl)thiophen-2-yl)-1,9-dioxa-3-azaspiro[5.5]undec-2-en-2-amine (102)

4-Methyl-4-(4-(5-(prop-1-ynyl)pyridin-3-yl)thiophen-2-yl)-1,9-dioxa-3-azaspiro[5.5]undec-2-en-2-amine 102 was prepared from 4-(4-bromothiophen-2-yl)-4-methyl-1,9-dioxa-3-azaspiro[5.5]undec-2-en-2-amine 27 (prepared as described in Example 2) and 5-(prop-1-ynyl)pyridin-3-yl-boronic acid 101 in one Step as follows:

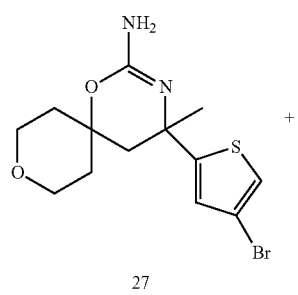

27

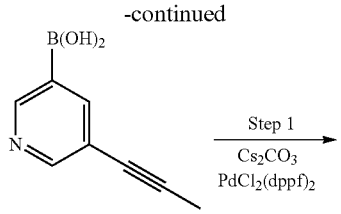

101

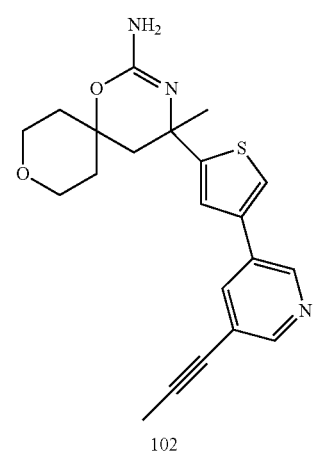

102

Step 1—synthesis of 4-methyl-4-(4-(5-(prop-1-ynyl)pyridin-3-yl)thiophen-2-yl)-1,9-dioxa-3-azaspiro[5.5]undec-2-en-2-amine (102)

4-(4-Bromothiophen-2-yl)-4-methyl-1,9-dioxa-3-azaspiro[5.5]undec-2-en-2-amine (27, 35 mg, 0.1 mmol), 5-(prop-1-ynyl)pyridin-3-ylboronic acid (101, 33 mg, 0.2 mmol), 1,1'-bis(diphenylphosphino)ferrocine palladium (II) dichloride (22 mg, 0.03 mmol) and Cs$_2$CO$_3$ (100 mg, 0.3 mmol) were combined in 2.5 mL of DME and 0.8 mL of water. The mixture was flushed with nitrogen for 2 minutes, then heated at 90° C. for 40 minutes. The mixture was diluted with 30 mL of EtOAc, washed with water and brine, and the organic phase was dried, filtered and the filtrate concentrated under vacuum. The resulting material was purified by HPLC (acetonitrile/water with 0.1% TFA). Appropriate fractions were combined and concentrated under vacuum to provide the desired compound as a di-TFA salt (102, 18 mg, 0.04 mmol). $^1$H NMR (400 MHz, CD$_3$OD) δ: 8.77 (s, 1H), 8.47 (s, 1H), 8.13 (s, 1H), 7.84 (d, 1H), 7.54 (d, 1H), 3.80-3.85 (m, 2H), 3.52-3.63 (m, 2H), 2.96 (d, 1H), 2.40 (d, 1H), 2.10 (s, 3H), 1.97-2.04 (m, 1H), 1.85-1.99 (m, 1H), 1.80 (s, 3H), 1.58-1.63 (m, 2H). MS: 382.1 m/z (M+H)$^+$.

Additional compounds are prepared following the methods of this example, wherein 4-(4-bromothiophen-2-yl)-4-methyl-1,9-dioxa-3-azaspiro[5.5]undec-2-en-2-amine 27 is optionally replaced with a suitable bromo-(hetero)aryl compound (prepared by the methods of Examples 2, 4, 5 or 7) and 5-(prop-1-ynyl)pyridin-3-ylboronic acid 101 is optionally replaced with a suitable boronic acid or boronic acid ester. The following compounds were prepared by this method:

8-methyl-8-(4-(5-(prop-1-ynyl)pyridin-3-yl)thiophen-2-yl)-5-oxa-7-azaspiro[3.5]non-6-en-6-amine (103),
(S)-4-methyl-4-(4-(5-(prop-1-ynyl)pyridin-3-yl)thiophen-2-yl)-1,9-dioxa-3-azaspiro[5.5]undec-2-en-2-amine (104),
(R)-4-methyl-4-(4-(5-(prop-1-ynyl)pyridin-3-yl)thiophen-2-yl)-1,9-dioxa-3-azaspiro[5.5]undec-2-en-2-amine (105),
4-(2-fluoro-5-(pyrimidin-5-yl)phenyl)-4-methyl-1,9-dioxa-3-azaspiro[5.5]undec-2-en-2-amine (106),
4-(2-fluoro-5-(1-propyl-1H-pyrazol-4-yl)phenyl)-4-methyl-1,9-dioxa-3-azaspiro[5.5]undec-2-en-2-amine (107),
(S)-4-methyl-4-(5-methyl-4-(5-(prop-1-ynyl)pyridin-3-yl)thiophen-2-yl)-1,9-dioxa-3-azaspiro[5.5]undec-2-en-2-amine (108),
9,9-difluoro-4-methyl-4-(4-(5-(prop-1-ynyl)pyridin-3-yl)thiophen-2-yl)-1-oxa-3-azaspiro[5.5]undec-2-en-2-amine (109),
(S)-9,9-difluoro-4-methyl-4-(4-(5-(prop-1-ynyl)pyridin-3-yl)thiophen-2-yl)-1-oxa-3-azaspiro[5.5]undec-2-en-2-amine (110),
(S)-8-(2-fluoro-5-(5-(prop-1-ynyl)pyridin-3-yl)phenyl)-8-methyl-5-oxa-7-azaspiro[3.5]non-6-en-6-amine (111),
8-methyl-8-(4-(5-(prop-1-ynyl)pyridin-3-yl)thiophen-2-yl)-2-oxa-5-thia-7-azaspiro[3.5]non-6-en-6-amine (112),
4-methyl-4-(4-(5-(prop-1-ynyl)pyridin-3-yl)thiophen-2-yl)-9-oxa-1-thia-3-azaspiro[5.5]undec-2-en-2-amine (113), and
5,5-difluoro-4-methyl-4-(4-(5-(prop-1-ynyl)pyridin-3-yl)thiophen-2-yl)-1,9-dioxa-3-azaspiro[5.5]undec-2-en-2-amine (114).

The following table provides the compound number (column 1), Br-(hetero)aryl compound used (column 2), and boronic acid compound used (column 3) to give the compound shown in column 4. Identification data is provided in column 5.

| Comp No. | Br-(hetero)aryl | Boronic acid | Structure | Identification |
|---|---|---|---|---|
| 103 | Ex. 2-26 | | 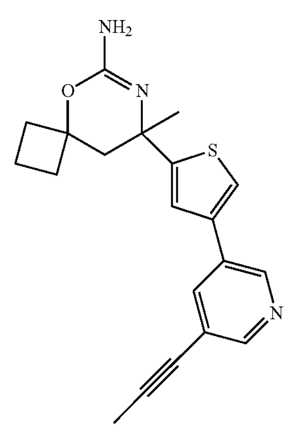 [SMILES: CC#Cc1cncc(-c2csc(C3(C)CC4(CCC4)OC(N)=N3)c2)c1] | MS: 352.1 m/z (M + H)$^+$ <br> $^1$H NMR (400 MHz, CD$_3$OD) δ: 8.78 (d, 1H), 8.48 (d, 1H), 8.17 (t, 1H), 7.85 (d, 1H), 7.52 (d, 1H), 2.94 (d, 1H), 2.44-2.55 (m, 2H), 2.32-2.43 (m, 1H), 2.11 (s, 3H), 1.87-1.97 (m, 1H), 1.83 (s, 3H), 1.65-1.75 (m, 1H). |

-continued

| Comp No. | Br-(hetero)aryl | Boronic acid | Structure | Identification |
|---|---|---|---|---|
| 104 | Ex. 2-28 | | 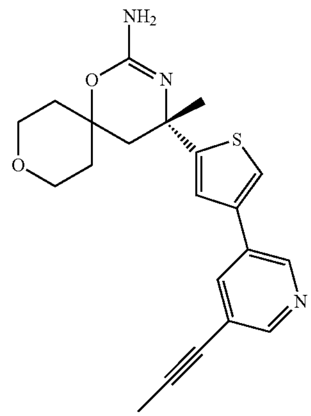 [SMILES: CC#Cc1cncc(-c2csc([C@]3(C)CC4(CCOCC4)OC(N)=N3)c2)c1] | MS: 382.1 m/z (M + H)+<br>1H NMR (400 MHz, CD3OD)<br>δ: 8.77 (d, 1H), 8.48 (d, 1H), 8.16 (t, 1H), 7.85 (d, 1H), 7.53 (d, 1H), 3.84 (m, 2H), 3.60 (m, 2H), 2.98 (d, 1H), 2.41 (d, 1H), 2.10 (s, 3H), 2.08-1.98 (m, 1H), 1.95-1.86 (m, 1H), 1.82 (s, 3H), 1.57 (m, 2H). |
| 105 | | | 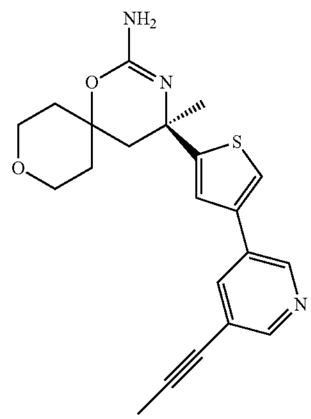 [SMILES: CC#Cc1cncc(-c2csc([C@@]3(C)CC4(CCOCC4)OC(N)=N3)c2)c1] | |
| 106 | Ex. 2-25 | | 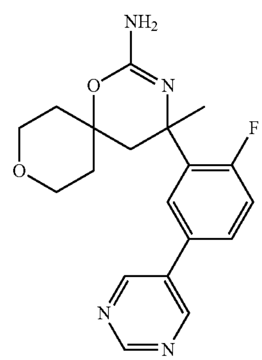 [SMILES: CC1(c2cc(-c3cncnc3)ccc2F)CC2(CCOCC2)OC(N)=N1] | MS: 357.2 m/z (M + H)+<br>1H NMR (400 MHz, CD3OD)<br>δ: 9.20 (s, 1H), 9.10 (s, 2H), 7.82 (m, 1H), 7.73 (dd, 1H), 7.44 (dd, 1H), 3.84 (m, 2H), 3.57 (m, 2H), 3.10 (d, 1H), 2.42 (d, 1H), 1.95-2.08 (m, 1H), 1.85-1.95 (m, 1H), 1.84 (s, 3H), 1.50 (m, 2H). |
| 107 | Ex. 2-25 | | 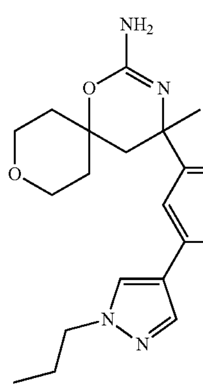 | MS: 387.2 m/z (M + H)+<br>1H NMR (400 MHz, CD3OD)<br>δ: 8.05 (s, 1H), 7.86 (d, 1H), 7.63 (m, 1H), 7.53 (dd, 1H), 7.23 (dd, 1H), 4.17 (t, 2H), 3.84 (m, 2H), 3.57 (m, 2H), 3.08 (d, 1H), 2.35 (d, 1H), 1.83-2.08 (m, 4H), 1.81 (s, 3H), 1.42-1.55 (m, 2H), 0.95 (t, 3H). |

-continued

| Comp No. | Br-(hetero)aryl | Boronic acid | Structure | Identification |
|---|---|---|---|---|
| 108 | Ex. 2-28 | | 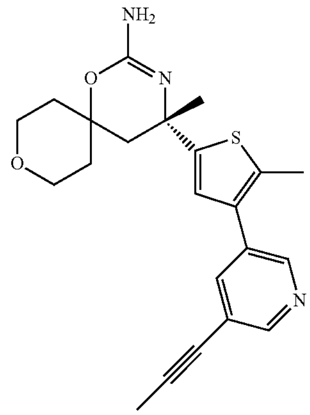 [SMILES: CC#Cc1cncc(-c2cc([C@]3(C)CC4(CCOCC4)OC(N)=N3)sc2C)c1] | MS: 396.1 m/z (M + H)+<br>1H NMR (400 MHz, CD3OD) δ: 8.52 (m, 2H), 7.90 (d, 1H), 7.05 (s, 1H), 3.89 (m, 2H), 3.65 (m, 2H), 2.90 (d, 1H), 2.50 (s, 3H), 2.38 (d, 1H), 2.11 (s, 3H), 2.08-1.98 (m, 1H), 1.95-1.86 (m, 1H), 1.79 (s, 3H), 1.67 (m, 2H). |
| 109 | Ex. 2-31 | | 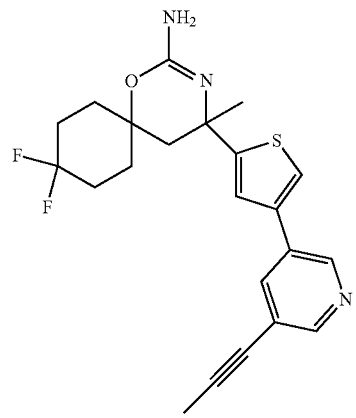 [SMILES: CC#Cc1cncc(-c2csc(C3(C)CC4(CCC(F)(F)CC4)OC(N)=N3)c2)c1] | MS: 416.2 m/z (M + H)+<br>1H NMR (400 MHz, CD3OD) δ: 8.77 (d, J = 2.0 Hz, 1H), 8.47 (d, J = 1.6 Hz, 1H), 8.16 (s, 1H), 7.85 (d, J = 1.4 Hz, 1H), 7.54 (d, J = 1.5 Hz, 1H), 2.93 (d, J = 15.0 Hz, 1H), 2.46 (d, J = 14.9 Hz, 1H), 2.30-2.00 (m, 3H), 2.09 (s, 3H), 2.00-1.80 (m, 2H), 1.79 (s, 3H), 1.70-1.50 (m, 1H). |
| 110 | Ex. 2-32 | | 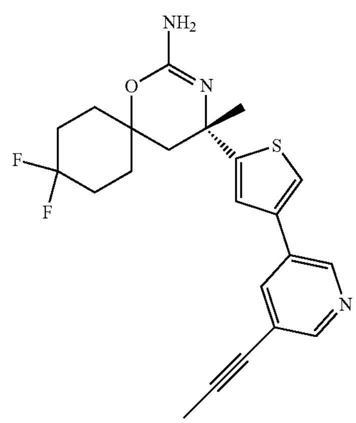 [SMILES: CC#Cc1cncc(-c2csc([C@]3(C)CC4(CCC(F)(F)CC4)OC(N)=N3)c2)c1] | MS: 416.2 m/z (M + H)+<br>1H NMR (400 MHz, CD3OD) δ: 8.77 (d, J = 2.0 Hz, 1H), 8.47 (d, J = 1.6 Hz, 1H), 8.16 (s, 1H), 7.85 (d, J = 1.4 Hz, 1H), 7.54 (d, J = 1.5 Hz, 1H), 2.93 (d, J = 15.0 Hz, 1H), 2.46 (d, J = 14.9 Hz, 1H), 2.30-2.00 (m, 3H), 2.09 (s, 3H), 2.00-1.80 (m, 2H), 1.79 (s, 3H), 1.70-1.50 (m, 1H). |
| 111 | Ex. 2-33 | | 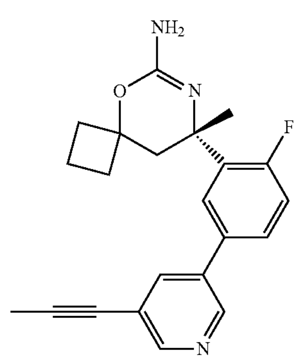 [SMILES: CC#Cc1cncc(-c2ccc(F)c([C@]3(C)CC4(CCC4)OC(N)=N3)c2)c1] | MS: 364.2 m/z (M + H)+<br>1H NMR (400 MHz, CD3OD) δ: 8.70 (d, 1H), 8.58 (d, 1H), 8.07 (m, 1H), 7.76 (m, 1H), 7.52 (d, 1H), 7.39 (dd, 1H), 3.11 (d, 1H), 2.50-2.39 (m, 2H), 2.38 (d, 1H), 2.12 (s, 3H), 1.97-1.87 (m, 2H), 1.83 (s, 3H), 1.65-1.75 (m, 1H), 1.63-1.54 (m, 1H). |

-continued

| Comp No. | Br-(hetero)aryl | Boronic acid | Structure | Identification |
|---|---|---|---|---|
| 112 | Ex. 4-63 | | 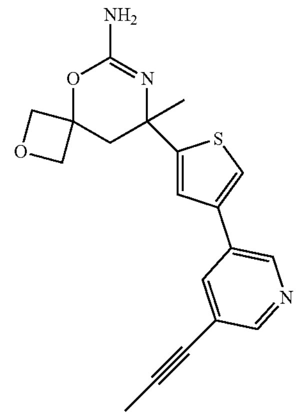 | MS: 370.1 m/z (M + H)+<br>¹H NMR (400 MHz, CDCl₃) δ: 8.72 (s, 1H), 8.55 (s, 1H), 7.91 (s, 1H), 7.49 (s, 1H), 7.18 (s, 1H), 3.73 (d, J = 10.4 Hz, 1H), 3.41 (d, J = 14.4 Hz, 1H), 3.30 (d, J = 10.4 Hz, 1H), 3.17 (d, J = 10.4 Hz, 1H), 2.55 (d, J = 10.4 Hz, 1H), 2.34-2.30 (m, 1H), 2.11 (s, 3H), 1.90 (s, 3H). |
| 113 | Ex. 5-72 | | 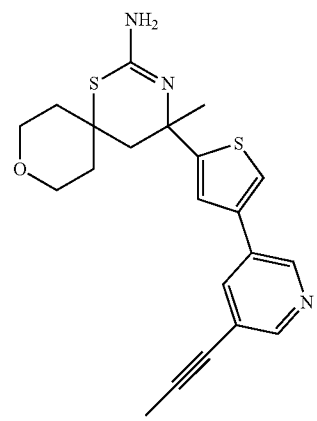 [SMILES: CC#Cc1cncc(-c2csc(C3(C)CC4(CCOCC4)SC(N)=N3)c2)c1] | MS: 398.1 m/z (M + H)+<br>¹H NMR (400 MHz, CD₃OD) δ: 8.77 (s, 1H), 8.47 (s, 1H), 8.15 (s, 1H), 7.84 (d, J = 1.4 Hz, 1H), 7.52 (d, J = 1.4 Hz, 1H), 3.87 (dt, J = 12.4, 4.0 Hz, 1H), 3.70-3.57 (m, 2H), 3.47 (dt, J = 10.1, 2.5 Hz, 1H), 3.00 (d, J = 14.9 Hz, 1H), 2.40 (d, J = 14.9 Hz, 1H), 2.10-2.00 (m, 1H), 2.09 (s, 3H), 1.95-1.83 (m, 1H), 1.86 (s, 3H), 1.62 (ddd, J = 14.3, 10.4, 4.2 Hz, 1H), 1.44 (d, J = 13.7 Hz, 1H). |
| 114 | Ex. 7-95 | | 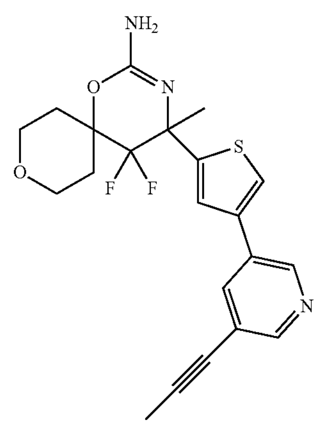 [SMILES: CC#Cc1cncc(-c2csc(C3(C)N=C(N)OC4(CCOCC4)C3(F)F)c2)c1] | MS: 418.1 m/z (M + H)+<br>¹H NMR (400 MHz, CD₃OD) δ: 8.82 (d, 1H), 8.52 (d, 1H), 8.20 (t, 1H), 8.03 (d, 1H), 7.67 (s, 1H), 4.01 (m, 1H), 3.79 (m, 2H), 3.61 (m, 1H), 2.05-2.25 (m, 2H), 2.13 (s, 3H), 1.97 (d, 3H), 1.84-1.97 (m, 1H), 1.57 (m, 1H). |

Example 9

Synthesis of N-(3-(2-amino-4-methyl-1,9-dioxa-3-azaspiro[5.5]undec-2-en-4-yl)-4-fluorophenyl)-5-fluoropicolinamide (120)

N-(3-(2-amino-4-methyl-1,9-dioxa-3-azaspiro[5.5]undec-2-en-4-yl)-4-fluorophenyl)-5-fluoropicolinamide 120 was prepared from 4-(5-bromo-2-fluorophenyl)-4-methyl-1,9-dioxa-3-azaspiro[5.5]undec-2-en-2-amine 25 (prepared as described in Example 2) in five Steps as follows:

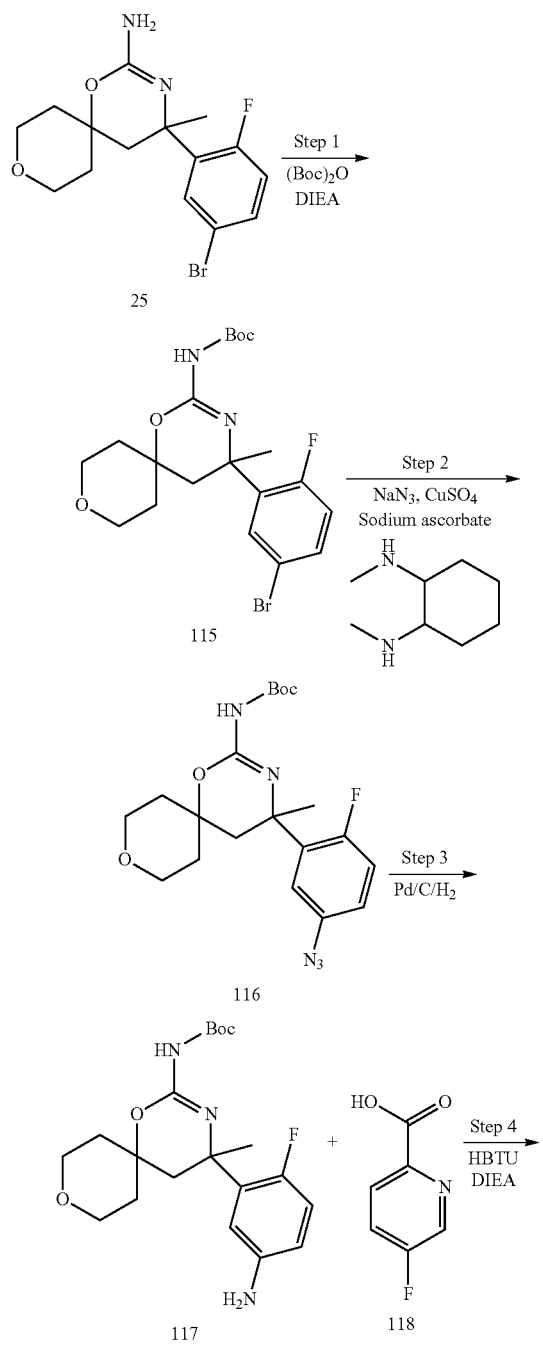

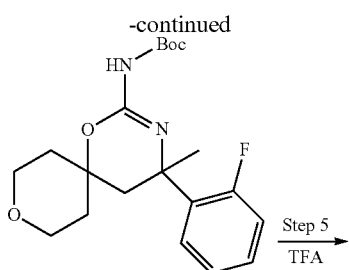

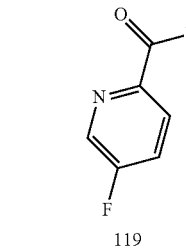

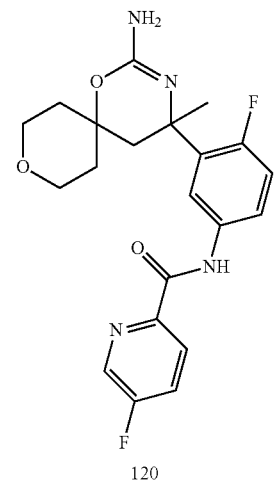

Step 1—synthesis of tert-butyl 4-(5-bromo-2-fluorophenyl)-4-methyl-1,9-dioxa-3-azaspiro[5.5]undec-2-en-2-ylcarbamate (115)

tert-Butoxycarbonyl tert-butyl carbonate (0.3 g, 1.0 mmol) and N-ethyl-N-isopropylpropan-2-amine (0.2 g, 2.0 mmol) and 4-(5-bromo-2-fluorophenyl)-4-methyl-1,9-dioxa-3-azaspiro[5.5]undec-2-en-2-amine (25, 0.3 g, 0.8 mmol) were combined in 10 mL of $CH_2Cl_2$. The mixture was stirred at room temperature for 8 hours, then concentrated under vacuum. The resulting material was purified by flash column chromatography (hexane/EtOAc 0-50%). Appropriate fractions were combined and concentrated under vacuum to provide the desired compound as a white solid (115, 0.4 g, 0.7 mmol).

Step 2—synthesis of tert-butyl 4-(5-azido-2-fluorophenyl)-4-methyl-1,9-dioxa-3-azaspiro[5.5]undec-2-en-2-ylcarbamate (116)

tert-butyl 4-(5-bromo-2-fluorophenyl)-4-methyl-1,9-dioxa-3-azaspiro[5.5]undec-2-en-2-ylcarbamate (115, 70 mg, 0.15 mmol), sodium ascorbate (24 mg, 0.12 mmol), sodium azide (30 mg, 0.46 mmol), N1,N2-dimethylcyclohexane-1,2-diamine (13 mg, 0.09 mmol), and copper sulfate pentahydrate (15 mg, 0.06 mmol) were combined in 1.6 mL of EtOH and 0.4 mL of water. The resulting mixture was flushed with nitrogen and heated at 80° C. for 1 hour. The reaction mixture was diluted with 30 mL of EtOAc, washed with saturated aqueous NaHCO$_3$ and brine and the organic portion was dried, filtered and the filtrate concentrated under vacuum to provide the desired compound as a yellow solid (116, 61 mg, 0.14 mmol).

Step 3—synthesis of tert-butyl 4-(5-amino-2-fluorophenyl)-4-methyl-1,9-dioxa-3-azaspiro[5.5]undec-2-en-2-ylcarbamate (117)

tert-butyl 4-(5-azido-2-fluorophenyl)-4-methyl-1,9-dioxa-3-azaspiro[5.5]undec-2-en-2-ylcarbamate (116, 45 mg, 0.11 mmol) was dissolved in 5 mL of EtOH, and 9 mg of 10% Pd/C was added. The mixture was hydrogenated at 30 psi under H$_2$ for 1.5 hours. The catalyst was removed by filtration, and the filtrate concentrated under vacuum to provide the desired compound as a white solid (117, 40 mg, 0.10 mmol).

Step 4—synthesis of tert-butyl 4-(2-fluoro-5-(5-fluoropicolinamido)phenyl)-4-methyl-1,9-dioxa-3-azaspiro[5.5]undec-2-en-2-ylcarbamate (119)

tert-Butyl 4-(5-amino-2-fluorophenyl)-4-methyl-1,9-dioxa-3-azaspiro[5.5]undec-2-en-2-ylcarbamate (117, 15 mg, 0.04 mmol), 5-fluoropicolinic acid (118, 6 mg, 0.045 mmol), and [benzotriazol-1-yloxy(dimethylamino)methylene]-dimethyl-ammonium hexafluorophosphate (19 mg, 0.05 mmol) were dissolved in 0.6 mL of DMF. The mixture was cooled over an ice-water bath and N-ethyl-N-isopropyl-propan-2-amine (7 mg, 0.057 mmol) was added. The mixture was stirred at room temperature for 30 minutes, then diluted with 10 mL of EtOAc, and washed with saturated aqueous NaHCO$_3$ and brine. The organic portion was dried, filtered and the filtrate concentrated under vacuum to provide the desired compound as a yellow solid (119, 18 mg, 0.035 mmol).

Step 5—synthesis of N-(3-(2-amino-4-methyl-1,9-dioxa-3-azaspiro[5.5]undec-2-en-4-yl)-4-fluorophenyl)-5-fluoropicolinamide (120)

tert-Butyl 4-(2-fluoro-5-(5-fluoropicolinamido)phenyl)-4-methyl-1,9-dioxa-3-azaspiro[5.5]undec-2-en-2-ylcarbamate (119, 18 mg, 0.035 mmol) was dissolved in 0.2 mL of CH$_2$Cl$_2$ and 0.2 mL of TFA was added. The resulting mixture was stirred at room temperature for 30 minutes, then concentrated under vacuum. The resulting material was purified by HPLC (acetonitrile/water with 0.1% TFA). Appropriate fractions were combined and concentrated under vacuum to provide the desired compound as a di-TFA salt (120, 14 mg, 0.033 mmol). MS: 417.2 m/z (M+H)$^+$. $^1$H NMR (400 MHz, CDCl$_3$) δ: 8.64 (d, J=2.76, 1H), 8.32 (dd, J=4.52, 8.88, 1H), 8.07 (dd, J=2.68, 7.48, 1H), 7.8 (dt, J=2.76, 8.48, 1H), 7.76 (m, 1H), 7.29 (dd, J=8.84, 11.96, 1H), 3.82-3.86 (m, 2H), 3.55-3.58 (m, 2H), 3.09 (d, J=15.04, 1H), 2.36 (d, J=15.04, 1H), 1.85-1.97 (m, 1H), 1.80 (s, 3H), 1.42-1.55 (m, 2H).

Additional compounds are prepared following the methods of this example, wherein 4-(5-bromo-2-fluorophenyl)-4-methyl-1,9-dioxa-3-azaspiro[5.5]undec-2-en-2-amine is optionally replaced with a suitable bromo-(hetero)aryl compound (prepared by the methods of Examples 2-7) in Step 1 and 5-fluoropicolinic acid 118 is optionally replaced with a suitable carboxylic acid in Step 4. The following compounds were prepared by this method:

N-(3-(2-amino-4-methyl-1,9-dioxa-3-azaspiro[5.5]undec-2-en-4-yl)-4-fluorophenyl)-5-chloropicolinamide (121), (S)—N-(3-(2-amino-4-methyl-1,9-dioxa-3-azaspiro[5.5]undec-2-en-4-yl)-4-fluorophenyl)-5-chloropicolinamide (122), (S)—N-(3-(2-amino-9,9-difluoro-4-methyl-1-oxa-3-azaspiro[5.5]undec-2-en-4-yl)-4-fluorophenyl)-5-fluoropicolinamide (123), (S)—N-(3-(2-amino-9,9-difluoro-4-methyl-1-oxa-3-azaspiro[5.5]undec-2-en-4-yl)-4-fluorophenyl)-5-chloropicolinamide (124), N-(3-(6-amino-8-methyl-5-oxa-7-azaspiro[3.5]non-6-en-8-yl)-4-fluorophenyl)-5-fluoropicolinamide (125), (S)—N-(3-(6-amino-8-methyl-5-oxa-7-azaspiro[3.5]non-6-en-8-yl)-4-fluorophenyl)-5-fluoropicolinamide (126), (R)—N-(3-(6-amino-8-methyl-5-oxa-7-azaspiro[3.5]non-6-en-8-yl)-4-fluorophenyl)-5-fluoropicolinamide (127), (S)—N-(3-(2-amino-4-methyl-1,9-dioxa-3-azaspiro[5.5]undec-2-en-4-yl)-4-fluorophenyl)-5-fluoropicolinamide (128), (S)—N-(3-(6-amino-8-methyl-5-oxa-7-azaspiro[3.5]non-6-en-8-yl)-4-fluorophenyl)-5-chloropicolinamide (129), (S)—N-(3-(6-amino-8-methyl-5-oxa-7-azaspiro[3.5]non-6-en-8-yl)-4-fluorophenyl)-5-cyanopicolinamide (130), (S)—N-(3-(6-amino-8-methyl-5-oxa-7-azaspiro[3.5]non-6-en-8-yl)-4-fluorophenyl)-5-chloro-3-fluoropicolinamide (131), (S)—N-(3-(2-amino-9,9-difluoro-4-methyl-1-oxa-3-azaspiro[5.5]undec-2-en-4-yl)-4-fluorophenyl)-5-(trifluoromethyl)picolinamide (132), (S)—N-(3-(2-amino-9,9-difluoro-4-methyl-1-oxa-3-azaspiro[5.5]undec-2-en-4-yl)-4-fluorophenyl)-5-chloro-3-fluoropicolinamide (133), (S)—N-(3-(2-amino-9,9-difluoro-4-methyl-1-oxa-3-azaspiro[5.5]undec-2-en-4-yl)-4-fluorophenyl)cyclopropanecarboxamide (134), (S)—N-(3-(6-amino-8-methyl-5-oxa-7-azaspiro[3.5]non-6-en-8-yl)-4-fluorophenyl)-5-methoxypyrazine-2-carboxamide (135), (S)—N-(3-(2-amino-9,9-difluoro-4-methyl-1-oxa-3-azaspiro[5.5]undec-2-en-4-yl)-4-fluorophenyl)-5-bromopicolinamide (136), (S)—N-(3-(2-amino-9,9-difluoro-4-methyl-1-oxa-3-azaspiro[5.5]undec-2-en-4-yl)-4-fluorophenyl)-5-cyclopropylpicolinamide (137), (S)—N-(3-(6-amino-8-methyl-5-oxa-7-azaspiro[3.5]non-6-en-8-yl)-4-fluorophenyl)-2-methyloxazole-4-carboxamide (138), N-(3-(2-amino-4-methyl-1,9-dioxa-3-azaspiro[5.5]undec-2-en-4-yl)-4-fluorophenyl)-5-cyanopicolinamide (139), (S)—N-(3-(6-amino-8-methyl-5-oxa-7-azaspiro[3.5]non-6-en-8-yl)-4-fluorophenyl)-4-chloro-2-methoxybenzamide (140), (S)—N-(3-(6-amino-8-methyl-5-oxa-7-azaspiro[3.5]non-6-en-8-yl)-4-fluorophenyl)-4-chlorobenzamide (141), N-(3-(2-amino-4-methyl-1-thia-3-azaspiro[5.5]undec-2-en-4-yl)-4-fluorophenyl)-5-fluoropicolinamide (142), (R)—N-(3-(6-amino-8-methyl-5-thia-7-azaspiro[3.5]non-6-en-8-yl)-4-fluorophenyl)-5-fluoropicolinamide (143), (S)—N-(3-(6-amino-8-methyl-5-thia-7-azaspiro[3.5]non-6-en-8-yl)-4-fluorophenyl)-5-fluoropicolinamide (144), (S)—N-(3-(6-amino-8-methyl-5-thia-7-azaspiro[3.5]non-6-en-8-yl)-4-fluorophenyl)-5-chloropicolinamide (145), (S)—N-(3-(6-amino-8-methyl-2-oxa-5-thia-7-azaspiro[3.5]non-6-en-8-yl)-4-fluorophenyl)-5-fluoropicolinamide (146), N-(3-(2-amino-4-methyl-9-oxa-1-thia-3-azaspiro[5.5]undec-2-en-4-yl)-4-fluorophenyl)-5-fluoropicolinamide (147), (S)—N-(3-(2-amino-4-methyl-9-oxa-1-thia-3-azaspiro[5.5]undec-2-en-4-yl)-4-fluorophenyl)-5-fluoropicolinamide (148),
(R)—N-(3-(2-amino-4-methyl-9-oxa-1-thia-3-azaspiro[5.5]undec-2-en-4-yl)-4-fluorophenyl)-5-fluoropicolinamide (149),
N-(3-(2-amino-4-methyl-9-oxa-1-thia-3-azaspiro[5.5]undec-2-en-4-yl)-4-fluorophenyl)-5-chloropicolinamide (150),
(S)—N-(3-(2-amino-4-methyl-9-oxa-1-thia-3-azaspiro[5.5]undec-2-en-4-yl)-4-fluorophenyl)-5-chloropicolinamide (151),
(R)—N-(3-(2-amino-4-methyl-9-oxa-1-thia-3-azaspiro[5.5]undec-2-en-4-yl)-4-fluorophenyl)-5-chloropicolinamide (152),
(S)—N-(3-(2-amino-4-methyl-9-oxa-1-thia-3-azaspiro[5.5]undec-2-en-4-yl)-4-fluorophenyl)-5-methoxypyrazine-2-carboxamide (153),
(S)—N-(3-(5-amino-7-methyl-4-oxa-6-azaspiro[2.5]oct-5-en-7-yl)-4-fluorophenyl)-5-chloropicolinamide (154),
N-(3-(2-amino-5,5-difluoro-4-methyl-1,9-dioxa-3-azaspiro[5.5]undec-2-en-4-yl)-4-fluorophenyl)-5-fluoropicolinamide (155),
(S)—N-(3-(2-amino-5,5-difluoro-4-methyl-1,9-dioxa-3-azaspiro[5.5]undec-2-en-4-yl)-4-fluorophenyl)-5-fluoropicolinamide (156),
(R)—N-(3-(2-amino-5,5-difluoro-4-methyl-1,9-dioxa-3-azaspiro[5.5]undec-2-en-4-yl)-4-fluorophenyl)-5-fluoropicolinamide (157),
N-(3-(2-amino-5,5-difluoro-4-methyl-1,9-dioxa-3-azaspiro[5.5]undec-2-en-4-yl)-4-fluorophenyl)-5-chloropicolinamide (158),
N-(3-(6-amino-9,9-difluoro-8-methyl-5-oxa-7-azaspiro[3.5]non-6-en-8-yl)-4-fluorophenyl)-5-fluoropicolinamide (159),
N-(3-(6-amino-9,9-difluoro-8-methyl-5-oxa-7-azaspiro[3.5]non-6-en-8-yl)-4-fluorophenyl)-5-chloropicolinamide (160),
N-(3-(6-amino-9,9-difluoro-8-methyl-5-oxa-7-azaspiro[3.5]non-6-en-8-yl)-4-fluorophenyl)-5-cyanopicolinamide (161),
(R)—N-(3-(6-amino-9,9-difluoro-8-methyl-5-oxa-7-azaspiro[3.5]non-6-en-8-yl)-4-fluorophenyl)-5-cyanopicolinamide (162),
(S)—N-(3-(6-amino-9,9-difluoro-8-methyl-5-oxa-7-azaspiro[3.5]non-6-en-8-yl)-4-fluorophenyl)-5-cyanopicolinamide (163),
N-(3-(6-amino-9,9-difluoro-8-methyl-5-oxa-7-azaspiro[3.5]non-6-en-8-yl)-4-fluorophenyl)-5-methoxypyrazine-2-carboxamide (164), and
N-(3-(6-amino-9,9-difluoro-8-methyl-5-oxa-7-azaspiro[3.5]non-6-en-8-yl)-4-fluorophenyl)-2-methyloxazole-4-carboxamide (165).

The following table provides the compound number (column 1), Br-(hetero)aryl compound used in Step 1 (column 2), and carboxylic acid compound used in Step 4 (column 3) to give the compound shown in column 4. Identification data is provided in column 5.

| Comp No. | Step 1 bromo | Step 4 acid | Structure | Identification |
|---|---|---|---|---|
| 121 | 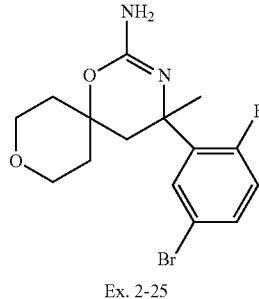 Ex. 2-25 | 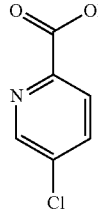 | 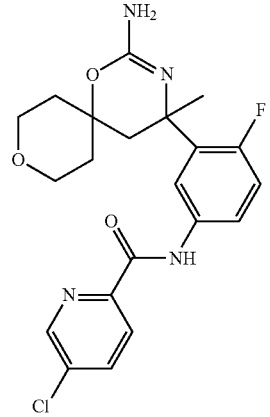 [SMILES: CC1(c2cc(NC(=O)c3ccc(Cl)cn3)ccc2F)CC2(CCOCC2)OC(N)=N1] | |
| 122 | 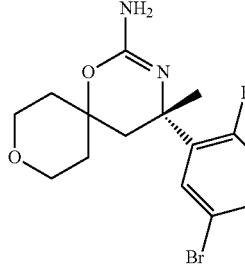 Ex. 2-37 | 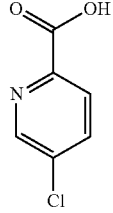 | 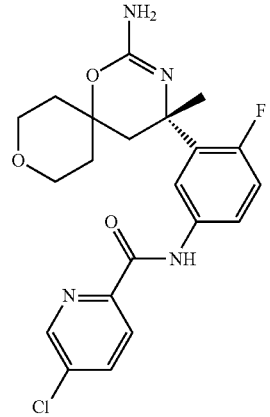 [SMILES: C[C@@]1(c2cc(NC(=O)c3ccc(Cl)cn3)ccc2F)CC2(CCOCC2)OC(N)=N1] | MS: 433.2 m/z (M + H)+ <br> 1H NMR (400 MHz, CD3OD) δ: 8.74 (d, 1H), 8.23 (dd, 1H), 8.11 (dd, 1H), 8.06 (dd, 1H), 7.77 (m, 1H), 7.27 (dd, 1H), 3.84 (m, 2H), 3.57 (m, 2H), 3.08 (d, 1H), 2.35 (d, 1H), 2.00 (m, 1H), 1.88 (m, 1H), 1.81 (s, 3H), 1.42-1.57 (m, 2H). |

-continued

| Comp No. | Step 1 bromo | Step 4 acid | Structure | Identification |
|---|---|---|---|---|
| 123 | Ex. 2-36 | | 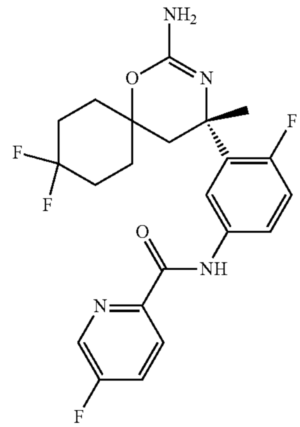 [SMILES: C[C@@]1(c2cc(NC(=O)c3ccc(F)cn3)ccc2F)CC2(CCC(F)(F)CC2)OC(N)=N1] | MS: 451.2 m/z (M + H)+<br>¹H NMR (400 MHz, CD₃OD) δ: 10.63 (s, 1H), 8.60 (d, J = 2.6 Hz, 1H), 8.28 (dd, J = 8.7, 4.5 Hz, 1H), 8.07-7.97 (m, 1H), 7.81 (dt, J = 8.6, 2.8 Hz, 1H), 7.78-7.68 (m, 1H), 7.24 (dd, J = 11.9, 8.9 Hz, 1H), 3.01 (d, J = 15.1 Hz, 1H), 2.38 (d, J = 15.1 Hz, 1H), 2.30-1.65 (m, 7H), 1.78 (s, 3H), 1.50-1.36 (m, 1H). |
| 124 | Ex. 2-36 | | 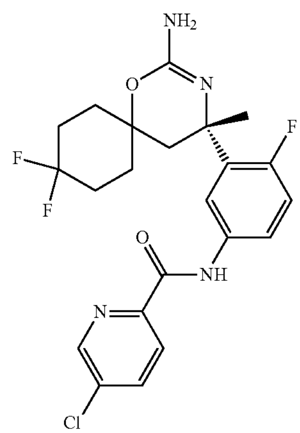 [SMILES: C[C@@]1(c2cc(NC(=O)c3ccc(Cl)cn3)ccc2F)CC2(CCC(F)(F)CC2)OC(N)=N1] | MS: 467.1 m/z (M + H)+<br>¹H NMR (400 MHz, CD₃OD) δ: 10.67 (s, 1H), 8.71 (d, J = 2.0 Hz, 1H), 8.19 (d, J = 8.0 Hz, 1H), 8.07 (dd, J = 8.4, 2.4 Hz, 1H), 8.03 (dd, J = 7.5, 2.7 Hz, 1H), 7.80-7.70 (m, 1H), 7.24 (dd, J = 12.0, 8.8 Hz, 1H), 3.01 (d, J = 15.1 Hz, 1H), 2.38 (d, J = 15.1 Hz, 1H), 2.30-1.65 (m, 7H), 1.78 (s, 3H), 1.50-1.36 (m, 1H). |
| 125 | Ex. 2-35 | | 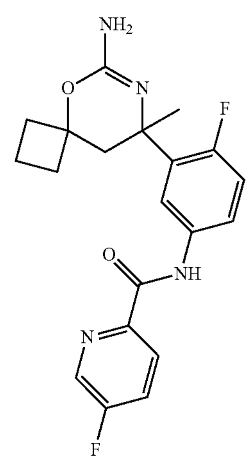 [SMILES: CC1(c2cc(NC(=O)c3ccc(F)cn3)ccc2F)CC2(CCC2)OC(N)=N1] | |

-continued

| Comp No. | Step 1 bromo | Step 4 acid | Structure | Identification |
|---|---|---|---|---|
| 126 | Ex. 2-33 | | 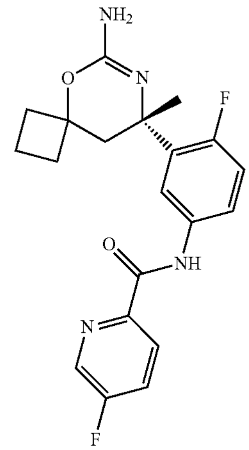 [SMILES: C[C@@]1(c2cc(NC(=O)c3ccc(F)cn3)ccc2F)CC2(CCC2)OC(N)=N1] | MS: 387.2 m/z (M + H)+<br>¹H NMR (400 MHz, CD₃OD) δ: 8.64 (d, 1H), 8.31 (dd, 1H), 8.00 (m, 1H), 7.80 (dt, 1H), 7.77 (m, 1H), 7.27 (dd, 1H), 3.10 (d, 1H), 2.44-2.52 (m, 1H), 2.32-2.43 (m, 2H), 1.86-2.05 (m, 2H), 1.83 (s, 3H), 1.61-1.74 (m, 1H), 1.49-1.58 (m, 1H). |
| 127 | Ex. 2-34 | | 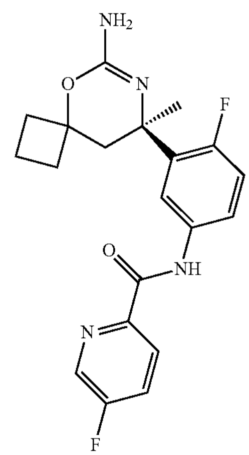 [SMILES: C[C@]1(c2cc(NC(=O)c3ccc(F)cn3)ccc2F)CC2(CCC2)OC(N)=N1] | |
| 128 | Ex. 2-37 | | 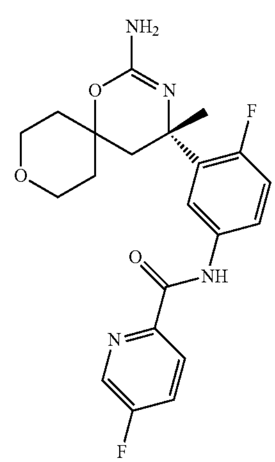 | MS: 417.2 m/z (M + H)+<br>¹H NMR (400 MHz, CD₃OD) δ: 8.64 (d, 1H), 8.31 (dd, 1H), 8.07 (dd, 1H), 7.83 (m, 1H), 7.76 (m, 1H), 7.27 (dd, 1H), 3.84 (m, 2H), 3.57 (m, 2H), 3.08 (d, 1H), 2.35 (d, 1H), 2.00 (m, 1H), 1.88 (m, 1H), 1.81 (s, 3H), 1.42-1.57 (m, 2H). |

| Comp No. | Step 1 bromo | Step 4 acid | Structure | Identification |
|---|---|---|---|---|
| 129 | Ex. 2-33 | | 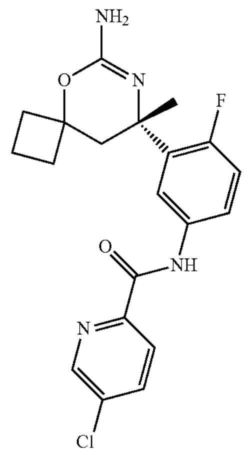 [SMILES: C[C@@]1(c2cc(NC(=O)c3ccc(Cl)cn3)ccc2F)CC2(CCC2)OC(N)=N1] | MS: 403.1 m/z (M + H)+<br>¹H NMR (400 MHz, CD₃OD) δ: 8.73 (m, 1H), 8.22 (m, 1H), 8.10 (dd, 1H), 8.00 (dd, 1H), 7.78 (m, 1H), 7.26 (dd, 1H), 3.10 (d, 1H), 2.42-2.54 (m, 1H), 2.32-2.43 (m, 2H), 1.86-2.05 (m, 2H), 1.83 (s, 3H), 1.61-1.74 (m, 1H), 1.49-1.58 (m, 1H). |
| 130 | Ex. 2-33 | | 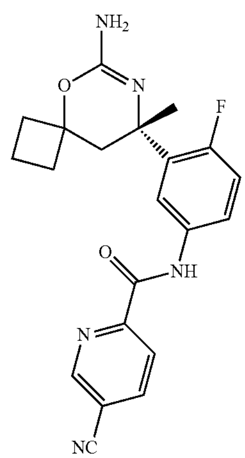 [SMILES: C[C@@]1(c2cc(NC(=O)c3ccc(C#N)cn3)ccc2F)CC2(CCC2)OC(N)=N1] | MS: 394.2 m/z (M + H)+<br>¹H NMR (400 MHz, CD₃OD) δ: 9.08 (m, 1H), 8.46 (dd, 1H), 8.38 (dd, 1H), 8.04 (dd, 1H), 7.82 (m, 1H), 7.28 (dd, 1H), 3.10 (d, 1H), 2.44-2.52 (m, 1H), 2.32-2.43 (m, 2H), 1.86-2.05 (m, 2H), 1.83 (s, 3H), 1.61-1.74 (m, 1H), 1.49-1.58 (m, 1H). |
| 131 | Ex. 2-33 | | 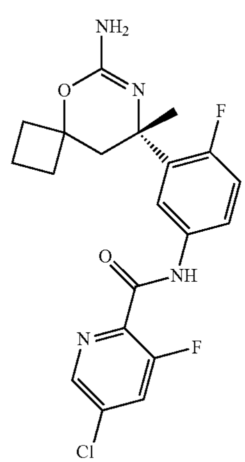 [SMILES: C[C@@]1(c2cc(NC(=O)c3ncc(Cl)cc3F)ccc2F)CC2(CCC2)OC(N)=N1] | MS: 421.1 m/z (M + H)+<br>¹H NMR (400 MHz, CD₃OD) δ: 8.59 (d, 1H), 8.04 (dd, 1H), 8.01 (dd, 1H), 7.69 (m, 1H), 7.26 (dd, 1H), 3.10 (d, 1H), 2.44-2.52 (m, 1H), 2.32-2.43 (m, 2H), 1.86-2.05 (m, 2H), 1.83 (s, 3H), 1.61-1.74 (m, 1H), 1.49-1.58 (m, 1H). |

| Comp No. | Step 1 bromo | Step 4 acid | Structure | Identification |
|---|---|---|---|---|
| 132 | Ex. 2-36 | CF₃-pyridine-carboxylic acid | 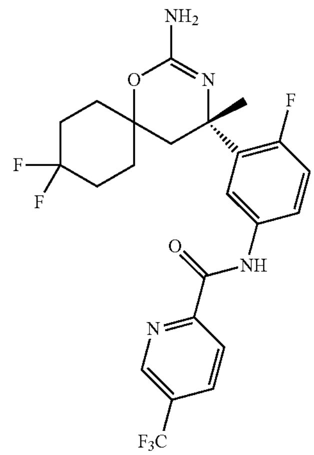 [SMILES: C[C@@]1(c2cc(NC(=O)c3ccc(C(F)(F)F)cn3)ccc2F)CC2(CCC(F)(F)CC2)OC(N)=N1] | MS: 501.2 m/z (M + H)⁺<br>¹H NMR (400 MHz, CD₃OD)<br>δ: 10.81 (s, 1H), 9.04 (s, 1H), 8.43-8.35 (m, 2H), 8.10-8.03 (m, 1H), 7.81-7.74 (m, 1H), 7.26 (dd, J = 11.9, 8.8 Hz, 1H), 3.02 (d, J = 15.2 Hz, 1H), 2.38 (d, J = 15.1 Hz, 1H), 2.30-1.65 (m, 7H), 1.78 (s, 3H), 1.50-1.36 (m, 1H). |
| 133 | Ex. 2-36 | 5-chloro-3-fluoropyridine-2-carboxylic acid | 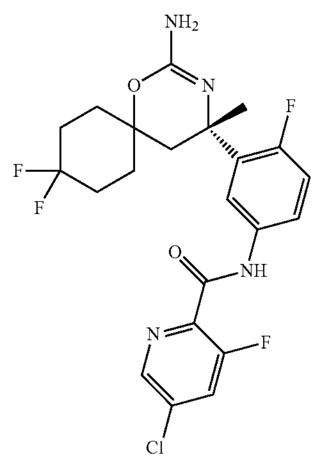 [SMILES: C[C@@]1(c2cc(NC(=O)c3ncc(Cl)cc3F)ccc2F)CC2(CCC(F)(F)CC2)OC(N)=N1] | MS: 485.1 m/z (M + H)⁺<br>¹H NMR (400 MHz, CD₃OD)<br>δ: 8.57 (d, J = 1.4 Hz, 1H), 8.10-8.04 (m, 1H), 8.02 (dd, J = 10.4, 1.9 Hz, 1H), 7.69-7.60 (m, 1H), 7.24 (dd, J = 11.9, 8.8 Hz, 1H), 3.01 (d, J = 15.1 Hz, 1H), 2.38 (d, J = 15.1 Hz, 1H), 2.30-1.65 (m, 7H), 1.77 (s, 3H), 1.50-1.36 (m, 1H). |
| 134 | Ex. 2-36 | cyclopropanecarboxylic acid | 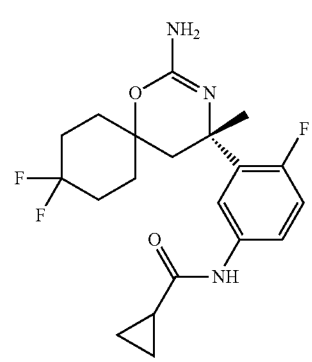 [SMILES: C[C@@]1(c2cc(NC(=O)C3CC3)ccc2F)CC2(CCC(F)(F)CC2)OC(N)=N1] | MS: 396.2 m/z (M + H)⁺<br>¹H NMR (400 MHz, CD₃OD)<br>δ: 10.19 (s, 1H), 7.87 (dd, J = 4.8, −2.6 Hz, 1H), 7.45-7.30 (m, 1H), 7.15 (dd, J = 11.9, 8.8 Hz, 1H), 2.98 (d, J = 15.1 Hz, 1H), 2.34 (d, J = 15.1 Hz, 1H), 2.30-1.60 (m, 9H), 1.73 (s, 3H), 1.00-0.90 (m, 2H), 0.90-0.80 (m, 2H). |

-continued

| Comp No. | Step 1 bromo | Step 4 acid | Structure | Identification |
|---|---|---|---|---|
| 135 | Ex. 2-33 | | 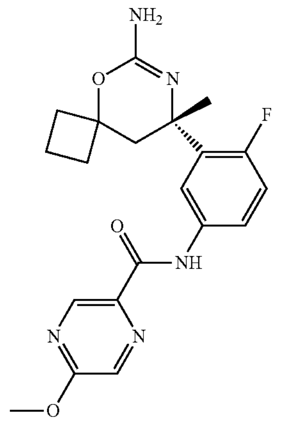 [SMILES: COc1cnc(C(=O)Nc2ccc(F)c([C@]3(C)CC4(CCC4)OC(N)=N3)c2)cn1] | MS: 400.2 m/z (M + H)+<br>1H NMR (400 MHz, CD3OD) δ: 8.94 (d, 1H), 8.32 (d, 1H), 8.31 (dd, 1H), 8.00 (m, 1H), 7.80 (dt, 1H), 7.77 (m, 1H), 7.26 (dd, 1H), 4.11 (S, 3H), 3.12 (d, 1H), 2.43-2.55 (m, 1H), 2.32-2.43 (m, 2H) 1.77-2.08 (m, 2H), 1.83 (s, 3H), 1.61-1.75 (m, 1H), 1.49-1.58 (m, 1H). |
| 136 | Ex. 2-36 | | 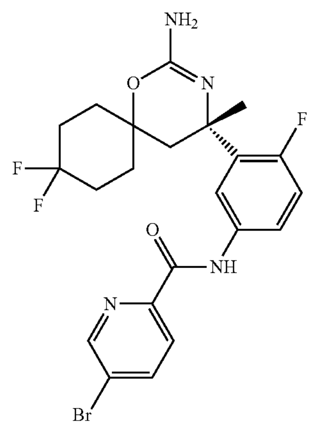 [SMILES: C[C@@]1(c2cc(NC(=O)c3ccc(Br)cn3)ccc2F)CC2(CCC(F)(F)CC2)OC(N)=N1] | MS: 511.1 m/z (M + H)+<br>1H NMR (400 MHz, CD3OD) δ: 8.80 (d, J = 2.0 Hz, 1H), 8.23 (dd, J = 8.4, 2.2 Hz, 1H), 8.12 (d, J = 8.3 Hz, 1H), 8.01 (dd, J = 7.4, 2.6 Hz, 1H), 7.76 (ddd, J = 8.8, 4.1, 2.7 Hz, 1H), 7.23 (dd, J = 11.9, 8.8 Hz, 1H), 7.15 (d, J = 4.0 Hz, 1H), 7.13-7.04 (m, 3H), 3.02 (d, J = 15.1 Hz, 1H), 2.38 (d, J = 15.1 Hz, 1H), 2.30-1.65 (m, 7H), 1.78 (s, 3H), 1.48-1.37 (m, 1H). |
| 137 | Ex. 2-36 | | 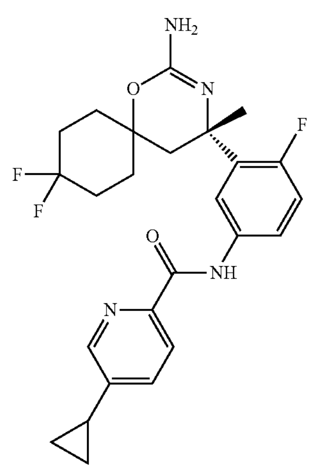 [SMILES: C[C@@]1(c2cc(NC(=O)c3ccc(C4CC4)cn3)ccc2F)CC2(CCC(F)(F)CC2)OC(N)=N1] | MS: 473.2 m/z (M + H)+<br>1H NMR (400 MHz, CD3OD) δ: 8.51 (d, J = 2.0 Hz, 1H), 8.07 (d, J = 8.2 Hz, 1H), 8.03 (dd, J = 7.4, 2.6 Hz, 1H), 7.73 (ddd, J = 8.8, 4.1, 2.7 Hz, 1H), 7.60 (dd, J = 8.2, 2.2 Hz, 1H), 7.23 (dd, J = 11.9, 8.9 Hz, 1H), 3.02 (d, J = 15.1 Hz, 1H), 2.37 (d, J = 15.1 Hz, 1H), 2.30-1.65 (m, 8H), 1.78 (s, 3H), 1.48-1.37 (m, 1H), 1.20-1.10 (m, 2H), 0.90-0.82 (m, 2H). |

-continued

| Comp No. | Step 1 bromo | Step 4 acid | Structure | Identification |
|---|---|---|---|---|
| 138 | Ex. 2-33 | 2-methyloxazole-4-carboxylic acid | 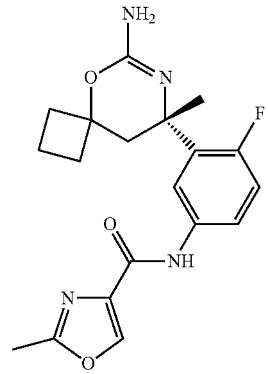 [SMILES: Cc1nc(C(=O)Nc2ccc(F)c([C@]3(C)CC4(CCC4)OC(N)=N3)c2)co1] | MS: 373.3 m/z (M + H)+<br>1H NMR (400 MHz, CD3OD) δ: 10.00 (s, 1H), 8.40 (s, 1H), 7.91 (m, 1H), 7.68 (m, 1H), 7.24 (dd, 1H), 3.09 (d, 1H), 2.55 (s, 3H), 2.42-2.53 (m, 1H), 2.32-2.42 (m, 2H), 1.88-2.04 (m, 2H), 1.82 (s, 3H), 1.62-1.73 (m, 1H), 1.47-1.57 (m, 1H). |
| 139 | Ex. 2-25 | 5-cyanopicolinic acid | 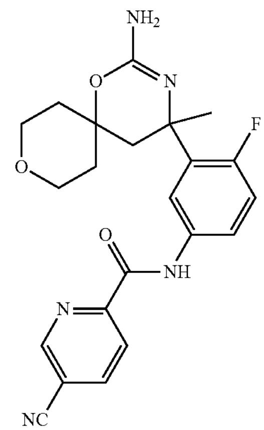 [SMILES: CC1(c2cc(NC(=O)c3ccc(C#N)cn3)ccc2F)CC2(CCOCC2)OC(N)=N1] | MS: 424.2 m/z (M + H)+<br>1H NMR (400 MHz, CD3OD) δ: 9.08 (m, 1H), 8.46 (dd, 1H), 8.38 (dd, 1H), 8.10 (dd, 1H), 7.80 (m, 1H), 7.29 (dd, 1H), 3.84 (m, 2H), 3.57 (m, 2H), 3.08 (d, 1H), 2.35 (d, 1H), 2.00 (m, 1H), 1.88 (m, 1H), 1.81 (s, 3H), 1.42-1.57 (m, 2H). |
| 140 | Ex. 2-33 | 4-chloro-2-methoxybenzoic acid | 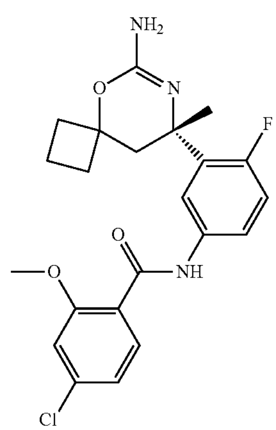 [SMILES: COc1cc(Cl)ccc1C(=O)Nc1ccc(F)c([C@]2(C)CC3(CCC3)OC(N)=N2)c1] | MS: 432.2 m/z (M + H)+<br>1H NMR (400 MHz, CD3OD) δ: 8.01 (m, 1H), 7.84 (d, 1H), 7.50 (m, 1H), 7.21-7.28 (m, 2H), 7.15 (dd, 1H), 4.04 (s, 3H), 3.11 (d, 1H), 2.43-2.55 (m, 1H), 2.34-2.43 (m, 2H), 1.90-2.05 (m, 2H), 1.82 (s, 3H), 1.63-1.75 (m, 1H), 1.50-1.60 (m, 1H). |

-continued

| Comp No. | Step 1 bromo | Step 4 acid | Structure | Identification |
|---|---|---|---|---|
| 141 | Ex. 2-33 | 4-chlorobenzoic acid | 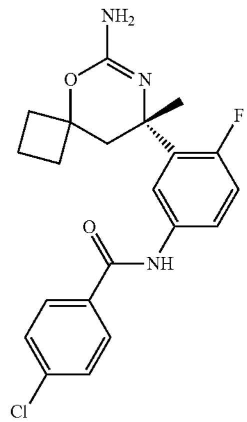 [SMILES: C[C@@]1(c2cc(NC(=O)c3ccc(Cl)cc3)ccc2F)CC2(CCC2)OC(N)=N1] | MS: 402.1 m/z (M + H)+<br>1H NMR (400 MHz, CD3OD) δ: 7.92-7.96 (m, 3H), 7.50-7.61 (m, 3H), 7.24 (dd, 1H), 3.10 (d, 1H), 2.44-2.52 (m, 1H), 2.30-2.41 (m, 2H), 1.86-2.05 (m, 2H), 1.82 (s, 3H), 1.63-1.75 (m, 1H), 1.49-1.59 (m, 1H). |
| 142 | Ex. 3-48 | 5-fluoropicolinic acid | 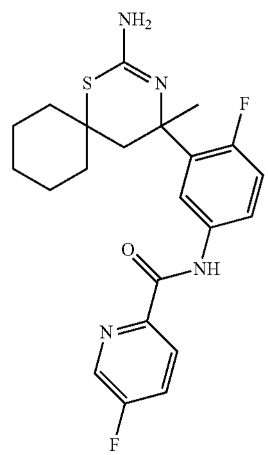 [SMILES: CC1(c2cc(NC(=O)c3ccc(F)cn3)ccc2F)CC2(CCCCC2)SC(N)=N1] | MS: 431.2 m/z (M + H)+<br>1H NMR (400 MHz, CDCl3) δ: 12.59 (s, 1H), 9.86 (s, 1H), 8.48 (d, J = 2.7 Hz, 1H), 8.31 (dd, J = 8.7, 4.6 Hz, 1H), 8.06 (m, 1H), 7.59 (m, 1H), 7.31 (dd, J = 7.2, 2.6 Hz, 1H), 7.09 (dd, J = 11.7, 8.8 Hz, 1H), 3.14 (d, J = 15.1 Hz, 1H), 2.06 (d, J = 15.1 Hz, 1H), 1.84 (s, 3H), 1.10-1.62 (m, 10H). |
| 143 | Ex. 3-49 | 5-fluoropicolinic acid | 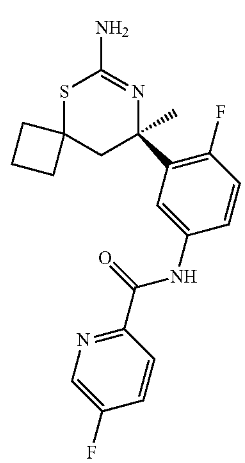 [SMILES: C[C@]1(c2cc(NC(=O)c3ccc(F)cn3)ccc2F)CC2(CCC2)SC(N)=N1] | MS: 403.2 m/z (M + H)+<br>1H NMR (400 MHz, CD3OD) δ: 8.59 (d, J = 2.8 Hz, 1H), 8.26 (dd, J = 8.8, 4.5 Hz, 1H), 7.89 (dt, J = 7.4, 2.9 Hz, 1H), 7.80 (dt, J = 8.6, 2.8 Hz, 1H), 7.77-7.70 (m, 1H), 7.22 (dd, J = 11.9, 8.8 Hz, 1H), 3.23 (d, J = 14.7 Hz, 1H), 2.52-2.41 (m, 1H), 2.39-2.30 (m, 1H), 2.25 (d, J = 14.7 Hz, 1H), 2.02-1.66 (m, 4H), 1.84 (s, 3H). |

| Comp No. | Step 1 bromo | Step 4 acid | Structure | Identification |
|---|---|---|---|---|
| 144 | Ex. 3-50 | | 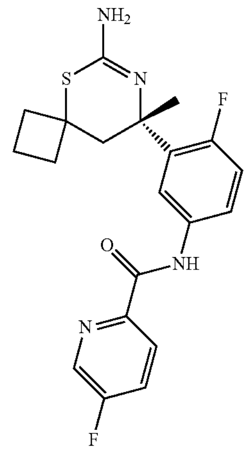 | MS: 403.1 m/z (M + H)+<br>¹H NMR (400 MHz, CD₃OD) δ: 8.60 (d, J = 2.8 Hz, 1H), 8.26 (dd, J = 8.8, 4.4 Hz, 1H), 7.93 (dt, J = 7.5, 2.6 Hz, 1H), 7.81 (dt, J = 8.6, 2.8 Hz, 1H), 7.76-7.70 (m, 1H), 7.22 (dd, J = 11.9, 8.9 Hz, 1H), 3.23 (d, J = 14.7 Hz, 1H), 2.52-2.41 (m, 1H), 2.39-2.30 (m, 1H), 2.25 (d, J = 14.7 Hz, 1H), 2.03-1.65 (m, 4H), 1.85 (s, 3H). |
| 145 | Ex. 3-50 | | 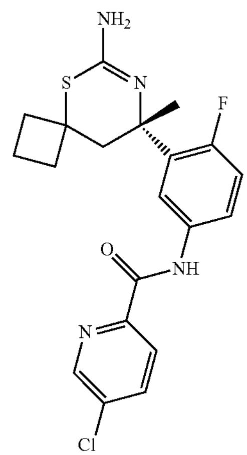 | MS: 419.1 m/z (M + H)+<br>¹H NMR (400 MHz, CD₃OD) δ: 8.70 (d, J = 2.2 Hz, 1H), 8.18 (d, J = 8.5 Hz, 1H), 8.07 (dd, J = 8.4, 2.4 Hz, 1H), 7.93 (dd, J = 7.4, 2.6 Hz, 1H), 7.74 (ddd, J = 9.0, 4.2, 2.7 Hz, 1H), 7.22 (dd, J = 11.9, 8.9 Hz, 1H), 3.23 (d, J = 14.8 Hz, 1H), 2.53-2.41 (m, 1H), 2.40-2.30 (m, 1H), 2.25 (d, J = 14.7 Hz, 1H), 2.03-1.65 (m, 4H), 1.85 (s, 3H). |
| 146 | Ex. 4-64 | | 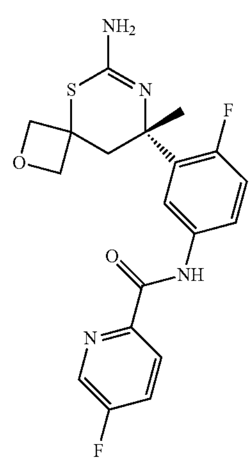 [SMILES: C[C@@]1(c2cc(NC(=O)c3ccc(F)cn3)ccc2F)CC2(COC2)SC(N)=N1] | MS: 405.1 m/z (M + H)+<br>¹H NMR (400 MHz, CD₃OD) δ: 8.63 (d, 1H), 8.31 (dd, 1H), 8.00 (dd, 1H), 7.83 (m, 1H), 7.79 (m, 1H), 7.30 (dd, 1H), 3.71 (d, 1H), 3.64 (d, 1H), 3.40 (d, 1H), 3.25 (d, 1H), 2.50 (d, 1H), 2.44 (d, 1H), 1.86 (s, 3H). |

| Comp No. | Step 1 bromo | Step 4 acid | Structure | Identification |
|---|---|---|---|---|
| 147 | Ex. 5-71 | | 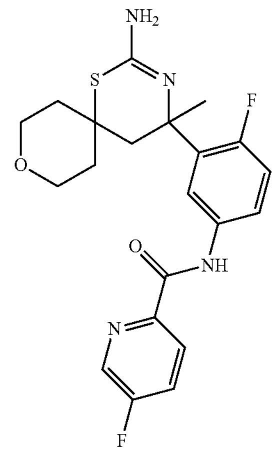 [SMILES: CC1(c2cc(NC(=O)c3ccc(F)cn3)ccc2F)CC2(CCOCC2)SC(N)=N1] | |
| 148 | Ex. 5-73 | | 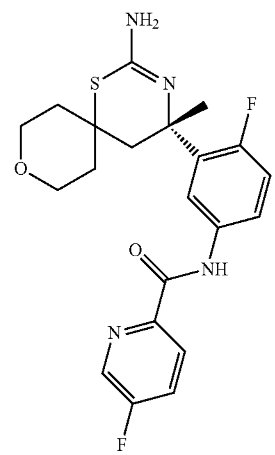 [SMILES: C[C@@]1(c2cc(NC(=O)c3ccc(F)cn3)ccc2F)CC2(CCOCC2)SC(N)=N1] | ¹H NMR (400 MHz, CD₃OD) δ: 8.63 (d, 1H), 8.30 (d, 1H), 8.01 (m, 1H), 7.84 (m, 1H), 7.77 (m, 1H), 7.27 (dd, 1H), 3.90 (dt, 1H), 3.65 (m, 2H), 3.40-3.48 (m, 1H), 3.20 (d, 1H), 2.31 (d, 1H), 2.04-2.12 (m, 1H), 1.88-1.94 (m, 1H), 1.87 (s, 3H), 1.47-1.57 (m, 1H), 1.30-1.37 (m, 1H). |
| 149 | Ex. 5-74 | | 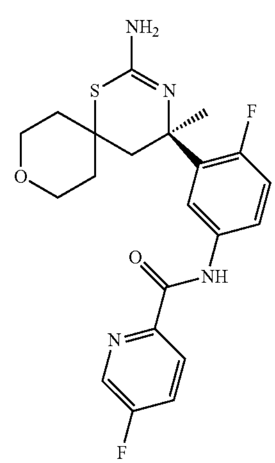 [SMILES: C[C@]1(c2cc(NC(=O)c3ccc(F)cn3)ccc2F)CC2(CCOCC2)SC(N)=N1] | |

-continued
| Comp No. | Step 1 bromo | Step 4 acid | Structure | Identification |
|---|---|---|---|---|
| 150 | 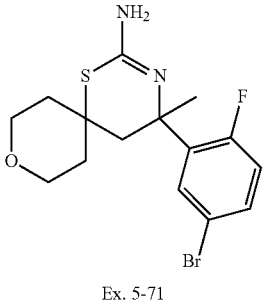 [SMILES: CC1(c2cc(Br)ccc2F)CC2(CCOCC2)SC(N)=N1]<br>Ex. 5-71 | 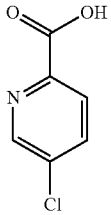 | 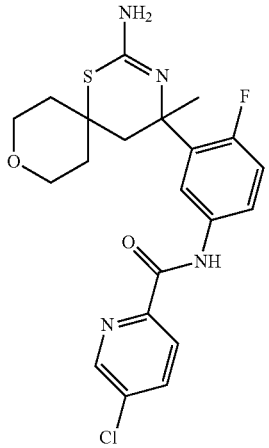 [SMILES: CC1(c2cc(NC(=O)c3ccc(Cl)cn3)ccc2F)CC2(CCOCC2)SC(N)=N1] | |
| 151 | 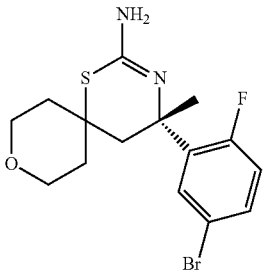<br>Ex. 5-73 | 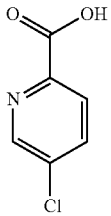 | 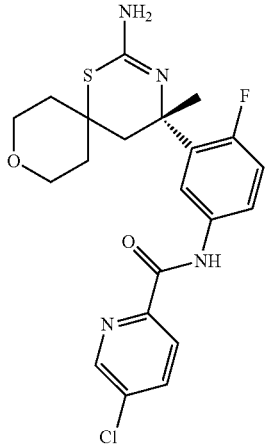 [SMILES: C[C@@]1(c2cc(NC(=O)c3ccc(Cl)cn3)ccc2F)CC2(CCOCC2)SC(N)=N1] | MS: 449.1 m/z (M + H)$^+$<br>$^1$H NMR (400 MHz, CD$_3$OD) δ: 8.73 (d, 1H), 8.21 (d, 1H), 8.10 (dd, 1H), 8.01 (dd, 1H), 7.76 (m, 1H), 7.26 (dd, 1H), 3.89 (dt, 1H), 3.65 (m, 2H), 3.39-3.54 (m, 1H), 3.19 (d, 1H), 2.30 (d, 1H), 2.04-2.12 (m, 1H), 1.88-1.94 (m, 1H), 1.86 (s, 3H), 1.47-1.57 (m, 1H), 1.30-1.37 (m, 1H). |
| 152 | 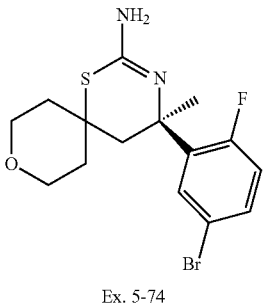 [SMILES: C[C@]1(c2cc(Br)ccc2F)CC2(CCOCC2)SC(N)=N1]<br>Ex. 5-74 | 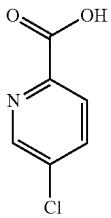 | 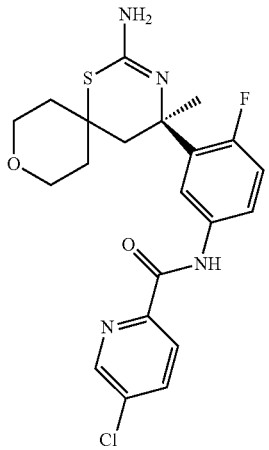 [SMILES: C[C@]1(c2cc(NC(=O)c3ccc(Cl)cn3)ccc2F)CC2(CCOCC2)SC(N)=N1] | |

-continued

| Comp No. | Step 1 bromo | Step 4 acid | Structure | Identification |
|---|---|---|---|---|
| 153 | Ex. 5-73 | | 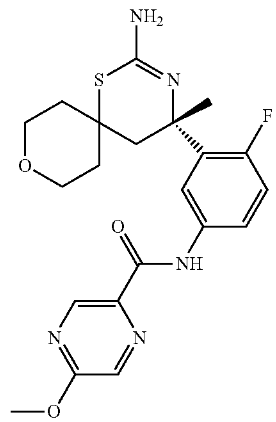 [SMILES: COc1cnc(C(=O)Nc2ccc(F)c([C@]3(C)CC4(CCOCC4)SC(N)=N3)c2)cn1] | MS: 446.1 m/z (M + H)+<br>¹H NMR (400 MHz, CD₃OD) δ: 8.94 (d, 1H), 8.32 (d, 1H), 8.01 (m, 1H), 7.72 (m, 1H), 7.26 (dd, 1H), 4.11 (s, 3H), 3.90 (dt, 1H), 3.65 (m, 2H), 3.41-3.52 (m, 1H), 3.17 (d, 1H), 2.30 (d, 1H), 2.04-2.12 (m, 1H), 1.88-1.94 (m, 1H), 1.87 (s, 3H), 1.47-1.57 (m, 1H), 1.30-1.37 (m, 1H). |
| 154 | Ex. 6-86 | | 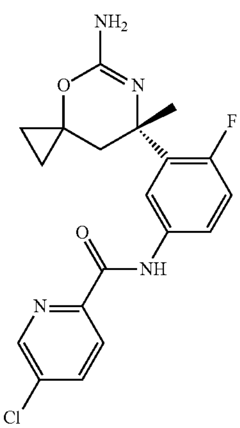 [SMILES: C[C@@]1(c2cc(NC(=O)c3ccc(Cl)cn3)ccc2F)CC2(CC2)OC(N)=N1] | MS: 389.1 m/z (M + H)+<br>¹H NMR (400 MHz, CD₃OD) δ: 8.74 (d, 1H), 8.23 (d, 1H), 8.05-8.15 (m, 2H), 7.81 (m, 1H), 7.26 (dd, 1H), 2.73 (d, 1H), 2.57 (d, 1H), 1.90 (s, 3H), 1.16 (m, 1H), 0.95 (m, 2H), 0.27 (m, 1H). |
| 155 | Ex. 7-94 | | 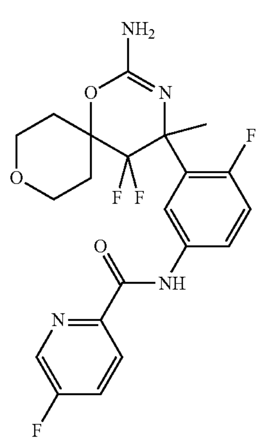 [SMILES: CC1(c2cc(NC(=O)c3ccc(F)cn3)ccc2F)N=C(N)OC2(CCOCC2)C1(F)F] | MS: 453.2 m/z (M + H)+<br>¹H NMR (400 MHz, CD₃OD) δ: 8.64 (d, 1H), 8.32 (m, 1H), 8.18 (m, 1H), 7.83-7.89 (m, 2H), 7.30 (dd, 1H), 4.01 (m, 1H), 3.90 (m, 1H), 3.71-3.79 (m, 2H), 2.23 (m, 2H), 1.98 (bs, 3H), 1.84-1.98 (m, 2H) |

-continued

| Comp No. | Step 1 bromo | Step 4 acid | Structure | Identification |
|---|---|---|---|---|
| 156 | Ex. 7-96 | | 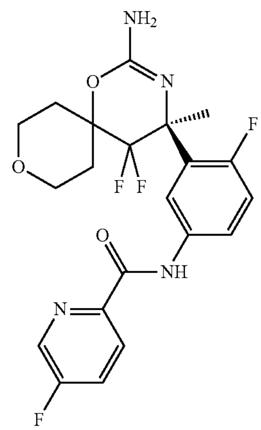 [SMILES: C[C@@]1(c2cc(NC(=O)c3ccc(F)cn3)ccc2F)N=C(N)OC2(CCOCC2)C1(F)F] | |
| 157 | Ex. 7-97 | | 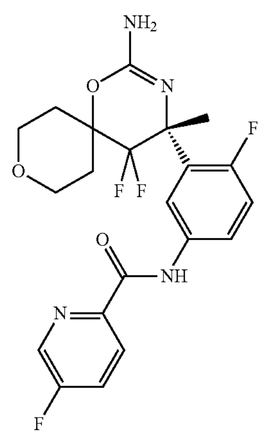 [SMILES: C[C@]1(c2cc(NC(=O)c3ccc(F)cn3)ccc2F)N=C(N)OC2(CCOCC2)C1(F)F] | MS: 453.2 m/z (M + H)+<br>1H NMR (400 MHz, CD3OD) δ: 8.63 (d, 1H), 8.31 (dd, 1H), 8.04 (dd, 1H), 7.84 (m, 2H), 7.18 (dd, 1H), 3.94 (m, 1H), 3.68-3.85 (m, 3H), 2.09 (m, 2H), 1.83 (bs, 3H), 1.79 (m, 2H) |
| 158 | Ex. 7-94 | | 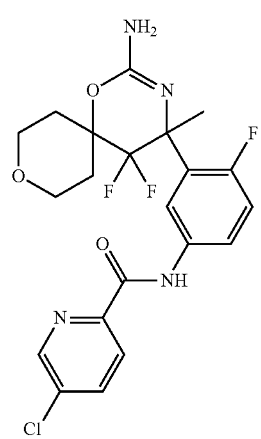 [SMILES: CC1(c2cc(NC(=O)c3ccc(Cl)cn3)ccc2F)N=C(N)OC2(CCOCC2)C1(F)F] | MS: 469.1 m/z (M + H)+<br>1H NMR (400 MHz, CD3OD) δ: 8.75 (d, 1H), 8.24 (d, 1H), 8.18 (m, 1H), 8.11 (dd, 1H), 7.88 (m, 2H), 7.30 (dd, 1H), 4.01 (m, 1H), 3.90 (m, 1H), 3.68-3.80 (m, 2H), 2.23 (m, 2H), 2.06 (bs, 3H), 1.84-2.00 (m, 2H) |

-continued

| Comp No. | Step 1 bromo | Step 4 acid | Structure | Identification |
|---|---|---|---|---|
| 159 | Ex. 7-98 | 5-fluoropyridine-2-carboxylic acid | 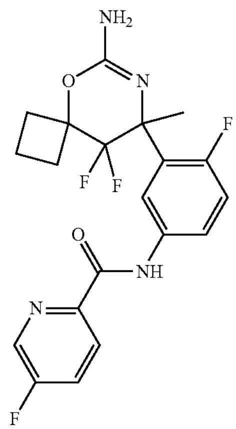 [SMILES: CC1(c2cc(NC(=O)c3ccc(F)cn3)ccc2F)N=C(N)OC2(CCC2)C1(F)F] | MS: 423.2 m/z (M + H)+<br>1H NMR (400 MHz, CD3OD) δ: 8.64 (d, 1H), 8.32 (dd, 1H), 8.20 (dd, 1H), 7.82-7.89 (m, 2H), 7.30 (dd, 1H), 2.90 (m, 1H), 2.50 (m, 1H), 2.30 (m, 1H), 2.11 (m, 2H), 2.03 (s, 3H), 1.83 (m, 1H) |
| 160 | Ex. 7-98 | 5-chloropyridine-2-carboxylic acid | 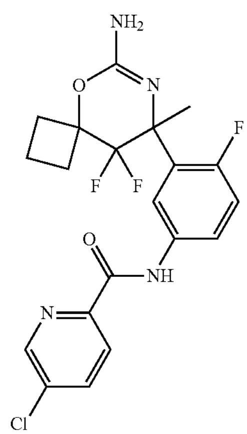 [SMILES: CC1(c2cc(NC(=O)c3ccc(Cl)cn3)ccc2F)N=C(N)OC2(CCC2)C1(F)F] | MS: 439.1 m/z (M + H)+<br>1H NMR (400 MHz, CD3OD) δ: 8.74 (d, 1H), 8.22 (d, 1H), 8.19 (dd, 1H), 8.10 (dd, 1H), 7.87 (m, 1H), 7.29 (dd, 1H), 2.90 (m, 1H), 2.49 (m, 1H), 2.29 (m, 1H), 2.11 (m, 2H), 2.02 (s, 3H), 1.82 (m, 1H) |
| 161 | Ex. 7-98 | 5-cyanopyridine-2-carboxylic acid | 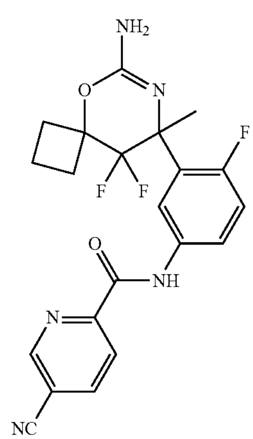 [SMILES: CC1(c2cc(NC(=O)c3ccc(C#N)cn3)ccc2F)N=C(N)OC2(CCC2)C1(F)F] | |

| Comp No. | Step 1 bromo | Step 4 acid | Structure | Identification |
|---|---|---|---|---|
| 162 | 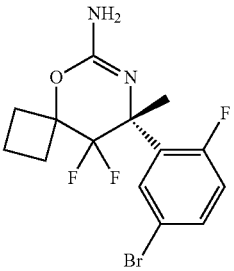 Ex. 7-100 | 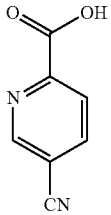 | 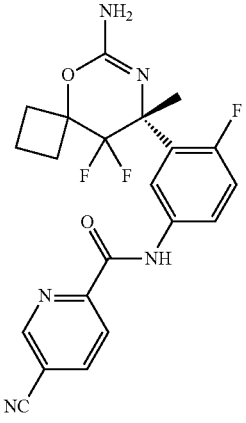 [SMILES: C[C@]1(c2cc(NC(=O)c3ccc(C#N)cn3)ccc2F)N=C(N)OC2(CCC2)C1(F)F] | MS: 430.2 m/z (M + H)$^+$<br>$^1$H NMR (400 MHz, CD$_3$OD) δ: 9.08 (d, 1H), 8.46 (dd, 1H), 8.39 (dd, 1H), 8.14 (dd, 1H), 7.89 (m, 1H), 7.26 (dd, 1H), 2.86 (m, 1H), 2.42 (m, 1H), 2.22 (m, 1H), 2.07 (m, 2H), 1.93 (s, 3H), 1.78 (m, 1H) |
| 163 | 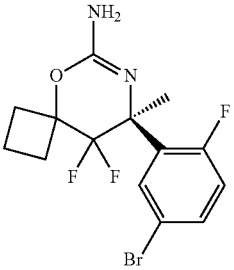 Ex. 7-99 | 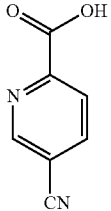 | 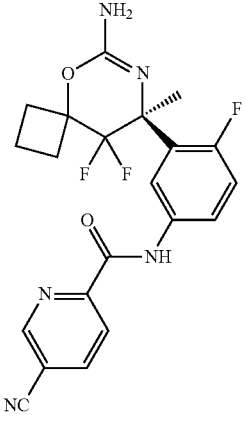 [SMILES: C[C@@]1(c2cc(NC(=O)c3ccc(C#N)cn3)ccc2F)N=C(N)OC2(CCC2)C1(F)F] | |
| 164 | 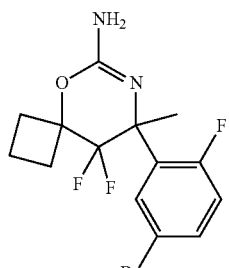 Ex. 7-98 | 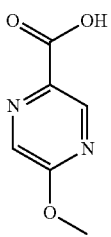 | 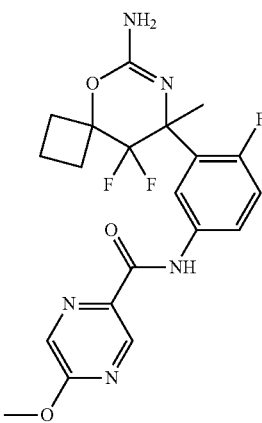 | MS: 436.2 m/z (M + H)$^+$<br>$^1$H NMR (400 MHz, CD$_3$OD) δ: 8.95 (d, 1H), 8.33 (d, 1H), 8.20 (dd, 1H), 7.84 (m, 1H), 7.30 (dd, 1H), 4.11 (s, 3H), 2.91 (m, 1H), 2.50 (m, 1H), 2.29 (m, 1H), 2.11 (m, 2H), 2.03 (s, 3H), 1.83 (m, 1H) |

-continued

| Comp No. | Step 1 bromo | Step 4 acid | Structure | Identification |
|---|---|---|---|---|
| 165 | Ex. 7-98 | 2-methyl oxazole-4-carboxylic acid | 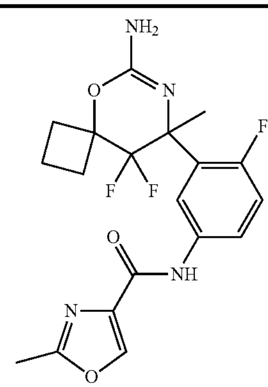 | MS: 409.2 m/z (M + H)+<br>1H NMR (400 MHz, CD3OD)<br>δ: 8.40 (s, 1H), 8.09 (dd, 1H),<br>7.76 (m, 1H), 7.30 (dd, 1H),<br>2.90 (m, 1H), 2.55 (s, 3H),<br>2.48 (m, 1H), 2.28 (m, 1H),<br>2.08 (m, 2H), 2.00 (s, 3H),<br>1.82 (m, 1H) |

Example 10
Synthesis of (S)-8-(2-fluoro-5-((5-fluoropyridin-2-yl)methylamino)phenyl)-8-methyl-5-oxa-7-azaspiro[3.5]non-6-en-6-amine (169)

(S)-8-(2-fluoro-5-((5-fluoropyridin-2-yl)methylamino)phenyl)-8-methyl-5-oxa-7-azaspiro[3.5]non-6-en-6-amine 169 was prepared in from (S)-tert-butyl 8-(5-amino-2-fluorophenyl)-8-methyl-5-oxa-7-azaspiro[3.5]non-6-en-6-ylcarbamate 166 (prepared by the methods of Example 9, for example isolating after Step 3 in the preparation of compound 126) and 5-fluoropicolinaldehyde 167 in two Steps as follows:

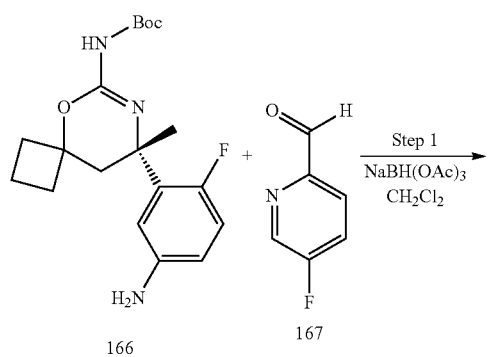

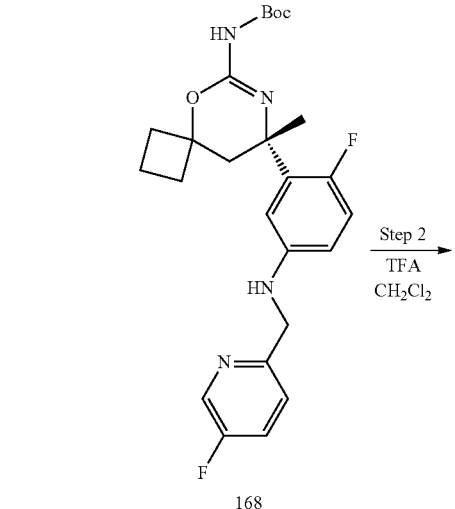

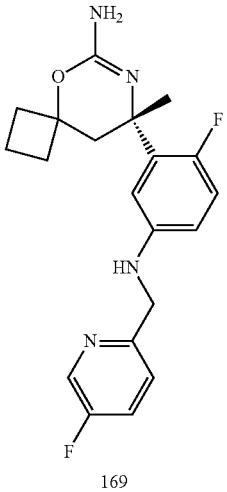

169

Step 1—synthesis of (S)-tert-butyl 8-(2-fluoro-5-((5-fluoropyridin-2-yl)methylamino)phenyl)-8-methyl-5-oxa-7-azaspiro[3.5]non-6-en-6-ylcarbamate (168)

Sodium triacetoxyborohydride (0.02624 g, 0.1238 mmol) was added to a solution of (S)-tert-butyl 8-(5-amino-2-fluorophenyl)-8-methyl-5-oxa-7-azaspiro[3.5]non-6-en-6-ylcarbamate (166, 0.03 g, 0.08255 mmol) and 5-fluoropicolinaldehyde (167, 0.01239 g, 0.09906 mmol) in 1 mL of CH3OH and the resulting solution was stirred at room temperature for 18 hours. The reaction mixture was concentrated under vacuum and the resulting material purified by silica gel chromatography (ISCO, hexane/EtOAc 0-100%). Appropriate fractions were combined and concentrated under vacuum to provide the desired compound (168, 0.022 g, 0.04656 mmol, 56.40%) MS: 473.3 m/z (M+H)+.

Step 2—synthesis of (S)-8-(2-fluoro-5-((5-fluoropyridin-2-yl)methylamino)phenyl)-8-methyl-5-oxa-7-azaspiro[3.5]non-6-en-6-amine (169)

Trifluoroacetic acid (0.5 mL) was added to a solution of (S)-tert-butyl 8-(2-fluoro-5-((5-fluoropyridin-2-yl)methylamino)phenyl)-8-methyl-5-oxa-7-azaspiro[3.5]non-6-en-6-ylcarbamate (168, 0.025 g, 0.05291 mmol) in 0.5 mL of CH$_2$Cl$_2$. The resulting solution was stirred at room temperature for 30 minutes, then concentrated under vacuum and the residue was purified by preparative HPLC. Appropriate fractions were combined and concentrated under vacuum to provide the desired compound (169, 0.009 g, 0.02417 mmol). MS: 373.2 m/z (M+H)$^+$. $^1$H NMR (400 MHz, CDCl$_3$) δ: 11.95 (s, 1H), 8.45 (s, 1H), 7.46 (m, 2H), 6.86 (dd, J=11.1, 8.7 Hz, 1H), 6.52 (m, 2H), 4.42 (s, 2H), 3.10 (d, J=14.6 Hz, 1H), 2.39 (m, 1H), 2.20 (m, 1H), 2.07 (d, J=14.6 Hz, 1H), 1.83 (m, 2H), 1.74 (s, 3H), 1.48-1.66 (m, 2H).

Example 11

Synthesis of (S)-8-(5-(7-chloroquinazolin-4-ylamino)-2-fluorophenyl)-8-methyl-5-oxa-7-azaspiro[3.5]non-6-en-6-amine (173)

(S)-8-(5-(7-chloroquinazolin-4-ylamino)-2-fluorophenyl)-8-methyl-5-oxa-7-azaspiro[3.5]non-6-en-6-amine 173 was prepared from 7-chloroquinazolin-4(3H)-one 170 in three Steps as follows:

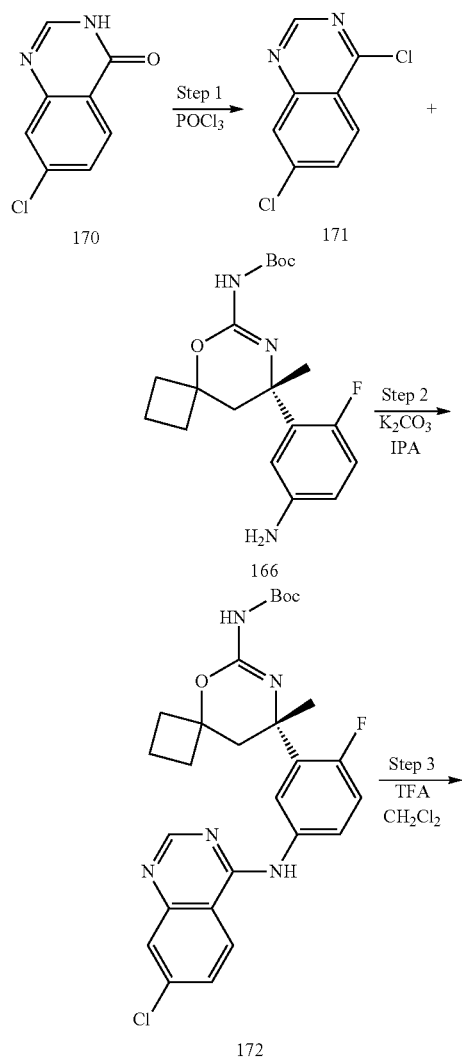

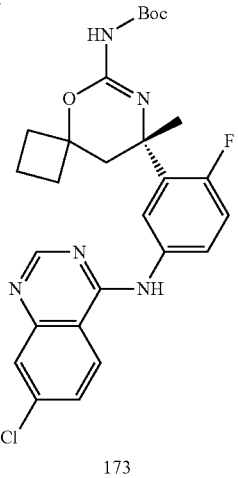

Step 1—synthesis of 4,7-dichloroquinazoline (171)

7-Chloro-3H-quinazolin-4-one (170, 0.155 g, 0.85830 mmol) was dissolved in 1 mL of POCl$_3$ in a screw cap vial. The vial was sealed and placed in a 100° C. oil bath for 3 hours. The resulting solution was concentrated under vacuum and co-concentrated from toluene three times to provide the desired compound (171, 0.162 g, 0.81391 mmol, 94.828%). MS: 199.0 m/z (M+H)$^+$.

Step 2—synthesis of (5)-tert-butyl 8-(5-(7-chloroquinazolin-4-ylamino)-2-fluorophenyl)-8-methyl-5-oxa-7-azaspiro[3.5]non-6-en-6-ylcarbamate (172)

(S)-tert-butyl 8-(5-amino-2-fluorophenyl)-8-methyl-5-oxa-7-azaspiro[3.5]non-6-en-6-ylcarbamate (166, 0.026 g, 0.07155 mmol), 4,7-dichloroquinazoline (171, 0.02136 g, 0.1073 mmol) and potassium carbonate (0.01978 g, 0.1431 mmol) were dissolved in 0.5 mL of isopropanol in a screw cap vial. The vial was sealed and placed in a 70° C. oil bath for 3 hours, then concentrated under vacuum and the residue was purified by silica gel chromatography (ISCO, CH$_2$Cl$_2$/MeOH 0-10%). Appropriate fractions were combined and concentrated under vacuum to provide the desired compound (172, 0.032 g, 0.06084 mmol, 85.03%). MS: 526.2 m/z (M+H)$^+$.

Step 3—synthesis of (S)-8-(5-(7-chloroquinazolin-4-ylamino)-2-fluorophenyl)-8-methyl-5-oxa-7-azaspiro[3.5]non-6-en-6-amine (173)

Trifluoroacetic acid (1 mL) was added to a solution of (5)-tert-butyl 8-(5-(7-chloroquinazolin-4-ylamino)-2-fluorophenyl)-8-methyl-5-oxa-7-azaspiro[3.5]non-6-en-6-ylcarbamate (172, 0.03 g, 0.05703 mmol) in 1 mL of CH$_2$Cl$_2$. The reaction was stirred at room temperature for 1 hour, then concentrated under vacuum, and the residue was purified by preparative HPLC. Appropriate fractions were combined and concentrated under vacuum to provide the desired compound (173, 0.018 g, 0.04226 mmol, 74.10%). MS: 426.1 m/z (M+H)+. $^1$H NMR (400 MHz, CDCl$_3$) δ: 11.20 (s, 1H), 8.75 (s, 1H), 8.61 (d, J=8.8 Hz, 1H), 8.15 (m, 1H), 7.92 (m, 2H), 7.55 (d, J=7.1 Hz, 1H), 7.18 (dd, J=11.5, 8.9 Hz, 1H), 3.11 (d, J=14.8 Hz, 1H), 2.46 (m, 1H), 2.28 (d, J=14.8 Hz, 1H), 1.99-2.25 (m, 5H), 1.69 (s, 3H), 1.52-1.60 (m, 2H).

Example 12

Synthesis of (S,E)-8-(2-fluoro-5-(4-fluorostyryl)phenyl)-8-methyl-5-oxa-7-azaspiro[3.5]non-6-en-6-amine (177)

(S,E)-8-(2-fluoro-5-(4-fluorostyryl)phenyl)-8-methyl-5-oxa-7-azaspiro[3.5]non-6-en-6-amine 177 was prepared from (5)-tert-butyl 8-(5-bromo-2-fluorophenyl)-8-methyl-5-oxa-7-azaspiro[3.5]non-6-en-6-ylcarbamate 174 (prepared by the methods of Step 1 of Example 9, starting from compound 33 of Example 2), and (E)-4-fluorostyrylboronic acid 175 in two Steps as follows:

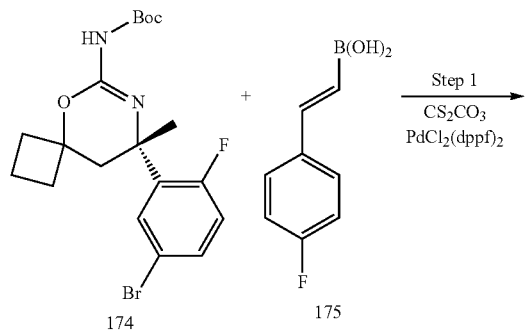

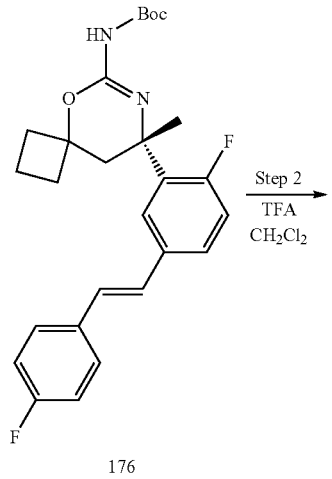

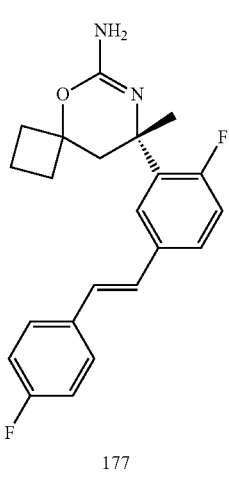

Step 1—synthesis of (S,E)-tert-butyl 8-(2-fluoro-5-(4-fluorostyryl)phenyl)-8-methyl-5-oxa-7-azaspiro[3.5]non-6-en-6-ylcarbamate (176)

(S)-tert-butyl 8-(5-bromo-2-fluorophenyl)-8-methyl-5-oxa-7-azaspiro[3.5]non-6-en-6-ylcarbamate (174, 51 mg, 0.12 mmol), (E)-4-fluorostyrylboronic acid (175, 40 mg, 0.24 mmol), 1,1'-bis(diphenylphosphino)ferrocene palladium (II) dichloride (26 mg, 0.036 mmol) and cesium carbonate (117 mg, 0.36 mmol) were combined in 3.25 mL of DME and 1 mL of water. The mixture was flushed with nitrogen for 2 minutes and then heated at 85° C. for 30 minutes. The mixture was cooled to room temperature, then diluted with 50 mL of EtOAc, washed with 10 mL, then 5 mL of water and 5 mL of brine. The organic extract was dried with $Na_2SO_4$, filtered and the filtrate concentrated under vacuum to provide the desired compound (176, 110 mg).

Step 2—synthesis of (S,E)-tert-butyl 8-(2-fluoro-5-(4-fluorostyryl)phenyl)-8-methyl-5-oxa-7-azaspiro[3.5]non-6-en-6-ylcarbamate (177)

(S,E)-tert-butyl 8-(2-fluoro-5-(4-fluorostyryl)phenyl)-8-methyl-5-oxa-7-azaspiro[3.5]non-6-en-6-ylcarbamate (176, 110 mg) was taken up into 2 mL of $CH_2Cl_2$ and 1 mL of TFA was added dropwise at room temperature. The mixture was stirred for 60 minutes at room temperature, then concentrated under vacuum. The resulting material was purified by preparative reverse-phase HPLC. Appropriate fractions were combined and concentrated under vacuum to provide the desired compound as a mono-TFA salt (177, 47 mg, ~81% yield). MS: 369.2 m/z (M+H)±. $^1$H NMR (400 MHz, $CDCl_3$) δ: 7.64-7.58 (m, 2H), 7.57-7.4 (m, 1H), 7.39 (dd, 1H), 7.13-7.04 (m, 3H), 7.00 (d, 2H), 3.11 (d, 1H), 2.50 (m, 1H), 2.28 (m, 1H) 2.21 (d, 1H), 1.97-1.84 (m, 2H), 1.85 (s, 3H), 1.68-1.59 (m, 1H), 1.58-1.43 (m, 1H).

Additional compounds are prepared following the methods of this example, optionally replacing (S)-tert-butyl 8-(5-bromo-2-fluorophenyl)-8-methyl-5-oxa-7-azaspiro[3.5]non-6-en-6-ylcarbamate 174 with a suitable Boc protected bromo-(hetero)aryl compound (similarly prepared by the methods of Examples 9 Step 1) and optionally replacing (E)-4-fluorostyrylboronic acid 175 with a suitable boronic acid in Step 1. The following compounds were prepared by this method:

(S,E)-8-(2-fluoro-5-(4-fluorostyryl)phenyl)-8-methyl-5-oxa-7-azaspiro[3.5]non-6-en-6-amine (178), and (S,E)-8-(5-(4-chlorostyryl)-2-fluorophenyl)-8-methyl-5-oxa-7-azaspiro[3.5]non-6-en-6-amine (179).

The following table provides the compound number (column 1), Br-(hetero)aryl compound used in Step 1 (column 2), and boronic acid compound used in Step 1 (column 3) to give the compound shown in column 4. Identification data is provided in column 5.

| Comp No. | Step 1 bromo | Step 1 boronic acid | Structure | Identification |
|---|---|---|---|---|
| 178 | (structure) | (structure) | (structure) | MS: 433.2 m/z (M + H)+<br>1H NMR (400 MHz, CD3OD) δ: 7.69-7.62 (m, 1H), 7.62-7.54 (m, 2H), 7.49 (dd, J = 8.0, 2.1 Hz, 1H), 7.21 (dd, J = 11.3, 8.5 Hz, 1H), 7.15 (d, J = 4.0 Hz, 1H), 7.13-7.04 (m, 3H), 3.03 (d, J = 15.1 Hz, 1H), 2.38 (d, J = 15.1 Hz, 1H), 2.30-1.60 (m, 7H), 1.77 (s, 3H), 1.52-1.38 (m, 1H). |
| 179 | (structure) | (structure) | (structure) | MS: 385.1 m/z (M + H)+<br>1H NMR (400 MHz, CD3OD) δ: 7.69-7.62 (m, 1H), 7.64-7.55 (m, 2H), 7.50-7.35 (m, 3H), 7.30-7.10 (m, 3H), 3.10 (d, 1H), 2.51 (m, 1H), 2.30 (m, 1H) 2.35 (d, 1H), 1.97-1.84 (m, 2H), 1.80 (s, 3H), 1.70-1.60 (m, 1H), 1.58-1.48 (m, 1H). |

Example 13

Synthesis of (S)-4-(2-fluoro-5-(3-methoxypyridin-2-ylamino)phenyl)-4-methyl-9-oxa-1-thia-3-azaspiro[5.5]undec-2-en-2-amine (182)

(S)-4-(2-fluoro-5-(3-methoxypyridin-2-ylamino)phenyl)-4-methyl-9-oxa-1-thia-3-azaspiro[5.5]undec-2-en-2-amine 182 was prepared from (S)-tert-butyl 4-(5-amino-2-fluorophenyl)-4-methyl-9-oxa-1-thia-3-azaspiro[5.5]undec-2-en-2-ylcarbamate 180 (prepared by the methods of Example 9, for example isolating after Step 3 in the preparation of compound 148), and 2-fluoro-3-methoxypyridine 181 in one Step as follows:

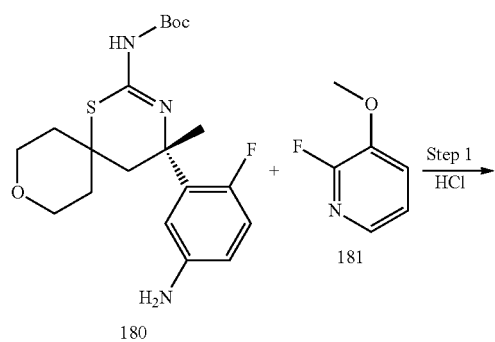

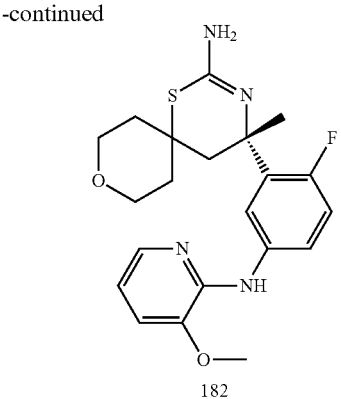

Step 1—synthesis of (S)-4-(2-fluoro-5-(3-methoxypyridin-2-ylamino)phenyl)-4-methyl-9-oxa-1-thia-3-azaspiro[5.5]undec-2-en-2-amine (182)

(S)-tert-butyl 4-(5-amino-2-fluorophenyl)-4-methyl-9-oxa-1-thia-3-azaspiro[5.5]undec-2-en-2-ylcarbamate (180, 20 mg, 0.048 mmol) was dissolved in 1 mL of isopropanol, and 2-fluoro-3-methoxypyridine (181, 12 mg, 0.098 mmol) was added. The mixture was stirred at room temperature for 5 minutes, then 0.1 mL of HCl (4N in dioxane) was added.

The resulting mixture was heated at 100° C. for 2 days, then concentrated under vacuum. The resulting material was purified by HPLC (acetonitrile/water with 0.1% TFA). Appropriate fractions were combined and concentrated under vacuum to provide the desired compound as a di-TFA salt (182, 8.3 mg, 0.02 mmol). MS: 417.2 m/z (M+H)$^+$. $^1$H NMR (400 MHz, CD$_3$OD) δ: 7.46-7.59 (m, 4H), 7.34 (dd, 1H), 6.97 (t, 1H), 4.07 (s, 3H), 3.89 (dt, 1H), 3.57-3.68 (m, 2H), 3.41-3.52 (m, 1H), 3.16 (d, 1H), 2.32 (d, 1H), 2.04-2.12 (m, 1H), 1.88-1.94 (m, 1H), 1.87 (s, 3H), 1.47-1.57 (m, 1H), 1.30-1.37 (m, 1H).

Example 14

Synthesis of Additional Compounds

The methods as described in Schemes 1-11, Examples 1-13, or variations as would be known to one of skill in the art are used to make additional compounds.
The following compounds are prepared:
4-methyl-4-(4-(5-(prop-1-ynyl)pyridin-3-yl)thiophen-2-yl)-1-oxa-3-azaspiro[5.5]undec-2-en-2-amine (500),
N-(3-(2-amino-4-methyl-1-thia-3-azaspiro[5.5]undec-2-en-4-yl)-4-fluorophenyl)-5-chloropicolinamide (502),
N-(3-(2-amino-4-methyl-1-thia-3-azaspiro[5.5]undec-2-en-4-yl)-4-fluorophenyl)-5-cyanopicolinamide (503),
7-methyl-7-(4-(5-(prop-1-ynyl)pyridin-3-yl)thiophen-2-yl)-4-thia-6-azaspiro[2.5]oct-5-en-5-amine (504),
7-methyl-7-(4-(5-(prop-1-ynyl)pyridin-3-yl)thiophen-2-yl)-4-oxa-6-azaspiro[2.5]oct-5-en-5-amine (505),
8-methyl-8-(4-(5-(prop-1-ynyl)pyridin-3-yl)thiophen-2-yl)-5-thia-7-azaspiro[3.5]non-6-en-6-amine (506),
4'-methyl-4'-(4-(5-(prop-1-ynyl)pyridin-3-yl)thiophen-2-yl)-4',5'-dihydrospiro[bicyclo[3.1.0]hexane-3,6'-[1,3]thiazin]-2'-amine (508),
7-methyl-7-(1-(5-(prop-1-ynyl)pyridin-3-yl)-1H-pyrazol-4-yl)-4-thia-6-azaspiro[2.5]oct-5-en-5-amine (509),
5-(5-(5-amino-7-methyl-4-thia-6-azaspiro[2.5]oct-5-en-7-yl)-4-chlorothiophen-2-yl)nicotinonitrile (510),
N-(3-(5-amino-7-methyl-4-thia-6-azaspiro[2.5]oct-5-en-7-yl)-4-fluorophenyl)-5-fluoropicolinamide (511),
N-(3-(5-amino-7-methyl-4-thia-6-azaspiro[2.5]oct-5-en-7-yl)-4-fluorophenyl)-5-fluoropicolinamide (512),
N-(3-(6-amino-8-methyl-5-thia-7-azaspiro[3.5]non-6-en-8-yl)-4-fluorophenyl)-5-fluoropicolinamide (513),
4-methyl-4-(4-(5-(prop-1-ynyl)pyridin-3-yl)thiophen-2-yl)-1,8-dioxa-3-azaspiro[5.5]undec-2-en-2-amine (515),
8-methyl-8-(4-(5-(prop-1-ynyl)pyridin-3-yl)thiophen-2-yl)-2,5-dioxa-7-azaspiro[3.5]non-6-en-6-amine (516),
5-(5-(6-amino-8-methyl-2,5-dioxa-7-azaspiro[3.5]non-6-en-8-yl)thiophen-3-yl)nicotinonitrile (517),
8-(4-(5-(cyclopropylethynyl)pyridin-3-yl)thiophen-2-yl)-8-methyl-2,5-dioxa-7-azaspiro[3.5]non-6-en-6-amine (518),
8-methyl-8-(1-(5-(prop-1-ynyl)pyridin-3-yl)-1H-pyrazol-4-yl)-2,5-dioxa-7-azaspiro[3.5]non-6-en-6-amine (519),
5-(5-(6-amino-8-methyl-2,5-dioxa-7-azaspiro[3.5]non-6-en-8-yl)-4-chlorothiophen-2-yl)nicotinonitrile (520),
N-(3-(6-amino-8-methyl-2,5-dioxa-7-azaspiro[3.5]non-6-en-8-yl)-4-fluorophenyl)-5-fluoropicolinamide (521),
4-methyl-4-(4-(5-(prop-1-ynyl)pyridin-3-yl)thiophen-2-yl)-8-oxa-1-thia-3-azaspiro[5.5]undec-2-en-2-amine (523),
5-(5-(6-amino-8-methyl-2-oxa-5-thia-7-azaspiro[3.5]non-6-en-8-yl)thiophen-3-yl)nicotinonitrile (524),
8-(4-(5-(cyclopropylethynyl)pyridin-3-yl)thiophen-2-yl)-8-methyl-2-oxa-5-thia-7-azaspiro[3.5]non-6-en-6-amine (525),
8-methyl-8-(1-(5-(prop-1-ynyl)pyridin-3-yl)-1H-pyrazol-4-yl)-2-oxa-5-thia-7-azaspiro[3.5]non-6-en-6-amine (526),
5-(5-(6-amino-8-methyl-2-oxa-5-thia-7-azaspiro[3.5]non-6-en-8-yl)-4-chlorothiophen-2-yl)nicotinonitrile (527),
N-(3-(6-amino-8-methyl-2-oxa-5-thia-7-azaspiro[3.5]non-6-en-8-yl)-4-fluorophenyl)-5-fluoropicolinamide (528),
8-methyl-8-(4-(5-(prop-1-ynyl)pyridin-3-yl)thiophen-2-yl)-2,5-dithia-7-azaspiro[3.5]non-6-en-6-amine-2,2-dioxide (529),
4-methyl-4-(4-(5-(prop-1-ynyl)pyridin-3-yl)thiophen-2-yl)-1-oxa-8-thia-3-azaspiro[5.5]undec-2-en-2-amine-8,8-dioxide (530),
8-methyl-8-(4-(5-(prop-1-ynyl)pyridin-3-yl)thiophen-2-yl)-5-oxa-2-thia-7-azaspiro[3.5]non-6-en-6-amine-2,2-dioxide (531),
5-(5-(6-amino-8-methyl-5-oxa-2-thia-7-azaspiro[3.5]non-6-en-8-yl-2,2-dioxide)thiophen-3-yl)nicotinonitrile (532),
8-(4-(5-(cyclopropylethynyl)pyridin-3-yl)thiophen-2-yl)-8-methyl-5-oxa-2-thia-7-azaspiro[3.5]non-6-en-6-amine-2,2-dioxide (533),
8-methyl-8-(1-(5-(prop-1-ynyl)pyridin-3-yl)-1H-pyrazol-4-yl)-5-oxa-2-thia-7-azaspiro[3.5]non-6-en-6-amine-2,2-dioxide (534),
5-(5-(6-amino-8-methyl-5-oxa-2-thia-7-azaspiro[3.5]non-6-en-8-yl-2,2-dioxide)-4-chlorothiophen-2-yl)nicotinonitrile (535),
N-(3-(6-amino-8-methyl-5-oxa-2-thia-7-azaspiro[3.5]non-6-en-8-yl-2,2-dioxide)-4-fluorophenyl)-5-fluoropicolinamide (536),
4-methyl-4-(4-(5-(prop-1-ynyl)pyridin-3-yl)thiophen-2-yl)-1,9-dithia-3-azaspiro[5.5]undec-2-en-2-amine-9,9-dioxide (537),
4-methyl-4-(4-(5-(prop-1-ynyl)pyridin-3-yl)thiophen-2-yl)-1-oxa-9-thia-3-azaspiro[5.5]undec-2-en-2-amine-9,9-dioxide (538),
4-methyl-4-(4-(5-(prop-1-ynyl)pyridin-3-yl)thiophen-2-yl)-1,8-dithia-3-azaspiro[5.5]undec-2-en-2-amine-8,8-dioxide (539),
5-(5-(6-amino-8-methyl-2,5-dithia-7-azaspiro[3.5]non-6-en-8-yl-2,2-dioxide)thiophen-3-yl)nicotinonitrile (540),
8-(4-(5-(cyclopropylethynyl)pyridin-3-yl)thiophen-2-yl)-8-methyl-2,5-dithia-7-azaspiro[3.5]non-6-en-6-amine-2,2-dioxide (541),
8-methyl-8-(1-(5-(prop-1-ynyl)pyridin-3-yl)-1H-pyrazol-4-yl)-2,5-dithia-7-azaspiro[3.5]non-6-en-6-amine-2,2-dioxide (542),
5-(5-(6-amino-8-methyl-2,5-dithia-7-azaspiro[3.5]non-6-en-8-yl-2,2-dioxide)-4-chlorothiophen-2-yl)nicotinonitrile (543),
N-(3-(6-amino-8-methyl-2,5-dithia-7-azaspiro[3.5]non-6-en-8-yl-2,2-dioxide)-4-fluorophenyl)-5-fluoropicolinamide (544),
1-(6-amino-8-methyl-8-(4-(5-(prop-1-ynyl)pyridin-3-yl)thiophen-2-yl)-5-thia-7-azaspiro[3.5]non-6-en-2-yl)ethanone (545),
1-(6-amino-8-methyl-8-(4-(5-(prop-1-ynyl)pyridin-3-yl)thiophen-2-yl)-5-oxa-7-azaspiro[3.5]non-6-en-2-yl)ethanone (546),
N-(3-(2-acetyl-6-amino-8-methyl-5-thia-7-azaspiro[3.5]non-6-en-8-yl)-4-fluorophenyl)-5-fluoropicolinamide (547),
N-(3-(2-acetyl-6-amino-8-methyl-5-oxa-7-azaspiro[3.5]non-6-en-8-yl)-4-fluorophenyl)-5-fluoropicolinamide (548),
N-(3-(6-amino-2,2-difluoro-8-methyl-5-oxa-7-azaspiro[3.5]non-6-en-8-yl)-4-fluorophenyl)-5-fluoropicolinamide (549), N-(3-(6-amino-2,2-difluoro-8-methyl-5-thia-7-azaspiro[3.5]non-6-en-8-yl)-4-fluorophenyl)-5-fluoropicolinamide (551),
N-(3-(2-amino-9,9-difluoro-4-methyl-1-thia-3-azaspiro[5.5]undec-2-en-4-yl)-4-fluorophenyl)-5-fluoropicolinamide (552),
2,2-difluoro-8-methyl-8-(4-(5-(prop-1-ynyl)pyridin-3-yl)thiophen-2-yl)-5-thia-7-azaspiro[3.5]non-6-en-6-amine (553),
9,9-difluoro-4-methyl-4-(4-(5-(prop-1-ynyl)pyridin-3-yl)thiophen-2-yl)-1-thia-3-azaspiro[5.5]undec-2-en-2-amine (554),
2,2,9,9-tetrafluoro-8-methyl-8-(4-(5-(prop-1-ynyl)pyridin-3-yl)thiophen-2-yl)-5-thia-7-azaspiro[3.5]non-6-en-6-amine (555),
5,5,9,9-tetrafluoro-4-methyl-4-(4-(5-(prop-1-ynyl)pyridin-3-yl)thiophen-2-yl)-1-thia-3-azaspiro[5.5]undec-2-en-2-amine (556),
9,9-difluoro-8-methyl-8-(4-(5-(prop-1-ynyl)pyridin-3-yl)thiophen-2-yl)-5-thia-7-azaspiro[3.5]non-6-en-6-amine (557),
10,10-difluoro-9-methyl-9-(4-(5-(prop-1-ynyl)pyridin-3-yl)thiophen-2-yl)-6-thia-8-azaspiro[4.5]dec-7-en-7-amine (558),
5,5-difluoro-4-methyl-4-(4-(5-(prop-1-ynyl)pyridin-3-yl)thiophen-2-yl)-1-thia-3-azaspiro[5.5]undec-2-en-2-amine (559),
5,5-difluoro-4-methyl-4-(4-(5-(prop-1-ynyl)pyridin-3-yl)thiophen-2-yl)-9-oxa-1-thia-3-azaspiro[5.5]undec-2-en-2-amine (560),
N-(3-(6-amino-2,2,9,9-tetrafluoro-8-methyl-5-oxa-7-azaspiro[3.5]non-6-en-8-yl)-4-fluorophenyl)-5-fluoropicolinamide (561),
N-(3-(2-amino-5,5,9,9-tetrafluoro-4-methyl-1-oxa-3-azaspiro[5.5]undec-2-en-4-yl)-4-fluorophenyl)-5-fluoropicolinamide (562),
N-(3-(7-amino-10,10-difluoro-9-methyl-6-oxa-8-azaspiro[4.5]dec-7-en-9-yl)-4-fluorophenyl)-5-fluoropicolinamide (564),
N-(3-(2-amino-5,5-difluoro-4-methyl-1-oxa-3-azaspiro[5.5]undec-2-en-4-yl)-4-fluorophenyl)-5-fluoropicolinamide (565),
3-(2-amino-4-methyl-9-oxa-1-thia-3-azaspiro[5.5]undec-2-en-4-yl)-4-fluoro-N-(5-fluoropyridin-2-yl)benzamide (569),
3-(2-amino-4-methyl-1,9-dioxa-3-azaspiro[5.5]undec-2-en-4-yl)-4-fluoro-N-(5-fluoropyridin-2-yl)benzamide (570),
3-(6-amino-8-methyl-5-oxa-7-azaspiro[3.5]non-6-en-8-yl)-4-fluoro-N-(5-fluoropyridin-2-yl)benzamide (571), and
3-(6-amino-8-methyl-5-thia-7-azaspiro[3.5]non-6-en-8-yl)-4-fluoro-N-(5-fluoropyridin-2-yl)benzamide (572)
4-methyl-4-(4-(5-(prop-1-ynyl)pyridin-3-yl)thiophen-2-yl)-1-thia-3-azaspiro[5.5]undec-2-en-2-amine (573),
9-methyl-9-(4-(5-(prop-1-ynyl)pyridin-3-yl)thiophen-2-yl)-6-thia-8-azaspiro[4.5]dec-7-en-7-amine (574),
(S)-4-methyl-4-(4-(5-(prop-1-ynyl)pyridin-3-yl)thiophen-2-yl)-1-thia-3-azaspiro[5.5]undec-2-en-2-amine (575),
(S)-9-methyl-9-(4-(5-(prop-1-ynyl)pyridin-3-yl)thiophen-2-yl)-6-thia-8-azaspiro[4.5]dec-7-en-7-amine (576),
9-methyl-9-(4-(5-(prop-1-ynyl)pyridin-3-yl)thiophen-2-yl)-1-(pyrrolidin-1-yl)-6-thia-8-azaspiro[4.5]dec-7-en-7-amine (577),
4-(1-(5-bromopyridin-3-yl)-1H-pyrazol-4-yl)-4-methyl-1-thia-3-azaspiro[5.5]undec-2-en-2-amine (578),
(R)-5-(5-(2-amino-4-methyl-1-thia-3-azaspiro[5.5]undec-2-en-4-yl)thiophen-3-yl)nicotinonitrile (579),
4-methyl-4-(1-(5-(prop-1-ynyl)pyridin-3-yl)-1H-pyrazol-4-yl)-1-thia-3-azaspiro[5.5]undec-2-en-2-amine (580),
(S)-4-methyl-4-(1-(5-(prop-1-ynyl)pyridin-3-yl)-1H-pyrazol-4-yl)-1-thia-3-azaspiro[5.5]undec-2-en-2-amine (581),
4-methyl-4-(1-methyl-3-(5-(prop-1-ynyl)pyridin-3-yl)-1H-pyrazol-5-yl)-1-thia-3-azaspiro[5.5]undec-2-en-2-amine (582),
(S)-4-(3-chloro-5-(5-(prop-1-ynyl)pyridin-3-yl)thiophen-2-yl)-4-methyl-1-thia-3-azaspiro[5.5]undec-2-en-2-amine (583),
4-(3-chloro-5-(5-(prop-1-ynyl)pyridin-3-yl)thiophen-2-yl)-4-methyl-1-thia-3-azaspiro[5.5]undec-2-en-2-amine (584),
(S)-5-(5-(2-amino-4-methyl-1-thia-3-azaspiro[5.5]undec-2-en-4-yl)-4-chlorothiophen-2-yl)nicotinonitrile (585),
5-(5-(2-amino-4-methyl-1-thia-3-azaspiro[5.5]undec-2-en-4-yl)-4-chlorothiophen-2-yl)nicotinonitrile (586), and
2,2-difluoro-8-methyl-8-(4-(5-(prop-1-ynyl)pyridin-3-yl)thiophen-2-yl)-5-oxa-7-azaspiro[3.5]non-6-en-6-amine (587).

These compounds having the following structures:

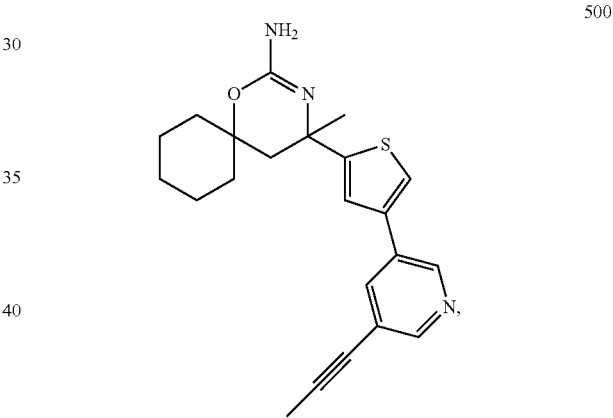

500

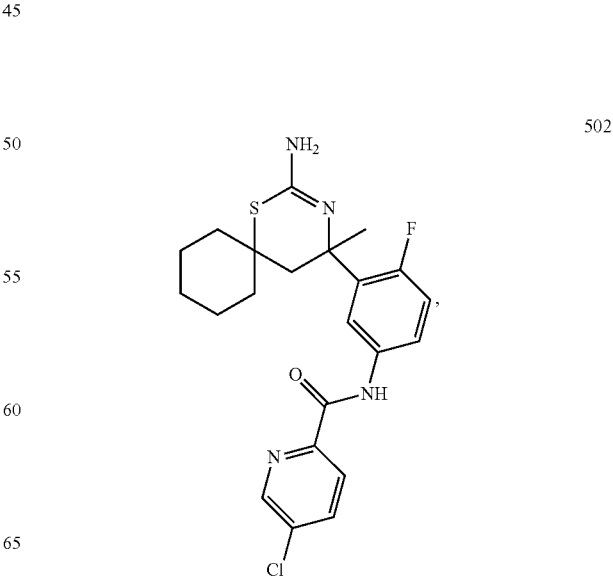

502

-continued
503
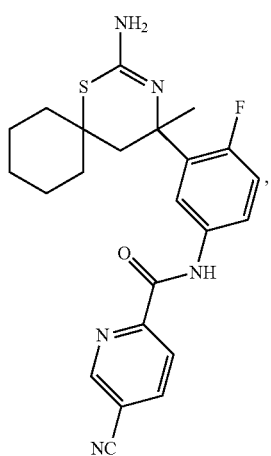
504
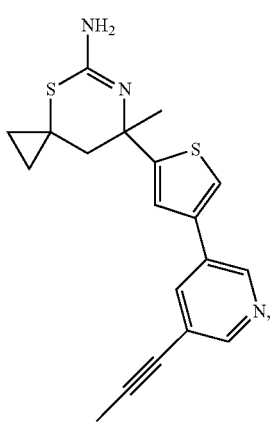
505
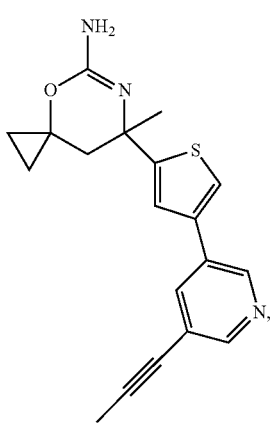
-continued
506
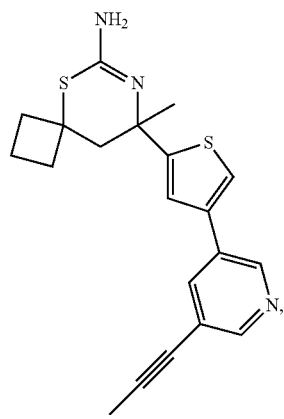
508
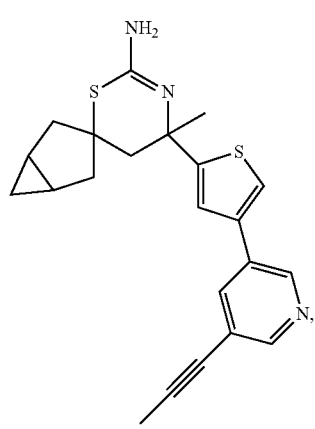
509
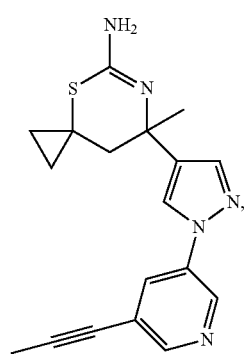
510
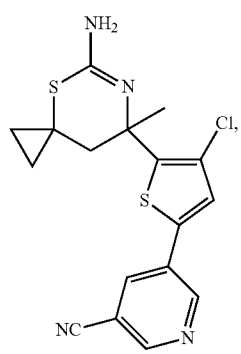

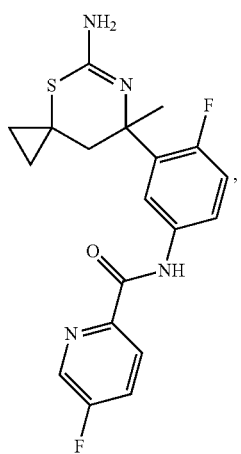
511
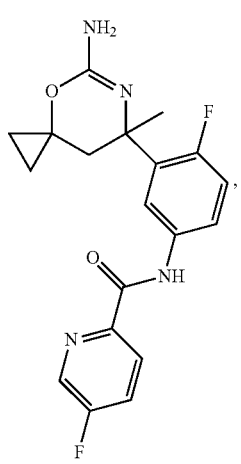
512
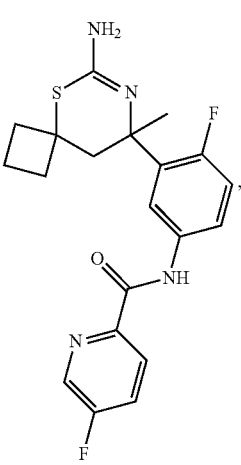
513
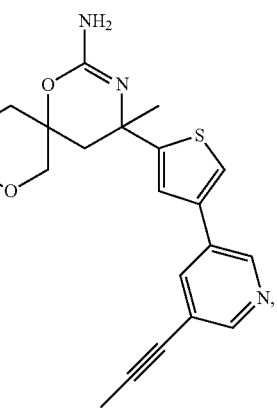
515
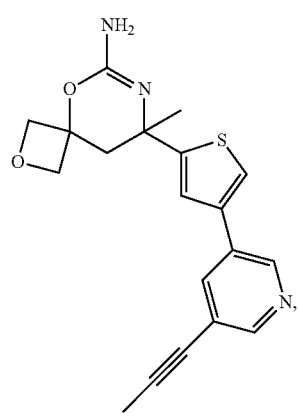
516
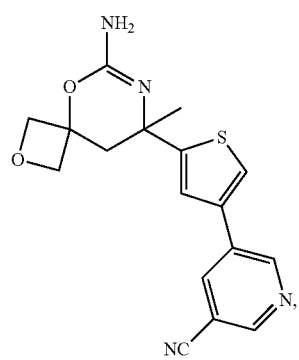
517
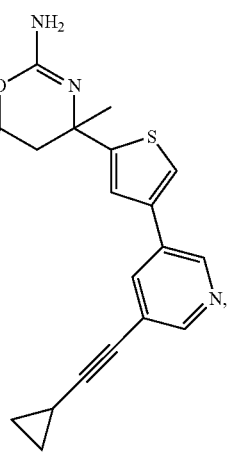
518

| | |
|---|---|
| 519 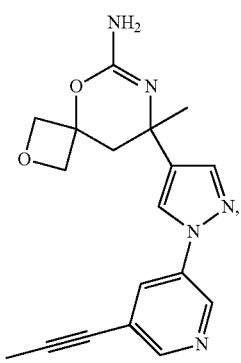 | 524 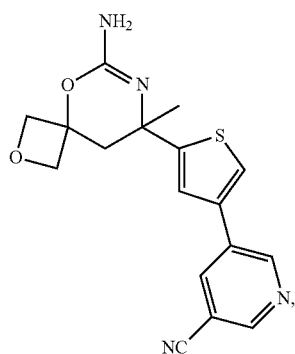 |
| 520 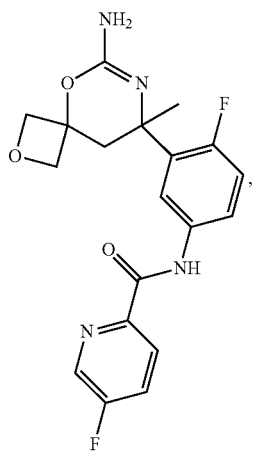 | 525 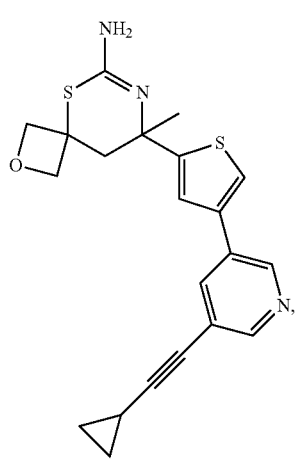 |
| 521 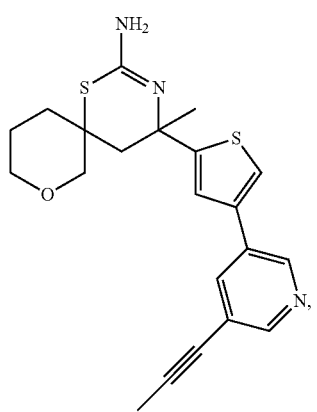 | 526 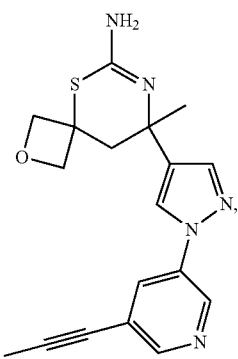 |
| 523 | 527 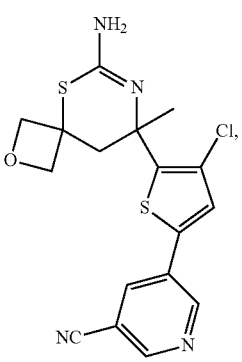 |

528
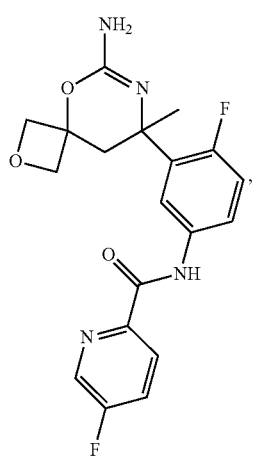
529
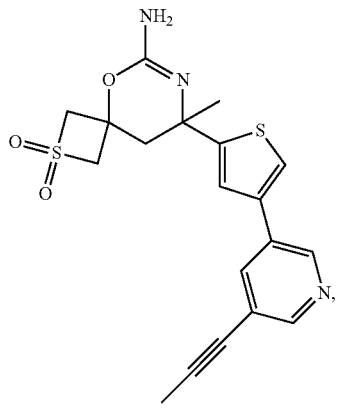
530
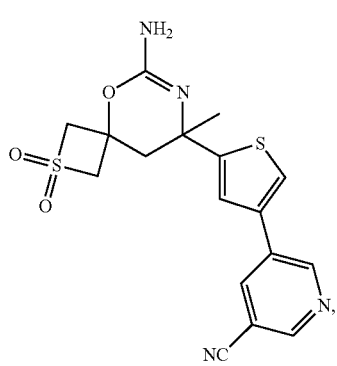
531
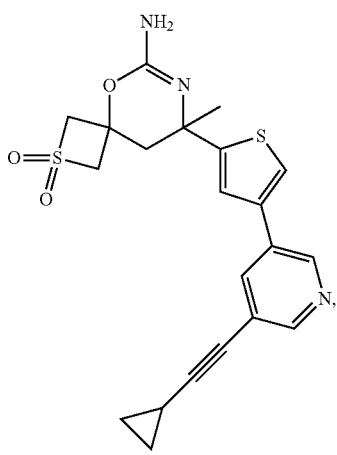
532
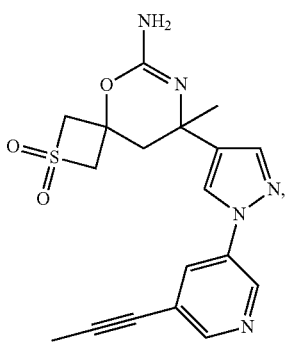

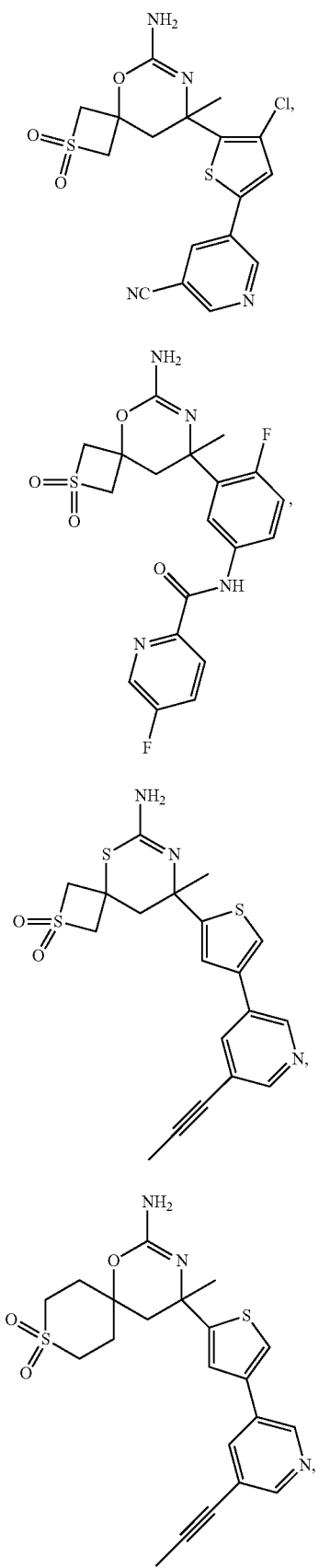
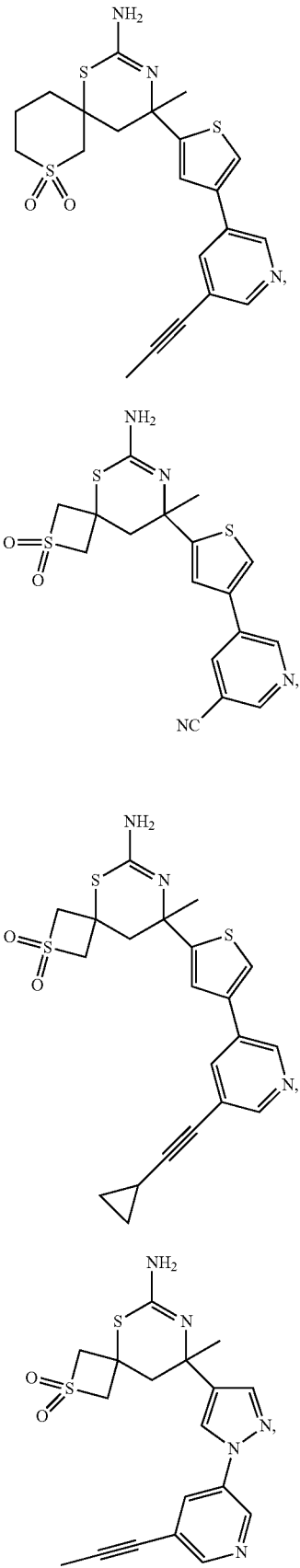

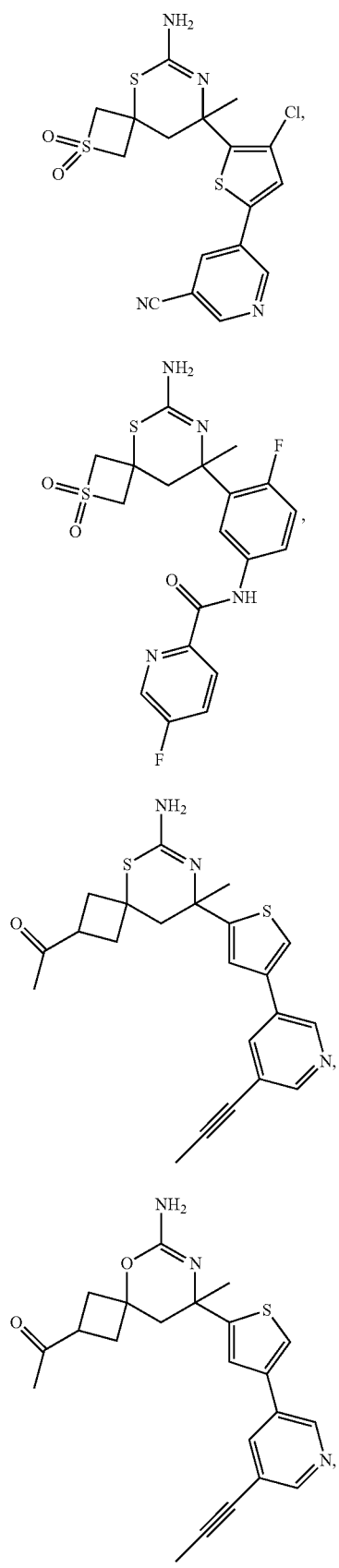
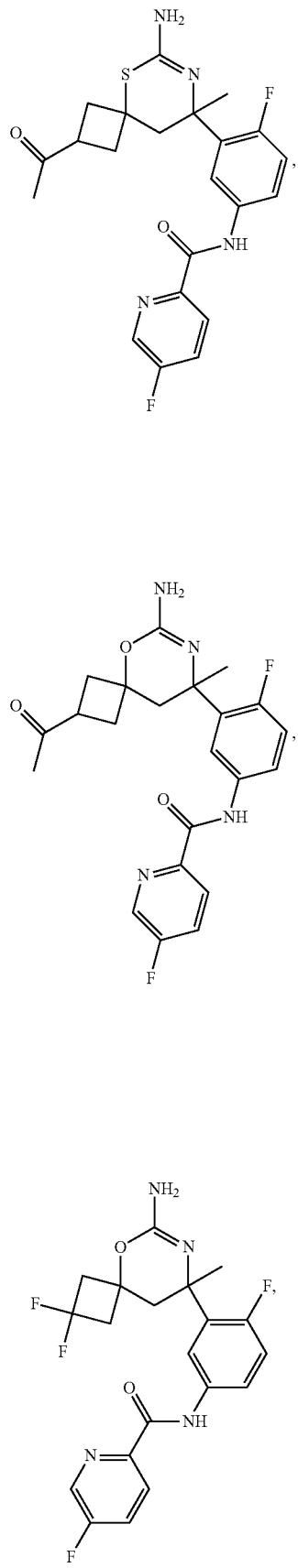

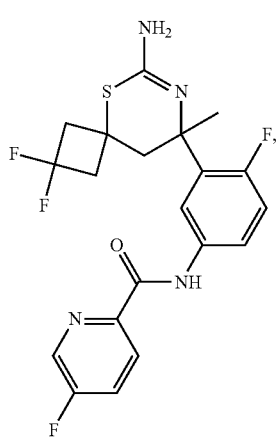
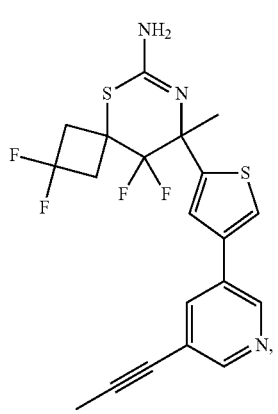
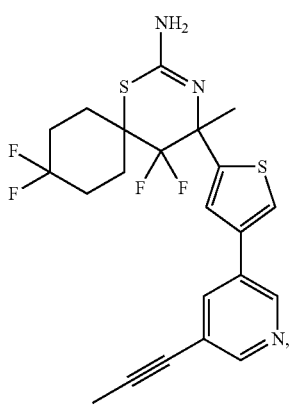
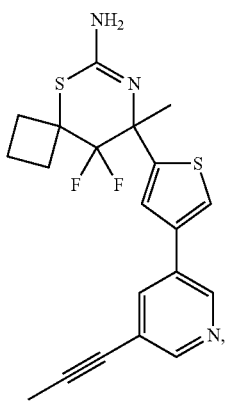
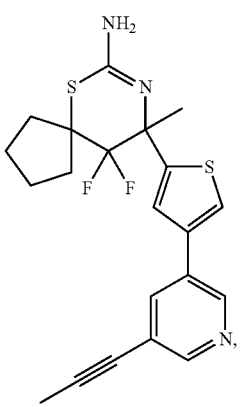

559 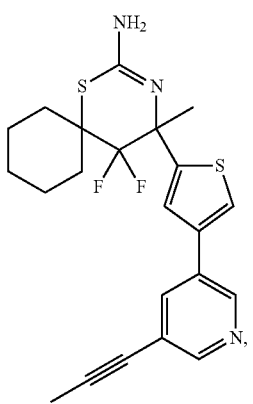
560 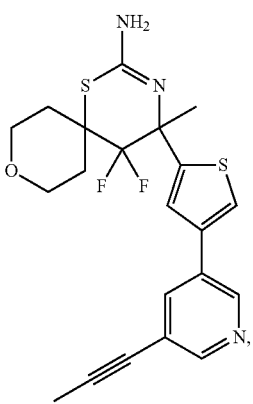
561 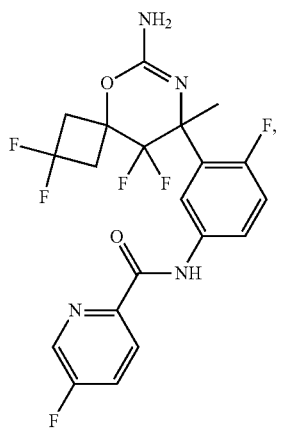
562 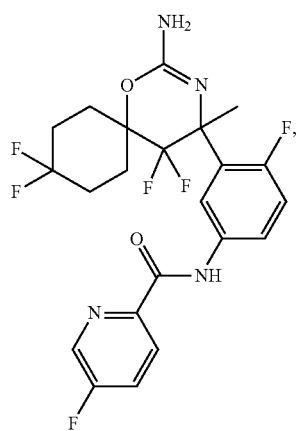
564 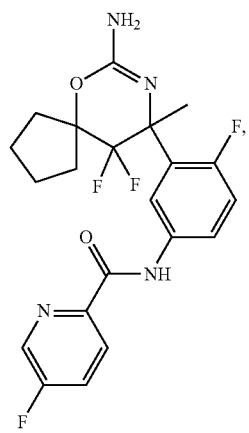
565 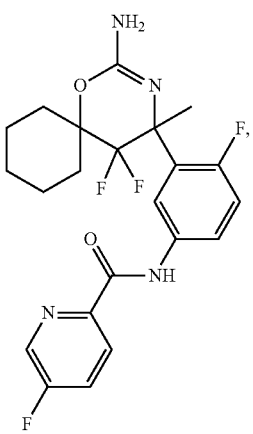
569 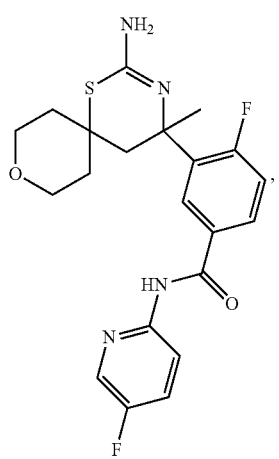

-continued
570
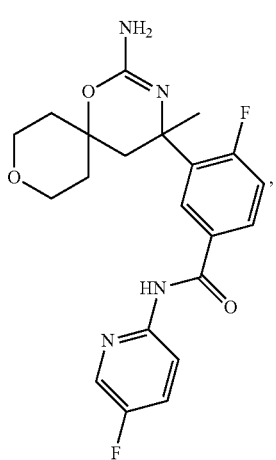
571
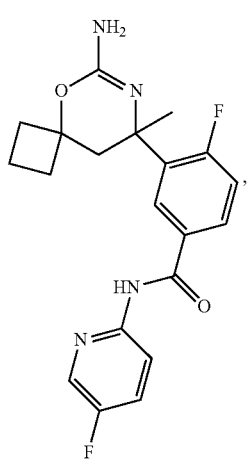
572
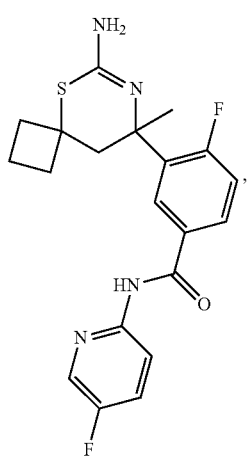
-continued
573
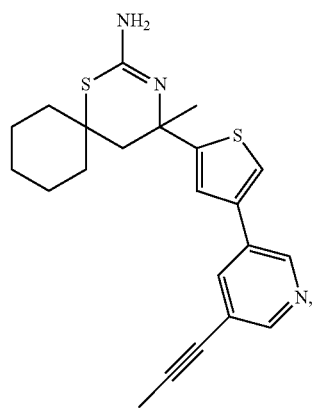
574
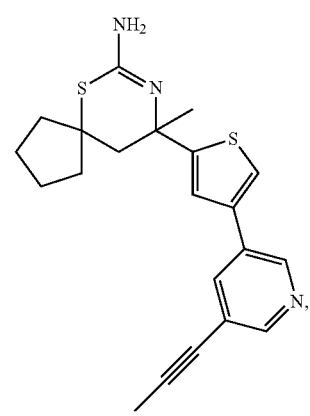
575
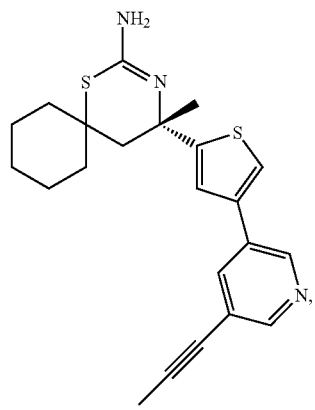
576
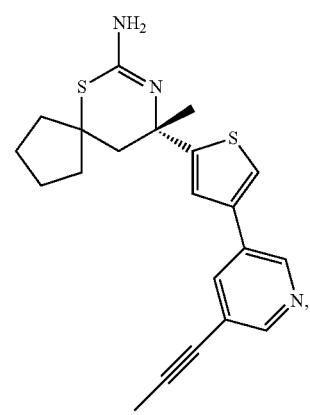

577 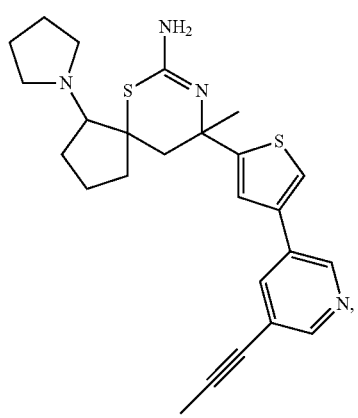
578 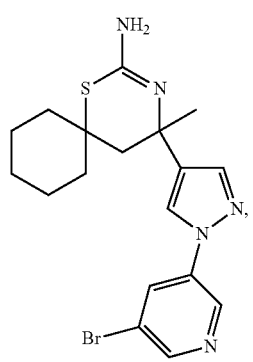
579 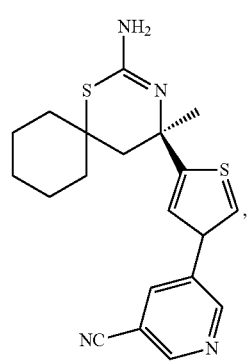
580 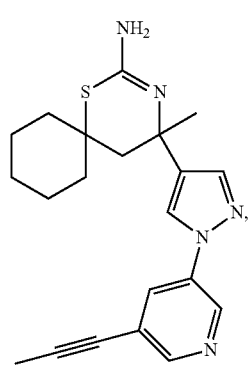
581 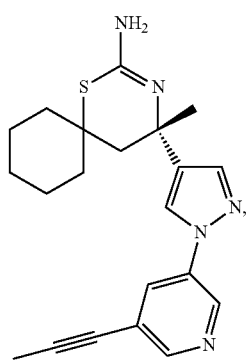
582 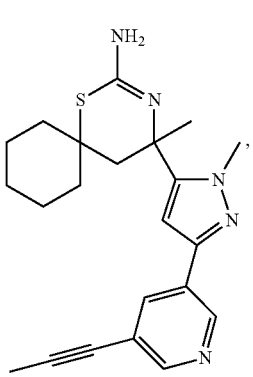
583 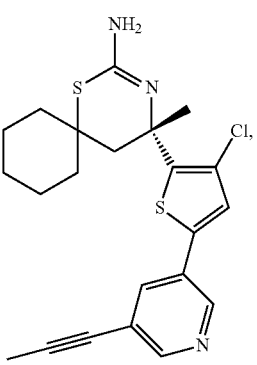
584 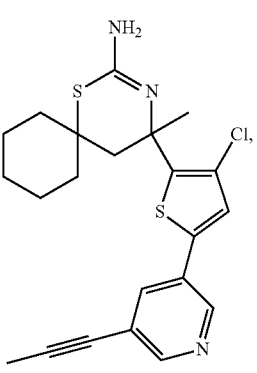

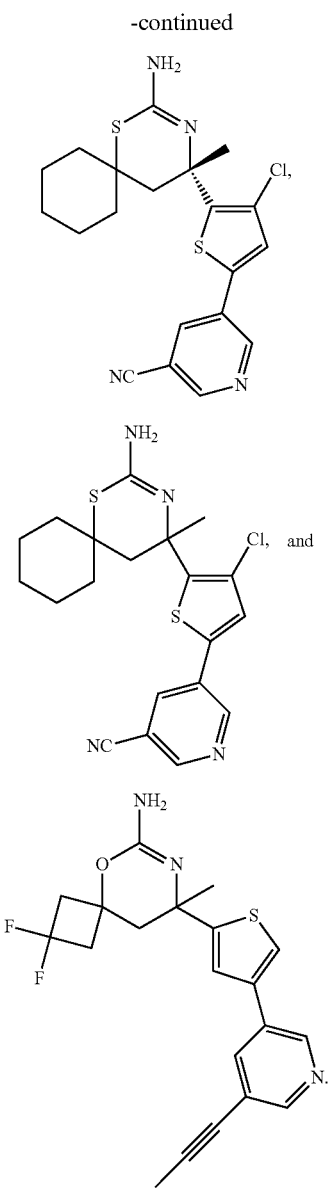

Example A

In Vitro Protease Activities

BACE1 activity can be assessed in an AlphaScreen® assay. Compounds to be assessed (e.g. compounds as described in the above examples) are serially diluted 1:4 in DMSO, then plated by diluting 10 µL of compound with 40 µl of assay buffer (1×PBS, 0.01% Tween-20, pH 7.0, 0.05% BSA). The diluted compound is transferred (4 µL per well) to a 386 well assay plate and 4 µL of BACE1 enzyme (20 mg/mL) is added and incubated for 15 minutes. This assay uses a probe that is a BACE1 binding sight ligand linked to biotin, which can be displaced by test compound dependent on compound binding affinity. This of biotinylated probe (4 µL) is added and incubated for 1 hour, followed with 4 µL of donor and acceptor bead mixture and incubated for 2 hours. The fluorescent signal is read on a plate reader and the value as a function of compound concentration is used to determine the $IC_{50}$. Compounds are also assessed for BACE1 and Cathepsin D activity using an FP Assay. Compounds to be assessed (e.g. compounds as described in the above examples) are serially diluted 1:3 with DMSO and each concentration point is transferred to a 96 well plate, 6 µL per well, followed by addition of 194 µL of assay buffer (100 mM sodium acetate, pH 4.5 with 0.001% Tween-20). A 10 µL compound sample from this plate is transferred to a well of a 384 well plate and combined with 10 µL per well of BACE1 enzyme (0.3 nM in assay buffer) or Cathepsin D enzyme (1.8 nM in assay buffer) and the plate is incubated at room temperature for 30 minutes. Substrate (0.45 µM for BACE1 or 0.45 nM for Cathepsin D in assay buffer) is added, 10 µL per well, and the plate is incubated at 37° C., 3 hours for BACE1 or 2 hours for Cathepsin D. The reaction is stopped by adding 30 µL per well of cold 1.5 µM Streptavidin Immunopure and incubated for 15 minutes at room temperature and the fluorescent signal determined, excitation 485-20 and Emission 530-25, and the value as a function of compound concentration is used to determine the $IC_{50}$.

BACE1 inhibition is also assessed in a cellular assay. HEKp293 cells transfected with APP751 gene (SWE293, American Type Culture Collection CRL-1563) are used to assess compounds for reduction in levels of Aβ peptide production. SWE293 cell medium is DMEM supplemented with 10% fetal bovine serum and 2 mM L-glutamine, 1.0 mM sodium pyruvate, 25 mM Hepes Buffer, 0.4 mg/mL geneticin (G418, Gibco BRL 860-181IIJ). Cells are maintained diluting 1:10 for 4 days in T-150 flask and 35 mL of cell media. For plating, cells are rinsed with 5 mL of 1×PBS, trypsinized with 4 mL of 0.05% Tripsin for 1 minute, and 12 mL of cell media is added. These are centrifuged at 1000 rpm for 4 minutes and the media aspirated, then 8 mL of media per flask is added. Based on cell count, appropriate amounts of cell and cell media are combined, and 180 µl per well are plated (96 well) and the plates are incubated overnight at 37° C., 5% $CO_2$. Compounds to be tested are serially diluted 1:3 in DMSO and twice in media (without G418) in V-bottom plates and incubated at room temperature. Plated cells are washed with media, 3×50 µL per well and 17 µL per well of appropriate dilution of compound is added. Plates are incubated for 2 hours, and the wash steps, compound addition and incubation are repeated. Sample is transferred to capture plate (prepared with 266 antibody, see e.g. Johnson-Wood et al., PNAS February 1997, 94: 1550-1555), along with a standard curve of Aβ-40. ELISA assay is used to assess Aβ levels, washing with TBS, 0.05% Tween20 pH 7.5, then adding 1.3 mg/mL 3D6 antibody 1:900 in specimen diluents with thimericol is added (100 µl per well) and incubated for 1 hour. Wash step is repeated and Streptavidin-AP diluted 1:1000 in specimen diluents with thimerisol is added (100 µL per well) and incubated for 1 hour. Wash step is repeated and fluorescent substrate is added, 100 µL per well and incubated for 10 minutes followed by reading the fluorescent signal on a plate reader. Fluorescent signal is compared to standard curve to assess Aβ peptide levels, which are plotted as a function of concentration to assess the effective concentration of the compound (dose at which Aβ level is reduced by 50%, $ED_{50}$).

Compounds as described herein (compounds of Formula I, e.g., compounds of the above Examples) are tested for their in vitro BACE1 or BACE2 activity in biochemical and cell assays. The following table summarizes exemplary compounds from the Examples above and their in vitro $IC_{50}$ values for BACE1 inhibition and compared to Cathepsin D, and their in vitro effective concentration ($ED_{50}$ values) for BACE1 inhibition in HEKp293 SWEAB cells as determined using the methods as described herein. Compounds are identified by the Example number and compound number identification given in the Example. For $IC_{50}$ values in the table, AS indicates values from the AlphaScreen® assay described above, while FP indicates values for the FP BACE1 or Cathepsin D assays as described above. SWE293 indicates the $ED_{50}$ value for the cellular assay. The following table summarizes exemplary compounds from the Examples above.

| Example/CompoundNo. | BACE1 AS $IC_{50}$ (µM) | BACE1 FP $IC_{50}$ (µM) | CatD FP $IC_{50}$ (µM) | SWE293 $ED_{50}$ (µM) |
|---|---|---|---|---|
| 8-102 | 0.069 | 2.29 | 4.43 | 0.365 |
| 8-103 | 0.030 | 1.36 | 7.92 | 0.582 |
| 8-104 | 0.016 | 0.406 | 14.8 | 0.157 |
| 8-105 | 1.33 | 84.9 | 5.25 | 7.47 |
| 8-106 | 0.569 | 12.6 | >30 | 0.673 |
| 8-107 | 1.677 | 34.1 | 20.8 | 1.725 |
| 8-108 | 0.0175 | 1.12 | 9.32 | 0.485 |
| 8-109 | 0.068 | 1.16 | 6.29 | 0.621 |
| 8-110 | 0.026 | 0.96 | 5.57 | 0.305 |
| 8-111 | 0.088 | 3.51 | 5.08 | 0.391 |
| 8-112 | 0.017 | 0.227 |  | 0.222 |
| 8-113 | <0.007 | 0.160 | 1.88 | 0.184 |
| 8-114 | 0.2205 | 0.626 | 5.54 | 2.12 |
| 9-120 | 0.019 | 0.282 | >30 | 0.013 |
| 9-121 | 0.009 | 0.073 | >30 | 0.006 |
| 9-122 | 0.012 | 0.059 | >30 | 0.004 |
| 9-123 | 0.0087 | 0.270 | >30 | 0.019 |
| 9-124 | 0.0045 | 0.060 | >30 | 0.011 |
| 9-125 | 0.029 | 0.366 | >30 | 0.067 |
| 9-126 | 0.011 | 0.321 | >30 | 0.080 |
| 9-127 | 1.306 | 7.44 | >30 | >10 |
| 9-128 | 0.004 | 0.112 | >30 | 0.009 |
| 9-129 | 0.0083 | 0.107 | >30 | 0.037 |
| 9-130 | 0.006 | 0.046 | >30 | 0.0054 |
| 9-131 | 0.0057 | 0.087 | >30 | 0.046 |
| 9-132 | 0.006 |  |  | 0.011 |
| 9-133 | 0.009 | 0.016 | >30 | 0.016 |
| 9-134 | 0.801 | 2.33 |  | 0.882 |
| 9-135 | 0.0105 | 0.281 | >30 | 0.027 |
| 9-136 | 0.007 | 0.050 | >30 | 0.0089 |
| 9-137 | 0.017 | 1.83 |  | 0.088 |
| 9-138 | 0.011 | 0.299 | >30 | 0.023 |
| 9-139 | 0.009 | 0.048 | >30 | 0.005 |
| 9-140 | 0.101 | 9.11 |  | 0.342 |
| 9-141 | 0.0175 | 0.839 | >30 | 0.109 |
| 9-142 | 0.006 | 0.028 |  | 0.012 |
| 9-143 | >7.5 | 51.8 | >30 | 6.22 |
| 9-144 | 0.008 | 0.027 | >30 | 0.009 |
| 9-145 | 0.0045 | 0.0019 | >30 | 0.002 |
| 9-146 | 0.0098 | 0.119 | >30 | 0.022 |
| 9-147 | 0.008 | 0.029 | 15.6 | <0.004 |
| 9-148 | 0.0068 | 0.029 | >30 | 0.0014 |
| 9-149 | >1 | 8.49 | 21.5 |  |
| 9-150 | 0.009 | 0.004 | 10.6 | <0.004 |
| 9-151 | 0.0097 | 0.005 | >30 | 0.0004 |
| 9-152 |  | 1.56 | 10.8 |  |
| 9-153 |  | 0.033 | >30 | <0.123 |
| 9-154 | 0.0075 | 0.113 | >30 | 0.020 |
| 9-155 | 0.031 | 0.277 | >30 | 0.177 |
| 9-156 | >30 | >30 |  | >30 |
| 9-157 |  | 0.045 | 0.300 | >30 | 0.166 |
| 9-158 | 0.015 | 0.094 | 19.6 | 0.182 |
| 9-159 | 0.040 | 0.210 | >30 | 0.225 |
| 9-160 | 0.0195 | 0.066 | >30 | 0.268 |
| 9-161 | 0.0135 | 0.066 | >30 | 0.038 |
| 9-162 | 0.015 | 0.040 | >30 | 0.039 |
| 9-163 | 13.4 | 38.1 |  | >30 |
| 9-164 | 0.0275 | 0.464 | >30 | 0.195 |
| 9-165 | 0.034 | 0.496 | >30 | 0.176 |
| 10-169 | 3.72 | 179 |  | 5.61 |
| 11-173 |  | 8.55 |  | 0.687 |
| 12-177 | 1.16 | 21.7 |  | 1.21 |
| 12-178 | 1.96 | 13.1 |  | 2.13 |
| 12-179 | 0.51 | 4.64 |  | 1.34 |
| 13-182 | 0.002 | 0.032 | 14.7 | <0.123 |

Example B

In Vivo Activities

Ability of a compound as described herein to reduce the level of Aβ peptide in vivo was determined in a Sprague Dawley rat model. Compounds were dosed orally in female Sprague Dawley rats, along with a vehicle control, five rats per dose group. Compounds were formulated in 5% DMSO/ 0.5% methylcellulose, and dosed at various amounts (10 mL/kg), and 10 mL/kg vehicle by oral gavage. CSF was collected from the cistern magna under isoflurane anesthesia, frozen on dry ice and stored at −80° C. until assessed for Aβ peptide levels. Rats were terminated 3 hours post dosing, and cortical brain samples were collected, frozen on dry ice and stored at −80° C. until assessed for Aβ peptide levels. Cortical brain samples were homogenized in 5 M guanidine and Aβ peptide was quantitated in these brain samples as well as plasma samples in an ELISA assay, where Aβ x-40 ELISA detects Aβ peptide N-terminal sequences containing the transmembrane region and ending at amino acid 40 at the C-terminus. The ELISA was performed as described in Johnson-Wood et al., PNAS February 1997, 94: 1550-1555, using capture antibody 266 (Aβ 16-23 specific) and biotinylated 2G3 (Aβ 40 specific) as reporter antibody. Results of cortical and plasma Aβ x-40 levels were statistically analyzed separately using a one-way Anova with a Dunnets post test analysis at the 0.05 significant level. Compound 125 from Example 9 at 30 or 100 mg/kg and compound 104 from Example 8 at 50 and 200 mg/kg showed no significant effect on brain Aβ x-40 levels. Compound 154 from Example 9 dosed at 100 mg/kg showed a statistically significant decrease of the mean compared to vehicle control of 25% in brain samples. Compound 148 from Example 9 dosed at 10, 30, 60 and 100 mg/kg showed a statistically significant decrease of the mean compared to vehicle control of 23%, 31%, 31%, and 40% respectively in brain samples. Compound 151 of Example 9 was also dosed at 30 mg/kg, and samples were taken at various timepoints, and demonstrated a reduction in Aβ x-40 levels for up to 12 hours in brain samples and longer in CSF. Thus, compounds 148, 151 and 154 showed a decrease in cortical brain levels of Aβ, with compound 151 demonstrating decreased levels of Aβ in both brain and CSF for as long as 12 hours.

Example C

Assays to Assess Pharmaceutical Properties

Various assays can be used to evaluate other pharmaceutical properties, such as Cyp inhibition, metabolic stability, measurement of pGp binding or as pGp substrate, solubility, cell permeability, brain penetration, and pharmacokinetic properties. For example, assays for in vitro permeability across a monolayer of MDCK cells, in vivo assay for P-gp efflux and brain penetration in an FVB mouse model, and in vivo oral availability in Sprague-Dawley rats are well known in the art. Compounds as described herein have little or no Cyp inhibition or pGp binding or do not act as pGp substrates, are relatively metabolically stable and show good oral availability and good brain penetration.

The disclosures in this document of all articles and references, including patents, are incorporated herein by reference in their entirety.

What is claimed is:
1. A method of treating a neurodegenerative disease, the method comprising:
administering to a mammalian subject in need thereof a pharmaceutically effective amount of a compound having a structure according to Formula I:

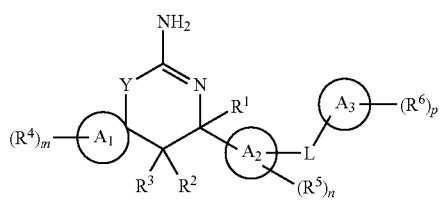

or a pharmaceutically acceptable salt thereof, wherein:
Y is S;
L is selected from the group consisting of a direct bond, —$CR^7R^8$—, —C(O)—, —O—, —$S(O)_z$—, —$NR^9$—, —$CR^7R^8$—$CR^{10}R^{11}$—, —$CR^7R^8$—C(O)—, —$CR^7R^8$—O—, —$CR^7R^8$—$S(O)_z$—, —$CR^7R^8$—$NR^9$—, —C(O)—$CR^{10}R^{11}$—, —C(O)—O—, —C(O)—$NR^9$—, —O—$CR^{10}R^{11}$—, —O—C(O)—, —$S(O)_2$—$CR^{10}R^{11}$—, —$S(O)_2$—$NR^9$—, —$NR^9$—$CR^{10}R^{11}$—, —$NR^9$—C(O)—, and —$NR^9$—$S(O)_2$—;
$A_1$ is a $C_{3-10}$ carbocyclic ring or a 3 to 10 membered heterocyclic ring;
$A_2$ is phenyl, naphthyl, or a heteroaryl ring;
$A_3$ is phenyl, naphthyl, or a heteroaryl ring;
$R^1$ is hydrogen, $C_{1-6}$ alkyl, or combines with $R^2$ to form a fused monocyclic $C_{3-7}$ carbocyclic ring or a 3 to 7 membered heterocyclic ring;
$R^2$ and $R^3$ are independently hydrogen or halogen, or $R^3$ is hydrogen and $R^2$ combines with $R^1$ to form a fused monocyclic $C_{3-7}$ carbocyclic ring or a 3 to 7 membered heterocyclic ring;
$R^4$ at each occurrence is independently selected from the group consisting of halogen, —CN, $C_{1-6}$ alkyl, $C_{2-6}$ alkenyl, $C_{2-6}$ alkynyl, $C_{3-6}$ cycloalkyl, —OH, =O, —$OR^{12}$, —$S(O)_zR^{12}$, —$C(O)R^{12}$, —$NR^{13}R^{14}$, and =$NR^{14}$, wherein said $C_{1-6}$ alkyl, $C_{2-6}$ alkenyl, $C_{2-6}$ alkynyl, and $C_{3-6}$ cycloalkyl are optionally substituted with one or more fluoro, —OH, —$NH_2$, —$OR^a$, —$S(O)_zR^a$, —$C(O)R^a$, —$NHR^a$, —$NR^aR^b$, or optionally fluoro substituted $C_{3-6}$ cycloalkyl;
$R^5$ and $R^6$ at each occurrence are independently selected from the group consisting of halogen, —CN, —OH, —$NH_2$, —$NO_2$, —C(O)—OH, —C(O)—$NH_2$, —$S(O)_2$—$NH_2$, and $L_1$-$R^{15}$;
$R^7$, $R^8$, $R^9$, $R^{10}$, and $R^{11}$ are independently selected from the group consisting of hydrogen and $C_{1-6}$ alkyl;
$L_1$ at each occurrence is independently selected from the group consisting of a direct bond, —C(O)—, —O—, —$S(O)_z$, —$NR^{16}$—, —C(O)—O—, —C(O)—$NR^{16}$—, —$NR^{16}$—C(O)—, —$S(O)_2$—$NR^{16}$—, and —$NR^{16}$—$S(O)_2$—;
$R^{12}$ at each occurrence is independently selected from the group consisting of $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —$NH_2$, —$OR^a$, —$S(O)_zR^a$, —$C(O)R^a$, —$NHR^a$, —$NR^aR^b$, and optionally fluoro substituted $C_{3-6}$ cycloalkyl;
$R^{13}$ and $R^{14}$ at each occurrence are independently selected from the group consisting of hydrogen, $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —$NH_2$, —$OR^a$, —$S(O)_zR^a$, —$C(O)R^a$, —$NHR^a$, —$NR^aR^b$, and optionally fluoro substituted $C_{3-6}$ cycloalkyl or $R^{13}$ and $R^{14}$ combine with the nitrogen to which they are attached to form a 4-7 membered monocyclic heterocyclic ring or a 5 or 7 membered heteroaryl ring, wherein said ring is optionally substituted with one or more substituents independently selected from the group consisting of halogen, —CN, =O, —OH, —$NH_2$, —$OR^a$, —$S(O)_zR^a$, —$C(O)R^a$, —$NHR^a$, —$NR^aR^b$, and optionally fluoro substituted $C_{1-6}$ alkyl, optionally Now substituted $C_{2-6}$ alkenyl, optionally fluoro substituted $C_{2-6}$ alkynyl, and optionally fluoro substituted $C_{3-6}$ cycloalkyl;
$R^{15}$ at each occurrence is independently selected from the group consisting of $C_{1-6}$ alkyl, $C_{2-6}$ alkenyl, $C_{2-6}$ alkynyl, and $C_{3-6}$ cycloalkyl, 3-7 membered heterocycloalkyl, phenyl, naphthyl, and heteroaryl, wherein phe naphthyl, and heteroaryl are optionally substituted with one or more substituents independently selected from the group consisting of —CN, —OH, —NO2, —C(O)—OH, $C_{1-6}$ alkyl, $C_{2-6}$ alkenyl, $C_{7-6}$ alkynyl, and $C_{3-6}$ cycloalkyl, 3-7 membered heterocycloalkyl, phenyl, 5 or 6 membered heteroaryl, —$OR^{17}$, —$S(O)_zR^{17}$, —$NR^{18}R^{19}$, —$C(O)R^{17}$, —C(O)—$OR^{17}$, —O—$C(O)R^{17}$, —C(O)—$NR^{18}R^{19}$, —$NR^{16}$—C(O) $R^{17}$, —$S(O)_2$—$NR^{18}R^{19}$, and —$NR^{16}$—$S(O)_2R^{17}$, and wherein $C_{1-6}$ alkyl, $C_{2-6}$ alkenyl, $C_{2-6}$ alkynyl, and $C_{3-6}$ cycloalkyl, 3-7 membered heterocycloalkyl, as $R^{15}$ or as a substituent of phenyl, naphthyl, or heteroaryl, are optionally substituted with one or more substituents independently selected from the group consisting of fluoro, —CN, —OH, =O, =NH, —$NO_2$, —C(O)—OH, $C_{3-6}$ cycloalkyl, 3-7 membered heterocycloalkyl, —$OR^{17}$, —$S(O)_zR^{17}$, =$NR^{17}$, —$NR^{18}R^{19}$, —$C(O)R^{17}$, —C(O)—$OR^{17}$, —O—$C(O)R^{17}$, —C(O)—$NR^{18}R^{19}$, —$NR^{16}$—$C(O)R^{17}$, —$S(O)_2$—$NR^{18}R^{19}$, and —$NR^{16}$—$S(O)_2R^{17}$;
$R^{16}$ at each occurrence is independently selected from the group consisting of hydrogen $C_{1-6}$ alkyl;
$R^{17}$ at each occurrence is independently selected from the group consisting of $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —$NH_2$, —$OR^a$, —$S(O)_zR^a$, —$C(O)R^a$, —$NHR^a$, —$NR^aR^b$, and optionally fluoro substituted $C_{3-6}$ cycloalkyl;
$R^{18}$ and $R^{19}$ at each occurrence are independently selected from the group consisting of hydrogen, $C_{1-6}$ alkyl, $C_{2-6}$ alkenyl, $C_{2-6}$ alkynyl, and $C_{3-6}$ cycloalkyl, wherein said $C_{1-6}$ alkyl, $C_{2-6}$ alkenyl, $C_{2-6}$ alkynyl, and $C_{3-6}$ cycloalkyl are optionally substituted with one or more substituents independently selected from the group consisting of fluoro, —OH, —NH$_2$, —OR$^a$, —S(O)$_z$R$^a$, —C(O)R$^a$, —NHR$^a$, —NR$^a$R$^b$, and optionally fluoro substituted C$_{1-6}$ cycloalkyl, or R$^{18}$ and R$^{19}$ combine with the nitrogen to which they are attached to form a 4-7 membered monocyclic heterocyclic ring or a 5 or 7 membered heteroaryl ring, wherein said ring is optionally substituted with one or more substituents independently selected from the group consisting of halogen, —CN, =O, —OH, —NH$_2$, —OR$^a$, —S(O)$_z$R$^a$, —C(O)R$^a$, —NHR$^a$, —NR$^a$R$^b$, optionally fluoro substituted C$_{1-6}$ alkyl, optionally fluoro substituted C$_{2-6}$ alkenyl, optionally fluoro substituted C$_{2-6}$ alkynyl, and optionally fluoro substituted C$_{3-6}$ cycloalkyl;

R$^a$ and R$^b$ at each occurrence are independently selected from the group consisting of optionally fluoro substituted C$_{1-6}$ alkyl, optionally fluoro substituted C$_{2-6}$ alkenyl, optionally fluoro substituted C$_{2-6}$ alkynyl, and optionally fluoro substituted C$_{3-6}$ cycloalkyl, or R$^a$ and R$^b$ combine with the nitrogen to which they are attached to form N-linked-heterocycloalkyl;

m is 0, 1, or 2;
n is 0, 1, 2, or 3;
p is 0, 1, 2, or 3; and
z is 0, 1, or 2, and
wherein the disease is associated with Aβ peptide aggregation, oligomerization, fibrillization, or plaque formation.

2. The method of claim 1, wherein, in formula (I):
L is a direct bond, —NR$^9$—, —C(O)—NR$^9$—, or —NR$^9$—C(O)—;
A$_2$ is phenyl, or a monocyclic 5-6 membered heteroaryl ring; and
A$_3$ is phenyl, or a monocyclic 5-6 membered heteroaryl ring.

3. The method of claim 1, wherein, in formula (I), A$_1$ is a C$_{3-10}$ carbocyclic ring.

4. The method of claim 3, wherein, in formula (I), A$_1$ is a C$_{3-6}$ monocyclic carbocyclic ring.

5. The method of claim 1, wherein, in formula (I), A$_1$ is a 3 to 10 membered heterocyclic ring.

6. The method of 5, wherein, in formula (I), A$_1$ is a 4 to 6 membered monocyclic heterocyclic ring that contains one oxygen atom or one sulfur atom as the only heteroatom.

7. The method of claim 1, wherein, in formula (I):
n is 0, 1, or 2;
p is 0, 1, or 2; and
each R$^5$ and R$^6$ are independently selected from the group consisting of —CN, halogen, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, alkylamino, N-linked-heterocycloalkyl, and C$_{3-6}$ cycloalkyl, wherein C$_{1-6}$ alkyl, C$_{2-6}$ alkenyl, C$_{2-6}$ alkynyl and the alkyl chains of C$_{1-6}$ alkoxy, C$_{1-6}$ alkylsulfonyl, C$_{1-6}$ alkylamino, or di-C$_{1-6}$ alkylamino are optionally substituted with one or more substituents independently selected from the group consisting of fluoro, —CN, C$_{3-6}$ cycloalkyl, C$_{1-6}$ alkoxy, C$_{1-6}$ haloalkoxy, C$_{1-6}$ alkylamino, di-C$_{1-6}$ alkylamino, and N-linked-heterocycloalkyl.

8. The method of claim 7, wherein, in formula (I):
n is 0 or 1;
R$^5$ is halogen, —CN, C$_{1-6}$ alkyl, C$_{1-6}$ haloalkoxy;
p is 0, 1, or 2; and
R$^6$ at each occurrence is independently selected from the group consisting of halogen, —CN, C$_{1-6}$ alkyl, C$_{2-6}$ alkenyl, C$_{2-6}$ alkynyl, C$_{1-6}$ alkoxy, C$_{1-6}$ alkylsulfonyl, C$_{1-6}$ alkylamino, di-C$_{1-6}$ alkylamino, N-linked-heterocycloalkyl, and C$_{3-6}$ cycloalkyl, wherein C$_{1-6}$ alkyl, C$_{2-6}$ alkenyl, C$_{2-6}$ alkynyl, and the alkyl chains of C$_{1-6}$ alkoxy, C$_{1-6}$ alkylsulfonyl, C$_{1-6}$ alkylamino, or di-C$_{1-6}$ alkylamino as R$^6$ are optionally substituted with one or more substituents independently selected from the group consisting of fluoro, —CN, C$_{3-6}$ cycloalkyl, C$_{1-6}$ alkoxy, C$_{1-6}$ haloalkoxy, C$_{1-6}$ alkylamino, di-C$_{1-6}$ alkylamino, and N-linked-heterocycloalkyl.

9. The method of claim 8, wherein, in formula (I):
R$^4$ is fluoro;
n is 1;
R$^5$ is halogen;
p is 0, 1, or 2; and
each R$^6$ is independently selected from the group consisting of —CN, halogen, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ alkynyl, and C$_{3-6}$ cycloalkyl.

10. The method of claim 1, wherein the compound of formula (I) has a structure according to Formula Ia:

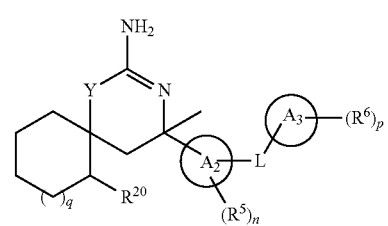

Ia or a pharmaceutically acceptable salt thereof, wherein:
q is 0 or 1; and
R$^{20}$ is selected from the group consisting of hydrogen, —OH, =O, —OR$^{12}$, —S(O)$_z$R$^{12}$, —NR$^{13}$R$^{14}$, and =NR$^{14}$.

11. The method of claim 1, wherein the compound of formula (I) has a structure according to Formula Ib:

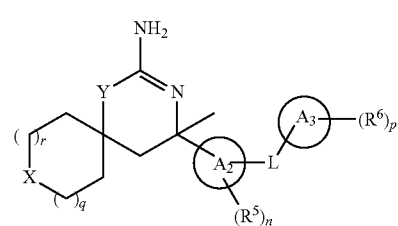

Ib or a pharmaceutically acceptable salt thereof, wherein:
X is O or S(O)$_2$;
r is 0, 1, or 2; and
s is 0, or 2.

12. The method of claim 1, wherein the compound of formula (I) has a structure according to Formula Ic:

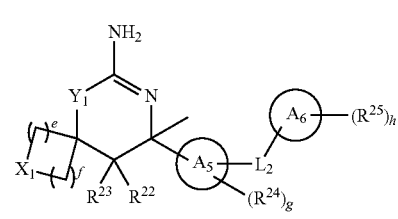

Ic or a pharmaceutically acceptable salt thereof, wherein:
$Y_1$ is S;
$L_2$ is selected from the group consisting of a direct bond, —NH—, and —NH—C(O)—;
$X_1$ is a direct bond and e and f are both 1; or
$X_1$ is $CH_2$, $CF_2$, or O, and e and f are independently 1 or 2;
$A_5$ is phenyl or thiophenyl;
$A_6$ is phenyl, pyridinyl, pyrazinyl or oxazolyl;
$R^{22}$ and $R^{23}$ are both hydrogen or both fluoro;
$R^{24}$ at each occurrence is independently selected from the group consisting of —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl;
$R^{25}$ at each occurrence is independently selected from the group consisting of —CN, halogen, $C_{1-6}$ alkyl, $C_{2-6}$ alkenyl, $C_{2-6}$ alkynyl, alkoxy, $C_{1-6}$ alkylsulfonyl, $C_{1-6}$ alkylamino, di-$C_{1-6}$ alkylamino, N-linked-heterocycloalkyl, and $C_{3-6}$ cycloalkyl, wherein $C_{1-6}$ alkyl, $C_{2-6}$ alkenyl, $C_{2-6}$ alkynyl, and the alkyl chains of $C_{1-6}$alkoxy, $C_{1-6}$ alkylsulfonyl, $C_{1-6}$ alkylamino, or di-$C_{1-6}$alkylamino are optionally substituted with one or more substituents independently selected from the group consisting of fluoro, —CN, $C_{3-6}$ cycloalkyl, $C_{1-6}$alkoxy, $C_{1-6}$ haloalkoxy, $C_{1-6}$alkylamino, di-$C_{1-6}$alkylamino, and N-linked-heterocycloalkyl;
g is 0, 1, or 2; and
h is 0, 1, or 2.

13. The method of claim 12, wherein, in formula (Ic):
g is 0 or 1;
$R^{24}$ is halogen, —CN, $C_{1-6}$ alkyl, $C_{1-6}$ haloalkyl, $C_{1-6}$ alkoxy, or $C_{1-6}$ haloalkoxy;
h is 0, 1, or 2; and
$R^{25}$ at each occurrence is independently selected from the group consisting of —CN, halogen, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $C_{3-6}$ cycloalkyl.

14. The method of claim 12, wherein the compound of formula (Ic) has a structure selected from the group consisting of:

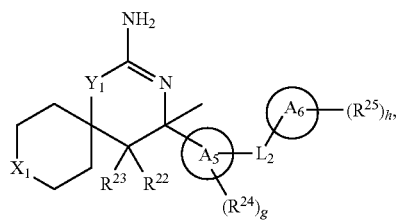

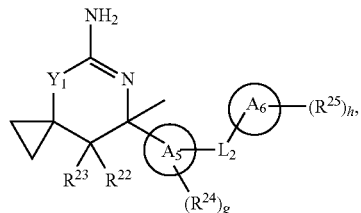

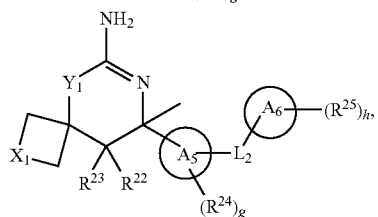

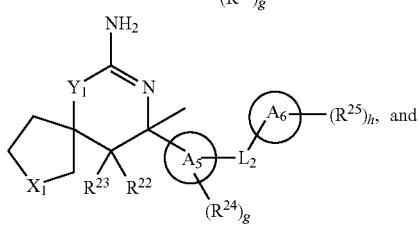

15. The method of claim 14, wherein the compound has a structure selected from the group consisting of:

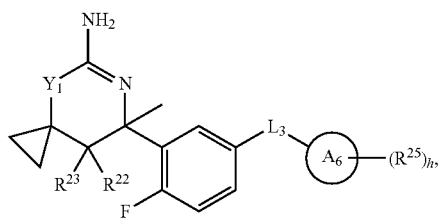

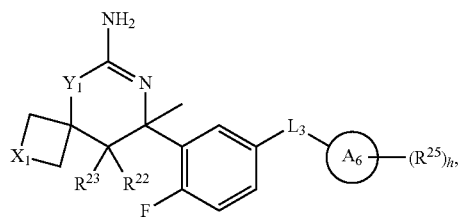

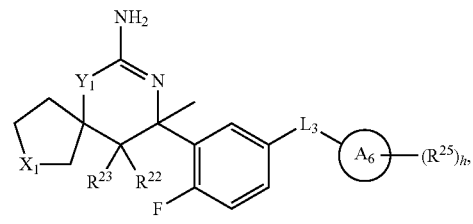

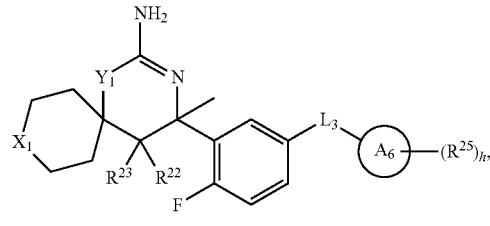

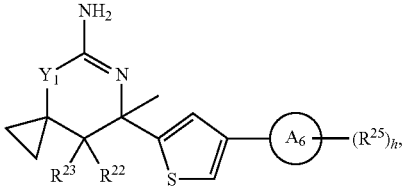

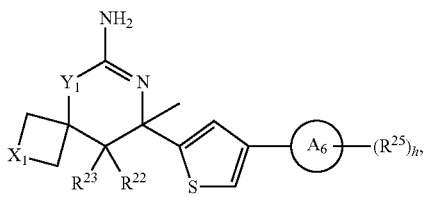

-continued

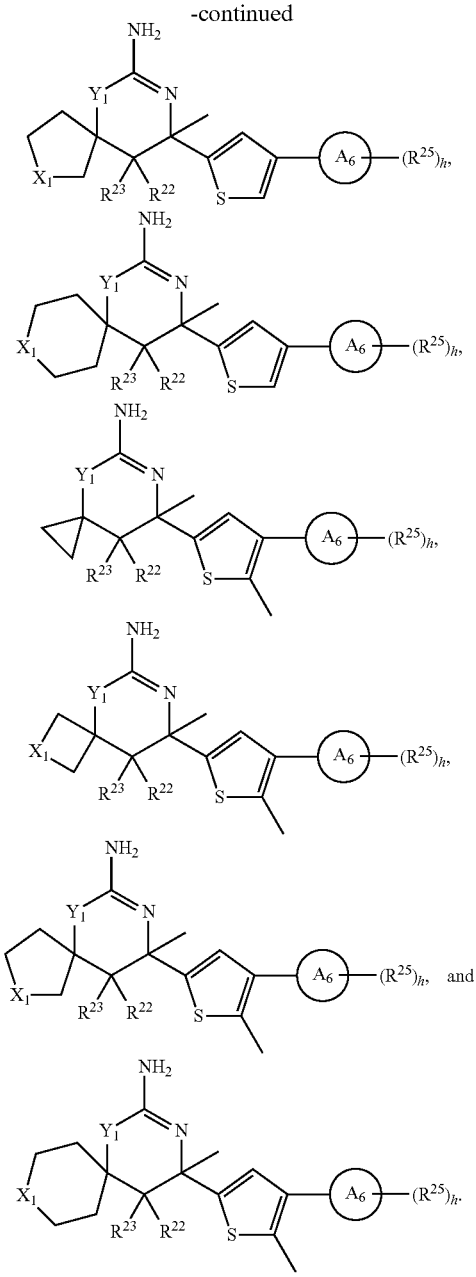

16. The method of claim 1, wherein the compound of formula (I) is selected from the group consisting of
4-methyl-4-(4-(5-(prop-1-ynyl)pyridin-3-yl)thiophen-2-yl)-1-thia-3-azaspiro[5.5]undec-2-en-2-amine,
(S)-4-methyl-4-(4-(5-(prop-1-ynyl)pyridin-3-yl)thiophen-2-yl)-1-thia-3-azaspiro[5.5]undec-2-en-2-amine,
9-methyl-9-(4-(5-(prop-1-ynyl)pyridin-3-yl)thiophen-2-yl)-6-thia-8-azaspiro[4.5]dec-7-en-7-amine,
(S)-9-methyl-9-(4-(5-(prop-1-ynyl)pyridin-3-yl)thiophen-2-yl)-6-thia-8-azaspiro[4.5]dec-7-en-7-amine,
9-methyl-9-(4-(5-(prop-1-ynyl)pyridin-3-yl)thiophen-2-yl)-1-(pyrrolidin-1-yl)-6-thia-8-azaspiro[4.5]dec-7-en-7-amine,
4-(1-(5-bromopyridin-3-yl)-1H-pyrazol-4-yl)-4-methyl-1-thia-3-azaspiro[5.5]undec-2-en-2-amine,
(R)-5-(5-(2-amino-4-methyl-1-thia-3-azaspiro[5.5]undec-2-en-4-yl)thiophen-3-yl)nicotinonitrile,
4-methyl-4-(1-(5-(prop-1-ynyl)pyridin-3-yl)-1H-pyrazol-4-yl)-1-thia-3-azaspiro[5.5]undec-2-en-2-amine,
(S)-4-methyl-4-(1-(5-(prop-1-ynyl)pyridin-3-yl)-1H-pyrazol-4-yl)-1-thia-3-azaspiro[5.5]undec-2-en-2-amine,
4-methyl-4-(1-methyl-3-(5-(prop-1-ynyl)pyridin-3-yl)-1H-pyrazol-5-yl)-1-thia-3-azaspiro[5.5]undec-2-en-2-amine,
(S)-4-(3-chloro-5-(5-(prop-1-ynyl)pyridin-3-yl)thiophen-2-yl)-4-methyl-1-thia-3-azaspiro[5.5]undec-2-en-2-amine,
4-(3-chloro-5-(5-(prop-1-ynyl)pyridin-3-yl)thiophen-2-yl)-4-methyl-1-thia-3-azaspiro[5.5]undec-2-en-2-amine,
(S)-5-(5-(2-amino-4-methyl-1-thia-3-azaspiro[5.5]undec-2-en-4-yl)-4-chlorothiophen-2-yl)nicotinonitrile,
5-(5-(2-amino-4-methyl-1-thia-3-azaspiro[5.5]undec-2-en-4-yl)-4-chlorothiophen-2-yl)nicotinonitrile,
8-methyl-8-(4-(5-(prop-1-ynyl)pyridin-3-yl)thiophen-2-yl)-2-oxa-5-thia-7-azaspiro[3.5]non-6-en-6-amine,
N-(3-(2-amino-4-methyl-1-thia-3-azaspiro[5.5]undec-2-en-4-yl)-4-fluorophenyl)-5-fluoropicolinamide,
N-(3-(2-amino-4-methyl-1-thia-3-azaspiro[5.5]undec-2-en-4-yl)-4-fluorophenyl)-5-chloropicolinamide,
N-(3-(2-amino-4-methyl-1-thia-3-azaspiro[5.5]undec-2-en-4-yl)-4-fluorophenyl)-5-cyanopicolinamide,
7-methyl-7-(4-(5-(prop-1-ynyl)pyridin-3-yl)thiophen-2-yl)-4-thia-6-azaspiro[2.5]oct-5-en-5-amine,
8-methyl-8-(4-(5-(prop-1-ynyl)pyridin-3-yl)thiophen-2-yl)-5-thia-7-azaspiro[3.5]non-6-en-6-amine,
4'-methyl-4'-(4-(5-(prop-1-ynyl)pyridin-3-yl)thiophen-2-yl)-4',5'-dihydrospiro[bicyclo[3.1.0]hexane-3,6'-[1,3]thiazin]-2'-amine,
7-methyl-7-(1-(5-(prop-1-ynyl)pyridin-3-yl)-1H-pyrazol-4-yl)-4-thia-6-azaspiro[2.5]oct-5-en-5-amine,
5-(5-(5-amino-7-methyl-4-thia-6-azaspiro[2.5]oct-5-en-7-yl)-4-chlorothiophen-2-yl)nicotinonitrile,
N-(3-(5-amino-7-methyl-4-thia-6-azaspiro[2.5]oct-5-en-7-yl)-4-fluorophenyl)-5-fluoropicolinamide,
N-(3-(6-amino-8-methyl-5-thia-7-azaspiro[3.5]non-6-en-8-yl)-4-fluorophenyl)-5-fluoropicolinamide,
4-methyl-4-(4-(5-(prop-1-ynyl)pyridin-3-yl)thiophen-2-yl)-9-oxa-1-thia-3-azaspiro[5.5]undec-2-en-2-amine,
4-methyl-4-(4-(5-(prop-1-ynyl)pyridin-3-yl)thiophen-2-yl)-8-oxa-1-thia-3-azaspiro[5.5]undec-2-en-2-amine,
5-(5-(6-amino-8-methyl-2-oxa-5-thia-7-azaspiro[3.5]non-6-en-8-yl)thiophen-3-yl)nicotinonitrile,
8-(4-(5-(cyclopropylethynyl)pyridin-3-yl)thiophen-2-yl)-8-methyl-2-oxa-5-thia-7-azaspiro[3.5]non-6-en-6-amine,
8-methyl-8-(1-(5-(prop-1-ynyl)pyridin-3-yl)-1H-pyrazol-4-yl)-2-oxa-5-thia-7-azaspiro[3.5]non-6-en-6-amine,
5-(5-(6-amino-8-methyl-2-oxa-5-thia-7-azaspiro[3.5]non-6-en-8-yl)-4-chlorothiophen-2-yl)nicotinonitrile,
N-(3-(6-amino-8-methyl-2-oxa-5-thia-7-azaspiro[3.5]non-6-en-8-yl)-4-fluorophenyl)-5-fluoropicolinamide,
(S)—N-(3-(6-amino-8-methyl-2-oxa-5-thia-7-azaspiro[3.5]non-6-en-8-yl)-4-fluorophenyl)-5-fluoropicolinamide,
8-methyl-8-(4-(5-(prop-1-ynyl)pyridin-3-yl)thiophen-2-yl)-2,5-dithia-7-azaspiro[3.5]non-6-en-6-amine-2,2-dioxide,
4-methyl-4-(4-(5-(prop-1-ynyl)pyridin-3-yl)thiophen-2-yl)-1,9-dithia-3-azaspiro[5.5]undec-2-en-2-amine-9,9-dioxide, 4-methyl-4-(4-(5-(prop-1-ynyl)pyridin-3-yl)thiophen-2-yl)-1,8-dithia-3-azaspiro[5.5]undec-2-en-2-amine-8,8-dioxide,
5-(5-(6-amino-8-methyl-2,5-dithia-7-azaspiro[3.5]non-6-en-8-yl-2,2-dioxide)thiophen-3-yl) nicotinonitrile,
8-(4-(5-(cyclopropylethynyl)pyridin-3-yl)thiophen-2-yl)-8-methyl-2,5-dithia-7-azaspiro[3.5]non-6-en-6-amine-2,2-dioxide,
8-methyl-8-(1-(5-(prop-1-ynyl)pyridin-3-yl)-1H-pyrazol-4-yl)-2,5-dithia-7-azaspiro[3.5]non-6-en-6-amine-2,2-dioxide,
5-(5-(6-amino-8-methyl-2,5-dithia-7-azaspiro[3.5]non-6-en-8-yl-2,2-dioxide)-4-chlorothiophen-2-yl)nicotinonitrile,
N-(3-(6-amino-8-methyl-2,5-dithia-7-azaspiro[3.5]non-6-en-8-yl-2,2-dioxide)-4-fluorophenyl)-5-fluoropicolinamide,
1-(6-amino-8-methyl-8-(4-(5-(prop-1-ynyl)pyridin-3-yl)thiophen-2-yl)-5-thia-7-azaspiro[3.5]non-6-en-2-yl)ethanone,
N-(3-(2-acetyl-6-amino-8-methyl-5-thia-7-azaspiro[3.5]non-6-en-8-yl)-4-fluorophenyl)-5-fluoropicolinamide,
N-(3-(6-amino-2,2-difluoro-8-methyl-5-thia-7-azaspiro[3.5]non-6-en-8-yl)-4-fluorophenyl)-5-fluoropicolinamide,
N-(3-(2-amino-9,9-difluoro-4-methyl-1-thia-3-azaspiro[5.5]undec-2-en-4-yl)-4-fluorophenyl)-5-fluoropicolinamide,
2,2-difluoro-8-methyl-8-(4-(5-(prop-1-ynyl)pyridin-3-yl)thiophen-2-yl)-5-thia-7-azaspiro[3.5]non-6-en-6-amine,
9,9-difluoro-4-methyl-4-(4-(5-(prop-1-ynyl)pyridin-3-yl)thiophen-2-yl)-1-thia-3-azaspiro[5.5]undec-2-en-2-amine,
2,2,9,9-tetrafluoro-8-methyl-8-(4-(5-(prop-1-yl)pyridin-3-yl)thiophen-2-yl)-5-thia-7-azaspiro[3.5]non-6-en-6-amine,
5,5,9,9-tetrafluoro-4-methyl-4-(4-(5-(prop-1-ynyl)pyridin-3-yl)thiophen-2-yl)-1-thia-3-azaspiro[5.5]undec-2-en-2-amine,
9,9-difluoro-8-methyl-8-(4-(5-(prop-1-ynyl)pyridin-3-yl)thiophen-2-yl)-5-thia-7-azaspiro[3.5]non-6-en-6-amine,
10,10-difluoro-9-methyl-9-(4-(5-(prop-1-ynyl)pyridin-3-yl)thiophen-2-yl)-6-thia-8-azaspiro[4.5]dec-7-en-7-amine,
5,5-difluoro-4-methyl-4-(4-(5-(prop-1-ynyl)pyridin-3-yl)thiophen-2-yl)-1-thia-3-azaspiro[5.5]undec-2-en-2-amine,
5,5-difluoro-4-methyl-4-(4-(5-(prop-1-ynyl)pyridin-3-yl)thiophen-2-yl)-9-oxa-1-thia-3-azaspiro[5.5]undec-2-en-2-amine,
N-(3-(2-amino-4-methyl-9-oxa-1-thia-3-azaspiro[5.5]undec-2-en-4-yl)-4-fluorophenyl)-5-fluoropicolinamide,
3-(2-amino-4-methyl-9-oxa-1-thia-3-azaspiro[5.5]undec-2-en-4-yl)-4-fluoro-N-(5-fluoropyridin-2-yl)benzamide,
3-(6-amino-8-methyl-5-thia-7-azaspiro[3.5]non-6-en-8-yl)-4-fluoro-N-(5-fluoropyridin-2-yl)benzamide,
N-(3-(2-amino-4-methyl-9-oxa-1-thia-3-azaspiro[5.5]undec-2-en-4-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-fluoropicolinamide,
(S)—N-(3-(6-amino-8-methyl-5-thia-7-azaspiro[3.5]non-6-en-8-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-methoxypyrazine-2-carboxamide,
(S)-4-(2-fluoro-5-(3-methoxypyridin-2-ylamino)phenyl)-4-methyl-9-oxa-1-thia-3-azaspiro[5.5]undec-2-en-2-amine, and
any pharmaceutically acceptable salt thereof.

17. The method of claim 1, wherein the compound of formula (I) is selected from the group consisting of
8-methyl-8-(4-(5-(prop-1-ynyl)pyridin-3-yl)thiophen-2-yl)-2-oxa-5-thia-7-azaspiro[3.5]non-6-en-6-amine,
N-(3-(2-amino-4-methyl-1-thia-3-azaspiro[5.5]undec-2-en-4-yl)-4-fluorophenyl)-5-fluoropicolinamide,
4-methyl-4-(4-(5-(prop-1-ynyl)pyridin-3-yl)thiophen-2-yl)-9-oxa-1-thia-3-azaspiro[5.5]undec-2-en-2-amine,
(S)—N-(3-(6-amino-8-methyl-2-oxa-5-thia-7-azaspiro[3.5]non-6-en-8-yl)-4-fluorophenyl)-5-fluoropicolinamide,
N-(3-(6-amino-9,9-difluoro-8-methyl-5-oxa-7-azaspiro[3.5]non-6-en-8-yl)-4-fluorophenyl)-5-fluoropicolinamide,
N-(3-(2-amino-4-methyl-9-oxa-1-thia-3-azaspiro[5.5]undec-2-en-4-yl)-4-fluorophenyl)-5-fluoropicolinamide,
N-(3-(2-amino-4-methyl-9-oxa-1-thia-3-azaspiro[5.5]undec-2-en-4-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-fluoropicolinamide,
(S)—N-(3-(6-amino-8-methyl-5-thia-7-azaspiro[3.5]non-6-en-8-yl)-4-fluorophenyl)-5-chloropicolinamide,
(S)—N-(3-(2-amino-4-methyl-9-oxa-1-thia-3-azaspiro[5.5]undec-2-en-4-yl)-4-fluorophenyl)-5-methoxypyrazine-2-carboxamide,
(S)-4-(2-fluoro-5-(3-methoxypyridin-2-ylamino)phenyl)-4-methyl-9-oxa-1-thia-3-azaspiro[5.5]undec-2-en-2-amine, and
any pharmaceutically acceptable salt thereof.

18. The method of claim 1, wherein the disease is selected from the group consisting of Alzheimer's disease, diffuse Lewy body type Alzheimer's disease, Parkinson's disease, frontotemporal dementias with parkinsonism, progressive supranuclear palsy, cortical basal degeneration, dementia with Lewy bodies, presenile dementia, senile dementia, multi-infarct dementia, dementia of mixed vascular and degenerative origin, mild cognitive impairment, Down syndrome, cerebral amyloid angiopathy, amyotrophic lateral sclerosis, multiple sclerosis, traumatic brain injury, brain inflammation, spinal cord injury, and nerve injury.

19. The method of claim 1, wherein the disease is Alzheimer's disease.

* * * * *